United States Patent
Matsunaga et al.

(10) Patent No.: US 11,795,172 B2
(45) Date of Patent: Oct. 24, 2023

(54) SUBSTITUTED IMIDAZO[1,2-B]PYRIDAZINES AND [1,2,4]TRIAZOLO[4,3-B]PYRIDAZINES AS CAMKII INHIBITORS

(71) Applicant: Cardurion Pharmaceuticals, INC., Burlington, MA (US)

(72) Inventors: Nobuyuki Matsunaga, Kanagawa (JP); Junya Shirai, Kanagawa (JP); Tomohiro Okawa, Kanagawa (JP); Yasufumi Miyamoto, Kanagawa (JP); Zenyu Shiokawa, Kanagawa (JP); Takashi Nakahata, Kanagawa (JP); Akito Shibuya, Kanagawa (JP); Akira Kawada, Kanagawa (JP); Malcolm MacCoss, Seabrook Island, SC (US)

(73) Assignee: Cardurion Pharmaceuticals, Inc., Burlington, MA (US)

( * ) Notice: Subject to any disclaimer, the term of this patent is extended or adjusted under 35 U.S.C. 154(b) by 0 days.

(21) Appl. No.: 17/485,137

(22) Filed: Sep. 24, 2021

(65) Prior Publication Data
US 2022/0098207 A1   Mar. 31, 2022

Related U.S. Application Data

(60) Provisional application No. 63/084,217, filed on Sep. 28, 2020.

(51) Int. Cl.
*A61K 31/5025*   (2006.01)
*C07D 487/04*   (2006.01)
*C07D 471/04*   (2006.01)

(52) U.S. Cl.
CPC ......... *C07D 487/04* (2013.01); *C07D 471/04* (2013.01)

(58) Field of Classification Search
CPC .......................... A61K 31/5025; C07D 487/04
USPC ........................................... 514/248; 544/236
See application file for complete search history.

(56) References Cited

U.S. PATENT DOCUMENTS

| 7,981,891 B2 | 7/2011 | Deak et al. |
| 2002/0198219 A1 | 12/2002 | Grant et al. |

FOREIGN PATENT DOCUMENTS

| WO | 0211724 A2 | 2/2002 |
| WO | 0224681 A2 | 3/2002 |
| WO | 2005021529 A1 | 3/2005 |
| WO | 2008124083 A2 | 10/2008 |
| WO | 2013052394 A1 | 4/2013 |
| WO | 2013157540 A1 | 10/2013 |
| WO | 2014100695 A1 | 6/2014 |
| WO | 2018183112 A1 | 10/2018 |
| WO | 2020150552 A2 | 7/2020 |

OTHER PUBLICATIONS

International Search Report and Written Opinion received for PCT Application No. PCTUS2021052025, dated Feb. 14, 2022, 10 pages.
Backs et al. (Feb. 17, 2009) "The δ Isoform of CaM Kinase II is Required for Pathological Cardiac Hypertrophy and Remodeling After Pressure Overload", Proceedings of the National Academy of Sciences, 106(7):2342-2347.
Colomer et al. (Feb. 2003) "Pressure Overload Selectively Up-Regulates Ca2+/ Calmodulin-Dependent Protein Kinase II in Vivo", Molecular Endocrinology, 17(2):183-192.
Erickson et al. (Oct. 17, 2013) "Diabetic Hyperglycaemia Activates CaMKII and Arrhythmias by O-linked Glycosylation", Nature, 502:372-376 (13 pages).
Fischer et al. (Sep. 8, 2014) "Ca(2+) /Calmodulin-Dependent Protein Kinase II Equally Induces Sarcoplasmic Reticulum Ca(2+) Leak in Human Ischaemic and Dilated Cardiomyopathy", European Journal of Heart Failure, 16(12):1292-1300.
Hoch et al. (Apr. 2, 1999) "Identification and Expression of 6-Isoforms of the Multifunctional Ca2+/Calmodulin-Dependent Protein Kinase in Failing and Nonfailing Human Myocardium", Circulation Research, 84(6):713-721.
House et al. (Dec. 20, 2007) "CaMKII-δ Isoform Regulation of Neointima Formation After Vascular Injury", Arteriosclerosis, Thrombosis, and Vascular Biology, 28(3):441-447.

(Continued)

*Primary Examiner* — Douglas M Willis
(74) *Attorney, Agent, or Firm* — Mintz, Levin, Cohn, Ferris, Glovsky and Popeo, P.C.

(57) ABSTRACT

The present invention provides a fused heteroaryl compound having a CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like.

The present invention relates to a compound represented by the formula (I):

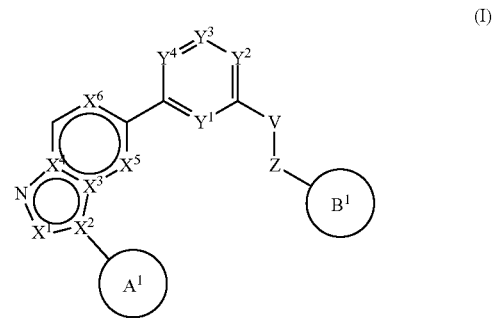

wherein each symbol is as defined in the description, or a pharmaceutically acceptable salt thereof.

15 Claims, No Drawings

(56) References Cited

OTHER PUBLICATIONS

Ling et al. (Mar. 15, 2013) "Ca2+/Calmodulin-Dependent Protein Kinase II δ Mediates Myocardial Ischemia/Reperfusion Injury Through Nuclear Factor-κB", Circulation Research, 112(6):935-944.

Liu et al. (Jan. 2011) "Calmodulin kinase II inhibition prevents arrhythmias in RyR2R4496C+/− mice with catecholaminergic polymorphic ventricular tachycardia", Journal of Molecular and Cellular Cardiology, 50(1):214-222.

Luo et al.( Apr. 2008) "Reversal of Chronic Inflammatory Pain by Acute Inhibition of Ca2+/Calmodulin-Dependent Protein Kinase II", Journal of Pharmacology and Experimental Therapeutics,325(1):267-275.

O'Hanlon et al. (Oct. 11, 2019) "An Influenza Virus Entry Inhibitor Targets Class II PI3 Kinase and Synergizes with Oseltamivir", ACS Infectious Diseases, 5(10):1779-1793(10 pages).

Soliman et al. (Mar. 2009) "Intracellular Calcium Signals Regulate Growth of Hepatic Stellate Cells Via Specific Effects on Cell Cycle Progression", Cell Calcium, 45(3):284-292 (21 pages).

Timmins et al. (Oct. 2009) "Calcium/Calmodulin-Dependent Protein Kinase II links ER Stress with Fas and Mitochondrial Apoptosis Pathways", The Journal of Clinical Investigation, 119(10):2925-2941.

Vest et al. (Jul. 2, 2010) "Effective Post-insult Neuroprotection by a Novel Ca2+/ Calmodulin-Dependent Protein Kinase II (CaMKII) Inhibitor", Journal of Biological Chemistry,285(27):20675-20682.

Wang et al. (2015) "The Emerging Role of CaMKII in Cancer", Oncotarget, 6(14):11725-11734.

Westra et al. (2010) "Expression and regulation of HIF-1alpha in macrophages under inflammatory conditions; significant reduction ofVEGF by CaMKII inhibitor", BMC Musculoskeletal Disorders, 30:11 pages.

Zhang et al. (May 2, 2003) "The δc Isoform of CaMKII Is Activated in Cardiac Hypertrophy and Induces Dilated Cardiomyopathy and Heart Failure", Circulation Research, 92(8):912-919.

SUBSTITUTED IMIDAZO[1,2-B]PYRIDAZINES AND [1,2,4]TRIAZOLO[4,3-B]PYRIDAZINES AS CAMKII INHIBITORS

CROSS REFERENCE TO RELATED APPLICATION

The present application claims priority to and the benefit of U.S. Provisional Application No. 63/084,217, filed on Sep. 28, 2020, which is incorporated herein by reference in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

(1) Field of the Invention

The present invention relates to a fused heteroaryl compound having a calcium/calmodulin-dependent protein kinase II (sometimes to be abbreviated as "CaMKII" in the present specification) inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like.

Cardiac diseases include heart failure, arrhythmia, myocardial infarction, angina, valvular heart disease and the like, and they are high-mortality diseases. In treatment of cardiac diseases with a drug, the symptoms are improved by control of each risk factor and symptomatic therapy. However, the satisfaction with treatment remains low level, and there is now no definitive therapy.

Calcium-calmodulin complex binds to $Ca^{2+}$/calmodulin-dependent protein kinase (CaMK) included in serine/threonine protein kinase, and activates the kinase. The CaMK family includes CaMKII, and four isoforms ($\alpha$, $\beta$, $\gamma$ and $\delta$) exist as CaMKII. CaMKII $\alpha$ and CaMKII $\beta$ are expressed mainly in cerebral tissue, and CaMKII $\gamma$ and CaMKII $\delta$ are expressed in many tissues including heart. CaMKII is activated by amino acid-modification due to oxidative stress or hyperglycemia, in addition to the binding of calcium-calmodulin complex. CaMKII regulates cell functions by phosphorylation of a transcription factor which is a substrate, a protein that plays a function in organelle uptake/excretion of $Ca^{2+}$, a protein that regulates contract and relax of muscles, a channel that regulates an intracellular ion concentration, and the like, due to its kinase activation.

(2) Description of Related Art

Some documents suggest that CaMKII plays a harmful role in progress of cardiac disease conditions. Expression and activity of CaMKII are increased in heart of human patient or animal with heart failure (Non-Patent Documents 1-4). In transgenic mouse overexpressing CaMKII $\delta$ in heart, onsets of cardiac hypertrophy and heart failure are reported (Non-Patent Document 4). By studies using an inhibitor by a pharmacological method, and studies using a gene deletion by genetic method, protecting effects on heart failure, cardiac hypertrophy, myocardial infarction and arrhythmia by an inhibition of CaMKII and an overexpression of CaMKII inhibitory protein are reported in mouse (Non-Patent Documents 5-7). For catecholaminergic polymorphic ventricular tachycardia, improving effects on disease conditions by CaMKII inhibitor in mutant ryanodine knock-in mouse ($RyR2^{R4496C+/-}$ mouse) are reported (Non-Patent Document 8). These findings suggest availabilities of CaMKII inhibitors in the prophylaxis and/or treatment of cardiac diseases including heart failure, cardiac hypertrophy, myocardial infarction and cardiac arrhythmia.

Recently, CaMKII exacerbating action on growth or metastasis of a certain type of cancer is suggested (Non-Patent Document 9). In addition, therapeutic effect on acute renal failure, intimal hypertrophy, hepatic fibrosis, stroke, pain, rheumatoid arthritis and the like by CaMKII inhibition are also indicated (Non-Patent Documents 10-15).

However, genetic methods achieve only deficiency of protein or overexpression of inhibitory protein, and they are different from a mechanism which inhibits temporarily kinase activity, and therefore, effects by kinase inhibitor cannot be always expected. In addition, inhibitors which have been already reported are not suitable for application as a medicament for a CaMKII selective inhibitor, because they have a low kinase selectivity to CaMKII, or they are not suitable for oral administration or chronic administration.

As a heterocyclic compound, the following compounds are known. Patent Document 1 describes that a compound represented by the following formula (I):

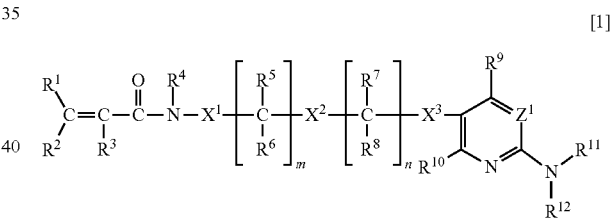

wherein each symbol is as defined in Patent Document 1, is a FLT3 inhibitor and useful for the treatment of acute myelogenous leukemia and the like.

Patent Document 2 describes that a compound represented by the following formula (I):

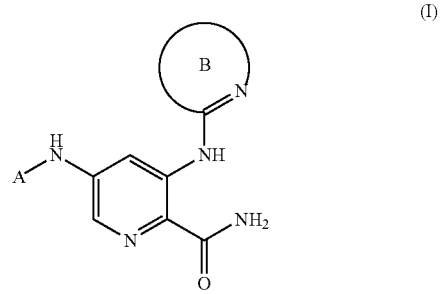

wherein each symbol is as defined in Patent Document 2, is a Syk (Spleen tyrosine kinase) inhibitor and useful for the treatment of diseases or conditions mediated by Syk (e.g., rheumatism).

Patent Document 3 describes that a compound represented by the following formula (I):

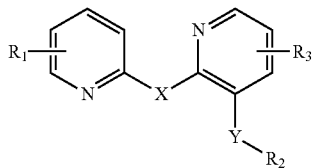

wherein each symbol is as defined in Patent Document 3, is a mGluR (metabotropic glutamate receptors) 5 modulator and useful for the treatment or prophylaxis of diseases or conditions in which mGluR5 is involved (e.g., pain disorder, anxiety, depression, Alzheimer's disease, Parkinson's disease, etc.).

Patent Document 4 describes that a compound represented by the following formula (I):

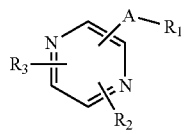

wherein each symbol is as defined in Patent Document 4, is a kinase inhibitor (particularly an inhibitor of kinase domain in VEGF receptor (VEGF receptor tyrosine kinase inhibitor)) and useful for the treatment of vascular abnormality, tumor, diabetic retinopathy, rheumatism, endometriosis, psoriasis and the like.

Patent Document 5 describes that a compound represented by the following formula (I):

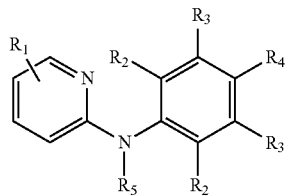

wherein each symbol is as defined in Patent Document 5, is a kinase (p38 kinase, etc.) inhibitor and useful for reduction of ischemic cell death (particularly reduction of traumatic neuronalcell death).

Patent Document 6 describes that a compound represented by the following formula (I):

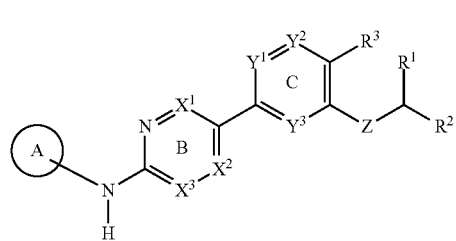

wherein each symbol is as defined in Patent Document 6, is a calcium/calmodulin-dependent protein kinase II inhibitor and useful for the prophylaxis or treatment of cardiac diseases.

Patent Document 1: WO 2013/157540
Patent Document 2: WO 2013/052394
Patent Document 3: WO 2005/021529
Patent Document 4: WO 2002/024681
Patent Document 5: WO 2002/011724
Patent Document 6: WO 2018/183112
Non-Patent Document 1: European Journal of Heart Failure, vol. 16, p. 1292-1300
Non-Patent Document 2: Circulation Research, vol. 84, p. 713-721
Non-Patent Document 3: Molecular Endocrinology, vol. 17, p. 183-192
Non-Patent Document 4: Circulation Research, vol. 92, p. 912-919
Non-Patent Document 5: Proceedings of the National Academy of Sciences, vol. 106, p. 2342-2347
Non-Patent Document 6: Circulation Research, vol. 112, p. 935-944
Non-Patent Document 7: Nature, vol. 502, p. 372-376
Non-Patent Document 8: Journal of Molecular and Cellular Cardiology, vol. 50, p. 214-222
Non-Patent Document 9: Oncotarget, vol. 20, p. 11725-11734
Non-Patent Document 10: Arterioscler Thromb Vasc Biol, vol. 28, p. 441-447
Non-Patent Document 11: Cell Calcium, vol. 45, p. 284-292
Non-Patent Document 12: J Clin Invest, vol. 119, p. 2925-2941
Non-Patent Document 13: J Biol Chem, vol. 285, p. 20675-20682
Non-Patent Document 14: J Pharmacol Exp Ther, vol. 325, p. 267-275
Non-Patent Document 15: BMC Musculoskelet Disord, vol. 30, p. 61

BRIEF SUMMARY OF THE INVENTION

An object of the present invention is to provide a fused heteroaryl compound having a CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like.

The present inventors have conducted intensive studies in an attempt to solve the above-mentioned problems and found that a compound represented by the following formula (I) has a CaMKII inhibitory action, and therefore, is expected to be useful as an agent for the prophylaxis or treatment of cardiac diseases (particularly catecholaminergic polymorphic ventricular tachycardia, postoperative atrial fibrillation, heart failure, fatal arrhythmia) and the like, which resulted in the completion of the present invention.

Accordingly, the present invention provides the following.

[1] A compound represented by the formula (I):

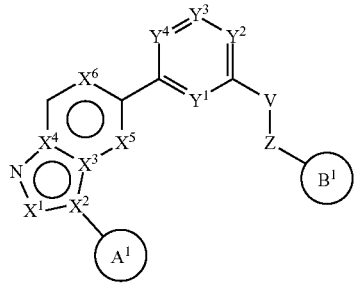

wherein
X$^1$ is N or CR$^{X1}$ wherein R$^{X1}$ is a hydrogen atom, a halogen atom or a C$_{1-6}$ alkyl group;
X$^2$, X$^3$ and X$^4$ are each independently C or N, and one of X$^2$, X$^3$ and
X$^4$ is N, and the other two are C;
X$^5$ is N or CR$^{X5}$ wherein R$^{X5}$ is a hydrogen atom;
X$^6$ is N or CR$^{X6}$ wherein R$^{X6}$ is a hydrogen atom;
Ring A$^1$ is an optionally further substituted C$_{6-14}$ aromatic hydrocarbon, an optionally further substituted aromatic heterocycle, or an optionally further substituted non-aromatic heterocycle, each of which is optionally fused with an optionally substituted 5- or 6-membered ring;
Y$^1$ is N or CR$^{Y1}$ wherein R$^{Y1}$ is a hydrogen atom;
Y$^2$ is N or CR$^{Y2}$ wherein R$^{Y2}$ is a hydrogen atom, a halogen atom or a cyano group;
Y$^3$ is N or CR$^{Y3}$ wherein R$^{Y3}$ is a hydrogen atom or a halogen atom;
Y$^4$ is N or CR$^{Y4}$ wherein R$^{Y4}$ is a hydrogen atom or a halogen atom; Ring B$^1$ is an optionally further substituted aromatic heterocycle;
V is O, S, S(O), S(O)$_2$ or N(R$^V$) wherein R$^V$ is a hydrogen atom or an optionally substituted C$_{1-6}$ alkyl group; and
Z is an optionally substituted C$_{1-6}$ alkylene group;
or a pharmaceutically acceptable salt thereof (hereinafter sometimes to be referred to as compound (I)).

[2] The compound or pharmaceutically acceptable salt according to the above-mentioned [1], wherein V is O.

[3] The compound or pharmaceutically acceptable salt according to the above-mentioned [1], wherein Ring B$^1$ is an optionally further substituted 5-membered aromatic heterocycle.

[4] The compound or pharmaceutically acceptable salt according to the above-mentioned [1], wherein Z is an optionally substituted ethylene group.

[5] The compound or pharmaceutically acceptable salt according to the above-mentioned [1], wherein X$^5$ is N.

[6] The compound or pharmaceutically acceptable salt according to the above-mentioned [1], wherein X$^6$ is CH.

[7] The compound or pharmaceutically acceptable salt according to the above-mentioned [1], wherein at least one of Y$^1$, Y$^2$, Y$^3$ and Y$^4$ are N.

[8] The compound or pharmaceutically acceptable salt according to the above-mentioned [1], which is a compound represented by the formula (I-1):

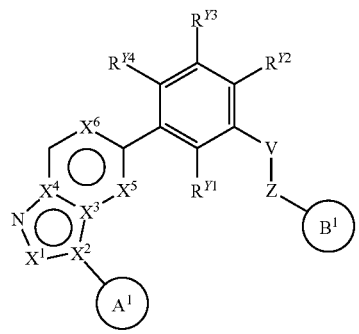

wherein each symbol is as defined in the above-mentioned [1], or a pharmaceutically acceptable salt thereof (hereinafter sometimes to be referred to as compound (I-1)).

[9] A compound represented by the formula (II):

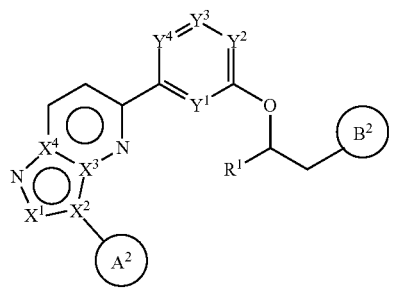

wherein
X$^1$ is N or CR$^{X1}$ wherein R$^{X1}$ is a hydrogen atom, a halogen atom or a C$_{1-6}$ alkyl group;
X$^2$, X$^3$ and X$^4$ are each independently C or N, and one of X$^2$, X$^3$ and
X$^4$ is N, and the other two are C;
Ring A$^2$ is an optionally further substituted benzene ring, an optionally further substituted 5- or 6-membered aromatic heterocycle, or an optionally further substituted 5- or 6-membered non-aromatic heterocycle, each of which is optionally fused with an optionally substituted 5- or 6-membered ring;
Y$^1$ is N or CR$^{Y1}$ wherein R$^{Y1}$ is a hydrogen atom;
Y$^2$ is N or CR$^{Y2}$ wherein R$^{Y2}$ is a hydrogen atom, a halogen atom or a cyano group;
Y$^3$ is N or CR$^{Y3}$ wherein R$^{Y3}$ is a hydrogen atom or a halogen atom;
Y$^4$ is N or CR$^{Y4}$ wherein R$^{Y4}$ is a hydrogen atom or a halogen atom;
Ring B$^2$ is an optionally further substituted 5-membered aromatic heterocycle; and
R$^1$ is a C$_{1-6}$ alkyl group;
or a pharmaceutically acceptable salt thereof (hereinafter sometimes to be referred to as compound (II)).

[10] The compound or pharmaceutically acceptable salt according to the above-mentioned [9], wherein X$^1$ is CH.

[11] The compound or pharmaceutically acceptable salt according to the above-mentioned [9], wherein Ring B$^2$ is tetrazole or triazole, each of which is bonded at its nitrogen.

[12] The compound or pharmaceutically acceptable salt according to the above-mentioned [9], wherein R$^1$ is methyl.

[13] The compound or pharmaceutically acceptable salt according to the above-mentioned [9], wherein Ring $A^2$ is a benzene ring, a 6-membered aromatic heterocycle, or a 6-membered non-aromatic heterocycle, each of which is further substituted by one cyano group and optionally further substituted.

[14] The compound or pharmaceutically acceptable salt according to the above-mentioned [9], wherein at least one of $Y^1$, $Y^2$, $Y^3$ and $Y^4$ are N.

[15] The compound or pharmaceutically acceptable salt according to the above-mentioned [9], which is a compound represented by the formula (II-1):

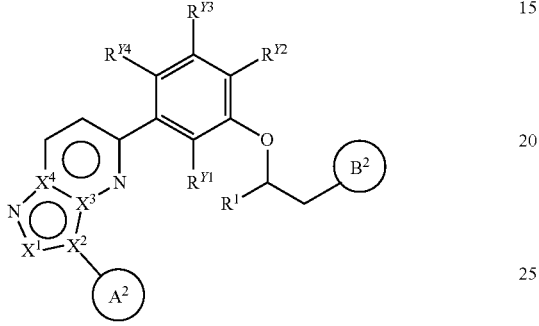

(II-1)

wherein each symbol is as defined in the above-mentioned [9], or a pharmaceutically acceptable salt thereof (hereinafter sometimes to be referred to as compound (II-1)).

[16] A compound represented by the formula (III):

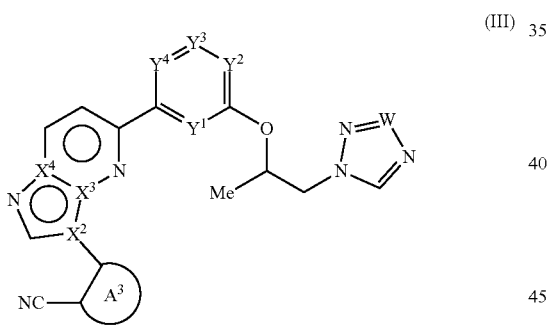

(III)

$X^2$, $X^3$ and $X^4$ are each independently C or N, and one of $X^2$, $X^3$ and $X^4$ is N, and the other two are C;

Ring $A^3$ is an optionally further substituted benzene ring, an optionally further substituted 6-membered nitrogen-containing aromatic heterocycle, or an optionally further substituted 6-membered nitrogen-containing non-aromatic heterocycle;

$Y^1$ is N or $CR^{Y1}$ wherein $R^Y$ is a hydrogen atom;

$Y^2$ is N or $CR^{Y2}$ wherein $R^{Y2}$ is a hydrogen atom, a halogen atom or a cyano group;

$Y^3$ is N or $CR^{Y3}$ wherein $R^{Y3}$ is a hydrogen atom or a halogen atom;

$Y^4$ is N or $CR^{Y4}$ wherein $R^{Y4}$ is a hydrogen atom or a halogen atom; and W is N or CH;

or a pharmaceutically acceptable salt thereof (hereinafter sometimes to be referred to as compound (III)).

[17] The compound or pharmaceutically acceptable salt according to the above-mentioned [16], wherein the partial structure represented by the formula;

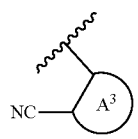

is a partial structure represented by the formula ($A^3$-1)-($A^3$-9);

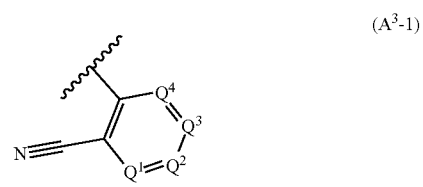
(A³-1)

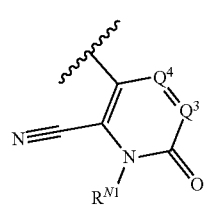
(A³-2)

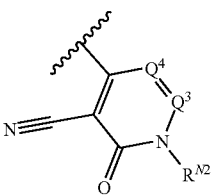
(A³-3)

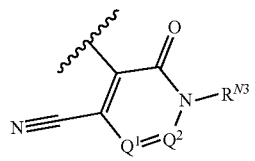
(A³-4)

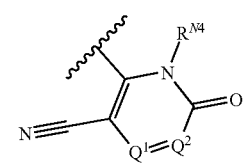
(A³-5)

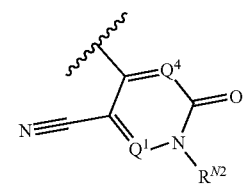
(A³-6)

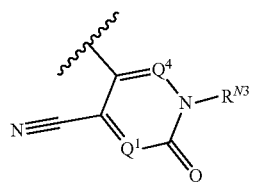
(A³-7)

-continued

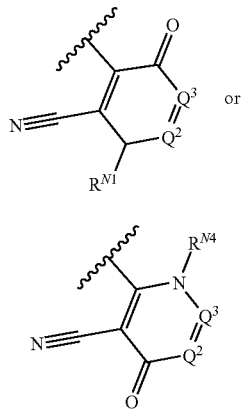

(A³-8)

(A³-9)

wherein
Q¹ is N or CR$^{Q1}$ wherein R$^{Q1}$ is
(a) a hydrogen atom,
(b) a cyano group,
(c) a halogen atom,
(d) a hydroxy group,
(e) a carboxy group,
(f) an amino group,
(g) an optionally substituted $C_{1-6}$ alkyl group,
(h) an optionally substituted $C_{1-6}$ alkoxy group,
(i) a $C_{1-6}$ alkyl-carbonyl group,
(j) a $C_{1-6}$ alkoxy-carbonyl group,
(k) an optionally substituted mono- or di-$C_{1-6}$ alkylamino group,
(l) an optionally substituted mono- or di-$C_{1-6}$ alkyl-carbonylamino group,
(m) a mono- or di-$C_{1-6}$ alkoxy-carbonylamino group,
(n) a mono- or di-$C_{1-6}$ alkyl-carbamoyl group,
(o) a di-$C_{1-6}$ alkylsulfinylidenamino group,
(p) a $C_{3-10}$ cycloalkyl group,
(q) an optionally substituted $C_{3-10}$ cycloalkyloxy group,
(r) a 3- to 8-membered monocyclic non-aromatic heterocyclic group,
(s) an optionally substituted 3- to 8-membered monocyclic non-aromatic heterocyclyloxy,
(t) an optionally substituted 3- to 8-membered monocyclic non-aromatic heterocyclylcarbonyl group, or
(u) a 3- to 8-membered monocyclic non-aromatic heterocyclylidenamino group,
Q² is N or CR$^{Q2}$ wherein R$^{Q2}$ is
(a) a hydrogen atom,
(b) a halogen atom, or
(c) a $C_{1-6}$ alkoxy group, Q³ is N or CR$^{Q3}$ wherein R$^{Q3}$ is
(a) a hydrogen atom,
(b) a cyano group,
(c) a halogen atom,
(d) a carboxy group,
(e) an optionally substituted $C_{1-6}$ alkyl group,
(f) an optionally substituted $C_{1-6}$ alkoxy group,
(g) a $C_{1-6}$ alkyl-carbonyl group,
(h) a $C_{1-6}$ alkoxy-carbonyl group,
(i) a mono- or di-$C_{1-6}$ alkylamino group,
(j) an optionally substituted mono- or di-$C_{1-6}$ alkyl-carbamoyl group,
(k) a di-$C_{1-6}$ alkylsulfinylidenamino group, or
(l) a 3- to 8-membered monocyclic non-aromatic heterocyclylidenamino group, Q⁴ is N or CR$^{Q4}$ wherein R$^{Q4}$ is
(a) a hydrogen atom, or
(b) a halogen atom, and
N of Q¹, Q², Q³ and Q⁴ is each optionally oxidized;
R$^{N1}$ is a hydrogen atom or a $C_{1-6}$ alkyl group;
R$^{N2}$ is a hydrogen atom or a $C_{1-6}$ alkyl group;
R$^{N3}$ is a hydrogen atom or a $C_{1-6}$ alkyl group; and
R$^{N4}$ is a hydrogen atom or a $C_{1-6}$ alkyl group optionally substituted by 1 to 3 halogen atoms.

[18] The compound or pharmaceutically acceptable salt according to the above-mentioned [16], wherein at least one of Y¹, Y², Y³ and Y⁴ are N.

[19] The compound or pharmaceutically acceptable salt according to the above-mentioned [16], which is a compound represented by the formula (III-1):

(III-1)

wherein each symbol is as defined in the above-mentioned [16], or a pharmaceutically acceptable salt thereof (hereinafter sometimes to be referred to as compound (III-1)).

[20] A compound selected from the group consisting of
2-[6-(4-fluoro-3-{[(2S)-1-(1H-tetrazol-1-yl)propan-2-yl]oxy}phenyl)imidazo[1,2-b]pyridazin-3-yl]benzonitrile,
2-[6-(4-fluoro-3-{[(2S)-1-(1H-tetrazol-1-yl)propan-2-yl]oxy}phenyl)imidazo[1,2-b]pyridazin-3-yl]pyridine-3-carbonitrile,
2-[6-(3-{[(2S)-1-(1H-tetrazol-1-yl)propan-2-yl]oxy}phenyl)imidazo[1,2-b]pyridazin-3-yl]pyridine-3-carbonitrile,
2-[5-(3-{[(2S)-1-(1H-tetrazol-1-yl)propan-2-yl]oxy}phenyl)-3H-imidazo[4,5-b]pyridin-3-yl]pyridine-3-carbonitrile,
4-fluoro-2-[6-(5-{[(2S)-1-(1H-tetrazol-1-yl)propan-2-yl]oxy}pyridin-3-yl)imidazo[1,2-b]pyridazin-3-yl]benzonitrile,
4-methoxy-2-[6-(3-{[(2S)-1-(1H-tetrazol-1-yl)propan-2-yl]oxy}phenyl)imidazo[1,2-b]pyridazin-3-yl]pyridine-3-carbonitrile,
2-[6-(4-fluoro-3-{[(2S)-1-(1H-tetrazol-1-yl)propan-2-yl]oxy}phenyl)imidazo[1,2-b]pyridazin-3-yl]-4-methoxypyridine-3-carbonitrile,
4-fluoro-2-[5-(6-{[(2S)-1-(1H-tetrazol-1-yl)propan-2-yl]oxy}pyridin-2-yl)-3H-imidazo[4,5-b]pyridin-3-yl]benzonitrile,
4-fluoro-2-methoxy-6-[6-(6-{[(2S)-1-(1H-tetrazol-1-yl)propan-2-yl]oxy}pyrazin-2-yl)imidazo[1,2-b]pyridazin-3-yl]benzonitrile,
4-fluoro-2-methoxy-6-[5-(6-{[(2S)-1-(1H-tetrazol-1-yl)propan-2-yl]oxy}pyridin-2-yl)-3H-imidazo[4,5-b]pyridin-3-yl]benzonitrile,
and 4-fluoro-2-methoxy-6-[6-(6-{[(2S)-1-(1H-tetrazol-1-yl)propan-2-yl]oxy}pyridin-2-yl)imidazo[1,2-b]pyridazin-3-yl]benzonitrile, or a pharmaceutically acceptable salt.

[21] A medicament comprising the compound or pharmaceutically acceptable salt according to the above-mentioned [1].

[22] The medicament according to the above-mentioned [21], which is a calcium/calmodulin-dependent protein kinase II inhibitor.

[23] The medicament according to the above-mentioned [21], which is an agent for the prophylaxis or treatment of cardiac diseases.

[24] The medicament according to the above-mentioned [23], wherein the cardiac disease is selected from catecholaminergic polymorphic ventricular tachycardia, postoperative atrial fibrillation, heart failure and fatal arrhythmia.

[25] The compound or pharmaceutically acceptable salt according to the above-mentioned [1] for use in the prophylaxis or treatment of cardiac diseases.

[26] The compound or pharmaceutically acceptable salt according to the above-mentioned [25], wherein the cardiac disease is selected from catecholaminergic polymorphic ventricular tachycardia, postoperative atrial fibrillation, heart failure and fatal arrhythmia.

[27] A method for inhibiting calcium/calmodulin-dependent protein kinase II in a mammal, which comprises administering an effective amount of the compound or pharmaceutically acceptable salt according to the above-mentioned [1] to the mammal.

[28] A method for preventing or treating cardiac diseases in a mammal, which comprises administering an effective amount of the compound or pharmaceutically acceptable salt according to the above-mentioned [1] to the mammal.

[29] The method according to the above-mentioned [28], wherein the cardiac disease is selected from catecholaminergic polymorphic ventricular tachycardia, postoperative atrial fibrillation, heart failure and fatal arrhythmia.

[30] Use of the compound or pharmaceutically acceptable salt according to the above-mentioned [1] for the production of an agent for the prophylaxis or treatment of cardiac diseases.

[31] The use according to the above-mentioned [30], wherein the cardiac disease is selected from catecholaminergic polymorphic ventricular tachycardia, postoperative atrial fibrillation, heart failure and fatal arrhythmia.

BRIEF DESCRIPTION OF THE SEVERAL VIEWS OF THE DRAWINGS

Not Applicable

DETAILED DESCRIPTION OF THE INVENTION

According to the present invention, a fused heteroaryl compound having a superior CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like can be provided.

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,

(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di- (optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di- (optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "$C_{6-14}$ aromatic hydrocarbon ring" include anthracene, phenanthrene, acenaphthylene, in addition to those exemplified as the above-mentioned "$C_{6-14}$ aromatic hydrocarbon ring".

The definition of each symbol in the formula (I) is explained in detail in the following.

$X^1$ is N or $CR^{X1}$ wherein $R^{X1}$ is a hydrogen atom, a halogen atom (e.g., a fluorine atom) or a $C_{1-6}$ alkyl group (e.g., methyl).

$X^1$ is preferably CH.

$X^2$, $X^3$ and $X^4$ are each independently C or N, and one of $X^2$, $X^3$ and $X^4$ is N, and the other two are C.

$X^5$ is N or $CR^{X5}$ wherein $R^{X5}$ is a hydrogen atom.

$X^5$ is preferably N.

$X^6$ is N or $CR^{X6}$ wherein $R^{X6}$ is a hydrogen atom.

$X^6$ is preferably CH.

The partial structure represented by the formula:

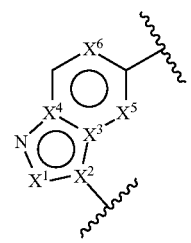

is specifically represented by the formula (Ia), (Ib) or (Ic):

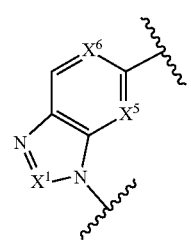

(Ia)

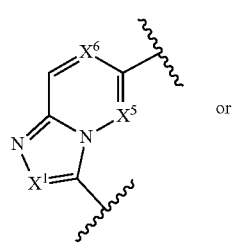

(Ib)

or

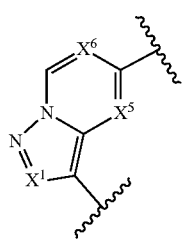
(Ic)

wherein each symbol is as defined above.

The partial structure represented by the formula:

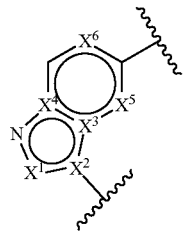

is preferably a partial structure represented by the formula (Ia1), (Ib1), (Ic1), (Ia2), (Ib2) or (Ic2):

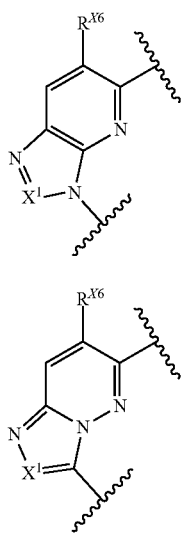

(Ia1)

(Ib1)

(Ic1)

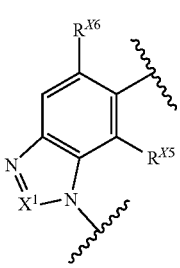
(Ia2)

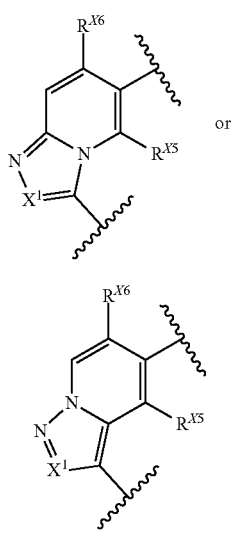
(Ib2)

or (Ic2)

wherein each symbol is as defined above.

In this embodiment, $X^1$ is N or $CR^{X1}$ wherein $R^{X1}$ is a hydrogen atom, a halogen atom (e.g., a fluorine atom) or a $C_{1-6}$ alkyl group (e.g., methyl), preferably CH.

In this embodiment, $R^{X5}$ is a hydrogen atom.

In this embodiment, $R^{X6}$ is a hydrogen atom.

The partial structure represented by the formula:

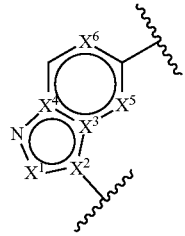

is more preferably a partial structure represented by the formula (Ia1), (Ib1), (Ic1) or (Ib2):

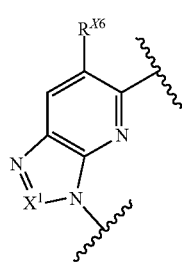

(Ia1)

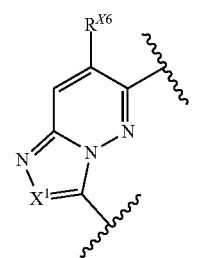
(Ib1)

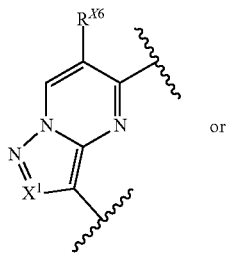
(Ic1)

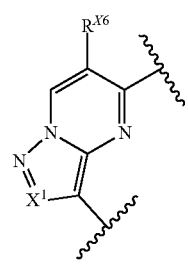
(Ic1)

wherein each symbol is as defined above.

The partial structure represented by the formula:

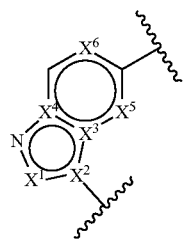

is still more preferably a partial structure represented by the formula (IIa), (IIb) or (IIc):

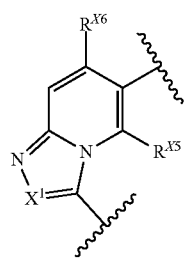
(Ib2)

wherein each symbol is as defined above, further more preferably a partial structure represented by the formula (Ia1), (Ib1) or (Ic1):

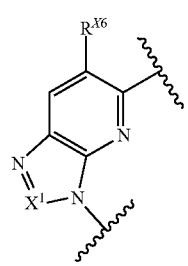
(Ia1)

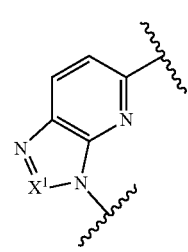
(IIa)

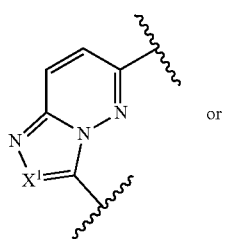
(IIb)

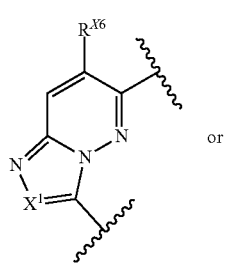
(Ib1) or

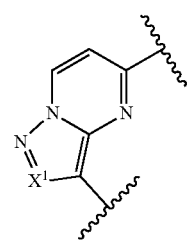
(IIc)

wherein each symbol is as defined above, and specifically represented by the formula (IIa1), (IIb1), (IIc1), (IIa2), (IIb2) or (IIc2):

(IIa1)
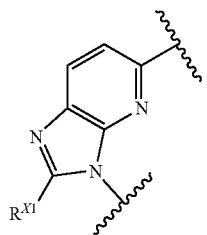

(IIb1)
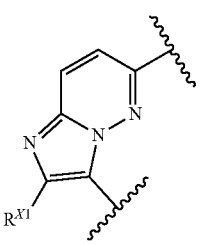

(IIc1)
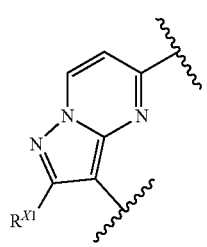

(IIa2)
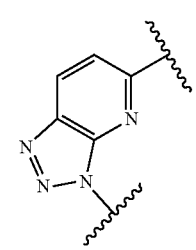

(IIb2)
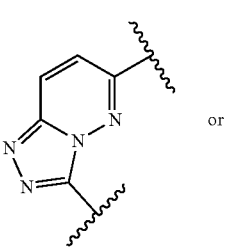

or (IIc2)
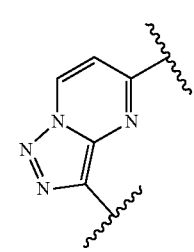

wherein each symbol is as defined above.

In this embodiment, $R^{X1}$ is a hydrogen atom, a halogen atom (e.g., a fluorine atom) or a $C_{1-6}$ alkyl group (e.g., methyl), preferably a hydrogen atom.

The partial structure represented by the formula:

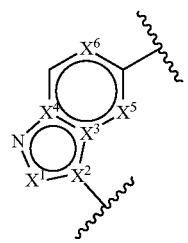

is still more preferably a partial structure represented by the formula (IIa1), (IIb1), (IIc1) or (IIb2):

(IIa1)
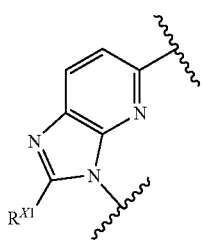

(IIb1)
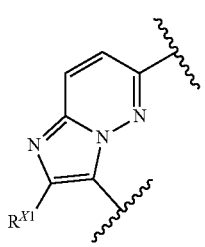

(IIc1)
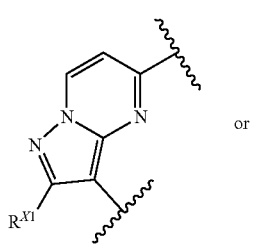

or (IIb2)
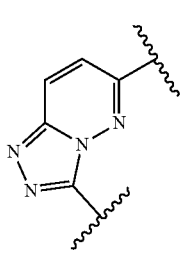

wherein each symbol is as defined above, even more preferably a partial structure represented by the formula (IIa1), (IIb1) or (IIc1):

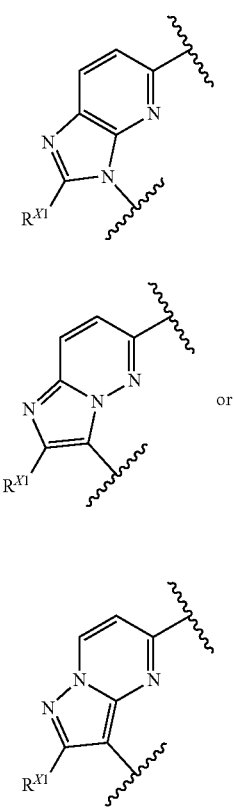

(IIa1)

(IIb1)

(IIc1)

wherein each symbol is as defined above.

The partial structure represented by the formula:

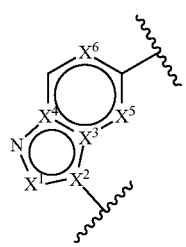

is particularly preferably a partial structure represented by the formula (IIIa), (IIIb) or (IIIc):

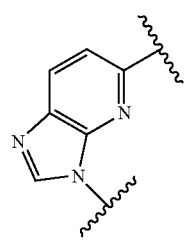

(IIIa)

-continued

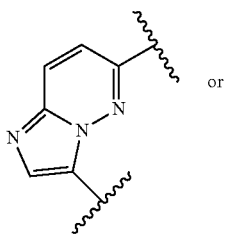

(IIIb)

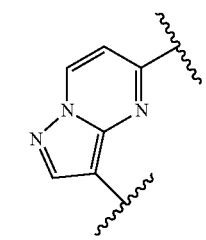

(IIIc)

wherein each symbol is as defined above.

$Y^1$ is N or $CR^{Y1}$ wherein $R^{Y1}$ is a hydrogen atom.

$Y^1$ is preferably CH.

$Y^2$ is N or $CR^{Y2}$ wherein $R^{Y2}$ is a hydrogen atom, a halogen atom (e.g., a fluorine atom, a chlorine atom) or a cyano group.

$Y^2$ is preferably N or $CR^{Y2}$ wherein $R^{Y2}$ is a hydrogen atom or a halogen atom (e.g., a fluorine atom, a chlorine atom), more preferably CH or CF, particularly preferably CF.

$Y^3$ is N or $CR^{Y3}$ wherein $R^{Y3}$ is a hydrogen atom or a halogen atom (e.g., a fluorine atom).

$Y^3$ is preferably CH.

$Y^4$ is N or $CR^{Y4}$ wherein $R^{Y4}$ is a hydrogen atom or a halogen atom (e.g., a fluorine atom).

$Y^4$ is preferably CH.

The partial structure represented by the formula:

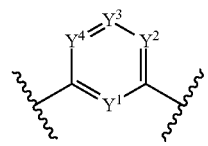

is specifically represented by the formula (Ar-1)-(Ar-12):

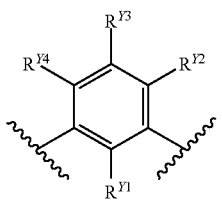

(Ar-1)

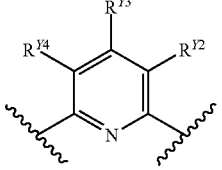

(Ar-2)

-continued (Ar-3) 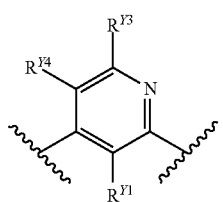

(Ar-4) 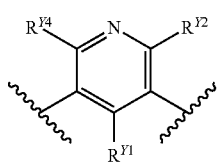

(Ar-5) 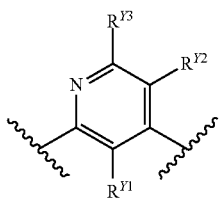

(Ar-6) 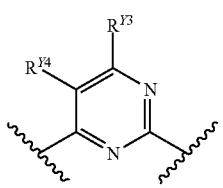

(Ar-7) 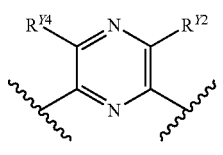

(Ar-8) 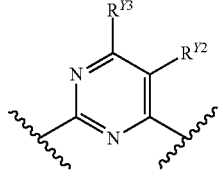

(Ar-9) 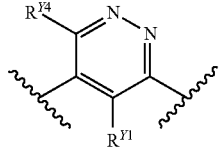

(Ar-10) 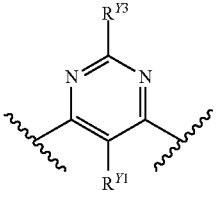

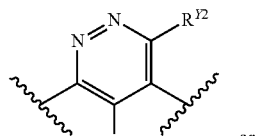 (Ar-11)

or

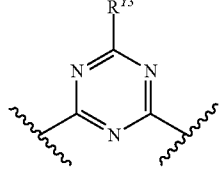 (Ar-12)

wherein each symbol is as defined above.

When $Y^1$, $Y^2$, $Y^3$ and $Y^4$ are all C, then the partial structure is represented by the formula (Ar-1).

When at least one of $Y^1$, $Y^2$, $Y^3$ and $Y^4$ are N, then the partial structure is represented by the formula (Ar-2)-(Ar-12). These partial structures are collectively represented by the formula:

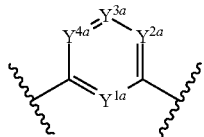

wherein
$Y^{1a}$ is N or $CR^{Y1a}$ wherein $R^{Y1a}$ is a hydrogen atom;
$Y^{2a}$ is N or $CR^{Y2a}$ wherein $R^{Y2a}$ is a hydrogen atom or a halogen atom (e.g., a fluorine atom);
$Y^{3a}$ is N or $CR^{Y3a}$ wherein $R^{Y3a}$ is a hydrogen atom;
$Y^{4a}$ is N or $CR^{Y4a}$ wherein $R^{Y4a}$ is a hydrogen atom; and
at least one of $Y^1a$, $Y^{2a}$, $Y^{3a}$ and $Y^{4a}$ are N.

$Y^{1a}$ is preferably N.
$Y^{2a}$ is preferably CH.
$Y^{3a}$ is preferably CH.
$Y^{4a}$ is preferably CH.

The partial structure represented by the formula:

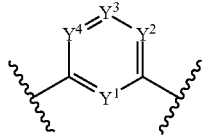

is preferably a partial structure represented by the formula (Ar-1)-(Ar-11):

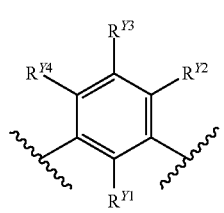 (Ar-1)

-continued (Ar-2) 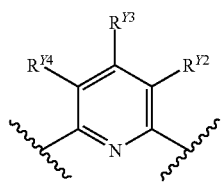

(Ar-3) 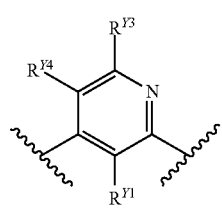

(Ar-4) 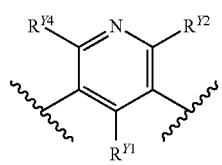

(Ar-5) 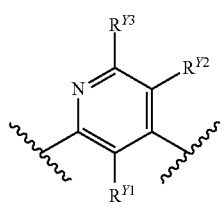

(Ar-6) 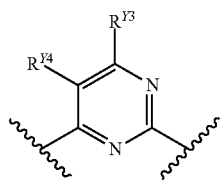

(Ar-7) 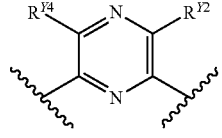

(Ar-8) 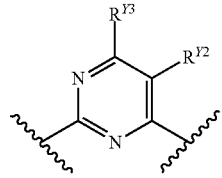

(Ar-9) 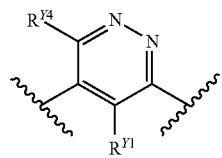

-continued (Ar-10) 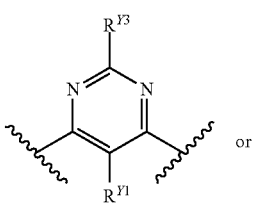  or (Ar-11) 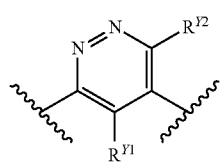

wherein each symbol is as defined above.

In this embodiment, $R^{Y1}$ is a hydrogen atom.

In this embodiment, $R^{Y2}$ is a hydrogen atom, a halogen atom (e.g., a fluorine atom, a chlorine atom) or a cyano group, preferably is a hydrogen atom or a halogen atom (e.g., a fluorine atom, a chlorine atom), more preferably a hydrogen atom or a fluorine atom, particularly preferably a fluorine atom.

In this embodiment, $R^{Y3}$ is a hydrogen atom or a halogen atom (e.g., a fluorine atom), preferably a hydrogen atom.

In this embodiment, $R^{Y4}$ is a hydrogen atom or a halogen atom (e.g., a fluorine atom), preferably a hydrogen atom.

The partial structure represented by the formula:

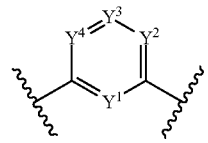

is more preferably a partial structure represented by the formula (Ar-1) or (Ar-2):

(Ar-1) 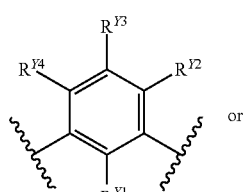  or (Ar-2) 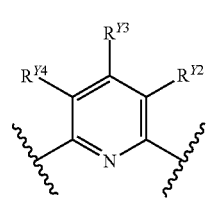

wherein each symbol is as defined above, further more preferably a partial structure represented by the formula (Ar-1-1) or (Ar-2-1):

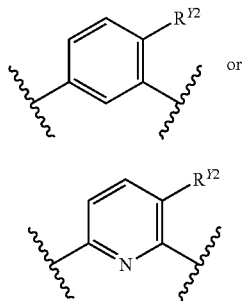

wherein each symbol is as defined above.

In this embodiment, $R^{y2}$ is a hydrogen atom, a halogen atom (e.g., a fluorine atom, a chlorine atom) or a cyano group, preferably is a hydrogen atom or a halogen atom (e.g., a fluorine atom, a chlorine atom), more preferably a hydrogen atom or a fluorine atom, particularly preferably a fluorine atom.

The partial structure represented by the formula:

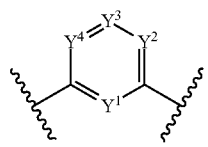

is particularly preferably a partial structure represented by the formula (Ar-1-1):

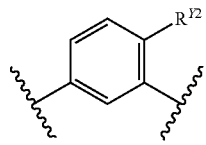

wherein each symbol is as defined above.

In this embodiment, $R^{y1}$ is a hydrogen atom, a halogen atom (e.g., a fluorine atom, a chlorine atom) or a cyano group, preferably is a hydrogen atom or a halogen atom (e.g., a fluorine atom, a chlorine atom), more preferably halogen atom (e.g., a fluorine atom, a chlorine atom), particularly preferably a fluorine atom.

Ring $A^1$ is an optionally further substituted $C_{6-14}$ aromatic hydrocarbon, an optionally further substituted aromatic heterocycle, or an optionally further substituted non-aromatic heterocycle, each of which is optionally fused with an optionally substituted 5- or 6-membered ring.

The "$C_{6-14}$ aromatic hydrocarbon" of the "optionally further substituted $C_{6-14}$ aromatic hydrocarbon" is preferably a benzene ring.

The "aromatic heterocycle" of the "optionally further substituted aromatic heterocycle" is preferably a 5- or 6-membered aromatic heterocycle.

The "non-aromatic heterocycle" of the "optionally further substituted non-aromatic heterocycle" is preferably a 5- or 6-membered non-aromatic heterocycle.

Examples of the "5- or 6-membered ring" of the "optionally substituted 5- or 6-membered ring" include a benzene ring, a $C_{5-6}$ cycloalkene, a 5- or 6-membered aromatic heterocycle and a 5- or 6-membered non-aromatic heterocycle.

The "$C_{6-14}$ aromatic hydrocarbon" of the "optionally further substituted $C_{6-14}$ aromatic hydrocarbon", the "aromatic heterocycle" of the "optionally further substituted aromatic heterocycle", the "non-aromatic heterocycle" of the "optionally further substituted non-aromatic heterocycle" and the "5- or 6-membered ring" of the "optionally substituted 5- or 6-membered ring" optionally further have 1 to 5 (preferably 1 to 3) substituents at substitutable position(s), in addition to the partial structure represented by the formula:

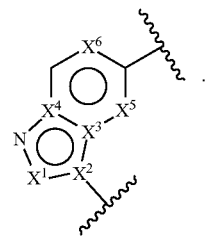

Examples of the substituent include substituents selected from the above-mentioned Substituent Group A. When the number of the substituents is two or more, the respective substituents may be the same or different. In addition, the above-mentioned Substituent Group A is optionally substituted by substituent(s) selected from Substituent Group A. The number of the substituents is, for example, 1 to 3. When the number of the substituents is two or more, the respective substituents may be the same or different.

Ring $A^1$ is preferably Ring $A^2$, i.e., an optionally further substituted benzene ring, an optionally further substituted 5- or 6-membered aromatic heterocycle, or an optionally further substituted 5- or 6-membered non-aromatic heterocycle, each of which is optionally fused with an optionally substituted 5- or 6-membered ring.

The "5- or 6-membered aromatic heterocycle" of the "optionally further substituted 5- or 6-membered aromatic heterocycle" is preferably a pyridine ring (optionally oxidized), a pyrimidine ring, a pyridazine ring, a pyrazine ring, a pyrazole ring, a thiazole ring, an imidazole ring, a thiophene ring or a furan ring.

The "5- or 6-membered non-aromatic heterocycle" of the "optionally further substituted 5- or 6-membered non-aromatic heterocycle" is preferably a dihydropyridine ring or a dihydropyrimidine ring.

Examples of the "5- or 6-membered ring" of the "optionally substituted 5- or 6-membered ring" include a benzene ring, a $C_{5-6}$ cycloalkene, a 5- or 6-membered aromatic heterocycle and a 5- or 6-membered non-aromatic heterocycle.

The "benzene ring" of the "optionally further substituted benzene ring", the "5- or 6-membered aromatic heterocycle" of the "optionally further substituted 5- or 6-membered aromatic heterocycle", the "5- or 6-membered non-aromatic heterocycle" of the "optionally further substituted 5- or 6-membered non-aromatic heterocycle" and the "5- or 6-membered ring" of the "optionally substituted 5- or 6-membered ring" optionally further have 1 to 5 (preferably 1 to 3) substituents at substitutable position(s), in addition to the partial structure represented by the formula:

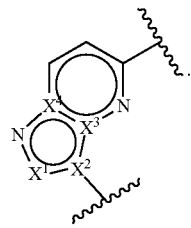

Examples of the substituent include substituents selected from the above-mentioned Substituent Group A. When the number of the substituents is two or more, the respective substituents may be the same or different. In addition, the above-mentioned Substituent Group A is optionally substituted by substituent(s) selected from Substituent Group A. The number of the substituents is, for example, 1 to 3. When the number of the substituents is two or more, the respective substituents may be the same or different.

Ring $A^2$ is preferably
(1) a benzene ring
optionally fused with a 5- to 6-membered monocyclic non-aromatic heterocycle (e.g., dihydrofuran, pyrroline) (i.e., the fused ring is dihydrobenzofuran, isoindoline) optionally substituted by 1 to 3 substituents selected from
(a) an oxo group, and
(b) a $C_{1-6}$ alkyl group (e.g., methyl, ethyl) optionally substituted by 1 to 3 $C_{1-6}$ alkoxy groups (e.g., methoxy), and optionally further substituted by 1 to 5 substituents selected from
(a) a cyano group,
(b) a halogen atom (e.g., a fluorine atom, a chlorine atom, a bromine atom),
(c) a hydroxy group,
(d) a carboxy group,
(e) a formyl group,
(f) an amino group,
(g) a carbamoyl group,
(h) a $C_{1-6}$ alkyl group (e.g., methyl, ethyl, isopropyl) optionally substituted by 1 to 3 substituents selected from
(i) a halogen atom (e.g., a fluorine atom),
(ii) a hydroxy group,
(iii) a $C_{1-6}$ alkoxy group (e.g., methoxy),
(iv) a mono- or di-$C_{1-6}$ alkylamino group (e.g., N,N-dimethylamino), and
(v) a di-$C_{1-6}$ alkylsulfinylidenamino group (e.g., N-dimethylsulfinylidenamino),
(i) a $C_{2-6}$ alkenyl group (e.g., vinyl),
(j) a $C_{2-6}$ alkynyl group (e.g., ethynyl),
(k) a $C_{1-6}$ alkoxy group (e.g., methoxy, ethoxy, propoxy, isopropoxy, isobutyloxy) optionally substituted by 1 to 3 substituents selected from
(i) a halogen atom (e.g., a fluorine atom),
(ii) a cyano group,
(iii) a carboxy group,
(iv) a carbamoyl group,
(v) a $C_{1-6}$ alkoxy group (e.g., methoxy, ethoxy) optionally substituted by 1 to 3 substituents selected from
(I) a $C_{1-6}$ alkoxy-$C_{1-6}$ alkoxy group (e.g., methoxyethoxy), and
(II) a mono- or di-$C_{1-6}$ alkylamino group (e.g., N,N-dimethylamino),
(vi) a mono- or di-$C_{1-6}$ alkyl-carbonylamino group (e.g., N-acetylamino),
(vii) a N—$C_{1-6}$ alkyl-N—$C_{1-6}$ alkyl-carbonylamino group (e.g., N-methyl-N-acetylamino),
(viii) a $C_{3-10}$ cycloalkyl group (e.g., cyclopropyl, cyclobutyl), and
(ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
(I) an oxo group, and
(II) a $C_{1-6}$ alkyl group (e.g., methyl),
(l) a $C_{1-6}$ alkyl-carbonyl group (e.g., acetyl),
(m) a $C_{1-6}$ alkoxy-carbonyl group (e.g., methoxycarbonyl, ethoxycarbonyl),
(n) a mono- or di-$C_{1-6}$ alkylamino group (e.g., N-ethylamino) optionally substituted by 1 to 3 $C_{1-6}$ alkoxy groups (e.g., methoxy),
(o) a mono- or di-$C_{1-6}$ alkyl-carbonylamino group (e.g., N-acetylamino, N-propanoylamino) optionally substituted by 1 to 3 $C_{1-6}$ alkoxy groups (e.g., methoxy),
(p) a mono- or di-$C_{1-6}$ alkyl-carbamoyl group (e.g., N-methylcarbamoyl, N,N-dimethylcarbamoyl, N-ethylcarbamoyl, N-propylcarbamoyl, N-butylcarbamoyl, N-isobutylcarbamoyl, N-isopentylcarbamoyl, N-neopentylcarbamoyl) optionally substituted by 1 to 3 substituents selected from
(i) a hydroxy group,
(ii) a $C_{1-6}$ alkoxy group (e.g., methoxy),
(iii) a mono- or di-$C_{1-6}$ alkylamino group (e.g., N,N-dimethylamino, N,N-diethylamino),
(iv) a mono- or di-$C_{1-6}$ alkyl-carbonylamino group (e.g., N-acetylamino),
(v) a mono- or di-$C_{1-6}$ alkyl-carbamoyl group (e.g., N-methylcarbamoyl, N,N-diethylcarbamoyl),
(vi) a $C_{3-10}$ cycloalkyl group (e.g., cyclopropyl, cyclohexyl),
(vii) a $C_{6-14}$ aryl group (e.g., phenyl),
(viii) a 5- or 6-membered monocyclic aromatic heterocyclic group (e.g., pyridyl, imidazolyl, triazolyl), and
(ix) a 3- to 8-membered monocyclic non-aromatic heterocyclic group (e.g., azetidinyl, morpholinyl, pyrrolidinyl, piperidyl, 1,1-dioxidothiomorpholinyl, tetrahydropyranyl) optionally substituted by 1 to 3 substituents selected from
(I) a hydroxy group,
(II) an oxo group, and
(III) a $C_{1-6}$ alkyl group (e.g., methyl),
(q) a di-$C_{1-6}$ alkylsulfinylidenamino group (e.g., N-dimethylsulfinylidenamino),
(r) a $C_{3-10}$ cycloalkyloxy group (e.g., cyclohexyloxy) optionally substituted by 1 to 3 substituents selected from
(i) a 3- 8-membered monocyclic non-aromatic heterocyclic group (e.g., morpholinyl) optionally substituted by 1 to 3 $C_{1-6}$ alkyl groups (e.g., methyl),
(s) a $C_{3-10}$ cycloalkylsulfonyl-carbamoyl group (e.g., cyclopropylsulfonylcarbamoyl),
(t) a $C_{6-14}$ aryl-carbamoyl group (e.g., phenylcarbamoyl), (u) a 3- to 8-membered monocyclic non-aromatic heterocyclic group (e.g., morpholinyl, piperazinyl) optionally substituted by 1 to 3 $C_{1-6}$ alkyl-carbonyl groups (e.g., acetyl),
(v) a 3- to 8-membered monocyclic non-aromatic heterocyclyloxy group (e.g., pyrrolidinyloxy) optionally substituted by 1 to 3 oxo groups,
(w) a 3- to 8-membered monocyclic non-aromatic heterocyclylcarbonyl group (e.g., azetidinylcarbonyl, piperidylcarbonyl, morpholinylcarbonyl) optionally substituted by 1 to 3 substituents selected from
  (i) a hydroxy group,
  (ii) a $C_{1-6}$ alkyl group (e.g., methyl),
  (iii) a $C_{1-6}$ alkoxy group (e.g., methoxy),
  (iv) a mono- or di-$C_{1-6}$ alkyl-carbonylamino group (e.g., N-acetylamino), and
  (v) a 3- to 8-membered monocyclic non-aromatic heterocyclic group (e.g., morpholinyl),
(x) a 9- to 14-membered bicyclic non-aromatic heterocyclylcarbonyl group (e.g., tetrahydroimidazopyrazinylcarbonyl tetrahydrotriazolopyrazinylcarbonyl),
(y) a 5- or 6-membered monocyclic aromatic heterocyclylcarbamoyl group (e.g., pyrazolylcarbamoyl, pyridylcarbamoyl) optionally substituted by 1 to 3 $C_{1-6}$ alkyl groups (e.g., methyl),
(z) a 3- to 8-membered monocyclic non-aromatic heterocyclylcarbamoyl group (e.g., azetidinylcarbamoyl, piperidylcarbamoyl, pyrrolidinylcarbamoyl) optionally substituted by 1 to 3 substituents selected from
  (i) an oxo group,
  (ii) a $C_{1-6}$ alkyl group (e.g., methyl),
  (iii) a $C_{1-6}$ alkyl-carbonyl group (e.g., acetyl), and
  (iv) a $C_{7-16}$ aralkyl group (e.g., benzyl), and
(aa) a 3- to 8-membered monocyclic non-aromatic heterocyclylidenamino group (e.g., 1-oxido-thiolan-1-ylidenamino),
(2) a 5- or 6-membered aromatic heterocycle (e.g., pyridine (optionally oxidized), pyrimidine, pyridazine, pyrazine, pyrazole, imidazole, thiophene, thiazole, furan) optionally fused with a 5- or 6-membered monocyclic aromatic heterocycle (e.g., imidazole) (i.e., the fused ring is imidazopyridine), and
optionally further substituted by 1 to 4 substituents selected from
(a) a cyano group,
(b) a halogen atom (e.g., a fluorine atom, a chlorine atom),
(c) a carboxy group,
(d) an amino group,
(e) a carbamoyl group,
(f) a $C_{1-6}$ alkyl group (e.g., methyl, ethyl, propyl) optionally substituted by 1 to 3 substituents selected from
  (i) a halogen atom (e.g., a fluorine atom),
  (ii) a cyano group,
  (iii) a hydroxy group,
  (iv) a carboxy group,
  (v) a $C_{1-6}$ alkoxy group (e.g., methoxy),
  (vi) a $C_{7-16}$ aralkyloxy-carbonyl group (e.g., benzyloxycarbonyl),
  (vii) a mono- or di-$C_{1-6}$ alkyl-carbamoyl group (e.g., N-ethylcarbamoyl, N-propylcarbamoyl) optionally substituted by 1 to 3 substituents selected from
    (I) a $C_{1-6}$ alkoxy group (e.g., methoxy), and
    (II) a 3- to 8-membered monocyclic non-aromatic heterocyclic group (e.g., morpholinyl), and
  (viii) a 3- to 8-membered monocyclic non-aromatic heterocyclic group (e.g., morpholinyl),
(g) a $C_{1-6}$ alkoxy group (e.g., methoxy, ethoxy) optionally substituted by 1 to 3 substituents selected from
  (i) a halogen atom (e.g., a fluorine atom),
  (ii) a cyano group,
  (iii) a $C_{1-6}$ alkoxy group (e.g., methoxy), and
  (iv) a 3- to 8-membered monocyclic non-aromatic heterocyclic group (e.g., oxetanyl),
(h) a $C_{3-10}$ cycloalkyl group (e.g., cyclopropyl),
(i) a $C_{1-6}$ alkyl-carbonyl group (e.g., acetyl),
(j) a $C_{1-6}$ alkoxy-carbonyl group (e.g., methoxycarbonyl, propoxycarbonyl, tert-butoxycarbonyl) optionally substituted by 1 to 3 $C_{1-6}$ alkoxy groups (e.g., methoxy),
(k) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
(l) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 substituents selected from
  (I) a $C_{1-6}$ alkoxy group (e.g., methoxy), and
  (II) a mono- or di-$C_{1-6}$ alkylamino groups (e.g., N,N-diethylamino),
(m) a mono- or di-$C_{1-6}$ alkoxy-carbonylamino group (e.g., N-tert-butoxycarbonylamino, N,N-di-tert-butoxycarbonylamino), and
(n) a 3- to 8-membered monocyclic non-aromatic heterocyclic group (e.g., azetidinyl, pyrrolidinyl), or
(3) a 5- or 6-membered non-aromatic heterocycle (e.g., dihydropyridine, dihydropyrimidine) optionally further substituted by 1 to 4 substituents selected from
(a) an oxo group,
(b) a cyano group,
(c) a halogen atom (e.g., a fluorine atom, a chlorine atom), and
(d) a $C_{1-6}$ alkyl group (e.g., methyl, ethyl) optionally substituted by 1 to 3 substituents selected from
  (I) a halogen atom (e.g., a fluorine atom),
  (II) a cyano group, and
  (III) a $C_{1-6}$ alkoxy group (e.g., methoxy, ethoxy) optionally substituted by 1 to 3 halogen atoms (e.g., a fluorine atom).

In another embodiment, Ring $A^2$ is preferably
(1) a benzene ring
optionally fused with a 5- to 6-membered monocyclic non-aromatic heterocycle (e.g., dihydrofuran, pyrroline) (i.e., the fused ring is dihydrobenzofuran, isoindoline) optionally substituted by 1 to 3 substituents selected from
(a) an oxo group, and
(b) a $C_{1-6}$ alkyl group (e.g., methyl, ethyl) optionally substituted by 1 to 3 $C_{1-6}$ alkoxy groups (e.g., methoxy), and optionally further substituted by 1 to 5 substituents selected from
(a) a cyano group,
(b) a halogen atom (e.g., a fluorine atom, a chlorine atom, a bromine atom),
(c) a hydroxy group,
(d) a carboxy group,
(e) a formyl group,
(f) an amino group, (g) a carbamoyl group,
(h) a $C_{1-6}$ alkyl group (e.g., methyl, ethyl, isopropyl) optionally substituted by 1 to 3 substituents selected from
  (i) a halogen atom (e.g., a fluorine atom),
  (ii) a hydroxy group,
  (iii) a mono- or di-$C_{1-6}$ alkylamino group (e.g., N,N-dimethylamino), and
  (iv) a di-$C_{1-6}$ alkylsulfinylidenamino group (e.g., N-dimethylsulfinylidenamino),
(i) a $C_{2-6}$ alkenyl group (e.g., vinyl),
(j) a $C_{2-6}$ alkynyl group (e.g., ethynyl),
(k) a $C_{1-6}$ alkoxy group (e.g., methoxy, ethoxy, propoxy, isopropoxy, isobutyloxy) optionally substituted by 1 to 3 substituents selected from
  (i) a halogen atom (e.g., a fluorine atom),
  (ii) a cyano group,
  (iii) a carboxy group,
  (iv) a carbamoyl group,
  (v) a $C_{1-6}$ alkoxy group (e.g., methoxy, ethoxy) optionally substituted by 1 to 3 substituents selected from
    (I) a $C_{1-6}$ alkoxy-$C_{1-6}$ alkoxy group (e.g., methoxyethoxy), and
    (II) a mono- or di-$C_{1-6}$ alkylamino group (e.g., N,N-dimethylamino),
  (vi) a mono- or di-$C_{1-6}$ alkyl-carbonylamino group (e.g., N-acetylamino),
  (vii) a N—$C_{1-6}$ alkyl-N—$C_{1-6}$ alkyl-carbonylamino group (e.g., N-methyl-N-acetylamino),
  (viii) a $C_{3-10}$ cycloalkyl group (e.g., cyclopropyl, cyclobutyl), and
  (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
    (I) an oxo group, and
    (II) a $C_{1-6}$ alkyl group (e.g., methyl),
(l) a $C_{1-6}$ alkyl-carbonyl group (e.g., acetyl),
(m) a $C_{1-6}$ alkoxy-carbonyl group (e.g., methoxycarbonyl, ethoxycarbonyl),
(n) a mono- or di-$C_{1-6}$ alkylamino group (e.g., N-ethylamino) optionally substituted by 1 to 3 $C_{1-6}$ alkoxy groups (e.g., methoxy),
(o) a mono- or di-$C_{1-6}$ alkyl-carbonylamino group (e.g., N-acetylamino, N-propanoylamino) optionally substituted by 1 to 3 $C_{1-6}$ alkoxy groups (e.g., methoxy),
(p) a mono- or di-$C_{1-6}$ alkyl-carbamoyl group (e.g., N-methylcarbamoyl, N,N-dimethylcarbamoyl, N-ethylcarbamoyl, N-propylcarbamoyl, N-butylcarbamoyl, N-isobutylcarbamoyl, N-isopentylcarbamoyl, N-neopentylcarbamoyl) optionally substituted by 1 to 3 substituents selected from
  (i) a hydroxy group,
  (ii) a $C_{1-6}$ alkoxy group (e.g., methoxy),
  (iii) a mono- or di-$C_{1-6}$ alkylamino group (e.g., N,N-dimethylamino, N,N-diethylamino),
  (iv) a mono- or di-$C_{1-6}$ alkyl-carbonylamino group (e.g., N-acetylamino),
  (v) a mono- or di-$C_{1-6}$ alkyl-carbamoyl group (e.g., N-methylcarbamoyl, N,N-diethylcarbamoyl),
  (vi) a $C_{3-10}$ cycloalkyl group (e.g., cyclopropyl, cyclohexyl),
  (vii) a $C_{6-14}$ aryl group (e.g., phenyl),
  (viii) a 5- or 6-membered monocyclic aromatic heterocyclic group (e.g., pyridyl, imidazolyl, triazolyl), and
  (ix) a 3- to 8-membered monocyclic non-aromatic heterocyclic group (e.g., azetidinyl, morpholinyl, pyrrolidinyl, piperidyl, 1,1-dioxidothiomorpholinyl, tetrahydropyranyl) optionally substituted by 1 to 3 substituents selected from
    (I) a hydroxy group,
    (II) an oxo group, and
    (III) a $C_{1-6}$ alkyl group (e.g., methyl),
(q) a di-$C_{1-6}$ alkylsulfinylidenamino group (e.g., N-dimethylsulfinylidenamino),
(r) a $C_{3-10}$ cycloalkyloxy group (e.g., cyclohexyloxy) optionally substituted by 1 to 3 substituents selected from
  (i) a 3- to 8-membered monocyclic non-aromatic heterocyclic group (e.g., morpholinyl) optionally substituted by 1 to 3 $C_{1-6}$ alkyl groups (e.g., methyl),
(s) a $C_{3-10}$ cycloalkylsulfonyl-carbamoyl group (e.g., cyclopropylsulfonylcarbamoyl),
(t) a $C_{6-14}$ aryl-carbamoyl group (e.g., phenylcarbamoyl),
(u) a 3- to 8-membered monocyclic non-aromatic heterocyclic group (e.g., morpholinyl, piperazinyl) optionally substituted by 1 to 3 $C_{1-6}$ alkyl-carbonyl groups (e.g., acetyl),
(v) a 3- to 8-membered monocyclic non-aromatic heterocyclyloxy group (e.g., pyrrolidinyloxy) optionally substituted by 1 to 3 oxo groups,
(w) a 3- to 8-membered monocyclic non-aromatic heterocyclylcarbonyl group (e.g., azetidinylcarbonyl, piperidylcarbonyl, morpholinylcarbonyl) optionally substituted by 1 to 3 substituents selected from
  (i) a hydroxy group,
  (ii) a $C_{1-6}$ alkyl group (e.g., methyl),
  (iii) a $C_{1-6}$ alkoxy group (e.g., methoxy),
  (iv) a mono- or di-$C_{1-6}$ alkyl-carbonylamino group (e.g., N-acetylamino), and
  (v) a 3- to 8-membered monocyclic non-aromatic heterocyclic group (e.g., morpholinyl),
(x) a 9- to 14-membered bicyclic non-aromatic heterocyclylcarbonyl group (e.g., tetrahydroimidazopyrazinylcarbonyl tetrahydrotriazolopyrazinylcarbonyl),
(y) a 5- or 6-membered monocyclic aromatic heterocyclylcarbamoyl group (e.g., pyrazolylcarbamoyl, pyridylcarbamoyl) optionally substituted by 1 to 3 $C_{1-6}$ alkyl groups (e.g., methyl),
(z) a 3- to 8-membered monocyclic non-aromatic heterocyclylcarbamoyl group (e.g., azetidinylcarbamoyl, piperidylcarbamoyl, pyrrolidinylcarbamoyl) optionally substituted by 1 to 3 substituents selected from
  (i) an oxo group,
  (ii) a $C_{1-6}$ alkyl group (e.g., methyl),
  (iii) a $C_{1-6}$ alkyl-carbonyl group (e.g., acetyl), and
  (iv) a $C_{7-16}$ aralkyl group (e.g., benzyl), and
(aa) a 3- to 8-membered monocyclic non-aromatic heterocyclylidenamino group (e.g., 1-oxido-thiolan-1-ylidenamino),
(2) a 5- or 6-membered aromatic heterocycle (e.g., pyridine (optionally oxidized), pyrimidine, pyridazine, pyrazine, pyrazole, imidazole, thiophene, thiazole, furan)

optionally fused with a 5- or 6-membered monocyclic aromatic heterocycle (e.g., imidazole) (i.e., the fused ring is imidazopyridine), and
optionally further substituted by 1 to 4 substituents selected from
- (a) a cyano group,
- (b) a halogen atom (e.g., a fluorine atom, a chlorine atom),
- (c) a carboxy group,
- (d) an amino group,
- (e) a carbamoyl group,
- (f) a $C_{1-6}$ alkyl group (e.g., methyl, ethyl, propyl) optionally substituted by 1 to 3 substituents selected from
  - (i) a halogen atom (e.g., a fluorine atom),
  - (ii) a cyano group,
  - (iii) a hydroxy group,
  - (iv) a carboxy group,
  - (v) a $C_{1-6}$ alkoxy group (e.g., methoxy),
  - (vi) a $C_{7-16}$ aralkyloxy-carbonyl group (e.g., benzyloxycarbonyl),
  - (vii) a mono- or di-$C_{1-6}$ alkyl-carbamoyl group (e.g., N-ethylcarbamoyl, N-propylcarbamoyl) optionally substituted by 1 to 3 substituents selected from
    - (I) a $C_{1-6}$ alkoxy group (e.g., methoxy), and
    - (II) a 3- to 8-membered monocyclic non-aromatic heterocyclic group (e.g., morpholinyl), and
  - (viii) a 3- to 8-membered monocyclic non-aromatic heterocyclic group (e.g., morpholinyl),
- (g) a $C_{1-6}$ alkoxy group (e.g., methoxy, ethoxy) optionally substituted by 1 to 3 substituents selected from
  - (i) a halogen atom (e.g., a fluorine atom),
  - (ii) a cyano group,
  - (iii) a $C_{1-6}$ alkoxy group (e.g., methoxy), and
  - (iv) a 3- to 8-membered monocyclic non-aromatic heterocyclic group (e.g., oxetanyl),
- (h) a $C_{3-10}$ cycloalkyl group (e.g., cyclopropyl),
- (i) a $C_{1-6}$ alkyl-carbonyl group (e.g., acetyl),
- (j) a $C_{1-6}$ alkoxy-carbonyl group (e.g., methoxycarbonyl, propoxycarbonyl, tert-butoxycarbonyl) optionally substituted by 1 to 3 $C_{1-6}$ alkoxy groups (e.g., methoxy),
- (k) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
- (l) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 substituents selected from
  - (I) a $C_{1-6}$ alkoxy group (e.g., methoxy), and
  - (II) a mono- or di-$C_{1-6}$ alkylamino groups (e.g., N,N-diethylamino),
- (m) a mono- or di-$C_{1-6}$ alkoxy-carbonylamino group (e.g., N-tert-butoxycarbonylamino, N,N-di-tert-butoxycarbonylamino), and
- (n) a 3- to 8-membered monocyclic non-aromatic heterocyclic group (e.g., azetidinyl, pyrrolidinyl), or
(3) a 5- or 6-membered non-aromatic heterocycle (e.g., dihydropyridine, dihydropyrimidine) optionally further substituted by 1 to 4 substituents selected from
- (a) an oxo group,
- (b) a cyano group,
- (c) a halogen atom (e.g., a fluorine atom, a chlorine atom), and
- (d) a $C_{1-6}$ alkyl group (e.g., methyl, ethyl) optionally substituted by 1 to 3 substituents selected from
  - (I) a halogen atom (e.g., a fluorine atom),
  - (II) a cyano group, and
  - (III) a $C_{1-6}$ alkoxy group (e.g., methoxy, ethoxy) optionally substituted by 1 to 3 halogen atoms (e.g., a fluorine atom).

In another embodiment, Ring $A^2$ is preferably
(1) a benzene ring optionally further substituted by 1 to 5 substituents selected from
- (a) a cyano group,
- (b) a halogen atom (e.g., a fluorine atom, a chlorine atom),
- (c) a $C_{1-6}$ alkyl group (e.g., methyl) optionally substituted by 1 to 3 substituents selected from
  - (i) a halogen atom (e.g., a fluorine atom), and
  - (ii) a $C_{1-6}$ alkoxy group (e.g., methoxy),
- (d) a $C_{1-6}$ alkoxy group (e.g., methoxy) optionally substituted by 1 to 3 halogen atoms (e.g., a fluorine atom),
(2) a 5- or 6-membered aromatic heterocycle (e.g., pyridine (optionally oxidized), pyrimidine, pyridazine, pyrazine, pyrazole, imidazole, thiophene, thiazole, furan) optionally further substituted by 1 to 4 substituents selected from
- (a) a cyano group,
- (b) a $C_{1-6}$ alkyl group (e.g., methyl) optionally substituted by 1 to 3 halogen atoms (e.g., a fluorine atom), and
- (c) a $C_{1-6}$ alkoxy group (e.g., methoxy, ethoxy), or
(3) a 5- or 6-membered non-aromatic heterocycle (e.g., dihydropyridine, dihydropyrimidine) optionally further substituted by 1 to 4 substituents selected from
- (a) an oxo group,
- (b) a cyano group, and
- (c) a $C_{1-6}$ alkyl group (e.g., methyl).

Ring $A^2$ is more preferably
(1) a benzene ring optionally fused with a 5- to 6-membered monocyclic non-aromatic heterocycle (e.g., dihydrofuran, pyrroline) (i.e., the fused ring is dihydrobenzofuran, isoindoline) optionally substituted by 1 to 3 substituents selected from
- (a) an oxo group, and
- (b) a $C_{1-6}$ alkyl group (e.g., methyl, ethyl) optionally substituted by 1 to 3 $C_{1-6}$ alkoxy groups (e.g., methoxy), and
optionally further substituted by 1 to 5 substituents selected from
- (a) a cyano group,
- (b) a halogen atom (e.g., a fluorine atom, a chlorine atom, a bromine atom),
- (c) a hydroxy group,
- (d) a carboxy group,
- (e) a formyl group,
- (f) an amino group,
- (g) a carbamoyl group,
- (h) a $C_{1-6}$ alkyl group (e.g., methyl, ethyl, isopropyl) optionally substituted by 1 to 3 substituents selected from
  - (i) a halogen atom (e.g., a fluorine atom),
  - (ii) a hydroxy group,
  - (iii) a $C_{1-6}$ alkoxy group (e.g., methoxy),
  - (iv) a mono- or di-$C_{1-6}$ alkylamino group (e.g., N,N-dimethylamino), and
  - (v) a di-$C_{1-6}$ alkylsulfinylidenamino group (e.g., N-dimethylsulfinylidenamino), (i) a C$_{2-6}$ alkenyl group (e.g., vinyl),
(j) a C$_{2-6}$ alkynyl group (e.g., ethynyl),
(k) a C$_{1-6}$ alkoxy group (e.g., methoxy, ethoxy, propoxy, isopropoxy, isobutyloxy) optionally substituted by 1 to 3 substituents selected from
  (i) a halogen atom (e.g., a fluorine atom),
  (ii) a cyano group,
  (iii) a carboxy group,
  (iv) a carbamoyl group,
  (v) a C$_{1-6}$ alkoxy group (e.g., methoxy, ethoxy) optionally substituted by 1 to 3 substituents selected from
    (I) a C$_{1-6}$ alkoxy-C$_{1-6}$ alkoxy group (e.g., methoxyethoxy), and
    (II) a mono- or di-C$_{1-6}$ alkylamino group (e.g., N,N-dimethylamino),
  (vi) a mono- or di-C$_{1-6}$ alkyl-carbonylamino group (e.g., N-acetylamino),
  (vii) a N—C$_{1-6}$ alkyl-N—C$_{1-6}$ alkyl-carbonylamino group (e.g., N-methyl-N-acetylamino),
  (viii) a C$_{3-10}$ cycloalkyl group (e.g., cyclopropyl, cyclobutyl), and
  (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
    (I) an oxo group, and
    (II) a C$_{1-6}$ alkyl group (e.g., methyl),
(l) a C$_{1-6}$ alkyl-carbonyl group (e.g., acetyl),
(m) a C$_{1-6}$ alkoxy-carbonyl group (e.g., methoxycarbonyl, ethoxycarbonyl),
(n) a mono- or di-C$_{1-6}$ alkylamino group (e.g., N-ethylamino) optionally substituted by 1 to 3 C$_{1-6}$ alkoxy groups (e.g., methoxy),
(o) a mono- or di-C$_{1-6}$ alkyl-carbonylamino group (e.g., N-acetylamino, N-propanoylamino) optionally substituted by 1 to 3 C$_{1-6}$ alkoxy groups (e.g., methoxy),
(p) a mono- or di-C$_{1-6}$ alkyl-carbamoyl group (e.g., N-methylcarbamoyl, N,N-dimethylcarbamoyl, N-ethylcarbamoyl, N-propylcarbamoyl, N-butylcarbamoyl, N-isobutylcarbamoyl, N-isopentylcarbamoyl, N-neopentylcarbamoyl) optionally substituted by 1 to 3 substituents selected from
  (i) a hydroxy group,
  (ii) a C$_{1-6}$ alkoxy group (e.g., methoxy),
  (iii) a mono- or di-C$_{1-6}$ alkylamino group (e.g., N,N-dimethylamino, N,N-diethylamino),
  (iv) a mono- or di-C$_{1-6}$ alkyl-carbonylamino group (e.g., N-acetylamino),
  (v) a mono- or di-C$_{1-6}$ alkyl-carbamoyl group (e.g., N-methylcarbamoyl, N,N-diethylcarbamoyl),
  (vi) a C$_{3-10}$ cycloalkyl group (e.g., cyclopropyl, cyclohexyl),
  (vii) a C$_{6-14}$ aryl group (e.g., phenyl),
  (viii) a 5- or 6-membered monocyclic aromatic heterocyclic group (e.g., pyridyl, imidazolyl, triazolyl), and
  (ix) a 3- to 8-membered monocyclic non-aromatic heterocyclic group (e.g., azetidinyl, morpholinyl, pyrrolidinyl, piperidyl, 1,1-dioxidothiomorpholinyl, tetrahydropyranyl) optionally substituted by 1 to 3 substituents selected from
    (I) a hydroxy group,
    (II) an oxo group, and
    (III) a C$_{1-6}$ alkyl group (e.g., methyl),
(q) a di-C$_{1-6}$ alkylsulfinylidenamino group (e.g., N-dimethylsulfinylidenamino),
(r) a C$_{3-10}$ cycloalkyloxy group (e.g., cyclohexyloxy) optionally substituted by 1 to 3 substituents selected from
  (i) a 3- to 8-membered monocyclic non-aromatic heterocyclic group (e.g., morpholinyl) optionally substituted by 1 to 3 C$_{1-6}$ alkyl groups (e.g., methyl),
(s) a C$_{3-10}$ cycloalkylsulfonyl-carbamoyl group (e.g., cyclopropylsulfonylcarbamoyl),
(t) a C$_{6-14}$ aryl-carbamoyl group (e.g., phenylcarbamoyl),
(u) a 3- to 8-membered monocyclic non-aromatic heterocyclic group (e.g., morpholinyl, piperazinyl) optionally substituted by 1 to 3 C$_{1-6}$ alkyl-carbonyl groups (e.g., acetyl),
(v) a 3- to 8-membered monocyclic non-aromatic heterocyclyloxy group (e.g., pyrrolidinyloxy) optionally substituted by 1 to 3 oxo groups,
(w) a 3- to 8-membered monocyclic non-aromatic heterocyclylcarbonyl group (e.g., azetidinylcarbonyl, piperidylcarbonyl, morpholinylcarbonyl) optionally substituted by 1 to 3 substituents selected from
  (i) a hydroxy group,
  (ii) a C$_{1-6}$ alkyl group (e.g., methyl),
  (iii) a C$_{1-6}$ alkoxy group (e.g., methoxy),
  (iv) a mono- or di-C$_{1-6}$ alkyl-carbonylamino group (e.g., N-acetylamino), and
  (v) a 3- to 8-membered monocyclic non-aromatic heterocyclic group (e.g., morpholinyl),
(x) a 9- to 14-membered bicyclic non-aromatic heterocyclylcarbonyl group (e.g., tetrahydroimidazopyrazinylcarbonyl tetrahydrotriazolopyrazinylcarbonyl),
(y) a 5- or 6-membered monocyclic aromatic heterocyclylcarbamoyl group (e.g., pyrazolylcarbamoyl, pyridylcarbamoyl) optionally substituted by 1 to 3 C$_{1-6}$ alkyl groups (e.g., methyl),
(z) a 3- to 8-membered monocyclic non-aromatic heterocyclylcarbamoyl group (e.g., azetidinylcarbamoyl, piperidylcarbamoyl, pyrrolidinylcarbamoyl) optionally substituted by 1 to 3 substituents selected from
  (i) an oxo group,
  (ii) a C$_{1-6}$ alkyl group (e.g., methyl),
  (iii) a C$_{1-6}$ alkyl-carbonyl group (e.g., acetyl), and
  (iv) a C$_{7-16}$ aralkyl group (e.g., benzyl), and
(aa) a 3- to 8-membered monocyclic non-aromatic heterocyclylidenamino group (e.g., 1-oxido-thiolan-1-ylidenamino),
(2) a pyridine ring (optionally oxidized)
optionally fused with a 5- or 6-membered monocyclic aromatic heterocycle (e.g., imidazole) (i.e., the fused ring is imidazopyridine), and
optionally further substituted by 1 to 4 substituents selected from
(a) a cyano group,
(b) a halogen atom (e.g., a fluorine atom, a chlorine atom),
(c) an amino group,
(d) a carbamoyl group,
(e) a C$_{1-6}$ alkyl group (e.g., methyl, ethyl) optionally substituted by 1 to 3 substituents selected from
  (i) a halogen atom (e.g., a fluorine atom), and
  (ii) a hydroxy group, (f) a $C_{1-6}$ alkoxy group (e.g., methoxy, ethoxy) optionally substituted by 1 to 3 substituents selected from
  (i) a halogen atom (e.g., a fluorine atom),
  (ii) a cyano group,
  (iii) a $C_{1-6}$ alkoxy group (e.g., methoxy), and
  (iv) a 3- to 8-membered monocyclic non-aromatic heterocyclic group (e.g., oxetanyl),
(g) a $C_{3-10}$ cycloalkyl group (e.g., cyclopropyl),
(h) a $C_{1-6}$ alkyl-carbonyl group (e.g., acetyl),
(i) a $C_{1-6}$ alkoxy-carbonyl group (e.g., methoxycarbonyl),
(j) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
(k) a mono- or di-$C_{1-6}$ alkyl-carbamoyl group (e.g., N-methylcarbamoyl, N-ethylcarbamoyl) optionally substituted by 1 to 3 of mono- or di-$C_{1-6}$ alkylamino groups (e.g., N,N-diethylamino),
(l) a mono- or di-$C_{1-6}$ alkoxy-carbonylamino group (e.g., N-tert-butoxycarbonylamino, N,N-di-tert-butoxycarbonylamino), and
(m) a 3- to 8-membered monocyclic non-aromatic heterocyclic group (e.g., azetidinyl, pyrrolidinyl),
(3) a pyrimidine ring optionally further substituted by 1 to 3 substituents selected from
  (a) a cyano group,
  (b) an amino group,
  (c) a $C_{1-6}$ alkoxy group (e.g., methoxy, ethoxy), and
  (d) a mono- or di-$C_{1-6}$ alkylamino group (e.g., N,N-dimethylamino),
(4) a pyridazine ring optionally further substituted by 1 to 3 cyano groups,
(5) a pyrazine ring optionally further substituted by 1 to 3 substituents selected from
  (a) a cyano group,
  (b) a $C_{1-6}$ alkyl group (e.g., methyl), and
  (c) a $C_{1-6}$ alkoxy group (e.g., methoxy),
(6) a pyrazole ring optionally further substituted by 1 to 3 substituents selected from
  (a) a cyano group,
  (b) a carboxy group,
  (c) a $C_{1-6}$ alkyl group (e.g., methyl, ethyl, propyl) optionally substituted by 1 to 3 substituents selected from
    (i) a halogen atom (e.g., a fluorine atom),
    (ii) a cyano group,
    (iii) a hydroxy group,
    (iv) a carboxy group,
    (v) a $C_{1-6}$ alkoxy group (e.g., methoxy),
    (vi) a $C_{7-16}$ aralkyloxy-carbonyl group (e.g., benzyloxycarbonyl),
    (vii) a mono- or di-$C_{1-6}$ alkyl-carbamoyl group (e.g., N-ethylcarbamoyl, N-propylcarbamoyl) optionally substituted by 1 to 3 substituents selected from
      (I) a $C_{1-6}$ alkoxy group (e.g., methoxy), and
      (II) a 3- to 8-membered monocyclic non-aromatic heterocyclic group (e.g., morpholinyl), and
    (viii) a 3- to 8-membered monocyclic non-aromatic heterocyclic group (e.g., morpholinyl),
  (d) a $C_{1-6}$ alkoxy-carbonyl group (e.g., propoxycarbonyl, tert-butoxycarbonyl) optionally substituted by 1 to 3 $C_{1-6}$ alkoxy groups (e.g., methoxy), and
  (e) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 $C_{1-6}$ alkoxy groups (e.g., methoxy),
(7) an imidazole ring optionally further substituted by 1 to 3 substituents selected from
  (a) a cyano group, and
  (b) a $C_{1-6}$ alkyl group (e.g., methyl),
(8) a thiazole ring optionally further substituted by 1 or 2 $C_{1-6}$ alkyl groups (e.g., methyl),
(9) a thiophene ring optionally further substituted by 1 to 3 substituents selected from
  (a) a cyano group,
  (b) a carboxy group,
  (c) a $C_{1-6}$ alkoxy-carbonyl group (e.g., methoxycarbonyl), and
  (d) a mono- or di-$C_{1-6}$ alkyl-carbamoyl group (e.g., N-methylcarbamoyl),
(10) a furan ring,
(11) a dihydropyridine ring optionally further substituted by 1 to 4 substituents selected from
  (a) a cyano group,
  (b) an oxo group,
  (c) a halogen atom (e.g., a fluorine atom, a chlorine atom), and
  (d) a $C_{1-6}$ alkyl group (e.g., methyl, ethyl) optionally substituted by 1 to 3 substituents selected from
    (I) a halogen atom (e.g., a fluorine atom),
    (II) a cyano group, and
    (III) a $C_{1-6}$ alkoxy group (e.g., methoxy, ethoxy) optionally substituted by 1 to 3 halogen atoms (e.g., a fluorine atom), or
(12) a dihydropyrimidine ring optionally further substituted by 1 to 4 substituents selected from
  (a) a cyano group, and
  (b) an oxo group.

In another embodiment, Ring $A^2$ is more preferably
(1) a benzene ring
optionally fused with a 5- to 6-membered monocyclic non-aromatic heterocycle (e.g., dihydrofuran, pyrroline) (i.e., the fused ring is dihydrobenzofuran, isoindoline) optionally substituted by 1 to 3 substituents selected from
  (a) an oxo group, and
  (b) a $C_{1-6}$ alkyl group (e.g., methyl, ethyl) optionally substituted by 1 to 3 $C_{1-6}$ alkoxy groups (e.g., methoxy), and optionally further substituted by 1 to 5 substituents selected from
  (a) a cyano group,
  (b) a halogen atom (e.g., a fluorine atom, a chlorine atom, a bromine atom),
  (c) a hydroxy group,
  (d) a carboxy group,
  (e) a formyl group,
  (f) an amino group,
  (g) a carbamoyl group,
  (h) a $C_{1-6}$ alkyl group (e.g., methyl, ethyl, isopropyl) optionally substituted by 1 to 3 substituents selected from
    (i) a halogen atom (e.g., a fluorine atom),
    (ii) a hydroxy group,
    (iii) a mono- or di-$C_{1-6}$ alkylamino group (e.g., N,N-dimethylamino), and
    (iv) a di-$C_{1-6}$ alkylsulfinylidenamino group (e.g., N-dimethylsulfinylidenamino),
  (i) a $C_{2-6}$ alkenyl group (e.g., vinyl),
  (j) a $C_{2-6}$ alkynyl group (e.g., ethynyl), (k) a $C_{1-6}$ alkoxy group (e.g., methoxy, ethoxy, propoxy, isopropoxy, isobutyloxy) optionally substituted by 1 to 3 substituents selected from
  (i) a halogen atom (e.g., a fluorine atom),
  (ii) a cyano group,
  (iii) a carboxy group,
  (iv) a carbamoyl group,
  (v) a $C_{1-6}$ alkoxy group (e.g., methoxy, ethoxy) optionally substituted by 1 to 3 substituents selected from
    (I) a $C_{1-6}$ alkoxy-$C_{1-6}$ alkoxy group (e.g., methoxyethoxy), and
    (II) a mono- or di-$C_{1-6}$ alkylamino group (e.g., N,N-dimethylamino),
  (vi) a mono- or di-$C_{1-6}$ alkyl-carbonylamino group (e.g., N-acetylamino),
  (vii) a N—$C_{1-6}$ alkyl-N—$C_{1-6}$ alkyl-carbonylamino group (e.g., N-methyl-N-acetylamino),
  (viii) a $C_{3-10}$ cycloalkyl group (e.g., cyclopropyl, cyclobutyl), and
  (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
    (I) an oxo group, and
    (II) a $C_{1-6}$ alkyl group (e.g., methyl),
(l) a $C_{1-6}$ alkyl-carbonyl group (e.g., acetyl),
(m) a $C_{1-6}$ alkoxy-carbonyl group (e.g., methoxycarbonyl, ethoxycarbonyl),
(n) a mono- or di-$C_{1-6}$ alkylamino group (e.g., N-ethylamino) optionally substituted by 1 to 3 $C_{1-6}$ alkoxy groups (e.g., methoxy),
(o) a mono- or di-$C_{1-6}$ alkyl-carbonylamino group (e.g., N-acetylamino, N-propanoylamino) optionally substituted by 1 to 3 $C_{1-6}$ alkoxy groups (e.g., methoxy),
(p) a mono- or di-$C_{1-6}$ alkyl-carbamoyl group (e.g., N-methylcarbamoyl, N,N-dimethylcarbamoyl, N-ethylcarbamoyl, N-propylcarbamoyl, N-butylcarbamoyl, N-isobutylcarbamoyl, N-isopentylcarbamoyl, N-neopentylcarbamoyl) optionally substituted by 1 to 3 substituents selected from
  (i) a hydroxy group,
  (ii) a $C_{1-6}$ alkoxy group (e.g., methoxy),
  (iii) a mono- or di-$C_{1-6}$ alkylamino group (e.g., N,N-dimethylamino, N,N-diethylamino),
  (iv) a mono- or di-$C_{1-6}$ alkyl-carbonylamino group (e.g., N-acetylamino),
  (v) a mono- or di-$C_{1-6}$ alkyl-carbamoyl group (e.g., N-methylcarbamoyl, N,N-diethylcarbamoyl),
  (vi) a $C_{3-10}$ cycloalkyl group (e.g., cyclopropyl, cyclohexyl),
  (vii) a $C_{6-14}$ aryl group (e.g., phenyl),
  (viii) a 5- or 6-membered monocyclic aromatic heterocyclic group (e.g., pyridyl, imidazolyl, triazolyl), and
  (ix) a 3- to 8-membered monocyclic non-aromatic heterocyclic group (e.g., azetidinyl, morpholinyl, pyrrolidinyl, piperidyl, 1,1-dioxidothiomorpholinyl, tetrahydropyranyl) optionally substituted by 1 to 3 substituents selected from
    (I) a hydroxy group,
    (II) an oxo group, and
    (III) a $C_{1-6}$ alkyl group (e.g., methyl),
(q) a di-$C_{1-6}$ alkylsulfinylidenamino group (e.g., N-dimethylsulfinylidenamino),
(r) a $C_{3-10}$ cycloalkyloxy group (e.g., cyclohexyloxy) optionally substituted by 1 to 3 substituents selected from
  (i) a 3- to 8-membered monocyclic non-aromatic heterocyclic group (e.g., morpholinyl) optionally substituted by 1 to 3 $C_{1-6}$ alkyl groups (e.g., methyl),
(s) a $C_{3-10}$ cycloalkylsulfonyl-carbamoyl group (e.g., cyclopropylsulfonylcarbamoyl),
(t) a $C_{6-14}$ aryl-carbamoyl group (e.g., phenylcarbamoyl),
(u) a 3- to 8-membered monocyclic non-aromatic heterocyclic group (e.g., morpholinyl, piperazinyl) optionally substituted by 1 to 3 $C_{1-6}$ alkyl-carbonyl groups (e.g., acetyl),
(v) a 3- to 8-membered monocyclic non-aromatic heterocyclyloxy group (e.g., pyrrolidinyloxy) optionally substituted by 1 to 3 oxo groups,
(w) a 3- to 8-membered monocyclic non-aromatic heterocyclylcarbonyl group (e.g., azetidinylcarbonyl, piperidylcarbonyl, morpholinylcarbonyl) optionally substituted by 1 to 3 substituents selected from
  (i) a hydroxy group,
  (ii) a $C_{1-6}$ alkyl group (e.g., methyl),
  (iii) a $C_{1-6}$ alkoxy group (e.g., methoxy),
  (iv) a mono- or di-$C_{1-6}$ alkyl-carbonylamino group (e.g., N-acetylamino), and
  (v) a 3- to 8-membered monocyclic non-aromatic heterocyclic group (e.g., morpholinyl),
(x) a 9- to 14-membered bicyclic non-aromatic heterocyclylcarbonyl group (e.g., tetrahydroimidazopyrazinylcarbonyl tetrahydrotriazolopyrazinylcarbonyl),
(y) a 5- or 6-membered monocyclic aromatic heterocyclylcarbamoyl group (e.g., pyrazolylcarbamoyl, pyridylcarbamoyl) optionally substituted by 1 to 3 $C_{1-6}$ alkyl groups (e.g., methyl),
(z) a 3- to 8-membered monocyclic non-aromatic heterocyclylcarbamoyl group (e.g., azetidinylcarbamoyl, piperidylcarbamoyl, pyrrolidinylcarbamoyl) optionally substituted by 1 to 3 substituents selected from
  (i) an oxo group,
  (ii) a $C_{1-6}$ alkyl group (e.g., methyl),
  (iii) a $C_{1-6}$ alkyl-carbonyl group (e.g., acetyl), and
  (iv) a $C_{7-16}$ aralkyl group (e.g., benzyl), and (aa) a 3- to 8-membered monocyclic non-aromatic heterocyclylidenamino group (e.g., 1-oxido-thiolan-1-ylidenamino),
(2) a pyridine ring (optionally oxidized)
optionally fused with a 5- or 6-membered monocyclic aromatic heterocycle (e.g., imidazole) (i.e., the fused ring is imidazopyridine), and
optionally further substituted by 1 to 4 substituents selected from
  (a) a cyano group,
  (b) a halogen atom (e.g., a fluorine atom, a chlorine atom),
  (c) an amino group,
  (d) a carbamoyl group,
  (e) a $C_{1-6}$ alkyl group (e.g., methyl, ethyl) optionally substituted by 1 to 3 substituents selected from
    (i) a halogen atom (e.g., a fluorine atom), and
    (ii) a hydroxy group,
  (f) a $C_{1-6}$ alkoxy group (e.g., methoxy, ethoxy) optionally substituted by 1 to 3 substituents selected from (i) a halogen atom (e.g., a fluorine atom),
(ii) a cyano group,
(iii) a $C_{1-6}$ alkoxy group (e.g., methoxy), and
(iv) a 3- to 8-membered monocyclic non-aromatic heterocyclic group (e.g., oxetanyl),
(g) a $C_{3-10}$ cycloalkyl group (e.g., cyclopropyl),
(h) a $C_{1-6}$ alkyl-carbonyl group (e.g., acetyl),
(i) a $C_{1-6}$ alkoxy-carbonyl group (e.g., methoxycarbonyl),
(j) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
(k) a mono- or di-$C_{1-6}$ alkyl-carbamoyl group (e.g., N-methylcarbamoyl, N-ethylcarbamoyl) optionally substituted by 1 to 3 of mono- or di-$C_{1-6}$ alkylamino groups (e.g., N,N-diethylamino),
(l) a mono- or di-$C_{1-6}$ alkoxy-carbonylamino group (e.g., N-tert-butoxycarbonylamino, N,N-di-tert-butoxycarbonylamino), and
(m) a 3- to 8-membered monocyclic non-aromatic heterocyclic group (e.g., azetidinyl, pyrrolidinyl),
(3) a pyrimidine ring optionally further substituted by 1 to 3 substituents selected from
(a) a cyano group,
(b) an amino group,
(c) a $C_{1-6}$ alkoxy group (e.g., methoxy, ethoxy), and
(d) a mono- or di-$C_{1-6}$ alkylamino group (e.g., N,N-dimethylamino),
(4) a pyridazine ring optionally further substituted by 1 to 3 cyano groups,
(5) a pyrazine ring optionally further substituted by 1 to 3 substituents selected from
(a) a cyano group,
(b) a $C_{1-6}$ alkyl group (e.g., methyl), and
(c) a $C_{1-6}$ alkoxy group (e.g., methoxy),
(6) a pyrazole ring optionally further substituted by 1 to 3 substituents selected from
(a) a cyano group,
(b) a carboxy group,
(c) a $C_{1-6}$ alkyl group (e.g., methyl, ethyl, propyl) optionally substituted by 1 to 3 substituents selected from
(i) a halogen atom (e.g., a fluorine atom),
(ii) a cyano group,
(iii) a hydroxy group,
(iv) a carboxy group,
(v) a $C_{1-6}$ alkoxy group (e.g., methoxy),
(vi) a $C_{7-16}$ aralkyloxy-carbonyl group (e.g., benzyloxycarbonyl),
(vii) a mono- or di-$C_{16}$ alkyl-carbamoyl group (e.g., N-ethylcarbamoyl, N-propylcarbamoyl) optionally substituted by 1 to 3 substituents selected from
(I) a $C_{1-6}$ alkoxy group (e.g., methoxy), and
(II) a 3- to 8-membered monocyclic non-aromatic heterocyclic group (e.g., morpholinyl), and
(viii) a 3- to 8-membered monocyclic non-aromatic heterocyclic group (e.g., morpholinyl),
(d) a $C_{1-6}$ alkoxy-carbonyl group (e.g., propoxycarbonyl, tert-butoxycarbonyl) optionally substituted by 1 to 3 $C_{1-6}$ alkoxy groups (e.g., methoxy), and
(e) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 $C_{1-6}$ alkoxy groups (e.g., methoxy),
(7) an imidazole ring optionally further substituted by 1 to 3 substituents selected from
(a) a cyano group, and
(b) a $C_{1-6}$ alkyl group (e.g., methyl),
(8) a thiazole ring optionally further substituted by 1 or 2 $C_{1-6}$ alkyl groups (e.g., methyl),
(9) a thiophene ring optionally further substituted by 1 to 3 substituents selected from
(a) a cyano group,
(b) a carboxy group,
(c) a $C_{1-6}$ alkoxy-carbonyl group (e.g., methoxycarbonyl), and
(d) a mono- or di-$C_{1-6}$ alkyl-carbamoyl group (e.g., N-methylcarbamoyl),
(10) a furan ring,
(11) a dihydropyridine ring optionally further substituted by 1 to 4 substituents selected from
(a) a cyano group,
(b) an oxo group,
(c) a halogen atom (e.g., a fluorine atom, a chlorine atom), and
(d) a $C_{1-6}$ alkyl group (e.g., methyl, ethyl) optionally substituted by 1 to 3 substituents selected from
(I) a halogen atom (e.g., a fluorine atom),
(II) a cyano group, and
(III) a $C_{1-6}$ alkoxy group (e.g., methoxy, ethoxy) optionally substituted by 1 to 3 halogen atoms (e.g., a fluorine atom), or
(12) a dihydropyrimidine ring optionally further substituted by 1 to 4 substituents selected from
(a) a cyano group, and
(b) an oxo group.
In another embodiment, Ring $A^2$ is more preferably
(1) a benzene ring optionally further substituted by 1 to 5 substituents selected from
(a) a cyano group,
(b) a halogen atom (e.g., a fluorine atom, a chlorine atom),
(c) a $C_{1-6}$ alkyl group (e.g., methyl) optionally substituted by 1 to 3 substituents selected from
(i) a halogen atom (e.g., a fluorine atom), and
(ii) a $C_{1-6}$ alkoxy group (e.g., methoxy),
(d) a $C_{1-6}$ alkoxy group (e.g., methoxy) optionally substituted by 1 to 3 halogen atoms (e.g., a fluorine atom),
(2) a pyridine ring (optionally oxidized) optionally further substituted by 1 to 4 substituents selected from
(a) a cyano group,
(b) a $C_{1-6}$ alkyl group (e.g., methyl) optionally substituted by 1 to 3 halogen atoms (e.g., a fluorine atom), and
(c) a $C_{1-6}$ alkoxy group (e.g., methoxy, ethoxy),
(3) a pyrimidine ring optionally further substituted by 1 to 3 substituents selected from
(a) a cyano group, and
(b) a $C_{1-6}$ alkoxy group (e.g., methoxy), or
(4) a dihydropyridine ring optionally further substituted by 1 to 4 substituents selected from
(a) a cyano group,
(b) an oxo group, and
(b) a $C_{1-6}$ alkyl group (e.g., methyl).
In another embodiment, Ring $A^2$ is preferably a benzene ring, a 6-membered aromatic heterocycle, or a 6-membered non-aromatic heterocycle, each of which is further substituted by one cyano group and optionally further substituted.

The "6-membered aromatic heterocycle" is preferably a pyridine ring (optionally oxidized), a pyrimidine ring, a pyridazine ring or a pyrazine ring, particularly preferably a pyridine ring.

The "6-membered non-aromatic heterocycle" is preferably a dihydropyridine ring or a dihydropyrimidine ring.

The "benzene ring", "6-membered aromatic heterocycle" and 15 "6-membered non-aromatic heterocycle" have one cyano group and optionally further have 1 to 5 (preferably 1 to 3) substituents at substitutable position(s), in addition to the partial structure represented by the formula:

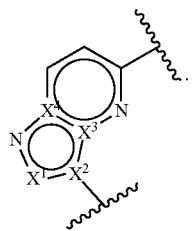

Examples of the substituent include substituents selected from the above-mentioned Substituent Group A. When the number of the substituents is two or more, the respective substituents may be the same or different. In addition, the above-mentioned Substituent Group A is optionally substituted by substituent(s) selected from Substituent Group A. The number of the substituents is, for example, 1 to 3. When the number of the substituents is two or more, the respective substituents may be the same or different.

Ring $A^2$ is more preferably
(1) a benzene ring
further substituted by one cyano group, and
optionally further substituted by 1 to 5 substituents selected from
  (a) a cyano group,
  (b) a halogen atom (e.g., a fluorine atom, a chlorine atom), (c) a hydroxy group,
  (d) a carboxy group,
  (e) an amino group,
  (f) a $C_{1-6}$ alkyl group (e.g., methyl, ethyl) optionally substituted by 1 to 3 substituents selected from
    (i) a halogen atom (e.g., a fluorine atom), and
    (ii) a $C_{1-6}$ alkoxy group (e.g., methoxy),
  (g) a $C_{1-6}$ alkoxy group (e.g., methoxy, ethoxy, propoxy, isopropoxy, isobutyloxy) optionally substituted by 1 to 3 substituents selected from
    (i) a halogen atom (e.g., a fluorine atom),
    (ii) a cyano group,
    (iii) a carboxy group,
    (iv) a carbamoyl group,
    (v) a $C_{1-6}$ alkoxy group (e.g., methoxy, ethoxy) optionally substituted by 1 to 3 substituents selected from
      (I) a $C_{1-6}$ alkoxy-$C_{1-6}$ alkoxy group (e.g., methoxyethoxy), and
      (II) a mono- or di-$C_{1-6}$ alkylamino group (e.g., N,N-dimethylamino),
    (vi) a mono- or di-$C_{1-6}$ alkyl-carbonylamino group (e.g., N-acetylamino),
    (vii) a N—$C_{1-6}$ alkyl-N—$C_{1-6}$ alkyl-carbonylamino group (e.g., N-methyl-N-acetylamino),
    (viii) a $C_{3-10}$ cycloalkyl group (e.g., cyclobutyl), and
    (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
      (I) an oxo group, and
      (II) a $C_{1-6}$ alkyl group (e.g., methyl),
  (h) a $C_{1-6}$ alkyl-carbonyl group (e.g., acetyl),
  (i) a $C_{1-6}$ alkoxy-carbonyl group (e.g., methoxycarbonyl, ethoxycarbonyl),
  (j) a mono- or di-$C_{1-6}$ alkylamino group (e.g., N-ethylamino) optionally substituted by 1 to 3 $C_{1-6}$ alkoxy groups (e.g., methoxy),
  (k) a mono- or di-$C_{1-6}$ alkyl-carbonylamino group (e.g., N-propanoylamino) optionally substituted by 1 to 3 $C_{1-6}$ alkoxy groups (e.g., methoxy),
  (l) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 of 3- to 8-membered monocyclic non-aromatic heterocyclic groups (e.g., morpholinyl),
  (m) a di-$C_{1-6}$ alkylsulfinylidenamino group (e.g., N-dimethylsulfinylidenamino),
  (n) a $C_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl),
  (o) a 3- to 8-membered monocyclic non-aromatic heterocyclyloxy group (e.g., pyrrolidinyloxy) optionally substituted by 1 to 3 oxo groups,
  (p) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), and
  (q) a 3- to 8-membered monocyclic non-aromatic heterocyclylidenamino group (e.g., 1-oxido-thiolan-1-ylidenamino),
(2) a 6-membered aromatic heterocycle (e.g., pyridine (optionally oxidized), pyrimidine, pyridazine, pyrazine)
optionally fused with a 5- or 6-membered monocyclic aromatic heterocycle (e.g., imidazole) (i.e., the fused ring is imidazopyridine),
further substituted by one cyano group, and
optionally further substituted by 1 to 4 substituents selected from
  (a) a halogen atom (e.g., a fluorine atom, a chlorine atom),
  (b) an amino group,
  (c) a $C_{1-6}$ alkyl group (e.g., methyl, ethyl) optionally substituted by 1 to 3 substituents selected from
    (i) a halogen atom (e.g., a fluorine atom), and
    (ii) a hydroxy group,
  (d) a $C_{1-6}$ alkoxy group (e.g., methoxy, ethoxy) optionally substituted by 1 to 3 substituents selected from
    (i) a halogen atom (e.g., a fluorine atom),
    (ii) a $C_{1-6}$ alkoxy group (e.g., methoxy), and
    (iii) a 3- to 8-membered monocyclic non-aromatic heterocyclic group (e.g., oxetanyl),
  (e) a $C_{3-10}$ cycloalkyl group (e.g., cyclopropyl),
  (f) a $C_{1-6}$ alkyl-carbonyl group (e.g., acetyl),
  (g) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
  (h) a mono- or di-$C_{1-6}$ alkoxy-carbonylamino group (e.g., N-tert-butoxycarbonylamino, N,N-di-tert-butoxycarbonylamino), and (i) a 3- to 8-membered monocyclic non-aromatic heterocyclic group (e.g., azetidinyl, pyrrolidinyl), or
(3) a 6-membered non-aromatic heterocycle (e.g., dihydropyridine, dihydropyrimidine)
further substituted by one cyano group, and
optionally further substituted by 1 to 4 substituents selected from
  (a) an oxo group, and
  (b) a $C_{1-6}$ alkyl group (e.g., methyl) optionally substituted by 1 to 3 halogen atoms (e.g., a fluorine atom).
In another embodiment, Ring $A^2$ is more preferably
(1) a benzene ring
further substituted by one cyano group, and
optionally further substituted by 1 to 5 substituents selected from
  (a) a cyano group,
  (b) a halogen atom (e.g., a fluorine atom),
  (c) a hydroxy group,
  (d) a carboxy group,
  (e) an amino group,
  (f) a $C_{1-6}$ alkyl group (e.g., methyl, ethyl) optionally substituted by 1 to 3 halogen atoms (e.g., a fluorine atom),
  (g) a $C_{1-6}$ alkoxy group (e.g., methoxy, ethoxy, propoxy, isopropoxy, isobutyloxy) optionally substituted by 1 to 3 substituents selected from
    (i) a halogen atom (e.g., a fluorine atom),
    (ii) a cyano group,
    (iii) a carboxy group,
    (iv) a carbamoyl group,
    (v) a $C_{1-6}$ alkoxy group (e.g., methoxy, ethoxy) optionally substituted by 1 to 3 substituents selected from
      (I) a $C_{1-6}$ alkoxy-$C_{1-6}$ alkoxy group (e.g., methoxyethoxy), and
      (II) a mono- or di-$C_{1-6}$ alkylamino group (e.g., N,N-dimethylamino),
    (vi) a mono- or di-$C_{1-6}$ alkyl-carbonylamino group (e.g., N-acetylamino),
    (vii) a N—$C_{1-6}$ alkyl-N—$C_{1-6}$ alkyl-carbonylamino group (e.g., N-methyl-N-acetylamino),
    (viii) a $C_{3-10}$ cycloalkyl group (e.g., cyclobutyl), and
    (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
      (I) an oxo group, and
      (II) a $C_{1-6}$ alkyl group (e.g., methyl),
  (h) a $C_{1-6}$ alkyl-carbonyl group (e.g., acetyl),
  (i) a $C_{1-6}$ alkoxy-carbonyl group (e.g., methoxycarbonyl, ethoxycarbonyl),
  (j) a mono- or di-$C_{1-6}$ alkylamino group (e.g., N-ethylamino) optionally substituted by 1 to 3 $C_{1-6}$ alkoxy groups (e.g., methoxy),
  (k) a mono- or di-$C_{1-6}$ alkyl-carbonylamino group (e.g., N-propanoylamino) optionally substituted by 1 to 3 $C_{1-6}$ alkoxy groups (e.g., methoxy),
  (l) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 of 3- to 8-membered monocyclic non-aromatic heterocyclic groups (e.g., morpholinyl),
  (m) a di-$C_{1-6}$ alkylsulfinylidenamino group (e.g., N-di-methylsulfinylidenamino),
  (n) a $C_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl),
  (o) a 3- to 8-membered monocyclic non-aromatic heterocyclyloxy group (e.g., pyrrolidinyloxy) optionally substituted by 1 to 3 oxo groups,
  (p) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), and
  (q) a 3- to 8-membered monocyclic non-aromatic heterocyclylidenamino group (e.g., 1-oxido-thiolan-1-ylidenamino),
(2) a 6-membered aromatic heterocycle (e.g., pyridine (optionally oxidized), pyrimidine, pyridazine, pyrazine)
optionally fused with a 5- or 6-membered monocyclic aromatic heterocycle (e.g., imidazole) (i.e., the fused ring is imidazopyridine),
further substituted by one cyano group, and
optionally further substituted by 1 to 4 substituents selected from
  (a) a halogen atom (e.g., a fluorine atom, a chlorine atom),
  (b) an amino group,
  (c) a $C_{1-6}$ alkyl group (e.g., methyl, ethyl) optionally substituted by 1 to 3 substituents selected from
    (i) a halogen atom (e.g., a fluorine atom), and
    (ii) a hydroxy group,
  (d) a $C_{1-6}$ alkoxy group (e.g., methoxy, ethoxy) optionally substituted by 1 to 3 substituents selected from
    (i) a halogen atom (e.g., a fluorine atom),
    (ii) a $C_{1-6}$ alkoxy group (e.g., methoxy), and
    (iii) a 3- to 8-membered monocyclic non-aromatic heterocyclic group (e.g., oxetanyl),
  (e) a $C_{3-10}$ cycloalkyl group (e.g., cyclopropyl),
  (f) a $C_{1-6}$ alkyl-carbonyl group (e.g., acetyl),
  (g) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
  (h) a mono- or di-$C_{1-6}$ alkoxy-carbonylamino group (e.g., N-tert-butoxycarbonylamino, N,N-di-tert-butoxycarbonylamino), and
  (i) a 3- to 8-membered monocyclic non-aromatic heterocyclic group (e.g., azetidinyl, pyrrolidinyl), or
(3) a 6-membered non-aromatic heterocycle (e.g., dihydropyridine, dihydropyrimidine)
further substituted by one cyano group, and
optionally further substituted by 1 to 4 substituents selected from
  (a) an oxo group, and
  (b) a $C_{1-6}$ alkyl group (e.g., methyl) optionally substituted by 1 to 3 halogen atoms (e.g., a fluorine atom).
In another embodiment, Ring $A^2$ is more preferably
(1) a benzene ring
further substituted by one cyano group, and
optionally further substituted by 1 to 5 substituents selected from
  (a) a halogen atom (e.g., a fluorine atom, a chlorine atom),
  (b) a $C_{1-6}$ alkyl group (e.g., methyl) optionally substituted by 1 to 3 substituents selected from
    (i) a halogen atom (e.g., a fluorine atom), and
    (ii) a $C_{1-6}$ alkoxy group (e.g., methoxy), and (c) a $C_{1-6}$ alkoxy group (e.g., methoxy) optionally substituted by 1 to 3 halogen atoms (e.g., a fluorine atom), (2) a 6-membered aromatic heterocycle (e.g., pyridine, pyrimidine)

further substituted by one cyano group, and optionally further substituted by 1 to 4 substituents selected from (a) a $C_{1-6}$ alkyl group (e.g., methyl) optionally substituted by 1 to 3 halogen atoms (e.g., a fluorine atom), and (b) a $C_{1-6}$ alkoxy group (e.g., methoxy, ethoxy), or (3) a 6-membered non-aromatic heterocycle (e.g., dihydropyridine)

further substituted by one cyano group, and optionally further substituted by 1 to 4 substituents selected from (a) an oxo group, and (b) a $C_{1-6}$ alkyl group (e.g., methyl).

Ring $A^2$ is further more preferably (1) a benzene ring further substituted by one cyano group, and optionally further substituted by 1 to 5 substituents selected from (a) a cyano group, (b) a halogen atom (e.g., a fluorine atom, a chlorine atom), (c) a hydroxy group, (d) a carboxy group, (e) an amino group, (f) a $C_{1-6}$ alkyl group (e.g., methyl, ethyl) optionally substituted by 1 to 3 substituents selected from (i) a halogen atom (e.g., a fluorine atom), and (ii) a $C_{1-6}$ alkoxy group (e.g., methoxy), (g) a $C_{1-6}$ alkoxy group (e.g., methoxy, ethoxy, propoxy, isopropoxy, isobutyloxy) optionally substituted by 1 to 3 substituents selected from (i) a halogen atom (e.g., a fluorine atom), (ii) a cyano group, (iii) a carboxy group, (iv) a carbamoyl group, (v) a $C_{1-6}$ alkoxy group (e.g., methoxy, ethoxy) optionally substituted by 1 to 3 substituents selected from (I) a $C_{1-6}$ alkoxy-$C_{1-6}$ alkoxy group (e.g., methoxyethoxy), and (II) a mono- or di-$C_{1-6}$ alkylamino group (e.g., N,N-dimethylamino), (vi) a mono- or di-$C_{1-6}$ alkyl-carbonylamino group (e.g., N-acetylamino), (vii) a N—$C_{1-6}$ alkyl-N—$C_{1-6}$ alkyl-carbonylamino group (e.g., N-methyl-N-acetylamino), (viii) a $C_{3-10}$ cycloalkyl group (e.g., cyclobutyl), and (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from (I) an oxo group, and (II) a $C_{1-6}$ alkyl group (e.g., methyl), (h) a $C_{1-6}$ alkyl-carbonyl group (e.g., acetyl), (i) a $C_{1-6}$ alkoxy-carbonyl group (e.g., methoxycarbonyl, ethoxycarbonyl), (j) a mono- or di-$C_{1-6}$ alkylamino group (e.g., N-ethylamino) optionally substituted by 1 to 3 $C_{1-6}$ alkoxy groups (e.g., methoxy), (k) a mono- or di-$C_{1-6}$ alkyl-carbonylamino group (e.g., N-propanoylamino) optionally substituted by 1 to 3 $C_{1-6}$ alkoxy groups (e.g., methoxy), (l) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 of 3- to 8-membered monocyclic non-aromatic heterocyclic groups (e.g., morpholinyl), (m) a di-$C_{1-6}$ alkylsulfinylidenamino group (e.g., N-dimethylsulfinylidenamino), (n) a $C_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl), (o) a 3- to 8-membered monocyclic non-aromatic heterocyclyloxy group (e.g., pyrrolidinyloxy) optionally substituted by 1 to 3 oxo groups, (p) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), and (q) a 3- to 8-membered monocyclic non-aromatic heterocyclylidenamino group (e.g., 1-oxido-thiolan-1-ylidenamino), (2) a pyridine ring (optionally oxidized)

optionally fused with a 5- or 6-membered monocyclic aromatic heterocycle (e.g., imidazole) (i.e., the fused ring is imidazopyridine), further substituted by one cyano group, and optionally further substituted by 1 to 4 substituents selected from (a) a halogen atom (e.g., a fluorine atom, a chlorine atom), (b) an amino group, (c) a $C_{1-6}$ alkyl group (e.g., methyl, ethyl) optionally substituted by 1 to 3 substituents selected from (i) a halogen atom (e.g., a fluorine atom), and (ii) a hydroxy group, (d) a $C_{1-6}$ alkoxy group (e.g., methoxy, ethoxy) optionally substituted by 1 to 3 substituents selected from (i) a halogen atom (e.g., a fluorine atom), (ii) a $C_{1-6}$ alkoxy group (e.g., methoxy), and (iii) a 3- to 8-membered monocyclic non-aromatic heterocyclic group (e.g., oxetanyl), (e) a $C_{3-10}$ cycloalkyl group (e.g., cyclopropyl), (f) a $C_{1-6}$ alkyl-carbonyl group (e.g., acetyl), (g) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom), (h) a mono- or di-$C_{1-6}$ alkoxy-carbonylamino group (e.g., N-tert-butoxycarbonylamino, N,N-di-tert-butoxycarbonylamino), and (i) a 3- to 8-membered monocyclic non-aromatic heterocyclic group (e.g., azetidinyl, pyrrolidinyl), (3) a pyrimidine ring further substituted by one cyano group, and optionally further substituted by 1 to 3 substituents selected from (a) an amino group, (b) a $C_{1-6}$ alkoxy group (e.g., methoxy, ethoxy), and (c) a mono- or di-$C_{16}$ alkylamino group (e.g., N,N-dimethylamino), (4) a pyridazine ring further substituted by one cyano group, (5) a pyrazine ring
further substituted by one cyano group, and
optionally further substituted by 1 to 3 substituents selected from
  (a) a $C_{1-6}$ alkyl group (e.g., methyl), and
  (b) a $C_{1-6}$ alkoxy group (e.g., methoxy),
(6) a dihydropyridine ring
further substituted by one cyano group, and
optionally further substituted by 1 to 4 substituents selected from
  (a) an oxo group, and
  (b) a $C_{1-6}$ alkyl group (e.g., methyl) optionally substituted by 1 to 3 halogen atoms (e.g., a fluorine atom), or
(7) a dihydropyrimidine ring
further substituted by one cyano group, and
optionally further substituted by 1 or 2 oxo groups.

In another embodiment, Ring $A^2$ is further more preferably
(1) a benzene ring
further substituted by one cyano group, and
optionally further substituted by 1 to 5 substituents selected from
  (a) a cyano group,
  (b) a halogen atom (e.g., a fluorine atom),
  (c) a hydroxy group,
  (d) a carboxy group,
  (e) an amino group,
  (f) a $C_{1-6}$ alkyl group (e.g., methyl, ethyl) optionally substituted by 1 to 3 halogen atoms (e.g., a fluorine atom),
  (g) a $C_{1-6}$ alkoxy group (e.g., methoxy, ethoxy, propoxy, isopropoxy, isobutyloxy) optionally substituted by 1 to 3 substituents selected from
    (i) a halogen atom (e.g., a fluorine atom),
    (ii) a cyano group,
    (iii) a carboxy group,
    (iv) a carbamoyl group,
    (v) a $C_{1-6}$ alkoxy group (e.g., methoxy, ethoxy) optionally substituted by 1 to 3 substituents selected from
      (I) a $C_{1-6}$ alkoxy-$C_{1-6}$ alkoxy group (e.g., methoxyethoxy), and
      (II) a mono- or di-$C_{1-6}$ alkylamino group (e.g., N,N-dimethylamino),
    (vi) a mono- or di-$C_{1-6}$ alkyl-carbonylamino group (e.g., N-acetylamino),
    (vii) a N—$C_{1-6}$ alkyl-N—$C_{1-6}$ alkyl-carbonylamino group (e.g., N-methyl-N-acetylamino),
    (viii) a $C_{3-10}$ cycloalkyl group (e.g., cyclobutyl), and
    (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
      (I) an oxo group, and
      (II) a $C_{1-6}$ alkyl group (e.g., methyl),
  (h) a $C_{1-6}$ alkyl-carbonyl group (e.g., acetyl),
  (i) a $C_{1-6}$ alkoxy-carbonyl group (e.g., methoxycarbonyl, ethoxycarbonyl),
  (j) a mono- or di-$C_{1-6}$ alkylamino group (e.g., N-ethylamino) optionally substituted by 1 to 3 $C_{1-6}$ alkoxy groups (e.g., methoxy),
  (k) a mono- or di-$C_{1-6}$ alkyl-carbonylamino group (e.g., N-propanoylamino) optionally substituted by 1 to 3 $C_{1-6}$ alkoxy groups (e.g., methoxy),
  (l) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 of 3- to 8-membered monocyclic non-aromatic heterocyclic groups (e.g., morpholinyl),
  (m) a di-$C_{1-6}$ alkylsulfinylidenamino group (e.g., N-dimethylsulfinylidenamino),
  (n) a $C_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl),
  (o) a 3- to 8-membered monocyclic non-aromatic heterocyclyloxy group (e.g., pyrrolidinyloxy) optionally substituted by 1 to 3 oxo groups,
  (p) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), and
  (q) a 3- to 8-membered monocyclic non-aromatic heterocyclylidenamino group (e.g., 1-oxido-thiolan-1-ylidenamino),
(2) a pyridine ring (optionally oxidized)
optionally fused with a 5- or 6-membered monocyclic aromatic heterocycle (e.g., imidazole) (i.e., the fused ring is imidazopyridine),
further substituted by one cyano group, and
optionally further substituted by 1 to 4 substituents selected from
  (a) a halogen atom (e.g., a fluorine atom, a chlorine atom),
  (b) an amino group,
  (c) a $C_{1-6}$ alkyl group (e.g., methyl, ethyl) optionally substituted by 1 to 3 substituents selected from
    (i) a halogen atom (e.g., a fluorine atom), and
    (ii) a hydroxy group,
  (d) a $C_{1-6}$ alkoxy group (e.g., methoxy, ethoxy) optionally substituted by 1 to 3 substituents selected from
    (i) a halogen atom (e.g., a fluorine atom),
    (ii) a $C_{1-6}$ alkoxy group (e.g., methoxy), and
    (iii) a 3- to 8-membered monocyclic non-aromatic heterocyclic group (e.g., oxetanyl),
  (e) a $C_{3-10}$ cycloalkyl group (e.g., cyclopropyl),
  (f) a $C_{1-6}$ alkyl-carbonyl group (e.g., acetyl),
  (g) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
  (h) a mono- or di-$C_{1-6}$ alkoxy-carbonylamino group (e.g., N-tert-butoxycarbonylamino, N,N-di-tert-butoxycarbonylamino), and
  (i) a 3- to 8-membered monocyclic non-aromatic heterocyclic group (e.g., azetidinyl, pyrrolidinyl),
(3) a pyrimidine ring
further substituted by one cyano group, and
optionally further substituted by 1 to 3 substituents selected from
  (a) an amino group,
  (b) a $C_{1-6}$ alkoxy group (e.g., methoxy, ethoxy), and
  (c) a mono- or di-$C_{1-6}$ alkylamino group (e.g., N,N-dimethylamino),
(4) a pyridazine ring further substituted by one cyano group,
(5) a pyrazine ring
further substituted by one cyano group, and
optionally further substituted by 1 to 3 substituents selected from (a) a $C_{1-6}$ alkyl group (e.g., methyl), and
(b) a $C_{1-6}$ alkoxy group (e.g., methoxy),
(6) a dihydropyridine ring
further substituted by one cyano group, and
optionally further substituted by 1 to 4 substituents selected from
  (a) an oxo group, and
  (b) a $C_{1-6}$ alkyl group (e.g., methyl) optionally substituted by 1 to 3 halogen atoms (e.g., a fluorine atom), or
(7) a dihydropyrimidine ring
further substituted by one cyano group, and
optionally further substituted by 1 or 2 oxo groups.

In another embodiment, Ring $A^2$ is further more preferably
(1) a benzene ring
further substituted by one cyano group, and
optionally further substituted by 1 to 5 substituents selected from
  (a) a halogen atom (e.g., a fluorine atom, a chlorine atom),
  (b) a $C_{1-6}$ alkyl group (e.g., methyl) optionally substituted by 1 to 3 substituents selected from
    (i) a halogen atom (e.g., a fluorine atom), and
    (ii) a $C_{1-6}$ alkoxy group (e.g., methoxy), and
  (c) a $C_{1-6}$ alkoxy group (e.g., methoxy) optionally substituted by 1 to 3 halogen atoms (e.g., a fluorine atom),
(2) a pyridine ring
further substituted by one cyano group, and
optionally further substituted by 1 to 4 substituents selected from
  (a) a $C_{1-6}$ alkyl group (e.g., methyl) optionally substituted by 1 to 3 halogen atoms (e.g., a fluorine atom), and
  (b) a $C_{1-6}$ alkoxy group (e.g., methoxy, ethoxy),
(3) a pyrimidine ring
further substituted by one cyano group, and
optionally further substituted by 1 to 4 $C_{1-6}$ alkoxy groups (e.g., methoxy), or
(4) a dihydropyridine ring
further substituted by one cyano group, and
optionally further substituted by 1 to 4 substituents selected from
  (a) an oxo group, and
  (b) a $C_{1-6}$ alkyl group (e.g., methyl).

In another embodiment, Ring $A^2$ is more preferably a partial structure represented by the following formula:

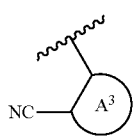

wherein Ring $A^3$ is an optionally further substituted benzene ring, an optionally further substituted 6-membered nitrogen-containing aromatic heterocycle, or an optionally further substituted 6-membered nitrogen-containing non-aromatic heterocycle. The cyano group is bonded to the carbon atom adjacent to the carbon atom to which the partial structure represented by the formula:

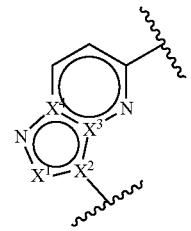

is bonded.

The "6-membered nitrogen-containing aromatic heterocycle" of the "optionally further substituted 6-membered nitrogen-containing aromatic heterocycle" is preferably a pyridine ring (optionally oxidized), a pyrimidine ring, a pyridazine ring or a pyrazine ring, particularly preferably a pyridine ring.

The "6-membered nitrogen-containing non-aromatic heterocycle" of the "optionally further substituted 6-membered nitrogen-containing non-aromatic heterocycle" is preferably a dihydropyridine ring or a dihydropyrimidine ring.

The "benzene ring" of the "optionally further substituted benzene ring", the "6-membered nitrogen-containing aromatic heterocycle" of the "optionally further substituted 6-membered nitrogen-containing aromatic heterocycle" and "6-membered nitrogen-containing non-aromatic heterocycle" of the "optionally further substituted 6-membered nitrogen-containing non-aromatic heterocycle" optionally further have 1 to 3 substituents at substitutable position(s), in addition to the cyano group and the partial structure represented by the formula:

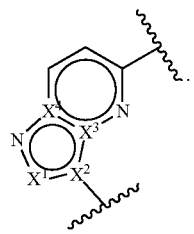

Examples of the substituent include substituents selected from the above-mentioned Substituent Group A. When the number of the substituents is two or more, the respective substituents may be the same or different. In addition, the above-mentioned Substituent Group A is optionally substituted by substituent(s) selected from Substituent Group A. The number of the substituents is, for example, 1 to 3. When the number of the substituents is two or more, the respective substituents may be the same or different.

Ring $A^3$ is preferably
(1) a benzene ring optionally further substituted by 1 to 5 substituents selected from
  (a) a cyano group,
  (b) a halogen atom (e.g., a fluorine atom, a chlorine atom),
  (c) a hydroxy group,
  (d) a carboxy group,
  (e) an amino group,
  (f) a $C_{1-6}$ alkyl group (e.g., methyl, ethyl) optionally substituted by 1 to 3 substituents selected from
    (i) a halogen atom (e.g., a fluorine atom), and
    (ii) a $C_{1-6}$ alkoxy group (e.g., methoxy), (g) a $C_{1-6}$ alkoxy group (e.g., methoxy, ethoxy, propoxy, isopropoxy, isobutyloxy) optionally substituted by 1 to 3 substituents selected from
  (i) a halogen atom (e.g., a fluorine atom),
  (ii) a cyano group,
  (iii) a carboxy group,
  (iv) a carbamoyl group,
  (v) a $C_{1-6}$ alkoxy group (e.g., methoxy, ethoxy) optionally substituted by 1 to 3 substituents selected from
    (I) a $C_{1-6}$ alkoxy-$C_{1-6}$ alkoxy group (e.g., methoxyethoxy), and
    (II) a mono- or di-$C_{1-6}$ alkylamino group (e.g., N,N-dimethylamino),
  (vi) a mono- or di-$C_{1-6}$ alkyl-carbonylamino group (e.g., N-acetylamino),
  (vii) a N—$C_{1-6}$ alkyl-N—$C_{1-6}$ alkyl-carbonylamino group (e.g., N-methyl-N-acetylamino),
  (viii) a $C_{3-10}$ cycloalkyl group (e.g., cyclobutyl), and
  (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
    (I) an oxo group, and
    (II) a $C_{1-6}$ alkyl group (e.g., methyl),
(h) a $C_{1-6}$ alkyl-carbonyl group (e.g., acetyl),
(i) a $C_{1-6}$ alkoxy-carbonyl group (e.g., methoxycarbonyl, ethoxycarbonyl),
(j) a mono- or di-$C_{1-6}$ alkylamino group (e.g., N-ethylamino) optionally substituted by 1 to 3 $C_{1-6}$ alkoxy groups (e.g., methoxy),
(k) a mono- or di-$C_{1-6}$ alkyl-carbonylamino group (e.g., N-propanoylamino) optionally substituted by 1 to 3 $C_{1-6}$ alkoxy groups (e.g., methoxy),
(l) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 of 3- to 8-membered monocyclic non-aromatic heterocyclic groups (e.g., morpholinyl),
(m) a di-$C_{1-6}$ alkylsulfinylidenamino group (e.g., N-dimethylsulfinylidenamino),
(n) a $C_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl),
(o) a 3- to 8-membered monocyclic non-aromatic heterocyclyloxy group (e.g., pyrrolidinyloxy) optionally substituted by 1 to 3 oxo groups,
(p) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), and
(q) a 3- to 8-membered monocyclic non-aromatic heterocyclylidenamino group (e.g., 1-oxido-thiolan-1-ylidenamino),
(2) a 6-membered aromatic heterocycle (e.g., pyridine (optionally oxidized), pyrimidine, pyridazine, pyrazine)
optionally fused with a 5- or 6-membered monocyclic aromatic heterocycle (e.g., imidazole) (i.e., the fused ring is imidazopyridine), and
optionally further substituted by 1 to 4 substituents selected from
  (a) a halogen atom (e.g., a fluorine atom, a chlorine atom),
  (b) an amino group,
  (c) a $C_{1-6}$ alkyl group (e.g., methyl, ethyl) optionally substituted by 1 to 3 substituents selected from
    (i) a halogen atom (e.g., a fluorine atom), and
    (ii) a hydroxy group,
  (d) a $C_{1-6}$ alkoxy group (e.g., methoxy, ethoxy) optionally substituted by 1 to 3 substituents selected from
    (i) a halogen atom (e.g., a fluorine atom),
    (ii) a $C_{1-6}$ alkoxy group (e.g., methoxy), and
    (iii) a 3- to 8-membered monocyclic non-aromatic heterocyclic group (e.g., oxetanyl),
  (e) a $C_{3-10}$ cycloalkyl group (e.g., cyclopropyl),
  (f) a $C_{1-6}$ alkyl-carbonyl group (e.g., acetyl),
  (g) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
  (h) a mono- or di-$C_{1-6}$ alkoxy-carbonylamino group (e.g., N-tert-butoxycarbonylamino, N,N-di-tert-butoxycarbonylamino), and
  (i) a 3- to 8-membered monocyclic non-aromatic heterocyclic group (e.g., azetidinyl, pyrrolidinyl), or
(3) a 6-membered non-aromatic heterocycle (e.g., dihydropyridine, dihydropyrimidine) optionally further substituted by 1 to 4 substituents selected from
  (a) an oxo group, and
  (b) a $C_{1-6}$ alkyl group (e.g., methyl) optionally substituted by 1 to 3 halogen atoms (e.g., a fluorine atom).
In another embodiment, Ring $A^3$ is preferably
(1) a benzene ring optionally further substituted by 1 to 5 substituents selected from
  (a) a cyano group,
  (b) a halogen atom (e.g., a fluorine atom),
  (c) a hydroxy group,
  (d) a carboxy group,
  (e) an amino group,
  (f) a $C_{1-6}$ alkyl group (e.g., methyl, ethyl) optionally substituted by 1 to 3 halogen atoms (e.g., a fluorine atom),
  (g) a $C_{1-6}$ alkoxy group (e.g., methoxy, ethoxy, propoxy, isopropoxy, isobutyloxy) optionally substituted by 1 to 3 substituents selected from
    (i) a halogen atom (e.g., a fluorine atom),
    (ii) a cyano group,
    (iii) a carboxy group,
    (iv) a carbamoyl group,
    (v) a $C_{1-6}$ alkoxy group (e.g., methoxy, ethoxy) optionally substituted by 1 to 3 substituents selected from
      (I) a $C_{1-6}$ alkoxy-$C_{1-6}$ alkoxy group (e.g., methoxyethoxy), and
      (II) a mono- or di-$C_{1-6}$ alkylamino group (e.g., N,N-dimethylamino),
    (vi) a mono- or di-$C_{1-6}$ alkyl-carbonylamino group (e.g., N-acetylamino),
    (vii) a N—$C_{1-6}$ alkyl-N—$C_{1-6}$ alkyl-carbonylamino group (e.g., N-methyl-N-acetylamino),
    (viii) a $C_{3-10}$ cycloalkyl group (e.g., cyclobutyl), and
    (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
      (I) an oxo group, and
      (II) a $C_{1-6}$ alkyl group (e.g., methyl), (h) a $C_{1-6}$ alkyl-carbonyl group (e.g., acetyl),
(i) a $C_{1-6}$ alkoxy-carbonyl group (e.g., methoxycarbonyl, ethoxycarbonyl),
(j) a mono- or di-$C_{1-6}$ alkylamino group (e.g., N-ethylamino) optionally substituted by 1 to 3 $C_{1-6}$ alkoxy groups (e.g., methoxy),
(k) a mono- or di-$C_{1-6}$ alkyl-carbonylamino group (e.g., N-propanoylamino) optionally substituted by 1 to 3 $C_{1-6}$ alkoxy groups (e.g., methoxy),
(l) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 of 3- to 8-membered monocyclic non-aromatic heterocyclic groups (e.g., morpholinyl),
(m) a di-$C_{1-6}$ alkylsulfinylidenamino group (e.g., N-dimethylsulfinylidenamino),
(n) a $C_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl),
(o) a 3- to 8-membered monocyclic non-aromatic heterocyclyloxy group (e.g., pyrrolidinyloxy) optionally substituted by 1 to 3 oxo groups,
(p) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), and
(q) a 3- to 8-membered monocyclic non-aromatic heterocyclylidenamino group (e.g., 1-oxido-thiolan-1-ylidenamino),
(2) a 6-membered aromatic heterocycle (e.g., pyridine (optionally oxidized), pyrimidine, pyridazine, pyrazine)
optionally fused with a 5- or 6-membered monocyclic aromatic heterocycle (e.g., imidazole) (i.e., the fused ring is imidazopyridine), and
optionally further substituted by 1 to 4 substituents selected from
(a) a halogen atom (e.g., a fluorine atom, a chlorine atom),
(b) an amino group,
(c) a $C_{1-6}$ alkyl group (e.g., methyl, ethyl) optionally substituted by 1 to 3 substituents selected from
(i) a halogen atom (e.g., a fluorine atom), and
(ii) a hydroxy group,
(d) a $C_{1-6}$ alkoxy group (e.g., methoxy, ethoxy) optionally substituted by 1 to 3 substituents selected from
(i) a halogen atom (e.g., a fluorine atom),
(ii) a $C_{1-6}$ alkoxy group (e.g., methoxy), and
(iii) a 3- to 8-membered monocyclic non-aromatic heterocyclic group (e.g., oxetanyl),
(e) a $C_{3-10}$ cycloalkyl group (e.g., cyclopropyl),
(f) a $C_{1-6}$ alkyl-carbonyl group (e.g., acetyl),
(g) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
(h) a mono- or di-$C_{1-6}$ alkoxy-carbonylamino group (e.g., N-tert-butoxycarbonylamino, N,N-di-tert-butoxycarbonylamino), and
(i) a 3- to 8-membered monocyclic non-aromatic heterocyclic group (e.g., azetidinyl, pyrrolidinyl), or
(3) a 6-membered non-aromatic heterocycle (e.g., dihydropyridine, dihydropyrimidine) optionally further substituted by 1 to 4 substituents selected from
(a) an oxo group, and
(b) a $C_{1-6}$ alkyl group (e.g., methyl) optionally substituted by 1 to 3 halogen atoms (e.g., a fluorine atom).

In another embodiment, Ring $A^3$ is preferably
(1) a benzene ring optionally further substituted by 1 to 5 substituents selected from
(a) a halogen atom (e.g., a fluorine atom, a chlorine atom),
(b) a $C_{1-6}$ alkyl group (e.g., methyl) optionally substituted by 1 to 3 substituents selected from
(i) a halogen atom (e.g., a fluorine atom), and
(ii) a $C_{1-6}$ alkoxy group (e.g., methoxy), and
(c) a $C_{1-6}$ alkoxy group (e.g., methoxy) optionally substituted by 1 to 3 halogen atoms (e.g., a fluorine atom),
(2) a 6-membered aromatic heterocycle (e.g., pyridine, pyrimidine) optionally further substituted by 1 to 4 substituents selected from
(a) a $C_{1-6}$ alkyl group (e.g., methyl) optionally substituted by 1 to 3 halogen atoms (e.g., a fluorine atom), and
(b) a $C_{1-6}$ alkoxy group (e.g., methoxy, ethoxy), or
(3) a 6-membered non-aromatic heterocycle (e.g., dihydropyridine) optionally further substituted by 1 to 4 substituents selected from
(a) an oxo group, and
(b) a $C_{1-6}$ alkyl group (e.g., methyl).

Ring $A^3$ is more preferably
(1) a benzene ring optionally further substituted by 1 to 5 substituents selected from
(a) a cyano group,
(b) a halogen atom (e.g., a fluorine atom, a chlorine atom),
(c) a hydroxy group,
(d) a carboxy group,
(e) an amino group,
(f) a $C_{1-6}$ alkyl group (e.g., methyl, ethyl) optionally substituted by 1 to 3 substituents selected from
(i) a halogen atom (e.g., a fluorine atom), and
(ii) a $C_{1-6}$ alkoxy group (e.g., methoxy),
(g) a $C_{1-6}$ alkoxy group (e.g., methoxy, ethoxy, propoxy, isopropoxy, isobutyloxy) optionally substituted by 1 to 3 substituents selected from
(i) a halogen atom (e.g., a fluorine atom),
(ii) a cyano group,
(iii) a carboxy group,
(iv) a carbamoyl group,
(v) a $C_{1-6}$ alkoxy group (e.g., methoxy, ethoxy) optionally substituted by 1 to 3 substituents selected from
(I) a $C_{1-6}$ alkoxy-$C_{1-6}$ alkoxy group (e.g., methoxyethoxy), and
(II) a mono- or di-$C_{1-6}$ alkylamino group (e.g., N,N-dimethylamino),
(vi) a mono- or di-$C_{1-6}$ alkyl-carbonylamino group (e.g., N-acetylamino),
(vii) a N—$C_{1-6}$ alkyl-N—$C_{1-6}$ alkyl-carbonylamino group (e.g., N-methyl-N-acetylamino),
(viii) a $C_{3-10}$ cycloalkyl group (e.g., cyclobutyl), and
(ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
(I) an oxo group, and
(II) a $C_{1-6}$ alkyl group (e.g., methyl), (h) a C$_{1-6}$ alkyl-carbonyl group (e.g., acetyl),
(i) a C$_{1-6}$ alkoxy-carbonyl group (e.g., methoxycarbonyl, ethoxycarbonyl),
(j) a mono- or di-C$_{1-6}$ alkylamino group (e.g., N-ethylamino) optionally substituted by 1 to 3 C$_{1-6}$ alkoxy groups (e.g., methoxy),
(k) a mono- or di-C$_{1-6}$ alkyl-carbonylamino group (e.g., N-propanoylamino) optionally substituted by 1 to 3 C$_{1-6}$ alkoxy groups (e.g., methoxy),
(l) a mono- or di-C$_{1-6}$ alkyl-carbamoyl group (e.g., N-methylcarbamoyl, N,N-dimethylcarbamoyl, N-ethylcarbamoyl) optionally substituted by 1 to 3 of 3- to 8-membered monocyclic non-aromatic heterocyclic groups (e.g., morpholinyl),
(m) a di-C$_{1-6}$ alkylsulfinylidenamino group (e.g., N-dimethylsulfinylidenamino),
(n) a C$_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 C$_{1-6}$ alkyl groups (e.g., methyl),
(o) a 3- to 8-membered monocyclic non-aromatic heterocyclyloxy group (e.g., pyrrolidinyloxy) optionally substituted by 1 to 3 oxo groups,
(p) a 3- to 8-membered monocyclic non-aromatic heterocyclylcarbonyl group (e.g., azetidinylcarbonyl) optionally substituted by 1 to 3 C$_{1-6}$ alkoxy groups (e.g., methoxy), and
(q) a 3- to 8-membered monocyclic non-aromatic heterocyclylidenamino group (e.g., 1-oxido-thiolan-1-ylidenamino),
(2) a pyridine ring (optionally oxidized)
optionally fused with a 5- or 6-membered monocyclic aromatic heterocycle (e.g., imidazole) (i.e., the fused ring is imidazopyridine), and
optionally further substituted by 1 to 4 substituents selected from
  (a) a halogen atom (e.g., a fluorine atom, a chlorine atom),
  (b) an amino group,
  (c) a C$_{1-6}$ alkyl group (e.g., methyl, ethyl) optionally substituted by 1 to 3 substituents selected from
    (i) a halogen atom (e.g., a fluorine atom), and
    (ii) a hydroxy group,
  (d) a C$_{1-6}$ alkoxy group (e.g., methoxy, ethoxy) optionally substituted by 1 to 3 substituents selected from
    (i) a halogen atom (e.g., a fluorine atom),
    (ii) a C$_{1-6}$ alkoxy group (e.g., methoxy), and
    (iii) a 3- to 8-membered monocyclic non-aromatic heterocyclic group (e.g., oxetanyl),
  (e) a C$_{3-10}$ cycloalkyl group (e.g., cyclopropyl),
  (f) a C$_{1-6}$ alkyl-carbonyl group (e.g., acetyl),
  (g) a mono- or di-C$_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
  (h) a mono- or di-C$_{1-6}$ alkoxy-carbonylamino group (e.g., N-tert-butoxycarbonylamino, N,N-di-tert-butoxycarbonylamino), and
    (i) a 3- to 8-membered monocyclic non-aromatic heterocyclic group (e.g., azetidinyl, pyrrolidinyl),
(3) a pyrimidine ring optionally further substituted by 1 to 3 substituents selected from
  (a) an amino group,
  (b) a C$_{1-6}$ alkoxy group (e.g., methoxy, ethoxy), and
  (c) a mono- or di-C$_{1-6}$ alkylamino group (e.g., N,N-dimethylamino),
(4) a pyridazine ring,
(5) a pyrazine ring optionally further substituted by 1 to 3 substituents selected from
  (a) a C$_{1-6}$ alkyl group (e.g., methyl), and
  (b) a C$_{1-6}$ alkoxy group (e.g., methoxy),
(6) a dihydropyridine ring optionally further substituted by 1 to 4 substituents selected from
  (a) an oxo group, and
  (b) a C$_{1-6}$ alkyl group (e.g., methyl) optionally substituted by 1 to 3 halogen atoms (e.g., a fluorine atom), or
(7) a dihydropyrimidine ring optionally further substituted by 1 or 2 oxo groups.

In another embodiment, Ring A$^3$ is more preferably
(1) a benzene ring optionally further substituted by 1 to 5 substituents selected from
  (a) a cyano group,
  (b) a halogen atom (e.g., a fluorine atom),
  (c) a hydroxy group,
  (d) a carboxy group,
  (e) an amino group,
  (f) a C$_{1-6}$ alkyl group (e.g., methyl, ethyl) optionally substituted by 1 to 3 halogen atoms (e.g., a fluorine atom),
  (g) a C$_{1-6}$ alkoxy group (e.g., methoxy, ethoxy, propoxy, isopropoxy, isobutyloxy) optionally substituted by 1 to 3 substituents selected from
    (i) a halogen atom (e.g., a fluorine atom),
    (ii) a cyano group,
    (iii) a carboxy group,
    (iv) a carbamoyl group,
    (v) a C$_{1-6}$ alkoxy group (e.g., methoxy, ethoxy) optionally substituted by 1 to 3 substituents selected from
      (I) a C$_{1-6}$ alkoxy-C$_{1-6}$ alkoxy group (e.g., methoxyethoxy), and
      (II) a mono- or di-C$_{1-6}$ alkylamino group (e.g., N,N-dimethylamino),
    (vi) a mono- or di-C$_{1-6}$ alkyl-carbonylamino group (e.g., N-acetylamino),
    (vii) a N—C$_{1-6}$ alkyl-N—C$_{1-6}$ alkyl-carbonylamino group (e.g., N-methyl-N-acetylamino),
    (viii) a C$_{3-10}$ cycloalkyl group (e.g., cyclobutyl), and
    (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
      (I) an oxo group, and
      (II) a C$_{1-6}$ alkyl group (e.g., methyl),
  (h) a C$_{1-6}$ alkyl-carbonyl group (e.g., acetyl),
  (i) a C$_{1-6}$ alkoxy-carbonyl group (e.g., methoxycarbonyl, ethoxycarbonyl),
  (j) a mono- or di-C$_{1-6}$ alkylamino group (e.g., N-ethylamino) optionally substituted by 1 to 3 C$_{1-6}$ alkoxy groups (e.g., methoxy),
  (k) a mono- or di-C$_{1-6}$ alkyl-carbonylamino group (e.g., N-propanoylamino) optionally substituted by 1 to 3 C$_{1-6}$ alkoxy groups (e.g., methoxy),
  (l) a mono- or di-C$_{1-6}$ alkyl-carbamoyl group (e.g., N-methylcarbamoyl, N,N-dimethylcarbamoyl, N-ethylcarbamoyl) optionally substituted by 1 to 3 of 3- to 8-membered monocyclic non-aromatic heterocyclic groups (e.g., morpholinyl),
  (m) a di-C$_{1-6}$ alkylsulfinylidenamino group (e.g., N-dimethylsulfinylidenamino),
  (n) a C$_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl),
- (o) a 3- to 8-membered monocyclic non-aromatic heterocyclyloxy group (e.g., pyrrolidinyloxy) optionally substituted by 1 to 3 oxo groups,
- (p) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), and
- (q) a 3- to 8-membered monocyclic non-aromatic heterocyclylidenamino group (e.g., 1-oxido-thiolan-1-ylidenamino), (2) a pyridine ring (optionally oxidized)

optionally fused with a 5- or 6-membered monocyclic aromatic heterocycle (e.g., imidazole) (i.e., the fused ring is imidazopyridine), and optionally further substituted by 1 to 4 substituents selected from
- (a) a halogen atom (e.g., a fluorine atom, a chlorine atom),
- (b) an amino group,
- (c) a $C_{1-6}$ alkyl group (e.g., methyl, ethyl) optionally substituted by 1 to 3 substituents selected from
  - (i) a halogen atom (e.g., a fluorine atom), and
  - (ii) a hydroxy group,
- (d) a $C_{1-6}$ alkoxy group (e.g., methoxy, ethoxy) optionally substituted by 1 to 3 substituents selected from
  - (i) a halogen atom (e.g., a fluorine atom),
  - (ii) a $C_{1-6}$ alkoxy group (e.g., methoxy), and
  - (iii) a 3- to 8-membered monocyclic non-aromatic heterocyclic group (e.g., oxetanyl),
- (e) a $C_{3-10}$ cycloalkyl group (e.g., cyclopropyl),
- (f) a $C_{1-6}$ alkyl-carbonyl group (e.g., acetyl),
- (g) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
- (h) a mono- or di-$C_{16}$ alkoxy-carbonylamino group (e.g., N-tert-butoxycarbonylamino, N,N-di-tert-butoxycarbonylamino), and
- (i) a 3- to 8-membered monocyclic non-aromatic heterocyclic group (e.g., azetidinyl, pyrrolidinyl), (3) a pyrimidine ring optionally further substituted by 1 to 3 substituents selected from
- (a) an amino group,
- (b) a $C_{1-6}$ alkoxy group (e.g., methoxy, ethoxy), and
- (c) a mono- or di-$C_{16}$ alkylamino group (e.g., N,N-dimethylamino), (4) a pyridazine ring, (5) a pyrazine ring optionally further substituted by 1 to 3 substituents selected from
- (a) a $C_{1-6}$ alkyl group (e.g., methyl), and
- (b) a $C_{1-6}$ alkoxy group (e.g., methoxy), (6) a dihydropyridine ring optionally further substituted by 1 to 4 substituents selected from
- (a) an oxo group, and
- (b) a $C_{1-6}$ alkyl group (e.g., methyl) optionally substituted by 1 to 3 halogen atoms (e.g., a fluorine atom), or (7) a dihydropyrimidine ring optionally further substituted by 1 or 2 oxo groups.

In another embodiment, Ring $A^3$ is more preferably (1) a benzene ring optionally further substituted by 1 to 5 substituents selected from
- (a) a halogen atom (e.g., a fluorine atom, a chlorine atom),
- (b) a $C_{1-6}$ alkyl group (e.g., methyl) optionally substituted by 1 to 3 substituents selected from
  - (i) a halogen atom (e.g., a fluorine atom), and
  - (ii) a $C_{1-6}$ alkoxy group (e.g., methoxy), and
- (c) a $C_{1-6}$ alkoxy group (e.g., methoxy) optionally substituted by 1 to 3 halogen atoms (e.g., a fluorine atom), (2) a pyridine ring optionally further substituted by 1 to 4 substituents selected from
- (a) a $C_{1-6}$ alkyl group (e.g., methyl) optionally substituted by 1 to 3 halogen atoms (e.g., a fluorine atom), and
- (b) a $C_{1-6}$ alkoxy group (e.g., methoxy, ethoxy), (3) a pyrimidine ring optionally further substituted by 1 to 4 $C_{1-6}$ alkoxy groups (e.g., methoxy), or (4) a dihydropyridine ring optionally further substituted by 1 to 4 substituents selected from
- (a) an oxo group, and
- (b) a $C_{1-6}$ alkyl group (e.g., methyl).

The partial structure represented by the formula;

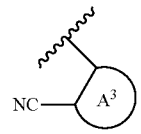

is preferably a partial structure represented by the formula $(A^3-1)$-$(A^3-9)$;

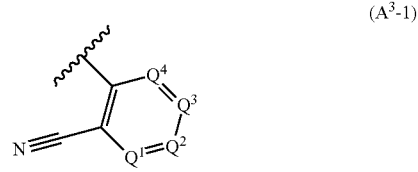

(A³-1)

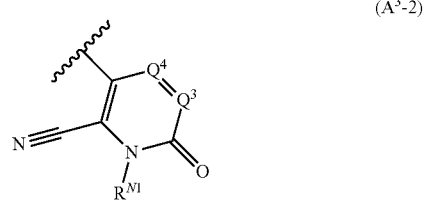

(A³-2)

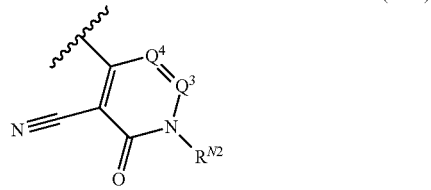

(A³-3)

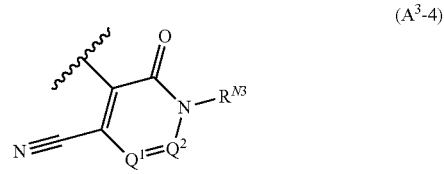

(A³-4)

-continued

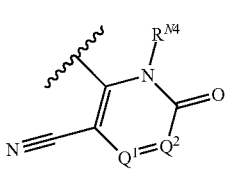
(A³-5)

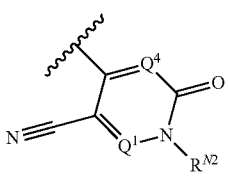
(A³-6)

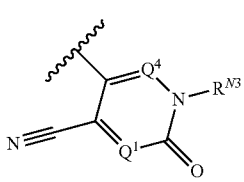
(A³-7)

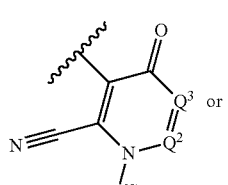
(A³-8)

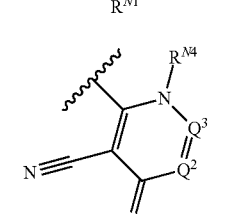
(A³-9)

wherein
$Q^1$ is N or $CR^{Q1}$ wherein $R^{Q1}$ is
(a) a hydrogen atom,
(b) a cyano group,
(c) a halogen atom,
(d) a hydroxy group,
(e) a carboxy group,
(f) an amino group,
(g) an optionally substituted $C_{1-6}$ alkyl group,
(h) an optionally substituted $C_{1-6}$ alkoxy group,
(i) a $C_{1-6}$ alkyl-carbonyl group,
(j) a $C_{1-6}$ alkoxy-carbonyl group,
(k) an optionally substituted mono- or di-$C_{1-6}$ alkylamino group,
(l) an optionally substituted mono- or di-$C_{1-6}$ alkyl-carbonylamino group,
(m) a mono- or di-$C_{1-6}$ alkoxy-carbonylamino group,
(n) a mono- or di-$C_{1-6}$ alkyl-carbamoyl group,
(o) a di-$C_{1-6}$ alkylsulfinylidenamino group,
(p) a $C_{3-10}$ cycloalkyl group,
(q) an optionally substituted $C_{3-10}$ cycloalkyloxy group,
(r) a 3- to 8-membered monocyclic non-aromatic heterocyclic group,
(s) an optionally substituted 3- to 8-membered monocyclic non-aromatic heterocyclyloxy,
(t) an optionally substituted 3- to 8-membered monocyclic non-aromatic heterocyclylcarbonyl group, or
(u) a 3- to 8-membered monocyclic non-aromatic heterocyclylidenamino group,
$Q^2$ is N or $CR^{Q2}$ wherein $R^{Q2}$ is
(a) a hydrogen atom,
(b) a halogen atom, or
(c) a $C_{1-6}$ alkoxy group,
$Q^3$ is N or $CR^{Q3}$ wherein $R^{Q3}$ is
(a) a hydrogen atom,
(b) a cyano group,
(c) a halogen atom,
(d) a carboxy group,
(e) an optionally substituted $C_{1-6}$ alkyl group,
(f) an optionally substituted $C_{1-6}$ alkoxy group,
(g) a $C_{1-6}$ alkyl-carbonyl group,
(h) a $C_{1-6}$ alkoxy-carbonyl group,
(i) a mono- or di-$C_{1-6}$ alkylamino group,
(j) an optionally substituted mono- or di-$C_{1-6}$ alkyl-carbamoyl group,
(k) a di-$C_{1-6}$ alkylsulfinylidenamino group, or
(l) a 3- to 8-membered monocyclic non-aromatic heterocyclylidenamino group, $Q^4$ is N or $CR^{Q4}$ wherein $R^{Q4}$ is
(a) a hydrogen atom, or
(b) a halogen atom, and
N of $Q^1$, $Q^2$, $Q^3$ and $Q^4$ is each optionally oxidized;
$R^{N1}$ is a hydrogen atom or a $C_{1-6}$ alkyl group;
$R^{N2}$ is a hydrogen atom or a $C_{1-6}$ alkyl group;
$R^{N3}$ is a hydrogen atom or a $C_{1-6}$ alkyl group; and
$R^{N4}$ is a hydrogen atom or a $C_{1-6}$ alkyl group optionally substituted by 1 to 3 halogen atoms.

The partial structure represented by the formula;

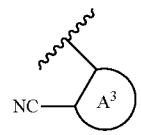

is more preferably a partial structure represented by the formula (A³-1), (A³-2), (A³-3), (A³-5), (A³-6) or (A³-9);

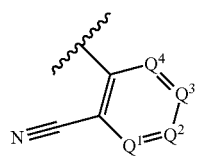
(A³-1)

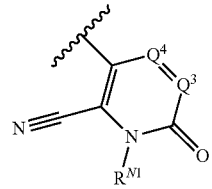
(A³-2)

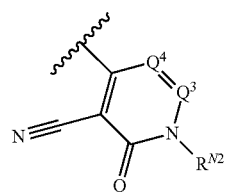
(A³-3)

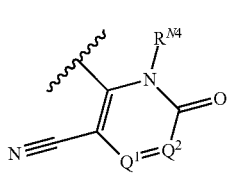
(A³-5)

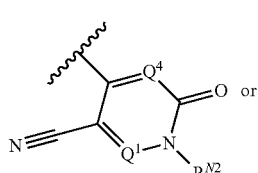
(A³-6)

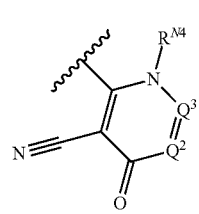
(A³-9)

wherein each symbol is as defined above.

In the formula (A³-1), $Q^1$ is preferably N or $CR^{Q1}$ wherein $R^{Q1}$ is
(a) a hydrogen atom,
(b) a cyano group,
(c) a halogen atom (e.g., a fluorine atom, a chlorine atom),
(d) a hydroxy group,
(e) a carboxy group,
(f) an amino group,
(g) a $C_{1-6}$ alkyl group (e.g., methyl, ethyl) optionally substituted by 1 to 3 substituents selected from
  (i) a halogen atom (e.g., a fluorine atom), and
  (ii) a $C_{1-6}$ alkoxy group (e.g., methoxy),
(h) a $C_{1-6}$ alkoxy group (e.g., methoxy, ethoxy, propoxy, isopropoxy, isobutyloxy) optionally substituted by 1 to 3 substituents selected from
  (i) a halogen atom (e.g., a fluorine atom),
  (ii) a cyano group,
  (iii) a carboxy group,
  (iv) a carbamoyl group,
  (v) a $C_{1-6}$ alkoxy group (e.g., methoxy, ethoxy) optionally substituted by 1 to 3 substituents selected from
    (I) a $C_{1-6}$ alkoxy-$C_{1-6}$ alkoxy group (e.g., methoxyethoxy), and
    (II) a mono- or di-$C_{1-6}$ alkylamino group (e.g., N,N-dimethylamino),
  (vi) a mono- or di-$C_{1-6}$ alkyl-carbonylamino group (e.g., N-acetylamino),
  (vii) a N—$C_{1-6}$ alkyl-N—$C_{1-6}$ alkyl-carbonylamino group (e.g., N-methyl-N-acetylamino),
  (viii) a $C_{3-10}$ cycloalkyl group (e.g., cyclobutyl), and
  (ix) a 3- to 8-membered monocyclic non-aromatic heterocyclic group (e.g., morpholinyl, azetidinyl, pyrrolidinyl, piperidyl, tetrahydropyranyl, oxetanyl) optionally substituted by 1 to 3 substituents selected from
    (I) an oxo group, and
    (II) a $C_{1-6}$ alkyl group (e.g., methyl),
(i) a $C_{1-6}$ alkyl-carbonyl group (e.g., acetyl),
(j) a $C_{1-6}$ alkoxy-carbonyl group (e.g., methoxycarbonyl),
(k) a mono- or di-$C_{1-6}$ alkylamino group (e.g., N-methylamino, N,N-dimethylamino, N-ethylamino, N-ethyl-N-methylamino) optionally substituted by 1 to 3 substituents selected from
  (i) a halogen atom (e.g., a fluorine atom), and
  (ii) a $C_{1-6}$ alkoxy group (e.g., methoxy),
(l) a mono- or di-$C_{1-6}$ alkyl-carbonylamino group (e.g., N-propanoylamino) optionally substituted by 1 to 3 $C_{1-6}$ alkoxy groups (e.g., methoxy),
(m) a mono- or di-$C_{1-6}$ alkoxy-carbonylamino group (e.g., N-tert-butoxycarbonylamino, N,N-di-tert-butoxycarbonylamino),
(n) a mono- or di-$C_{1-6}$ alkyl-carbamoyl group (e.g., N,N-dimethylcarbamoyl),
(o) a di-$C_{1-6}$ alkylsulfinylidenamino group (e.g., N-dimethylsulfinylidenamino),
(p) a $C_{3-10}$ cycloalkyl group (e.g., cyclopropyl),
(q) a $C_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl),
(r) a 3- to 8-membered monocyclic non-aromatic heterocyclic group (e.g., azetidinyl, pyrrolidinyl),
(s) a 3- to 8-membered monocyclic non-aromatic heterocyclyloxy group (e.g., pyrrolidinyloxy) optionally substituted by 1 to 3 oxo groups,
(t) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), or
(u) a 3- to 8-membered monocyclic non-aromatic heterocyclylidenamino group (e.g., 1-oxido-thiolan-1-ylidenamino).

In another embodiment, in the formula (A³-1), $Q^1$ is preferably N or $CR^{Q1}$ wherein $R^{Q1}$ is
(a) a hydrogen atom,
(b) a cyano group,
(c) a halogen atom (e.g., a fluorine atom, a chlorine atom),
(d) a hydroxy group,
(e) a carboxy group,
(f) an amino group,
(g) a $C_{1-6}$ alkyl group (e.g., methyl, ethyl) optionally substituted by 1 to 3 halogen atoms (e.g., a fluorine atom),
(h) a $C_{1-6}$ alkoxy group (e.g., methoxy, ethoxy, propoxy, isopropoxy, isobutyloxy) optionally substituted by 1 to 3 substituents selected from
  (i) a halogen atom (e.g., a fluorine atom),
  (ii) a cyano group,
  (iii) a carboxy group,
  (iv) a carbamoyl group,
  (v) a $C_{1-6}$ alkoxy group (e.g., methoxy, ethoxy) optionally substituted by 1 to 3 substituents selected from
    (I) a $C_{1-6}$ alkoxy-$C_{1-6}$ alkoxy group (e.g., methoxyethoxy), and
    (II) a mono- or di-$C_{1-6}$ alkylamino group (e.g., N,N-dimethylamino),
  (vi) a mono- or di-$C_{1-6}$ alkyl-carbonylamino group (e.g., N-acetylamino),
  (vii) a N—$C_{1-6}$ alkyl-N—$C_{1-6}$ alkyl-carbonylamino group (e.g., N-methyl-N-acetylamino), (viii) a $C_{3-10}$ cycloalkyl group (e.g., cyclobutyl), and
(ix) a 3- to 8-membered monocyclic non-aromatic heterocyclic group (e.g., morpholinyl, azetidinyl, pyrrolidinyl, piperidyl, tetrahydropyranyl, oxetanyl) optionally substituted by 1 to 3 substituents selected from
(I) an oxo group, and
(II) a $C_{1-6}$ alkyl group (e.g., methyl),
(i) a $C_{1-6}$ alkyl-carbonyl group (e.g., acetyl),
(j) a $C_{1-6}$ alkoxy-carbonyl group (e.g., methoxycarbonyl),
(k) a mono- or di-$C_{1-6}$ alkylamino group (e.g., N-methylamino, N,N-dimethylamino, N-ethylamino, N-ethyl-N-methylamino) optionally substituted by 1 to 3 substituents selected from
(i) a halogen atom (e.g., a fluorine atom), and
(ii) a $C_{1-6}$ alkoxy group (e.g., methoxy),
(l) a mono- or di-$C_{1-6}$ alkyl-carbonylamino group (e.g., N-propanoylamino) optionally substituted by 1 to 3 $C_{1-6}$ alkoxy groups (e.g., methoxy),
(m) a mono- or di-$C_{1-6}$ alkoxy-carbonylamino group (e.g., N-tert-butoxycarbonylamino, N,N-di-tert-butoxycarbonylamino),
(n) a mono- or di-$C_{1-6}$ alkyl-carbamoyl group (e.g., N,N-dimethylcarbamoyl),
(o) a di-$C_{1-6}$ alkylsulfinylidenamino group (e.g., N-dimethylsulfinylidenamino),
(p) a $C_{3-10}$ cycloalkyl group (e.g., cyclopropyl),
(q) a $C_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl),
(r) a 3- to 8-membered monocyclic non-aromatic heterocyclic group (e.g., azetidinyl, pyrrolidinyl),
(s) a 3- to 8-membered monocyclic non-aromatic heterocyclyloxy group (e.g., pyrrolidinyloxy) optionally substituted by 1 to 3 oxo groups,
(t) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), or
(u) a 3- to 8-membered monocyclic non-aromatic heterocyclylidenamino group (e.g., 1-oxido-thiolan-1-ylidenamino).

In another embodiment, in the formula ($A^3$-1),
$Q^1$ is preferably $CR^{Q1}$ wherein $R^{Q1}$ is
(a) a hydrogen atom,
(b) a halogen atom (e.g., a fluorine atom, a chlorine atom),
(c) a $C_{1-6}$ alkyl group (e.g., methyl) optionally substituted by 1 to 3 substituents selected from
(i) a halogen atom (e.g., a fluorine atom), and
(ii) a $C_{1-6}$ alkoxy group (e.g., methoxy), or
(d) a $C_{1-6}$ alkoxy group (e.g., methoxy, ethoxy) optionally substituted by 1 to 3 halogen atoms (e.g., a fluorine atom).

In the formula ($A^3$-1),
$Q^2$ is preferably N (optionally oxidized) or $CR^{Q2}$ wherein $R^{Q2}$ is
(a) a hydrogen atom,
(b) a halogen atom (e.g., a fluorine atom), or
(c) a $C_{1-6}$ alkoxy group (e.g., methoxy).

In another embodiment, in the formula ($A^3$-1),
$Q^2$ is preferably $CR^{Q2}$ wherein $R^{Q2}$ is
(a) a hydrogen atom, or
(b) a halogen atom (e.g., a fluorine atom).

In the formula ($A^3$-1),
$Q^3$ is preferably N (optionally oxidized) or $CR^{Q3}$ wherein $R^{Q3}$ is
(a) a hydrogen atom,
(b) a cyano group,
(c) a halogen atom (e.g., a fluorine atom, a chlorine atom),
(d) a carboxy group,
(e) a $C_{1-6}$ alkyl group (e.g., methyl, ethyl) optionally substituted by 1 to 3 substituents selected from
(i) a halogen atom (e.g., a fluorine atom), and
(ii) a hydroxy group,
(f) a $C_{1-6}$ alkoxy group (e.g., methoxy) optionally substituted by 1 to 3 halogen atoms (e.g., a fluorine atom),
(g) a $C_{1-6}$ alkyl-carbonyl group (e.g., acetyl),
(h) a $C_{1-6}$ alkoxy-carbonyl group (e.g., ethoxycarbonyl),
(i) a mono- or di-$C_{1-6}$ alkylamino group (e.g., N-methylamino, N,N-dimethylamino),
(j) a mono- or di-$C_{1-6}$ alkyl-carbamoyl group (e.g., N-methylcarbamoyl, N-ethylcarbamoyl) optionally substituted by 1 to 3 of 3- to 8-membered monocyclic non-aromatic heterocyclic groups (e.g., morpholinyl),
(k) a di-$C_{1-6}$ alkylsulfinylidenamino group (e.g., N-dimethylsulfinylidenamino), or
(l) a 3- to 8-membered monocyclic non-aromatic heterocyclylidenamino group (e.g., 1-oxido-thiolan-1-ylidenamino).

In another embodiment, in the formula ($A^3$-1), $Q^3$ is preferably N (optionally oxidized) or $CR^{Q3}$ wherein $R^{Q3}$ is
(a) a hydrogen atom,
(b) a cyano group,
(c) a halogen atom (e.g., a fluorine atom, a chlorine atom),
(d) a carboxy group,
(e) a $C_{1-6}$ alkyl group (e.g., methyl, ethyl) optionally substituted by 1 to 3 substituents selected from
(i) a halogen atom (e.g., a fluorine atom), and
(ii) a hydroxy group,
(f) a $C_{1-6}$ alkoxy group (e.g., methoxy),
(g) a $C_{1-6}$ alkyl-carbonyl group (e.g., acetyl),
(h) a $C_{1-6}$ alkoxy-carbonyl group (e.g., ethoxycarbonyl),
(i) a mono- or di-$C_{1-6}$ alkylamino group (e.g., N-methylamino, N,N-dimethylamino),
(j) a mono- or di-$C_{1-6}$ alkyl-carbamoyl group (e.g., N-methylcarbamoyl, N-ethylcarbamoyl) optionally substituted by 1 to 3 of 3- to 8-membered monocyclic non-aromatic heterocyclic groups (e.g., morpholinyl),
(k) a di-$C_{1-6}$ alkylsulfinylidenamino group (e.g., N-dimethylsulfinylidenamino), or
(l) a 3- to 8-membered monocyclic non-aromatic heterocyclylidenamino group (e.g., 1-oxido-thiolan-1-ylidenamino).

In another embodiment, in the formula ($A^3$-1),
$Q^3$ is preferably $CR^{Q3}$ wherein $R^{Q3}$ is
(a) a hydrogen atom,
(b) a halogen atom (e.g., a fluorine atom, a chlorine atom),
(c) a $C_{1-6}$ alkyl group (e.g., methyl) optionally substituted by 1 to 3 halogen atoms (e.g., a fluorine atom), or
(d) a $C_{1-6}$ alkoxy group (e.g., methoxy) optionally substituted by 1 to 3 halogen atoms (e.g., a fluorine atom).

In the formula ($A^3$-1),
$Q^4$ is preferably N (optionally oxidized) or $CR^{Q4}$ wherein $R^{Q4}$ is
(a) a hydrogen atom, or
(b) a halogen atom (e.g., a fluorine atom).

In another embodiment, in the formula ($A^3$-1),
$Q^4$ is preferably N (optionally oxidized) or CH.
In another embodiment, in the formula ($A^3$-1),
$Q^4$ is preferably N or $CR^{Q4}$ wherein $R^{Q4}$ is
(a) a hydrogen atom, or
(b) a halogen atom (e.g., a fluorine atom).

In the formula ($A^3$-2),
$R^{N1}$ is preferably a hydrogen atom or a $C_{1-6}$ alkyl group (e.g., methyl),
$Q^3$ is preferably CH, and
$Q^4$ is preferably CH.

In the formula ($A^3$-3),
$R^{N2}$ is preferably a hydrogen atom or a $C_{1-6}$ alkyl group (e.g., methyl),
$Q^3$ is preferably CH, and
$Q^4$ is preferably N or CH.

In the formula ($A^3$-5),
$R^{N4}$ is preferably a hydrogen atom,
$Q^1$ is preferably CH, and
$Q^2$ is preferably CH.

In the formula ($A^3$-6),
$R^{N2}$ is preferably a hydrogen atom or a $C_{1-6}$ alkyl group (e.g., methyl),
$Q^1$ is preferably CH, and
$Q^4$ is preferably CH.

In the formula ($A^3$-9),
$R^{N4}$ is preferably a hydrogen atom or a $C_{1-6}$ alkyl group (e.g., methyl) optionally substituted by 1 to 3 halogen atoms (e.g., a fluorine atom),
$Q^2$ is preferably CH, and
$Q^3$ is preferably CH.

Ring $B^1$ is an optionally further substituted aromatic heterocycle.

The "aromatic heterocycle" of the "optionally further substituted aromatic heterocycle" optionally further has 1 to 5 (preferably 1 to 3) substituents at substitutable position(s), in addition to —V—Z-Ring $B^1$. Examples of the substituent include substituents selected from the above-mentioned Substituent Group A. When the number of the substituents is two or more, the respective substituents may be the same or different.

The "aromatic heterocycle" of the "optionally further substituted aromatic heterocycle" is preferably a 5-membered aromatic heterocycle.

Ring $B^1$ is preferably Ring $B^2$, i.e., an optionally further substituted 5-membered aromatic heterocycle.

The "5-membered aromatic heterocycle" of the "optionally further substituted 5-membered aromatic heterocycle" optionally further has 1 to 5 (preferably 1 to 3) substituents at substitutable position(s), in addition to —O—CH($R^1$)—$CH_2$—Ring $B^2$. Examples of the substituent include substituents selected from the above-mentioned Substituent Group A. When the number of the substituents is two or more, the respective substituents may be the same or different.

The "5-membered aromatic heterocycle" of the "optionally further substituted 5-membered aromatic heterocycle" is preferably a 5-membered nitrogen-containing aromatic heterocycle.

Examples of the 5-membered nitrogen-containing aromatic heterocycle include tetrazole, 1,2,3-triazole, 1,2,4-triazole, pyrazole, imidazole, pyrrole, thiazole, isothiazole, oxazole, isoxazole, 1,2,4-oxadiazole, 1,3,4-oxadiazole, 1,2,4-thiadiazole, 1,3,4-thiadiazole and the like.

Ring $B^2$ is
preferably an optionally further substituted 5-membered nitrogen-containing aromatic heterocycle,
more preferably tetrazole or triazole, each of which is optionally further substituted,
further more preferably tetrazole or triazole,
still more preferably tetrazole or triazole, each of which is bonded at its nitrogen.
even more preferably tetrazole or 1,2,4-triazole, each of which is bonded at its nitrogen,
particularly preferably tetrazol-1-yl or 1,2,4-triazol-1-yl.

V is O, S, S(O), S(O)$_2$ or N($R^V$) wherein $R^V$ is a hydrogen atom or an optionally substituted $C_{1-6}$ alkyl group.

The "$C_{1-6}$ alkyl group" of the "optionally substituted $C_{1-6}$ alkyl group" optionally further has 1 to 5 (preferably 1 to 3) substituents at substitutable position(s). Examples of the substituent include substituents selected from the above-mentioned Substituent Group A. When the number of the substituents is two or more, the respective substituents may be the same or different.

V is preferably O.

Z is an optionally substituted $C_{1-6}$ alkylene group.

The "$C_{1-6}$ alkylene group" of the "optionally substituted $C_{1-6}$ alkylene group" optionally further has 1 to 5 (preferably 1 to 3) substituents at substitutable position(s). Examples of the substituent include substituents selected from the above-mentioned Substituent Group A. When the number of the substituents is two or more, the respective substituents may be the same or different.

Z is preferably an optionally substituted ethylene group, more preferably —CH(R')—$CH_2$— wherein $R^1$ is a $C_{1-6}$ alkyl group.

$R^1$ is preferably methyl.

Z is particularly preferably —CH($CH_3$)—$CH_2$—.

Compound (I) is preferably compound (II), more preferably compound (III).

Compound (I) contains a compound represented by the formulas (I-1) and (I-2):

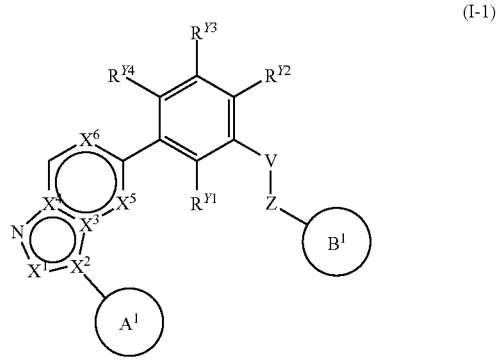

(I-1)

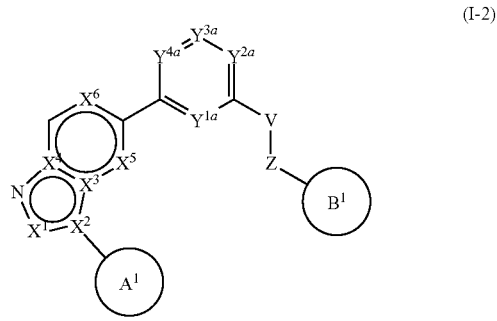

(I-2)

wherein each symbol is as defined above.

Compound (II) contains a compound represented by the formulas (II-1) and (II-2):

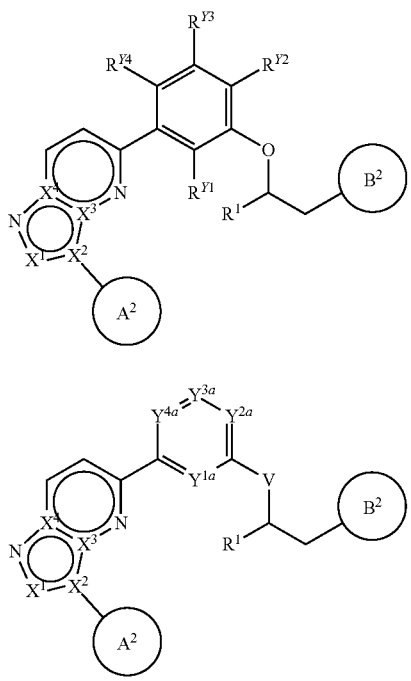

wherein each symbol is as defined above.

Compound (III) contains a compound represented by the formulas (III-1) and (III-2):

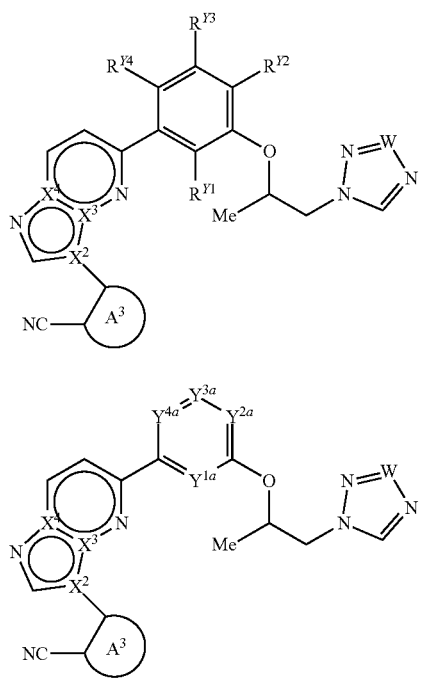

wherein each symbol is as defined above.

Preferable compounds (I)-(III) are as follows.
[Compound A]
Compound (II) wherein
$X^1$ is N or $CR^{X1}$ wherein $R^{X1}$ is a hydrogen atom, a halogen atom (e.g., a fluorine atom) or a $C_{1-6}$ alkyl group (e.g., methyl);
$X^2$, $X^3$ and $X^4$ are each independently C or N, and one of $X^2$, $X^3$ and
$X^4$ is N, and the other two are C;
Ring $A^2$ is
(1) a benzene ring
optionally fused with a 5- to 6-membered monocyclic non-aromatic heterocycle (e.g., dihydrofuran, pyrroline) (i.e., the fused ring is dihydrobenzofuran, isoindoline) optionally substituted by 1 to 3 substituents selected from
  (a) an oxo group, and
  (b) a $C_{1-6}$ alkyl group (e.g., methyl, ethyl) optionally substituted by 1 to 3 $C_{1-6}$ alkoxy groups (e.g., methoxy), and
optionally further substituted by 1 to 5 substituents selected from
  (a) a cyano group,
  (b) a halogen atom (e.g., a fluorine atom, a chlorine atom, a bromine atom),
  (c) a hydroxy group,
  (d) a carboxy group,
  (e) a formyl group,
  (f) an amino group,
  (g) a carbamoyl group,
  (h) a $C_{1-6}$ alkyl group (e.g., methyl, ethyl, isopropyl) optionally substituted by 1 to 3 substituents selected from
    (i) a halogen atom (e.g., a fluorine atom),
    (ii) a hydroxy group,
    (iii) a $C_{1-6}$ alkoxy group (e.g., methoxy),
    (iv) a mono- or di-$C_{1-6}$ alkylamino group (e.g., N,N-dimethylamino), and
    (v) a di-$C_{1-6}$ alkylsulfinylidenamino group (e.g., N-dimethylsulfinylidenamino),
  (i) a $C_{2-6}$ alkenyl group (e.g., vinyl),
  (j) a $C_{2-6}$ alkynyl group (e.g., ethynyl),
  (k) a $C_{1-6}$ alkoxy group (e.g., methoxy, ethoxy, propoxy, isopropoxy, isobutyloxy) optionally substituted by 1 to 3 substituents selected from
    (i) a halogen atom (e.g., a fluorine atom),
    (ii) a cyano group,
    (iii) a carboxy group,
    (iv) a carbamoyl group,
    (v) a $C_{1-6}$ alkoxy group (e.g., methoxy, ethoxy) optionally substituted by 1 to 3 substituents selected from
      (I) a $C_{1-6}$ alkoxy-$C_{1-6}$ alkoxy group (e.g., methoxyethoxy), and
      (II) a mono- or di-$C_{1-6}$ alkylamino group (e.g., N,N-dimethylamino),
    (vi) a mono- or di-$C_{1-6}$ alkyl-carbonylamino group (e.g., N-acetylamino),
    (vii) a N—$C_{1-6}$ alkyl-N—$C_{1-6}$ alkyl-carbonylamino group (e.g., N-methyl-N-acetylamino),
    (viii) a $C_{3-10}$ cycloalkyl group (e.g., cyclopropyl, cyclobutyl), and
    (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from (I) an oxo group, and
(II) a $C_{1-6}$ alkyl group (e.g., methyl),
(l) a $C_{1-6}$ alkyl-carbonyl group (e.g., acetyl),
(m) a $C_{1-6}$ alkoxy-carbonyl group (e.g., methoxycarbonyl, ethoxycarbonyl),
(n) a mono- or di-$C_{1-6}$ alkylamino group (e.g., N-ethylamino) optionally substituted by 1 to 3 $C_{1-6}$ alkoxy groups (e.g., methoxy),
(o) a mono- or di-$C_{1-6}$ alkyl-carbonylamino group (e.g., N-acetylamino, N-propanoylamino) optionally substituted by 1 to 3 $C_{1-6}$ alkoxy groups (e.g., methoxy),
(p) a mono- or di-$C_{1-6}$ alkyl-carbamoyl group (e.g., N-methylcarbamoyl, N,N-dimethylcarbamoyl, N-ethylcarbamoyl, N-propylcarbamoyl, N-butylcarbamoyl, N-isobutylcarbamoyl, N-isopentylcarbamoyl, N-neopentylcarbamoyl) optionally substituted by 1 to 3 substituents selected from
(i) a hydroxy group,
(ii) a $C_{1-6}$ alkoxy group (e.g., methoxy),
(iii) a mono- or di-$C_{1-6}$ alkylamino group (e.g., N,N-dimethylamino, N,N-diethylamino),
(iv) a mono- or di-$C_{1-6}$ alkyl-carbonylamino group (e.g., N-acetylamino),
(v) a mono- or di-$C_{1-6}$ alkyl-carbamoyl group (e.g., N-methylcarbamoyl, N,N-diethylcarbamoyl),
(vi) a $C_{3-10}$ cycloalkyl group (e.g., cyclopropyl, cyclohexyl),
(vii) a $C_{6-14}$ aryl group (e.g., phenyl),
(viii) a 5- or 6-membered monocyclic aromatic heterocyclic group (e.g., pyridyl, imidazolyl, triazolyl), and
(ix) a 3- to 8-membered monocyclic non-aromatic heterocyclic group (e.g., azetidinyl, morpholinyl, pyrrolidinyl, piperidyl, 1,1-dioxidothiomorpholinyl, tetrahydropyranyl) optionally substituted by 1 to 3 substituents selected from
(I) a hydroxy group,
(II) an oxo group, and
(III) a $C_{1-6}$ alkyl group (e.g., methyl),
(q) a di-$C_{1-6}$ alkylsulfinylidenamino group (e.g., N-dimethylsulfinylidenamino),
(r) a $C_{3-10}$ cycloalkyloxy group (e.g., cyclohexyloxy) optionally substituted by 1 to 3 substituents selected from
(i) a 3- to 8-membered monocyclic non-aromatic heterocyclic group (e.g., morpholinyl) optionally substituted by 1 to 3 $C_{1-6}$ alkyl groups (e.g., methyl),
(s) a $C_{3-10}$ cycloalkylsulfonyl-carbamoyl group (e.g., cyclopropylsulfonylcarbamoyl),
(t) a $C_{6-14}$ aryl-carbamoyl group (e.g., phenylcarbamoyl),
(u) a 3- to 8-membered monocyclic non-aromatic heterocyclic group (e.g., morpholinyl, piperazinyl) optionally substituted by 1 to 3 $C_{1-6}$ alkyl-carbonyl groups (e.g., acetyl),
(v) a 3- to 8-membered monocyclic non-aromatic heterocyclyloxy group (e.g., pyrrolidinyloxy) optionally substituted by 1 to 3 oxo groups,
(w) a 3- to 8-membered monocyclic non-aromatic heterocyclylcarbonyl group (e.g., azetidinylcarbonyl, piperidylcarbonyl, morpholinylcarbonyl) optionally substituted by 1 to 3 substituents selected from
(i) a hydroxy group,
(ii) a $C_{1-6}$ alkyl group (e.g., methyl),
(iii) a $C_{1-6}$ alkoxy group (e.g., methoxy),
(iv) a mono- or di-$C_{1-6}$ alkyl-carbonylamino group (e.g., N-acetylamino), and
(v) a 3- to 8-membered monocyclic non-aromatic heterocyclic group (e.g., morpholinyl),
(x) a 9- to 14-membered bicyclic non-aromatic heterocyclylcarbonyl group (e.g., tetrahydroimidazopyrazinylcarbonyl tetrahydrotriazolopyrazinylcarbonyl),
(y) a 5- or 6-membered monocyclic aromatic heterocyclylcarbamoyl group (e.g., pyrazolylcarbamoyl, pyridylcarbamoyl) optionally substituted by 1 to 3 $C_{1-6}$ alkyl groups (e.g., methyl),
(z) a 3- to 8-membered monocyclic non-aromatic heterocyclylcarbamoyl group (e.g., azetidinylcarbamoyl, piperidylcarbamoyl, pyrrolidinylcarbamoyl) optionally substituted by 1 to 3 substituents selected from
(i) an oxo group,
(ii) a $C_{1-6}$ alkyl group (e.g., methyl),
(iii) a $C_{1-6}$ alkyl-carbonyl group (e.g., acetyl), and
(iv) a $C_{7-16}$ aralkyl group (e.g., benzyl), and
(aa) a 3- to 8-membered monocyclic non-aromatic heterocyclylidenamino group (e.g., 1-oxido-thiolan-1-ylidenamino),
(2) a 5- or 6-membered aromatic heterocycle (e.g., pyridine (optionally oxidized), pyrimidine, pyridazine, pyrazine, pyrazole, imidazole, thiophene, thiazole, furan)
optionally fused with a 5- or 6-membered monocyclic aromatic heterocycle (e.g., imidazole) (i.e., the fused ring is imidazopyridine), and
optionally further substituted by 1 to 4 substituents selected from
(a) a cyano group,
(b) a halogen atom (e.g., a fluorine atom, a chlorine atom),
(c) a carboxy group,
(d) an amino group,
(e) a carbamoyl group,
(f) a $C_{1-6}$ alkyl group (e.g., methyl, ethyl, propyl) optionally substituted by 1 to 3 substituents selected from
(i) a halogen atom (e.g., a fluorine atom),
(ii) a cyano group,
(iii) a hydroxy group,
(iv) a carboxy group,
(v) a $C_{1-6}$ alkoxy group (e.g., methoxy),
(vi) a $C_{7-16}$ aralkyloxy-carbonyl group (e.g., benzyloxycarbonyl),
(vii) a mono- or di-$C_{1-6}$ alkyl-carbamoyl group (e.g., N-ethylcarbamoyl, N-propylcarbamoyl) optionally substituted by 1 to 3 substituents selected from
(I) a $C_{1-6}$ alkoxy group (e.g., methoxy), and
(II) a 3- to 8-membered monocyclic non-aromatic heterocyclic group (e.g., morpholinyl), and
(viii) a 3- to 8-membered monocyclic non-aromatic heterocyclic group (e.g., morpholinyl),
(g) a $C_{1-6}$ alkoxy group (e.g., methoxy, ethoxy) optionally substituted by 1 to 3 substituents selected from
(i) a halogen atom (e.g., a fluorine atom),
(ii) a cyano group,
(iii) a $C_{1-6}$ alkoxy group (e.g., methoxy), and
(iv) a 3- to 8-membered monocyclic non-aromatic heterocyclic group (e.g., oxetanyl),
(h) a $C_{3-10}$ cycloalkyl group (e.g., cyclopropyl),
(i) a $C_{1-6}$ alkyl-carbonyl group (e.g., acetyl), (j) a $C_{1-6}$ alkoxy-carbonyl group (e.g., methoxycarbonyl, propoxycarbonyl, tert-butoxycarbonyl) optionally substituted by 1 to 3 $C_{1-6}$ alkoxy groups (e.g., methoxy), (k) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom), (l) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 substituents selected from
  (I) a $C_{1-6}$ alkoxy group (e.g., methoxy), and
  (II) a mono- or di-$C_{1-6}$ alkylamino groups (e.g., N,N-diethylamino), (m) a mono- or di-$C_{1-6}$ alkoxy-carbonylamino group (e.g., N-tert-butoxycarbonylamino, N,N-di-tert-butoxycarbonylamino), and (n) a 3- to 8-membered monocyclic non-aromatic heterocyclic group (e.g., azetidinyl, pyrrolidinyl), or (3) a 5- or 6-membered non-aromatic heterocycle (e.g., dihydropyridine, dihydropyrimidine) optionally further substituted by 1 to 4 substituents selected from
  (a) an oxo group,
  (b) a cyano group,
  (c) a halogen atom (e.g., a fluorine atom, a chlorine atom), and
  (d) a $C_{1-6}$ alkyl group (e.g., methyl, ethyl) optionally substituted by 1 to 3 substituents selected from
    (I) a halogen atom (e.g., a fluorine atom),
    (II) a cyano group, and
    (III) a $C_{1-6}$ alkoxy group (e.g., methoxy, ethoxy) optionally substituted by 1 to 3 halogen atoms (e.g., a fluorine atom);

$Y^1$ is N or CH;

$Y^2$ is N or $CR^{Y2}$ wherein $R^{Y2}$ is a hydrogen atom, a halogen atom (e.g., a fluorine atom, a chlorine atom) or a cyano group;

$Y^3$ is N or $CR^{Y3}$ wherein $R^{Y3}$ is a hydrogen atom or a halogen atom (e.g., a fluorine atom);

$Y^4$ is N or $CR^{Y4}$ wherein $R^{Y4}$ is a hydrogen atom or a halogen atom (e.g., a fluorine atom);

Ring $B^2$ is a 5-membered aromatic heterocycle (preferably tetrazole or triazole (preferably 1,2,4-triazole), each of which is preferably bonded at its nitrogen); and $R^1$ is a $C_{1-6}$ alkyl group (preferably methyl).

[Compound B]

Compound (III) wherein $X^2$, $X^3$ and $X^4$ are each independently C or N, and one of $X^2$, $X^3$ and $X^4$ is N, and the other two are C;

Ring $A^3$ is (1) a benzene ring optionally further substituted by 1 to 5 substituents selected from
  (a) a cyano group,
  (b) a halogen atom (e.g., a fluorine atom, a chlorine atom),
  (c) a hydroxy group,
  (d) a carboxy group,
  (e) an amino group,
  (f) a $C_{1-6}$ alkyl group (e.g., methyl, ethyl) optionally substituted by 1 to 3 substituents selected from
    (i) a halogen atom (e.g., a fluorine atom), and
    (ii) a $C_{1-6}$ alkoxy group (e.g., methoxy),
  (g) a $C_{1-6}$ alkoxy group (e.g., methoxy, ethoxy, propoxy, isopropoxy, isobutyloxy) optionally substituted by 1 to 3 substituents selected from
    (i) a halogen atom (e.g., a fluorine atom),
    (ii) a cyano group,
    (iii) a carboxy group,
    (iv) a carbamoyl group,
    (v) a $C_{1-6}$ alkoxy group (e.g., methoxy, ethoxy) optionally substituted by 1 to 3 substituents selected from
      (I) a $C_{1-6}$ alkoxy-$C_{1-6}$ alkoxy group (e.g., methoxyethoxy), and
      (II) a mono- or di-$C_{1-6}$ alkylamino group (e.g., N,N-dimethylamino),
    (vi) a mono- or di-$C_{1-6}$ alkyl-carbonylamino group (e.g., N-acetylamino),
    (vii) a N—$C_{1-6}$ alkyl-N—$C_{1-6}$ alkyl-carbonylamino group (e.g., N-methyl-N-acetylamino),
    (viii) a $C_{3-10}$ cycloalkyl group (e.g., cyclobutyl), and
    (ix) a 3- to 8-membered monocyclic non-aromatic heterocyclic group (e.g., morpholinyl, azetidinyl, pyrrolidinyl, piperidyl, tetrahydropyranyl) optionally substituted by 1 to 3 substituents selected from
      (I) an oxo group, and
      (II) a $C_{1-6}$ alkyl group (e.g., methyl),
  (h) a $C_{1-6}$ alkyl-carbonyl group (e.g., acetyl),
  (i) a $C_{1-6}$ alkoxy-carbonyl group (e.g., methoxycarbonyl, ethoxycarbonyl),
  (j) a mono- or di-$C_{1-6}$ alkylamino group (e.g., N-ethylamino) optionally substituted by 1 to 3 $C_{1-6}$ alkoxy groups (e.g., methoxy),
  (k) a mono- or di-$C_{1-6}$ alkyl-carbonylamino group (e.g., N-propanoylamino) optionally substituted by 1 to 3 $C_{1-6}$ alkoxy groups (e.g., methoxy),
  (l) a mono- or di-$C_{1-6}$ alkyl-carbamoyl group (e.g., N-methylcarbamoyl, N,N-dimethylcarbamoyl, N-ethylcarbamoyl) optionally substituted by 1 to 3 of 3- to 8-membered monocyclic non-aromatic heterocyclic groups (e.g., morpholinyl),
  (m) a di-$C_{1-6}$ alkylsulfinylidenamino group (e.g., N-dimethylsulfinylidenamino),
  (n) a $C_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl),
  (o) a 3- to 8-membered monocyclic non-aromatic heterocyclyloxy group (e.g., pyrrolidinyloxy) optionally substituted by 1 to 3 oxo groups,
  (p) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), and
  (q) a 3- to 8-membered monocyclic non-aromatic heterocyclylidenamino group (e.g., 1-oxido-thiolan-1-ylidenamino), (2) a 6-membered aromatic heterocycle (e.g., pyridine (optionally oxidized), pyrimidine, pyridazine, pyrazine)

optionally fused with a 5- or 6-membered monocyclic aromatic heterocycle (e.g., imidazole) (i.e., the fused ring is imidazopyridine), and optionally further substituted by 1 to 4 substituents selected from
  (a) a halogen atom (e.g., a fluorine atom, a chlorine atom),
  (b) an amino group,
  (c) a $C_{1-6}$ alkyl group (e.g., methyl, ethyl) optionally substituted by 1 to 3 substituents selected from (i) a halogen atom (e.g., a fluorine atom), and
(ii) a hydroxy group,
(d) a $C_{1-6}$ alkoxy group (e.g., methoxy, ethoxy) optionally substituted by 1 to 3 substituents selected from
  (i) a halogen atom (e.g., a fluorine atom),
  (ii) a $C_{1-6}$ alkoxy group (e.g., methoxy), and
  (iii) a 3- to 8-membered monocyclic non-aromatic heterocyclic group (e.g., oxetanyl),
(e) a $C_{3-10}$ cycloalkyl group (e.g., cyclopropyl),
(f) a $C_{1-6}$ alkyl-carbonyl group (e.g., acetyl),
(g) a mono- or di-$C_{1-6}$ alkylamino group (e.g., N-methylamino, N,N-dimethylamino, N-ethylamino, N-ethyl-N-methylamino) optionally substituted by 1 to 3 halogen atoms (e.g., a fluorine atom),
(h) a mono- or di-$C_{1-6}$ alkoxy-carbonylamino group (e.g., N-tert-butoxycarbonylamino, N,N-di-tert-butoxycarbonylamino), and
(i) a 3- to 8-membered monocyclic non-aromatic heterocyclic group (e.g., azetidinyl, pyrrolidinyl), or
(3) a 6-membered non-aromatic heterocycle (e.g., dihydropyridine, dihydropyrimidine) optionally further substituted by 1 to 4 substituents selected from
  (a) an oxo group, and
  (b) a $C_{1-6}$ alkyl group (e.g., methyl) optionally substituted by 1 to 3 halogen atoms (e.g., a fluorine atom);
$Y^1$ is N or CH;
$Y^2$ is N or $CR^{Y2}$ wherein $R^{Y2}$ is a hydrogen atom or a halogen atom (e.g., a fluorine atom, a chlorine atom);
$Y^3$ is N or $CR^{Y3}$ wherein $R^{Y3}$ is a hydrogen atom or a halogen atom (e.g., a fluorine atom);
$Y^4$ is N or $CR^{Y4}$ wherein $R^{Y4}$ is a hydrogen atom or a halogen atom (e.g., a fluorine atom); and W is N or CH;

[Compound C]

[Compound B] wherein
the partial structure represented by the formula;

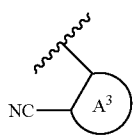

is a partial structure represented by the formula ($A^3$-1), ($A^3$-2), ($A^3$-3), ($A^3$-5), ($A^3$-6) or ($A^3$-9);

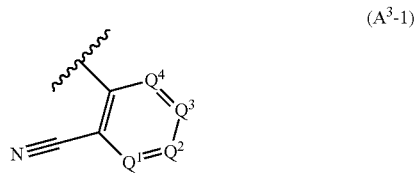

($A^3$-1)

($A^3$-2)

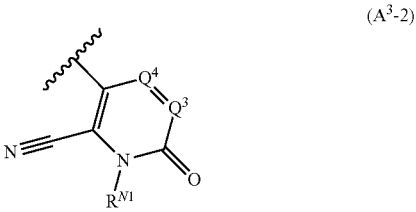

-continued

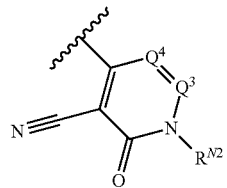

($A^3$-3)

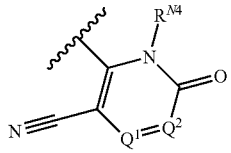

($A^3$-5)

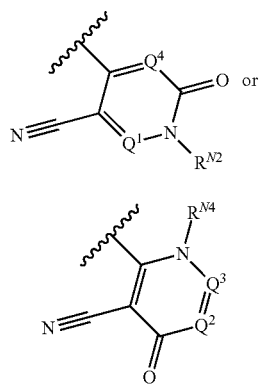

($A^3$-6)

($A^3$-9)

wherein
In the formula ($A^3$-1),
$Q^1$ is N or $CR^{Q1}$ wherein $R^{Q1}$ is
  (a) a hydrogen atom,
  (b) a cyano group,
  (c) a halogen atom (e.g., a fluorine atom, a chlorine atom),
  (d) a hydroxy group,
  (e) a carboxy group,
  (f) an amino group,
  (g) a $C_{1-6}$ alkyl group (e.g., methyl, ethyl) optionally substituted by 1 to 3 substituents selected from
    (i) a halogen atom (e.g., a fluorine atom), and
    (ii) a $C_{1-6}$ alkoxy group (e.g., methoxy),
  (h) a $C_{1-6}$ alkoxy group (e.g., methoxy, ethoxy, propoxy, isopropoxy, isobutyloxy) optionally substituted by 1 to 3 substituents selected from
    (i) a halogen atom (e.g., a fluorine atom),
    (ii) a cyano group,
    (iii) a carboxy group,
    (iv) a carbamoyl group,
    (v) a $C_{1-6}$ alkoxy group (e.g., methoxy, ethoxy) optionally substituted by 1 to 3 substituents selected from
      (I) a $C_{1-6}$ alkoxy-$C_{1-6}$ alkoxy group (e.g., methoxyethoxy), and
      (II) a mono- or di-$C_{1-6}$ alkylamino group (e.g., N,N-dimethylamino),
    (vi) a mono- or di-$C_{1-6}$ alkyl-carbonylamino group (e.g., N-acetylamino),
    (vii) a N—$C_{1-6}$ alkyl-N—$C_{1-6}$ alkyl-carbonylamino group (e.g., N-methyl-N-acetylamino),
    (viii) a $C_{3-10}$ cycloalkyl group (e.g., cyclobutyl), and (ix) a 3- to 8-membered monocyclic non-aromatic heterocyclic group (e.g., morpholinyl, azetidinyl, pyrrolidinyl, piperidyl, tetrahydropyranyl, oxetanyl) optionally substituted by 1 to 3 substituents selected from
  (I) an oxo group, and
  (II) a $C_{1-6}$ alkyl group (e.g., methyl),
(i) a $C_{1-6}$ alkyl-carbonyl group (e.g., acetyl),
(j) a $C_{1-6}$ alkoxy-carbonyl group (e.g., methoxycarbonyl),
(k) a mono- or di-$C_{1-6}$ alkylamino group (e.g., N-methylamino, N,N-dimethylamino, N-ethylamino, N-ethyl-N-methylamino) optionally substituted by 1 to 3 substituents selected from
  (i) a halogen atom (e.g., a fluorine atom), and
  (ii) a $C_{1-6}$ alkoxy group (e.g., methoxy),
(l) a mono- or di-$C_{1-6}$ alkyl-carbonylamino group (e.g., N-propanoylamino) optionally substituted by 1 to 3 $C_{1-6}$ alkoxy groups (e.g., methoxy),
(m) a mono- or di-$C_{1-6}$ alkoxy-carbonylamino group (e.g., N-tert-butoxycarbonylamino, N,N-di-tert-butoxycarbonylamino),
(n) a mono- or di-$C_{1-6}$ alkyl-carbamoyl group (e.g., N,N-dimethylcarbamoyl),
(o) a di-$C_{1-6}$ alkylsulfinylidenamino group (e.g., N-dimethylsulfinylidenamino),
(p) a $C_{3-10}$ cycloalkyl group (e.g., cyclopropyl),
(q) a $C_{3-10}$ cycloalkyloxy group (e.g., cyclohexyloxy) optionally substituted by 1 to 3 of 3- to 8-membered monocyclic non-aromatic heterocyclic groups (e.g., morpholinyl) optionally substituted by 1 to 3 $C_{1-6}$ alkyl groups (e.g., methyl),
(r) a 3- to 8-membered monocyclic non-aromatic heterocyclic group (e.g., azetidinyl, pyrrolidinyl),
(s) a 3- to 8-membered monocyclic non-aromatic heterocyclyloxy group (e.g., pyrrolidinyloxy) optionally substituted by 1 to 3 oxo groups,
(t) a 3- to 8-membered monocyclic non-aromatic heterocyclylcarbonyl group (e.g., azetidinylcarbonyl) optionally substituted by 1 to 3 $C_{1-6}$ alkoxy groups (e.g., methoxy), or
(u) a 3- to 8-membered monocyclic non-aromatic heterocyclylidenamino group (e.g., 1-oxido-thiolan-1-ylidenamino);
$Q^2$ is N (optionally oxidized) or $CR^{Q2}$ wherein $R^{Q2}$ is
  (a) a hydrogen atom,
  (b) a halogen atom (e.g., a fluorine atom), or
  (c) a $C_{1-6}$ alkoxy group (e.g., methoxy);
$Q^3$ is N (optionally oxidized) or $CR^{Q3}$ wherein $R^{Q3}$ is
  (a) a hydrogen atom,
  (b) a cyano group,
  (c) a halogen atom (e.g., a fluorine atom, a chlorine atom),
  (d) a carboxy group,
  (e) a $C_{1-6}$ alkyl group (e.g., methyl, ethyl) optionally substituted by 1 to 3 substituents selected from
    (i) a halogen atom (e.g., a fluorine atom), and
    (ii) a hydroxy group,
  (f) a $C_{1-6}$ alkoxy group (e.g., methoxy) optionally substituted by 1 to 3 halogen atoms (e.g., a fluorine atom),
  (g) a $C_{1-6}$ alkyl-carbonyl group (e.g., acetyl),
  (h) a $C_{1-6}$ alkoxy-carbonyl group (e.g., ethoxycarbonyl),
  (i) a mono- or di-$C_{1-6}$ alkylamino group (e.g., N-methylamino, N,N-dimethylamino),
  (j) a mono- or di-$C_{1-6}$ alkyl-carbamoyl group (e.g., N-methylcarbamoyl, N-ethylcarbamoyl) optionally substituted by 1 to 3 of 3- to 8-membered monocyclic non-aromatic heterocyclic groups (e.g., morpholinyl),
  (k) a di-$C_{1-6}$ alkylsulfinylidenamino group (e.g., N-dimethylsulfinylidenamino), or
  (l) a 3- to 8-membered monocyclic non-aromatic heterocyclylidenamino group (e.g., 1-oxido-thiolan-1-ylidenamino); and
$Q^4$ is N (optionally oxidized) or $CR^{Q4}$ wherein $R^{Q4}$ is
  (a) a hydrogen atom, or
  (b) a halogen atom (e.g., a fluorine atom);
In the formula ($A^3$-2),
$R^{N1}$ is a hydrogen atom or a $C_{1-6}$ alkyl group (e.g., methyl),
$Q^3$ is CH, and
$Q^4$ is CH;
In the formula ($A^3$-3),
$R^{N2}$ is a hydrogen atom or a $C_{1-6}$ alkyl group (e.g., methyl),
$Q^3$ is CH, and
$Q^4$ is N or CH;
In the formula ($A^3$-5),
$R^{N4}$ is a hydrogen atom,
$Q^1$ is CH, and
$Q^2$ is CH;
In the formula ($A^3$-6),
$R^{N2}$ is a hydrogen atom or a $C_{1-6}$ alkyl group (e.g., methyl),
$Q^1$ is CH, and
$Q^4$ is CH; and
In the formula ($A^3$-9),
$R^{N4}$ is a hydrogen atom or a $C_{1-6}$ alkyl group (e.g., methyl) optionally substituted by 1 to 3 halogen atoms (e.g., a fluorine atom),
$Q^2$ is CH, and
$Q^3$ is CH.

[Compound D]

2-[6-(4-fluoro-3-{[(2S)-1-(1H-tetrazol-1-yl)propan-2-yl]oxy}phenyl)imidazo[1,2-b]pyridazin-3-yl]benzonitrile, or a pharmaceutically acceptable salt (Example 121);

2-[6-(4-fluoro-3-{[(2S)-1-(1H-tetrazol-1-yl)propan-2-yl]oxy}phenyl)imidazo[1,2-b]pyridazin-3-yl]pyridine-3-carbonitrile, or a pharmaceutically acceptable salt (Example 247);

2-[6-(3-{[(2S)-1-(1H-tetrazol-1-yl)propan-2-yl]oxy}phenyl)imidazo[1,2-b]pyridazin-3-yl]pyridine-3-carbonitrile, or a pharmaceutically acceptable salt (Example 271);

2-[5-(3-{[(2S)-1-(1H-tetrazol-1-yl)propan-2-yl]oxy}phenyl)-3H-imidazo[4,5-b]pyridin-3-yl]pyridine-3-carbonitrile, or a pharmaceutically acceptable salt (Example 284);

4-fluoro-2-[6-(5-{[(2S)-1-(1H-tetrazol-1-yl)propan-2-yl]oxy}pyridin-3-yl)imidazo[1,2-b]pyridazin-3-yl]benzonitrile, or a pharmaceutically acceptable salt (Example 288);

4-methoxy-2-[6-(3-{[(2S)-1-(1H-tetrazol-1-yl)propan-2-yl]oxy}phenyl)imidazo[1,2-b]pyridazin-3-yl]pyridine-3-carbonitrile, or a pharmaceutically acceptable salt (Example 300);

2-[6-(4-fluoro-3-{[(2S)-1-(1H-tetrazol-1-yl)propan-2-yl]oxy}phenyl)imidazo[1,2-b]pyridazin-3-yl]-4-methoxypyridine-3-carbonitrile, or a pharmaceutically acceptable salt (Example 321);

4-fluoro-2-[5-(6-{[(2S)-1-(1H-tetrazol-1-yl)propan-2-yl]oxy}pyridin-2-yl)-3H-imidazo[4,5-b]pyridin-3-yl]benzonitrile,
or a pharmaceutically acceptable salt (Example 345);
4-fluoro-2-methoxy-6-[6-(6-{[(2S)-1-(1H-tetrazol-1-yl)propan-2-yl]oxy}pyrazin-2-yl)imidazo[1,2-b]pyridazin-3-yl]benzonitrile, or a pharmaceutically acceptable salt (Example 392);
4-fluoro-2-methoxy-6-[5-(6-{[(2S)-1-(1H-tetrazol-1-yl)propan-2-yl]oxy}pyridin-2-yl)-3H-imidazo[4,5-b]pyridin-3-yl]benzonitrile, or a pharmaceutically acceptable salt (Example 393); and
4-fluoro-2-methoxy-6-[6-(6-{[(2S)-1-(1H-tetrazol-1-yl)propan-2-yl]oxy}pyridin-2-yl)imidazo[1,2-b]pyridazin-3-yl]benzonitrile, or a pharmaceutically acceptable salt (Example 410).

Specific examples of compound (I) include the compounds of Examples 1 to 486.

When compound (I) is a salt, examples of the salt include metal salts, ammonium salts, salts with organic base, salts with inorganic acid, salts with organic acid, and salts with basic or acidic amino acid. Preferable examples of the metal salt include alkali metal salts such as sodium salts, potassium salts and the like; alkali earth metal salts such as calcium salts, magnesium salts, barium salts and the like; and aluminum salts. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acid include salts with arginine, lysine, ornithine and the like. Preferable examples of the salt with acidic amino acid include salts with aspartic acid, glutamic acid and the like. Among them, a pharmaceutically acceptable salt is preferable. For example, when a compound has an acidic functional group, examples of the salt include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples of the salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

When compound (I) contains isomers such as tautomers, optical isomers, stereoisomers, position isomers and rotational isomers, any of isomers or mixture are also encompassed in the compound of the present invention. Further, when compound (I) contains an optical isomer, the optical isomer separated from the racemate is encompassed in compound (I).

Compound (I) can be obtained in the crystal form. Either single crystalline form or crystalline mixture can be encompassed in compound (I).

Compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to co-crystallization method known per se.

Compound (I) may be a solvate (e.g., a hydrate) or a non-solvate and both are encompassed in compound (I).

Compounds labeled with or substituted by isotopes (e.g., $^2H$, $^3H$, $^{11}C$, $^{14}C$, $^{18}F$, $^{35}S$, $^{125}I$, etc.) are also encompassed in compound (I). The compound labeled with or substituted by isotopes can be used as, for example, a tracer used for Positron Emission Tomography (PET) (PET tracer), and are expected to be useful in the field of medical diagnosis and the like.

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature—300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a ligand, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol, benzyl alcohol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like; esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like; metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of a functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond or a nitro group or a benzyloxycarbonyl group is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ), oxone and the like.

When radical reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When nucleophilic substitution reaction is carried out in each step, examples of the base to be used include organic lithiums (e.g., lithium bis(trimehylsilyl)amide), metal alkoxides (e.g., potassium tert-butoxide), alkali metal hydrides (e.g., is sodium hydride), inorganic bases, organic bases and the like.

When aromatic nucleophilic substitution reaction is carried out in each step, a combination of a nucleophile (e.g., a hydroxy, an amine, imidazole etc.) and a base (e.g., an organic base etc.), or a combination of a nucleophile and an acid (e.g., an organic acid etc.) is used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, borane-2-methylpyridine complex, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, a combination of an azodicarboxylate (e.g., diethyl azodicarboxylate (DEAD), diisopropyl azodicarboxylate (DIAD) etc.) and triphenylphosphine, or a phosphorane reagent (e.g., cyanomethylenetributylphosphorane (Tsunoda reagent) is used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), tris(dibenzylideneacetone)dipalladium (0), [1,1'-bis(diphenylphosphino)ferrocene]dichloropalladium(II), bis(di-tert-butyl(4-dimethylaminophenyl)phosphine)dichloropalladium(II), (tri-tert-butylphosphine)palladium(0) and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide, copper(II) diacetate and the like; platinum compounds and the like. In addition, a base can be added to the reaction system, and examples thereof include organic bases (e.g., 1,8-diazabicyclo[5.4.0]undec-7-ene, N,N-diisopropylethylamine), inorganic bases and the like. Moreover, a ligand can be added to the reaction system, and examples thereof include organic amines such as N,N'-dimethylethylenediamine, N,N'-dimethyl-cyclohexane-1,2-diamine, 2,2-bipyridyl and the like; organophosphorus compounds such as triphenylphosphine, tri-tert-butylphosphine, 1,1'-bis(diphenylphosphino)ferrocene, di-tert-butyl(4-dimethylaminophenyl)phosphine, cataCXium® A (di(1-adamantyl)-n-butylphosphine) and the like; and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When cyanation reaction is carried out in each step, examples of the metal catalyst to be used include palladium compounds such as chloro(2-dicyclohexylphosphino-2',4',6'-tri-i-propyl-1,1'-biphenyl) (2'-amino-1,1'-biphenyl-2-yl) palladium(II), palladium(II) acetate, tetrakis(triphenylphosphine)palladium(0), dichlorobis(triphenylphosphine)palladium(II), tris(dibenzylideneacetone)dipalladium(0), 1,1'-bis(diphenylphosphino)ferrocene palladium(II) chloride, (tri-tert-butylphosphine)palladium(0) and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide, copper(II) diacetate and the like; platinum compounds and the like. Examples of the cyano compound to be used include potassium hexacyanoferrate(II) trihydrate, copper(I) cyanide, zinc cyanide, potassium cyanide, sodium cyanide and the like. In addition, a base can be added to the reaction system, and examples thereof include organic bases, inorganic bases and the like. Moreover, a ligand can be added to the reaction system, and examples thereof include organic amines such as N,N'-dimethylethylenediamine, N,N'-dimethyl-cyclohexane-1,2-diamine, 2,2-bipyridyl and the like; organophosphorus compounds such as 2-dicyclohexylphosphino-2',4',6'-triisopropylbiphenyl, triphenylphosphine, tri-tert-butylphosphine, tricyclohexylphosphine, BINAP (2,2'-bis(diphenylphosphino)-1,1-binaphthyl) and the like; and the like.

When nitration reaction is carried out in each step, examples of the nitrating agent to be used include mineral acids such as mixed acid, nitric acid and the like; nitrates such as potassium nitrate, sodium nitrate, tetramethylammonium nitrate, silver nitrate and the like.

When O-alkylation reaction or N-alkylation reaction is carried out in each step, a combination of an alkylating agent (e.g., an alkyl halide, an alkyl sulfonate ester etc.) and a base (e.g., an organic base, an inorganic base, alkali metal hydrides etc.) is used as a reagent.

Compound (I) of the present invention can be produced according to the methods explained below.

$A^1$, $B^1$, V, $X^1$-$X^6$, $Y^1$-$Y^4$ and Z in the following schemes are as defined above.

Compound (I) wherein $X^2$ is C, one of $X^3$ and $X^4$ is N, and the other is C can be produced from compound (2) according to the method shown in Scheme 1-1.

[Scheme 1-1]

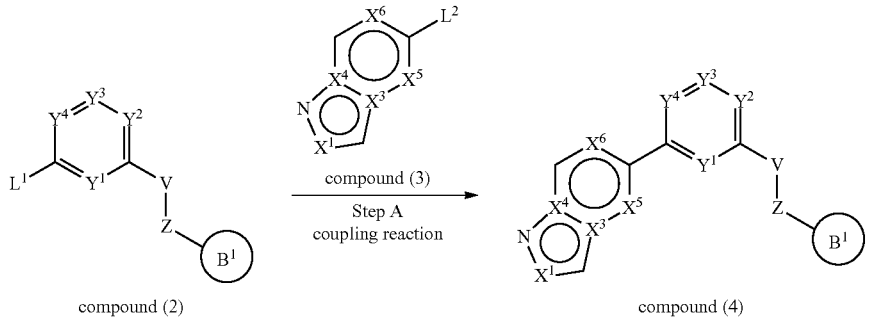

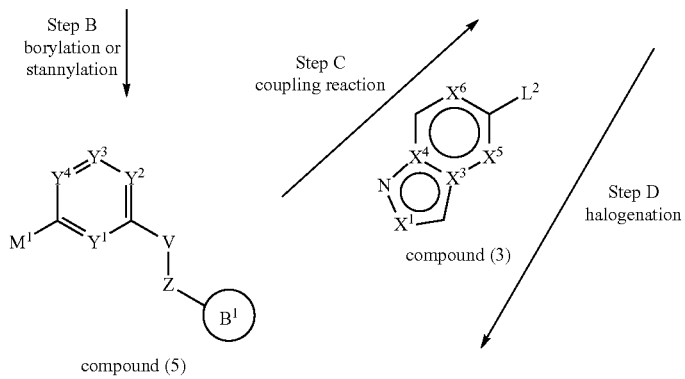

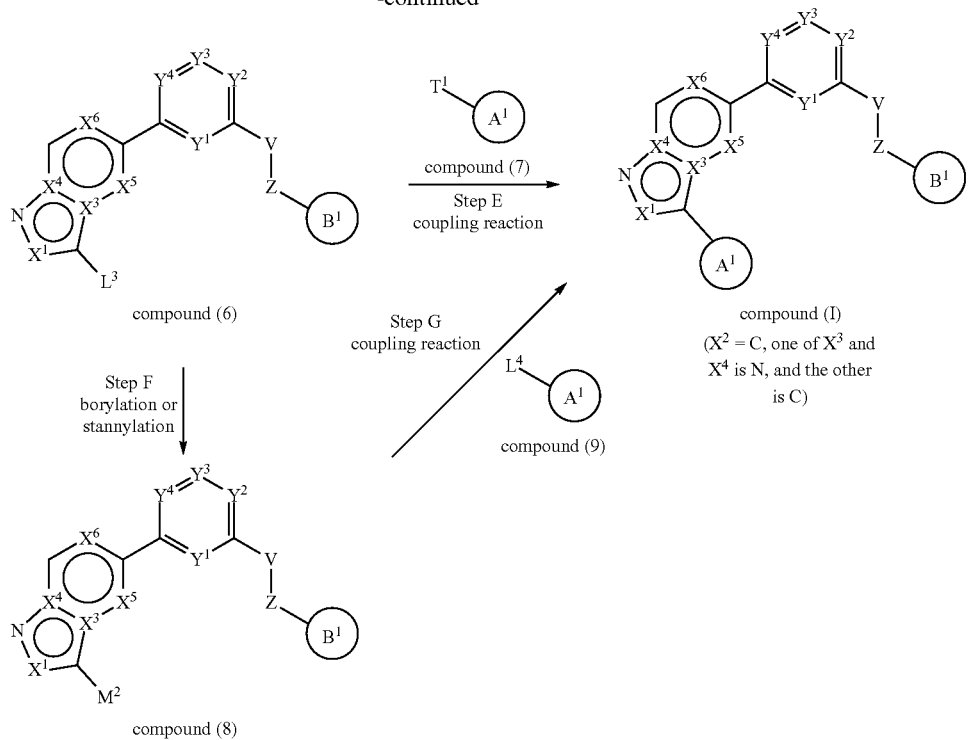

wherein $L^1$-$L^4$ are each independently a leaving group, $M^1$ and $M^2$ are each independently a metal group, $T^1$ is a leaving group or metal group, and the other symbols are as defined above.

Examples of the "leaving group" for $L^1$-$L^4$ and $T^1$ include a halogen atom (e.g., a fluorine atom, a chlorine atom, a bromine atom, an iodine atom etc.), an optionally halogenated $C_{1-6}$ alkylsulfonyloxy group (e.g., methanesulfonyloxy, ethanesulfonyloxy, trifluoromethanesulfonyloxy etc.), an optionally substituted $C_{6-14}$ arylsulfonyloxy group [e.g., a $C_{6-14}$ arylsulfonyloxy group optionally having 1 to 3 substituents selected from a $C_{1-6}$ alkyl group (e.g., methyl, etc.)], an optionally halogenated $C_{1-6}$ alkylsulfide group, an optionally substituted $C_{6-14}$ arylsulfide group, a $C_{1-6}$ alkoxy group (e.g., methoxy, etc.), a nitro group, m-nitrobenzenesulfonyloxy and naphthylsulfonyloxy and the like.

Examples of the "metal group" for $M^1$, $M^2$ and $T^1$ include a boronic acid group (—B(OH)$_2$), or a boronate ester group (—B(OR)$_2$; R is a $C_{1-6}$ alkyl group) or a cyclic group thereof (e.g., a 4,4,5,5-tetramethyl-1,3,2-dioxaborolan-2-yl, etc.), or trialkyl stannyl group and the like.

Compounds (2), (3), (7) and (9) may be a commercially available product, or can be produced according to a method known per se.

Compound (I) wherein $X^1$ is CH, $X^2$ and $X^4$ are C, $X^6$ is CH, and $X^3$ and $X^5$ are N, can also be produced from compound (9) according to the method shown in Scheme 1-2.

[Scheme 1-2]

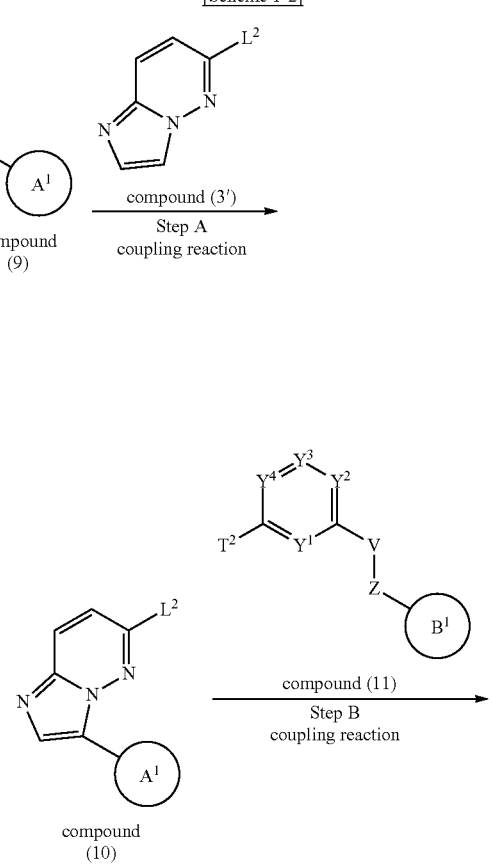

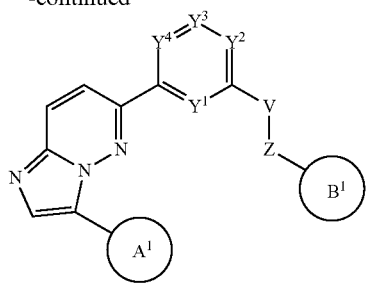

compound (I)
($X^1$ is CH, $X^2$ and $X^4$ are C,
$X^6$ is CH, and $X^3$ and $X^5$ are N)

wherein $T^2$ is a leaving group or a metal group, and the other symbols are as defined above.

Examples of the "leaving group" for $T^2$ include those exemplified as the "leaving group" for $T^1$.

Examples of the "metal group" for $T^2$ include those exemplified as the "metal group" for $T^1$.

Compounds (3'), (9) and (11) may be a commercially available product, or can be produced according to a method known per se.

Compound (I) wherein $X^1$ is $CR^{X1a}$, $X^3$ and $X^4$ are C, and $X^6$ is $CR^{X6}$, and $X^2$ and $X^5$ are N, can be produced from compound (12) according to the method shown in Scheme 1-3.

[Scheme 1-3]

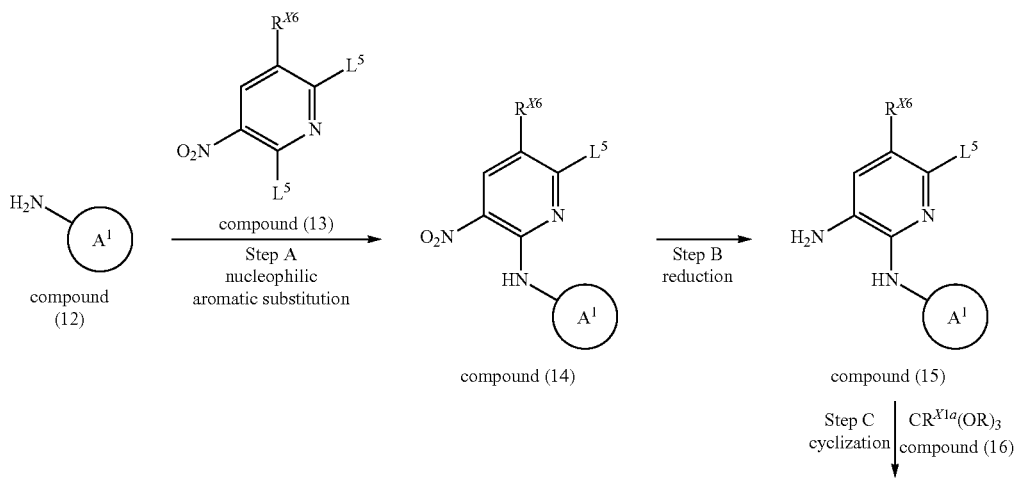

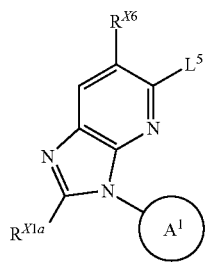

compound (17)

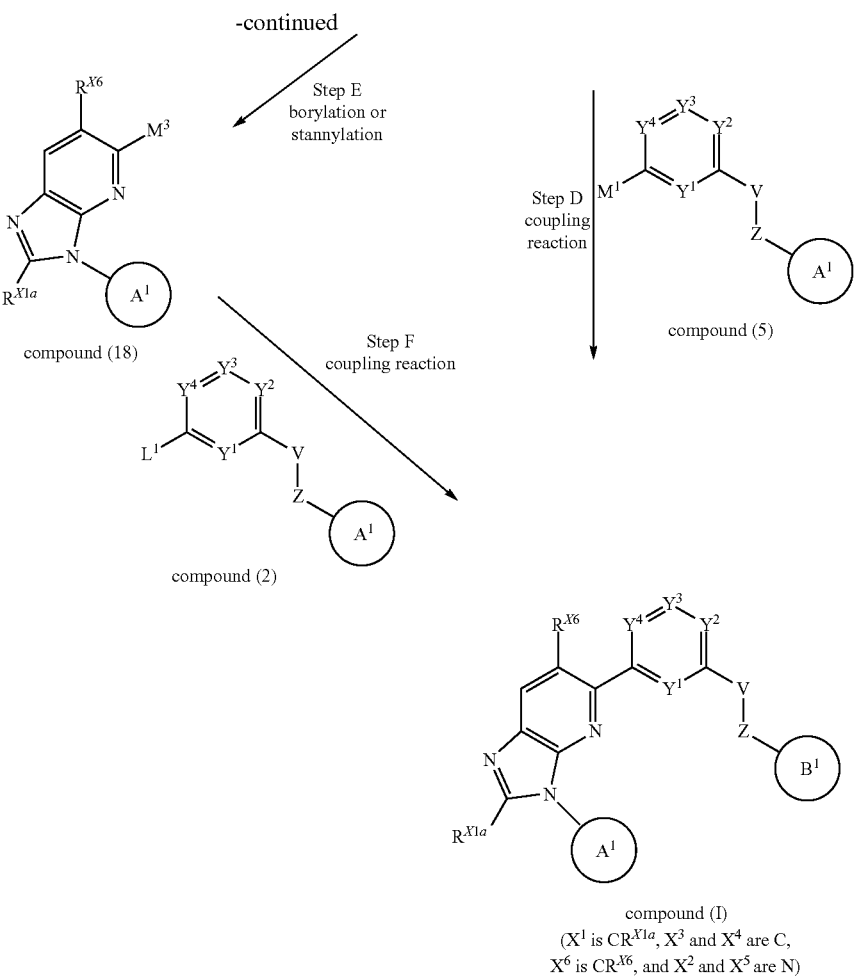

compound (I)
($X^1$ is $CR^{X1a}$, $X^3$ and $X^4$ are C,
$X^6$ is $CR^{X6}$, and $X^2$ and $X^5$ are N)

wherein $L^5$ is a leaving group, $M^3$ is a metal group, $R^{X1a}$ is a hydrogen atom or a $C_{1-2}$ alkyl group, R is a $C_{1-2}$ alkyl group, and the other symbols are as defined above.

Examples of the "leaving group" for $L^5$ include those exemplified as the "leaving group" for $L^1$-$L^4$.

Examples of the "metal group" for $M^3$ include those exemplified as the "metal group" for $M^1$ and $M^2$.

Compounds (2), (12), (13) and (16) may be a commercially available product, or can be produced according to a method known per se. Compound (5) can be produced according to Scheme 1-1.

Compound (2'), which is compound (2) wherein —V—Z-Ring $B^1$ is —O—CH($R^1$)—CH$_2$—Ring $B^2$, can be produced from compound (19) according to the method shown in Scheme 2-1 or a similar method known per se (WO 2018/183112 A1 and WO 2020/068854 A1).

[Scheme 2-1]

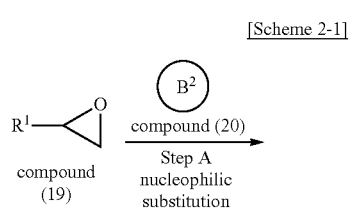

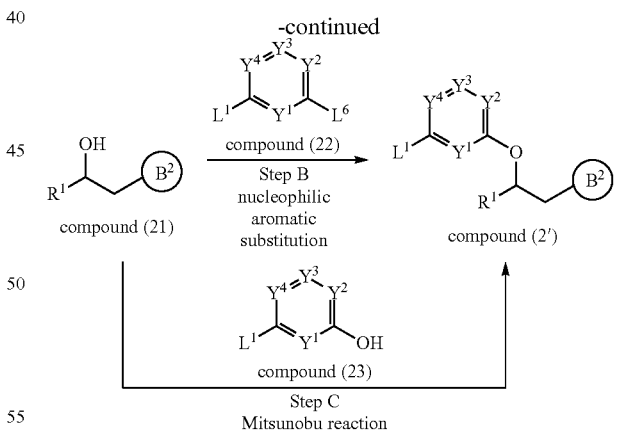

wherein $L^6$ is a leaving group, and the other symbols are as defined above.

Examples of the "leaving group" for $L^6$ include those exemplified as the "leaving group" for $L^1$-$L^4$.

Compounds (19), (20), (22) and (23) may be a commercially available product, or can be produced according to a method known per se.

The starting compound and/or production intermediate for compound (I) may form a salt. While the salt is not particularly limited as long as the reaction can be performed, examples thereof include those similar to the salts optionally formed by compound (I) and the like, and the like.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending on the kind of a substituent, and each stereoisomer and a mixture thereof are encompassed in the present invention.

Compound (I) may be a hydrate or a non-hydrate.

When desired, compound (I) can be synthesized by performing deprotection reaction, acylation reaction, alkylation reaction, hydrogenation reaction, oxidation reaction, reduction reaction, reaction of carbon chain extension, halogenation reaction, substituent exchange reaction, coupling reaction, reductive amination, nucleophilic addition reaction by a carbo anion, Grignard reagent and deoxofluorination reaction singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form can be isolated according to a conventional optical resolution.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

When compound (I) contains a configurational isomer, a diastereomer, a conformer and the like, each can be isolated according to the above-mentioned separation and purification methods, if desired. In addition, when compound (I) is racemic, S-form and R-form can be isolated according to a conventional optical resolution.

When compound (I) contains a stereoisomer, each isomer and a mixture thereof are encompassed in the present invention.

Compound (I) may be a prodrug. A prodrug of compound (I) means a compound which is converted to compound (I) with a reaction due to an enzyme, a gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

Compound (I) or a prodrug thereof (to be abbreviated as the compound of the present invention) is superior in vivo kinetics (e.g., plasma drug half-life, intracerebral transferability, metabolic stability), shows low toxicity (e.g., more superior as a medicament in terms of liver/hepatotoxicity, acute toxicity, chronic toxicity, genetic toxicity, reproductive toxicity, cardiotoxicity, cytotoxicity, drug interaction, carcinogenicity etc.; especially liver/hepatotoxicity). The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

Since the compound of the present invention has a superior CaMKII inhibitory action, it is expected to be useful for the prophylaxis or treatment of, for example, cardiac diseases (cardiac hypertrophy, acute heart failure and chronic heart failure including congestive heart failure, cardiomyopathy, angina, myocarditis, atrial/ventricular arrhythmia, tachycardia, myocardial infarction, etc.), myocardial ischemia, venous insufficiency, post-myocardial infarction transition to heart failure, hypertension, cor pulmonale, arteriosclerosis including atherosclerosis (aneurysm, coronary arterial sclerosis, cerebral arterial sclerosis, peripheral arterial sclerosis, etc.), vascular thickening, vascular thickening/occlusion and organ damages after intervention (percutaneous coronary angioplasty, stent placement, coronary angioscopy, intravascular ultrasound, coronary thrombolytic therapy, etc.), vascular reocclusion/restenosis after bypass surgery, cardiac hypofunction after artificial heart lung surgery, respiratory diseases (cold syndrome, pneumonia, asthma, pulmonary hypertension, pulmonary thrombus/pulmonary embolism, etc.), bone disorders (nonmetabolic bone disorders such as bone fracture, refracture, bone malformation/spondylosis deformans, osteosarcoma, myeloma, dysostosis and scoliosis, bone defect, osteoporosis, osteomalacia, rickets, osteitis fibrosis, renal osteodystrophy, Paget's disease of bone, myelitis with rigidity, chronic rheumatoid arthritis, gonarthrosis and articular tissue destruction in similar disorders thereof, etc.), inflammatory diseases (diabetic complication such as retinopathy, nephropathy, nerve damage, macroangiopathy etc.; arthritis such as chronic rheumatoid arthritis, osteoarthritis, rheumatoid myelitis, periostitis etc.; inflammation after surgery/trauma; reduction of swelling; pharyngitis; cystitis; pneumonia; atopic dermatitis; inflammatory enteric diseases such as Crohn's disease, ulcerative is colitis etc.; meningitis; inflammatory eye diseases; inflammatory pulmonary diseases such as pneumonia, silicosis, pulmonary sarcoidosis, pulmonary tuberculosis etc, and the like), allergic diseases (allergic rhinitis, conjunctivitis, gastrointestinal allergy, pollen allergy, anaphylaxis, etc.), drug dependence, neurodegenerative diseases (Alzheimer's disease, Parkinson's disease, amyotrophic lateral sclerosis, AIDS encephalopathy, etc.), central nervous system damage (disorders such as cerebral hemorrhage and cerebral infarction and aftereffects and complications thereof, head injury, spinal damage, cerebral edema, sensory dysfunction, sensory abnormality, autonomic dysfunction, abnormal autonomic function, multiple sclerosis etc.), dementia, disturbed memory, disturbed consciousness, amnesia, anxiety symptoms, nervous symptoms, unpleasant condition, mental disorders (depression, epilepsy, alcohol dependency, etc.), ischemic peripheral circulatory disorder, deep-vein thrombosis, occlusive peripheral circulatory disorder, arteriosclerosis obliterans (ASO), occlusive thromboangiitis, diabetes (type 1 diabetes, type 2 diabetes, pregnancy diabetes etc.), diabetic complications (nerve damage, nephropathy, retinopathy, cataract, macroangiopathy, osteopenia, diabetic hyperosmolar diabetic coma, infectious diseases, diabetic gangrene, xerostomia, deterioration in hearing, cerebrovascular damage, peripheral circulatory disorder, etc.), urinary incontinence, metabolic/nutritional disorders (obesity, hyperlipidemia, hypercholesterolemia, diabetes, impaired glucose tolerance, hyperuricemia, hyperkalemia, hypernatremia etc.), metabolic syndrome, vesceral obesity syndrome, male or female sexual dysfunction and the like, and for the prophylaxis or treatment of dysgeusia, smell disturbance, abnormal circadian rhythm of blood pressure, cerebrovascular damage (asymptomatic cerebrovascular damage, transient cerebral ischemia attack, stroke, cerebrovascular dementia, hypertensive encephalopathy, cerebral infarction, etc.), cerebral edema, cerebral circulatory disturbance, recurrence and aftereffects of cerebrovascular damages (neurological symptoms, mental symptoms, subjective symptoms, impairment of activities of daily living, etc.), kidney diseases (nephritis, glomerulonephritis, glomerulosclerosis, renal failure, thrombotic microangiopathy, diabetic nephropathy, nephrotic syndrome, hypertensive nephrosclerosis, complications of dialysis, organ damage including nephropathy by irradiation, etc.), erythrocytosis/hypertension/organ damage/vascular thickening after transplantation, rejection after transplantation, ocular disorders (glaucoma, ocular hypertension, etc.), thrombosis, multiple organ failure, endothelial dysfunction, hypertensive tinnitus, other circulatory diseases (ischemic cerebral circulatory disturbance, Raynaud's disease, Buerger's disease, etc.), chronic occlusive pulmonary diseases, interstitial pneumonia, carinii pneumonia, connective tissue disorders (e.g., systemic erythematosus, scleroderma, polyarteritis, etc.), liver disorders (hepatitis and cirrhosis including chronic types, etc.), portal hypertension, digestive disorders (gastritis, gastric ulcer, gastric cancer, disorder after gastric surgery, poor digestion, esophageal ulcer, pancreatitis, colon polyp, cholelithiasis, hemorrhoidal problem, esophageal and gastric variceal rupture, etc.), hematological/hematopoietic disorders (erythrocytosis, vascular purpura, autoimmune hemolytic anemia, disseminated intravascular coagulation syndrome, multiple myelosis, etc.), solid tumor, tumors (malignant melanoma, malignant lymphoma, digestive organs (e.g., stomach, intestine, etc.) cancers, etc.), cancers and cachexia associated therewith, cancer metastases, endocrine disorders (Addison's disease, Cushing's syndrome, pheochromocytoma, primary aldosteronism, etc.), Creutzfeldt-Jakob disease, urological/male genital diseases (cystitis, prostatic enlargement, prostate cancer, sexually transmitted diseases, etc.), gynecological disorders (menopausal disorders, pregnancy toxemia, endometriosis, uterine fibroid, ovarian diseases, mammary gland diseases, sexually transmitted diseases, etc.), diseases caused by environmental/occupational factor (e.g., radiation damage, damage from ultraviolet/infrared/laser beam, altitude sickness etc.), infectious diseases (viral infectious diseases of, for example, cytomegalovirus, influenza virus and herpesvirus, rickettsial infectious diseases, bacterial infectious diseases, etc.), toxemia (septicemia, septic shock, endotoxic shock, gram-negative septicemia, toxin shock syndrome, etc.), ear nose throat diseases (Ménière's disease, tinnitus, dysgeusia, vertigo, balance disorder, deglutition disorder etc.), cutaneous diseases (keloid, hemangioma, psoriasis, etc.), dialysis hypotension, myasthenia gravis, systemic diseases such as chronic fatigue syndrome, and the like, particularly cardiac diseases (particularly catecholaminergic polymorphic ventricular tachycardia, postoperative atrial fibrillation, heart failure, fatal arrhythmia) and the like, in animals, particularly mammals (e.g., humans, monkeys, cats, pigs, horses, bovines, mice, rats, guinea pigs, dogs, rabbits etc.).

Herein, the concept of prophylaxis of cardiac diseases include treatment of prognosis of myocardial infarction, angina attack, cardiac bypass surgery, thrombolytic therapy, coronary revascularization and the like, and the concept of treatment of cardiac diseases include suppress of progress or severity of heart failure (including both contractile failure HFrEF, and heart failure HFpEF with maintained ejection fraction), and maintenance of cardiac function when performing non-drug therapies (e.g., an implantable defibrillator, resection of cardiac sympathetic nerve, catheter ablation, cardiac pacemaker, intra aortic balloon pumping, auxiliary artificial heart, Batista operation, cell transplantation, gene therapy, heart transplantation and the like) for severe heart failure/arrhythmia, and the like. When the compound of the present invention is applied to prophylaxis or treatment of heart failure, improvement of heart contractility or atonicity is expected to be achieved by short-time administration, without side effects such as pressure decrease, tachycardia, reduced renal blood flow and the like, regardless of differences in causative diseases such as ischemic cardiac disease, cardiomyopathy, hypertension and the like and symptoms such as contractile failure, diastolic failure and the like. Moreover, long-term improvement of prognosis (survival rate, readmission rate, cardiac event rate etc.) is expected to be achieved, in addition to short-term improvement of cardiac function. When the compound of the present invention is applied to prophylaxis or treatment of arrhythmia, improvement or remission of the symptom is expected to be achieved, regardless of differences in etiology and atrial/ventricular. In addition, long-term improvement of prognosis (survival rate, readmission rate, cardiac event rate etc.) is expected to be achieved.

While the dose of the compound of the present invention varies depending on the administration route, symptom and the like, when, for example, the compound is orally administered to a patient with cardiac disease (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like. Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

When the compound of the present invention is applied to each of the above-mentioned diseases, it can be used in appropriate combination with a pharmaceutical agent (hereinafter to be abbreviated as a concomitant drug) or a treatment method generally employed for such diseases. For heart failure, for example, it can be used concurrently with angiotensin converting enzyme (ACE) inhibitors (e.g., alacepril, captopril, cilazapril, delapril, enalapril, lisinopril, temocapril, trandolapril, quinapril, imidapril, benazepril, perendopril and the like), angiotensin II receptor antagonists (e.g., losartan, candesartan cillexetil, valsartan, termisartan, irbesartan, forasartan and the like), angiotensin II receptor antagonist/NEP inhibitor combination agent (entresto), β receptor antagonists (e.g., propranolol, nadolol, timolol, nipradilol, bunitorolol, indenolol, penbutolol, carteolol, carvedilol, pindolol, acebutolol, atenolol, bisoprolol, metoprolol, labetalol, amosulalol, arotinolol and the like), Ca antagonists (e.g., manidipine, nicardipine, nilvadipine, nisoldipine, nitrendipine, benidipine, amlodipine, aranidipine and the like), diuretics (e.g., thiazide diuretics such as benzylhydrochlorothiazide, cyclopentiazide, ethiazide, hydrochlorothiazide, hydroflumethiazide, methyclothiazide, penfluthiazide, polythiazide, trichlormethiazide and the like; loop diuretics such as chlorthalidone, clofenamide, indapamide, mefruside, meticrane, sotolazone, tribamide, quinetazone, metolazone, furosemide, mefruside and the like; potassium retention diuretics such as spironolactone, triamterene and the like; and the like), digitalis preparations (e.g., digitoxin, digoxin, methyldigoxin, lanatoside C, proscillaridin and the like), ANP or BNP preparations, Ca sensitizers (e.g., pimobendan and the like), anticoagulants (e.g., warfarin, sodium citrate, activated protein C, tissue factor pathway inhibitor, antithrombin III, dalteparin sodium, aragatroban, gabexate, sodium ozagrel, ethyl icosapentate, beraprost sodium, alprostadil, pentoxifyline, tisokinase, streptokinase and the like), antiarrhythmic drugs (e.g., sodium channel blockers such as quinidine, procainamide, disopyramide, ajmaline, cibenzoline, lidocain, diphenylhydantoin, mexiletine, propafenone, flecainide, pilsicainide, phenytoin and the like; potassium channel blockers such as amiodarone and the like; calcium channel blockers such as verapamil, diltiazem and the like; and the like), PDE inhibitors (e.g., amrinone, milrinone, olprinone hydrochloride and the like), therapeutic drugs for diabetes (e.g., sulfonylureas such as tolbutamide, chlorpropamide, glyclopyramide, acetohexamide, tolazamide, glibenclamide, glybuzole and the like; biguanides such as metformin hydrochloride, buformin hydrochloride and the like; a-glucosidase inhibitors such as voglibose, acarbose and the like, insulin sensitizers such as pioglitazone, troglitazone and the like; SGLT2 inhibitors such as ipragliflozin, dapagliflozin, ruseogurifurojin, tofogliflozin, canagliflozin, empagliflozin and the like; insulin, glucagon; therapeutic drugs for diabetic complications such as epalrestat and the like; and the like), anti-obesity drugs and the like, and is also applicable when an implantable artificial heart, an implantable defibrillator, a ventricular pacing, Batista operation, heart transplantation or cell transplantation is performed. In addition, for arrhythmia, for example, it can be used concurrently with other antiarrhythmic drugs (e.g., sodium channel blockers such as flecainide, quinidine, procainamide, disopyramide, ajmaline, cibenzoline, lidocain, diphenylhydantoin, mexiletine, propafenone, pilsicainide, phenytoin and the like; potassium channel blockers such as amiodarone and the like; calcium channel blockers such as verapamil, diltiazem and the like, and the like) and β receptor antagonists, non-drug therapies (e.g., an implantable defibrillator, resection of cardiac sympathetic nerve, catheter ablation, cardiac pacemaker and the like). In addition, after acute myocardial infarction or during myocardial infarction prognosis, for example, the compound can be used in combination with antithrombotics (e.g., anticoagulants such as heparin sodium, heparin calcium, warfarin and the like; thrombolytic agents such as urokinase and the like; anti-platelet drugs such as aspirin, sulfinpyrazone (anturan), dipyridamole (persantin), ticropidine (panaldine), cilostazol (pletal), clopidogrel and the like; and the like), angiotensin converting enzyme inhibitors, angiotensin II receptor antagonists, β receptor antagonists, therapeutic drugs for diabetes, therapeutic drugs for hyperlipidemia (e.g., HMG-CoA reductase inhibitors such as pravastatine, fluvastatine, cerivastatine, atorvastatine and the like; fibrate drugs such as sinfibrate, clofibrate aluminum, clinofibrate, fenofibrate and the like; and the like), coronary vessel reconstructive surgery such as PTCA, CABG and the like; and the like. Furthermore, in chronic rheumatoid arthritis, for example, the compound can be used in combination with non-steroidal antiinflammatory agents (e.g., acetaminophen, phenacetin, ethenzamide, sulpyrine, antipyrine, migrenine, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesilate, ulinastatine, colchicine, probenecid, sulfinpyrazone, benzbromarone, allopurinol, sodium aurothiomalate, sodium hyaluronate, sodium salicylate, morphine hydrochloride, salicylic acid, atropine, scopolamine, morphine, pethidine, levorphanol, ketoprofen, naproxen, oxymorphone or a salt thereof and the like), immunomodulators or immunosuppressants (e.g., methotrexate, cyclosporine, tacrolimus, gusperimus, azathioprine, antilymphocyte serum, dried sulfonated immunoglobulin, erythropoietin, colony stimulating factor, interleukin, interferon and the like), steroids (e.g., dexamethasone, hexestrol, methimazole, betamethasone, triamcinolone, triamcinoloneacetonide, fluocinonide, fluocinoloneacetonide, prednisolone, methylprednisolone, cortisone acetate, hydrocortisone, fluorometholone, beclometasone dipropionate, estriol and the like), p38 MAP kinase inhibitors, anti-TNF-α drugs (e.g., etanercept, infliximab, D2E7, CDP-571, PASS TNF-α, soluble TNF-α receptor, TNF-α binding protein, anti-TNF-α antibody and the like), cyclooxygenase inhibitors (e.g., salicylic acid derivatives such as celecoxib, rofecoxib, aspirin and the like, MK-663, valdecoxib, SC-57666, tiracoxib, S-2474, diclofenac, indomethacin, loxoprofen and the like) and the like.

Moreover, it is possible to use the compound of the present invention in combination with biological products (e.g.: antibody, vaccine preparation and the like) when applying to the above-mentioned respective diseases, and it is also possible to apply the compound in combination with a gene therapy and the like as a combination therapy. As antibody and vaccine preparation, for example, vaccine preparation to angiotensin II, vaccine preparation to CETP, CETP antibody, TNF α antibody, antibody to other cytokine, amiloid β vaccine preparation, type 1 diabetes vaccine (DIAPEP-277 of Peptor Ltd. and the like), anti-HIV antibody, HIV vaccine preparation and the like, antibody and vaccine preparation to cytokine, renin-angiotensin enzyme and products thereof, antibody and vaccine preparation to enzyme and protein involved in blood lipid metabolism, antibody and vaccine preparation to enzyme and protein involved in blood coagulation-fibrinolytic system, antibody and vaccine preparation to protein involved in glucose metabolism and insulin resistance and the like can be mentioned. In addition, a combined use with biological products involved in growth factors such as GH, IGF and the like is possible. As a gene therapy, for example, a treatment method using a gene relating to cytokine, renin-angiotensin enzyme and products thereof, G protein, G protein-coupled receptor and phosphorylation enzyme thereof, a therapeutic method using a DNA decoy such as NFκB decoy and the like, a therapeutic method using antisense, a therapeutic method using a gene relating to enzyme and protein involved in blood lipid metabolism (e.g., gene relating to metabolism, excretion and absorption of cholesterol or triglyceride or HDL-cholesterol or blood phospholipid, and the like), a therapeutic method using a gene relating to enzyme and protein (e.g., growth factors such as HGF, VEGF and the like, and the like) involved in angiogenetic therapy aiming at obstruction of peripheral vessel and the like, a therapeutic method using a gene relating protein involved in glucose metabolism and insulin resistance, antisense to cytokine such as TNF-α and the like, and the like can be mentioned. In addition, it is possible to use the compound in combination with various organ regeneration methods such as heart regeneration, kidney regeneration, pancreas regeneration, blood vessel regeneration and the like, cell transplantation therapy using bone marrow cells (bone marrow mononuclear cell, bone marrow mesenchymal stem cell and the like), and artificial organs (artificial blood vessels and cardiac muscle cell sheet) using tissue engineering.

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination agent of the present invention exhibits low toxicity. For example, the compound of the present invention or (and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent of the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, an appropriate amount of conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

Unless particularly specified, the elution in column chromatography in Example was performed under observation by TLC (Thin Layer Chromatography). For TLC observation, 60$F_{254}$ manufactured by Merck was used as a TLC plate, and the solvent used as an elution solvent for column chromatography was used as a developing solvent. For detection, a UV detector was adopted. In silica gel column chromatography, NH means use of aminopropylsilane-bonded silica gel, and Diol means use of 3-(2,3-dihydroxypropoxy)propylsilane-bonded silica gel. In preparative HPLC (high performance liquid chromatography), $C_{18}$ means use of octadecyl-bonded silica gel. The ratios indicated for elution solvents are volume mixing ratios, unless otherwise specified.

For $^1$H NMR analysis, ACD/SpecManager (trade name) software and the like were used. Peaks of a hydroxy group, an amino group and the like, which having very mild protons, may not be described.

MS was measured by LC/MS. As ionization method, ESI method or APCI method was used. The data indicates actual measured value (found). Generally, molecular ion peaks are observed, and may be observed as a fragment ion. In the case of a salt, a molecular ion peak or fragment ion peak of free form is generally observed.

The unit of sample concentration (c) for optical rotation ($[α]_D$) is g/100 mL.

Elemental analysis value (Anal.) was described as calculated value (Calcd) and actual measured value (Found).

The peak by powder X-RAY diffraction in Example means the peak measured using Cu Kα-ray as a source by Ultima IV (Rigaku Corporation, Japan) at room temperature. The measurement conditions are as follows.

Electric pressure/Electric current: 40 kV/50 mA
Scan speed: 6 degree/min
Scan range of 2 Theta: 2-35 degree The crystallinity by powder X-RAY diffraction in Example was calculated by Hermans method.

In Examples, the following abbreviations are used.
mp: melting point
MS: mass spectrum
M: mol concentration
N: normality
$CDCl_3$: deuterochloroform
DMSO-$d_6$: deuterodimethyl sulfoxide
$CD_3OD$: deuteromethanol
$^1$H NMR: proton nuclear magnetic resonance
LC/MS: liquid chromatograph mass spectrometer
TLC: thin-layer chromatography
ESI: electrospray ionization, Electron Spray Ionization
APCI: atmospheric pressure chemical ionization, atmospheric pressure chemical ionization
AcOH: acetic acid
Boc: tert-butoxycarbonyl
(Boc)$_2$O: di-tert-butyl dicarbonate
(Bpin)$_2$: bis(pinacolato)diboron
brs: broad singlet
n-BuOH: normal butanol
n-BuLi: normal butyllithium
tBuXPhos: 2-di-tert-butylphosphino-2',4',6'-triisopropylbiphenyl
cataCXium® A: di(1-adamantyl)-n-butylphosphine
Cu(OAc)$_2$: copper(II) acetate
d: doublet
dd: double doublet
ddd: double double doublet
dt: double triplet
DCM: dichloromethane
DEAD: diethyl azodicarboxylate
Deoxo-Fluor®: bis(2-methoxyethyl)aminosulfur trifluoride
DIAD: diisopropyl azodicarboxylate
DIPEA: N,N-diisopropylethylamine
DMA: N,N-dimethylacetamide
DMAP: 4-dimethylaminopyridine
DMF: N,N-dimethylformamide
DME: 1,2-dimethoxyethane
DMSO: dimethyl sulfoxide
Et$_2$O: diethyl ether
EtOAc: ethyl acetate
EtOH: ethanol
FA: formic acid
HOBt-H$_2$O: 1-Hydroxybenzotriazole monohydrate
IPE: diisopropyl ether
KOAc: potassium acetate
m: multiplet
mCPBA: 3-chlorobenzene-1-carboperoxoic acid
MeOH: methanol
MsCl: methanesulfonyl chloride
NaOMe: sodium methoxide
NBS: N-bromosuccinimide
NMP: N-methylpyrrolidone
Pd(OAc)$_2$: palladium(II) acetate
Pd(amphos)Cl$_2$: bis(di-tert-butyl(4-dimethylaminophenyl)phosphine)dichloropalladium(II)
Pd($^t$Bu$_3$P)$_2$: bis(tri-tert-butylphosphine)palladium(0)
Pd$_2$(dba)$_3$: tris(dibenzylideneacetone)dipalladium(0)
Pd(dppf)Cl$_2$: [1,1'-bis(diphenylphosphino)ferrocene]dichloropalladium(II)
Pd(PPh$_3$)$_4$: tetrakis(triphenylphosphine)palladium(0)
Pd(PPh$_3$)$_2$Cl$_2$: bis(triphenylphosphine)palladium(II) dichloride
PE: petroleum ether
PPh$_3$: triphenylphosphine q: quartet
s: singlet
SEMCl: 2-(Chloromethoxy)ethyltrimethylsilane
t: triplet
TBAF: tetrabutylammonium fluoride
TBSCl: tert-butyldimethylchlorosilane
TEA: triethylamine
TFA: trifluoroacetic acid
TFE: 2,2,2-trifluoroethanol
THF: tetrahydrofuran
TMSCl: chlorotrimethylsilane
TsCl: p-toluenesulfonyl chloride
TsOH-H$_2$O: p-toluenesulfonic acid monohydrate
WSC—HCl: 1-(3-dimethylaminopropyl)-3-ethylcarbodiimide hydrochloride Example 1

3-[5-(4-cyano-3-{[(2S)-1-(1H-tetrazol-1-yl)propan-2-yl]oxy}phenyl)pyrazolo[1,5-a]pyrimidin-3-yl]-N-[2-(diethylamino)ethyl]benzamide A) methyl (2S)-2-(5-bromo-2-cyanophenoxy)propanoate To a mixture of 4-bromo-2-hydroxybenzonitrile (14.5 g), methyl (2R)-2-hydroxypropanoate (15.3 g), PPh$_3$ (57.6 g) and THF (150 mL) was added 2.2M DEAD toluene solution (120 mL) at 0° C. The mixture was stirred under nitrogen atmosphere at room temperature overnight. The mixture was diluted with water at room temperature and extracted with EtOAc. The organic layer was separated, washed with water and brine, dried over MgSO$_4$ and concentrated under reduced pressure. The residue was purified by silica gel column chromatography (EtOAc/hexane) to give the titled compound (20.0 g).
$^1$H NMR (300 MHz, DMSO-d$_6$) δ 7.72 (d, J=8.3 Hz, 1H), 7.47 (d, J=1.6 Hz, 1H), 7.35 (dd, J=8.3, 1.7 Hz, 1H), 5.40 (q, J=6.8 Hz, 1H), 3.71 (s, 3H), 1.57 (d, J=6.8 Hz, 3H).

B) 4-bromo-2-(((2S)-1-hydroxypropan-2-yl)oxy)benzonitrile

To a mixture of methyl (2S)-2-(5-bromo-2-cyanophenoxy)propanoate (72.0 g) in MeOH (200 mL) and THF (100 mL) was added NaBH$_4$ (4.76 g) at 0° C. The mixture was stirred under nitrogen atmosphere at room temperature for 10 hr. The mixture was quenched with saturated aqueous NH$_4$Cl solution at 0° C. and concentrated under reduced pressure. The residue was extracted with EtOAc. The organic layer was separated, washed with water and brine, dried over MgSO$_4$ and concentrated under reduced pressure. The residue was purified by silica gel column chromatography (EtOAc/hexane) to give the titled compound (65.0 g).
$^1$H NMR (300 MHz, DMSO-d$_6$) δ 7.66 (d, J=8.3 Hz, 1H), 7.60 (S, 1H), 7.28 (d, J=8.3 Hz, 1H), 4.97 (t, J=5.5 Hz, 1H), 4.65-4.78 (m, 1H), 3.54 (t, J=5.4 Hz, 2H), 1.24 (d, J=6.1 Hz, 3H).

C) (2S)-2-(5-bromo-2-cyanophenoxy)propyl methanesulfonate

To a solution of 4-bromo-2-(((2S)-1-hydroxypropan-2-yl)oxy)benzonitrile (21.0 g) and TEA (23 mL) in THF (100 mL) was added MsCl (8.9 mL) at 0° C. The mixture was stirred under nitrogen atmosphere at room temperature for 1 hr. The mixture was quenched with water at room temperature and extracted with EtOAc. The organic layer was separated, washed with water and brine, dried over MgSO$_4$ and concentrated under reduced pressure. The residue was filtered through an NH silica gel pad and concentrated under reduced pressure to give the titled compound (26.0 g).
$^1$H NMR (300 MHz, DMSO-d$_6$) δ 7.70 (d, J=8.3 Hz, 1H), 7.66 (d, J=1.6 Hz, 1H), 7.34 (dd, J=8.3, 1.7 Hz, 1H), 5.07 (td, J=6.2, 3.0 Hz, 1H), 4.42-4.48 (m, 1H), 4.31-4.39 (m, 1H), 3.22 (s, 3H), 1.33 (d, J=6.3 Hz 3H); m/z 335.2 [M+H]$^+$.

D) 4-bromo-2-(((2S)-1-(1H-tetrazol-1-yl)propan-2-yl)oxy)benzonitrile

To a mixture of (2S)-2-(5-bromo-2-cyanophenoxy)propyl methanesulfonate (25.0 g), 1H-tetrazole (10.5 g) and DMF (100 mL) was added K$_2$CO$_3$ (20.7 g) at room temperature and the mixture was stirred at 80° C. overnight. The mixture was diluted with water at room temperature and extracted with EtOAc. The organic layer was separated, washed with water and brine, dried over MgSO$_4$ and concentrated under reduced pressure. The residue was purified by silica gel column chromatography (EtOAc/hexane) to give the titled compound (10.3 g).
$^1$H NMR (300 MHz, CDCl$_3$) δ 8.88-9.02 (m, 1H), 7.42 (d, J=8.2 Hz, 1H), 7.21 (dd, J=8.3, 1.7 Hz, 1H), 7.01 (d, J=1.6 Hz, 1H), 4.79-4.89 (m, 2H), 4.64-4.77 (m, 1H), 1.44-1.51 (m, 3H); MS m/z 308.2 [M+H]$^+$.

E) 4-(4,4,5,5-tetramethyl-1,3,2-dioxaborolan-2-yl)-2-(((2S)-1-(1H-tetrazol-1-yl)propan-2-yl)oxy)benzonitrile To a mixture of 4-bromo-2-{[(2S)-1-(1H-tetrazol-1-yl)propan-2-yl]oxy}benzonitrile (5.00 g), (Bpin)$_2$ (4.52 g), KOAc (7.93 g) and DMF (50 mL) was added Pd(dppf)Cl$_2$—CH$_2$Cl$_2$ (594 mg). After being stirred under nitrogen atmosphere at 100° C. for 4 hr, the mixture was poured into water and extracted with EtOAc. The organic layer was separated, washed with brine, dried over MgSO$_4$ and concentrated under reduced pressure. The residue was purified by silica gel column chromatography (EtOAc/hexane) to give the titled compound (3.30 g).
MS m/z 356.2 [M+H]$^+$.

F) 4-{pyrazolo[1,5-a]pyrimidin-5-yl}-2-{[(2S)-1-(1H-tetrazol-1-yl)propan-2-yl]oxy}benzonitrile To a solution of 5-chloropyrazolo[1,5-a]pyrimidine (120 mg), 4-(4,4,5,5-tetramethyl-1,3,2-dioxaborolan-2-yl)-2-{[(2S)-1-(1H-tetrazol-1-yl)propan-2-yl]oxy}benzonitrile (666 mg) and Cs$_2$CO$_3$ (508 mg) in THF (10 mL) and water (2.0 mL) was added Pd($^t$Bu$_3$P)$_2$ (39.9 mg) and the mixture was stirred under nitrogen atmosphere at 70° C. for 10 hr. The mixture was quenched with water at room temperature and extracted with EtOAc. The organic layer was separated, washed with water and brine, dried over MgSO$_4$ and concentrated under reduced pressure. The residue was purified by silica gel column chromatography (NH, EtOAc/hexane) to give the titled compound (80.0 mg).
$^1$H NMR (300 MHz, DMSO-d$_6$) δ 9.38 (s, 1H), 9.31 (d, J=7.4 Hz, 1H), 8.31 (s, 1H), 7.85-7.97 (m, 3H), 7.80 (d, J=7.2 Hz, 1H), 6.85 (s, 1H), 5.36-5.48 (m, 1H), 4.84-5.01 (m, 2H), 1.39 (d, J=6.1 Hz, 3H); MS m/z 347.2 [M+H]$^+$.

G) 4-{3-bromopyrazolo[1,5-a]pyrimidin-5-yl}-2-{[(2S)-1-(1H-tetrazol-1-yl)propan-2-yl]oxy}benzonitrile To a mixture of 4-{pyrazolo[1,5-a]pyrimidin-5-yl}-2-{[(2S)-1-(1H-tetrazol-1-yl)propan-2-yl]oxy}benzonitrile (180 mg) in DMF (5.0 mL) was added NBS (101 mg) at 0° C. The mixture was stirred under nitrogen atmosphere at room temperature for 10 hr. The mixture was quenched with saturated aqueous NaHCO$_3$ solution at 0° C. and extracted with EtOAc. The organic layer was separated, washed with water and brine, dried over MgSO$_4$ and concentrated under reduced pressure to give the crude titled compound. The crude product was used for the next step without further purification.

MS m/z 425.0 [M+H]$^+$.

H) methyl 3-[5-(4-cyano-3-{[(2S)-1-(1H-tetrazol-1-yl)propan-2-yl]oxy}phenyl)pyrazolo[1,5-a]pyrimidin-3-yl]benzoate To a mixture of 4-{3-bromopyrazolo[1,5-a]pyrimidin-5-yl}-2-{[(2S)-1-(1H-tetrazol-1-yl)propan-2-yl]oxy}benzonitrile (220 mg) and [3-(methoxycarbonyl)phenyl]boronic acid (111 mg) in THF (20 mL) and water (4.0 mL) were added Cs$_2$CO$_3$ (252 mg) and Pd($^t$Bu$_3$P)$_2$ (26.4 mg) and the mixture was stirred under nitrogen atmosphere at 80° C. for 14 hr. The mixture was quenched with water at room temperature and extracted with EtOAc. The organic layer was separated, washed with water and brine, dried over MgSO$_4$ and concentrated under reduced pressure. The residue was purified by silica gel column chromatography (NH, EtOAc/hexane) to give the titled compound (160 mg).

$^1$H NMR (300 MHz, DMSO-d$_6$) δ 9.36-9.40 (m, 2H), 9.10 (s, 1H), 8.96 (s, 1H), 8.43 (d, J=8.3 Hz, 1H), 8.05-8.14 (m, 2H), 7.84-8.02 (m, 3H), 7.60-7.70 (m, 1H), 5.45-5.59 (m, 1H), 4.87-5.07 (m, 2H), 3.93 (s, 3H), 1.44 (d, J=5.8 Hz, 3H); MS m/z 481.2 [M+H]$^+$.

I) 3-[5-(4-cyano-3-{[(2S)-1-(1H-tetrazol-1-yl)propan-2-yl]oxy}phenyl)pyrazolo[1,5-a]pyrimidin-3-yl]benzoic acid To a mixture of methyl 3-[5-(4-cyano-3-{[(2S)-1-(1H-tetrazol-1-yl)propan-2-yl]oxy}phenyl)pyrazolo[1,5-a]pyrimidin-3-yl]benzoate (150 mg) in MeOH (10 mL) and THF (10 mL) was added 2M aqueous NaOH solution (0.16 mL). The mixture was stirred under nitrogen atmosphere at 50° C. for 10 hr. The mixture was acidified with 6M aqueous HCl solution (pH 2-3). The precipitate was collected by filtration and dried under reduced pressure to give the crude titled compound. The crude product was used for the next step without further purification.

MS m/z 467.2 [M+H]$^+$.

J) 3-[5-(4-cyano-3-{[(2S)-1-(1H-tetrazol-1-yl)propan-2-yl]oxy}phenyl)pyrazolo[1,5-a]pyrimidin-3-yl]-N-[2-(diethylamino)ethyl]benzamide To a mixture of 3-[5-(4-cyano-3-{[(2S)-1-(1H-tetrazol-1-yl)propan-2-yl]oxy}phenyl)pyrazolo[1,5-a]pyrimidin-3-yl]benzoic acid (145 mg), WSC—HCl (178 mg) and HOBt-H$_2$O (125 mg) in DMF (5.0 mL) were added (2-aminoethyl)diethylamine (72.2 mg) and TEA (0.13 mL). The mixture was stirred under nitrogen atmosphere for 16 hr. The mixture was quenched with water at room temperature and extracted with EtOAc. The organic layer was separated, washed with water and brine, dried over MgSO$_4$ and concentrated under reduced pressure. The residue was purified by silica gel column chromatography (NH, EtOAc/hexane), and then preparative HPLC (water/CH$_3$CN containing 0.1% TFA). The desired fraction was azeotroped with toluene under reduced pressure. The residue was dissolved in MeOH (5.0 mL) and Amberlyst® A21 was added to the mixture. The mixture was stirred at room temperature for 15 min and then the insoluble material was removed by filtration. The filtrate was concentrated under reduced pressure to give the titled compound (15.0 mg) as a yellow solid.

$^1$H NMR (300 MHz, DMSO-d$_6$) δ 9.34-9.40 (m, 2H), 8.91 (s, 1H), 8.87 (s, 1H), 8.46-8.53 (m, 1H), 8.35 (d, J=7.0 Hz, 1H), 8.15 (s, 1H), 8.03-8.08 (m, 1H), 7.87-7.98 (m, 2H), 7.74 (d, J=7.3 Hz, 1H), 7.55-7.62 (m, 1H), 5.52-5.65 (m, 1H), 4.87-5.06 (m, 2H), 3.33-3.46 (m, 4H), 2.52-2.67 (m, 4H), 1.43 (d, J=5.8 Hz, 3H), 0.98 (t, J=5.8 Hz, 6H); MS m/z 565.4 [M+H]$^+$.

Example 57

1-[(2S)-2-{2-fluoro-5-[2-methyl-3-(thiophen-2-yl)pyrazolo[1,5-a]pyrimidin-5-yl]phenoxy}propyl]-1H-tetrazole

A) methyl (2S)-2-(5-bromo-2-fluorophenoxy)propanoate

To a solution of 5-bromo-2-fluorophenol (74.0 g), methyl (2R)-2-hydroxypropanoate (80.7 g) and PPh$_3$ (152 g) in THF (1000 mL) was added portionwise DIAD (118 g) at 0° C. The mixture was stirred under nitrogen atmosphere at 25° C. for 12 hr. The mixture was diluted with water (1000 mL) and extracted with EtOAc (800 mL×3). The combined organic layer was washed with brine (1000 mL), dried over Na$_2$SO$_4$ and concentrated under reduced pressure. The residue was purified by silica gel column chromatography (EtOAc/PE) to give the titled compound (85.0 g).

$^1$H NMR (400 MHz, CDCl$_3$) δ 6.93-7.07 (m, 3H), 4.76 (q, J=7.2 Hz, 1H), 3.77 (s, 3H), 1.65 (d, J=6.8 Hz, 3H).

B) (2S)-2-(5-bromo-2-fluorophenoxy)propan-1-ol

To a solution of methyl (2S)-2-(5-bromo-2-fluorophenoxy)propanoate (85.0 g) in THF (330 mL) and MeOH (660 mL) was added portionwise NaBH$_4$ (17.4 g) at 0° C. over 0.5 hr. The mixture was stirred under nitrogen atmosphere at 25° C. for 12 hr. The mixture was diluted with saturated aqueous NH$_4$Cl solution (500 mL) and water (500 mL) at 0° C. The organic solvent was removed under reduced pressure. The residue was extracted with EtOAc (400 mL×3). The combined organic layer was washed with brine (800 mL), dried over Na$_2$SO$_4$ and concentrated under reduced pressure. The residue was purified by silica gel column chromatography (EtOAc/PE) to give the titled compound (75.0 g).

$^1$H NMR (400 MHz, CDCl$_3$) δ 7.16 (dd, J=7.2, 2.0 Hz, 1H), 7.04-7.10 (m, 1H), 6.92-6.97 (m, 1H), 4.42-4.46 (m, 1H), 3.74-3.80 (m, 2H), 2.58 (brs, 1H), 1.29 (d, J=6.0 Hz, 3H).

C) (2S)-2-(5-bromo-2-fluorophenoxy)propyl methanesulfonate

To a solution of (2S)-2-(5-bromo-2-fluorophenoxy)propan-1-ol (75.0 g) and TEA (60.9 g) in THF (1000 mL) was added dropwise MsCl (48.3 g) at 0° C. The mixture was stirred under nitrogen atmosphere at 25° C. for 1 hr. The mixture was diluted with water (800 mL) and extracted with EtOAc (1000 mL×3). The combined organic layer was washed with brine (800 mL), dried over $Na_2SO_4$ and concentrated under reduced pressure to give the titled compound (97.0 g).

$^1$H NMR (400 MHz, $CDCl_3$) δ 7.15 (dd, J=7.2, 2.4 Hz, 1H), 7.06-7.10 (m, 1H), 6.94-6.99 (m, 1H), 4.59-4.63 (m, 1H), 4.35-4.36 (m, 2H), 3.05 (s, 3H), 1.38 (d, J=6.4 Hz, 3H).

D) 1-[(2S)-2-(5-bromo-2-fluorophenoxy)propyl]-1H-tetrazole

To a mixture of (2S)-2-(5-bromo-2-fluorophenoxy)propyl methanesulfonate (97.0 g) and 1H-tetrazole (41.5 g) in DMF (1000 mL) was added $K_2CO_3$ (82.0 g). The mixture was stirred at 80° C. for 12 hr. The mixture was diluted with saturated aqueous $NH_4Cl$ solution (600 mL) and extracted with EtOAc (200 mL×3). The combined organic layer was washed with brine (600 mL), dried over $Na_2SO_4$ and concentrated under reduced pressure. The residue was purified by silica gel column chromatography (EtOAc/PE) to give the titled compound (31.0 g).

$^1$H NMR (400 MHz, $CDCl_3$) δ 8.80 (s, 1H), 7.05-7.17 (m, 1H), 6.90-7.04 (m, 2H), 4.75-4.85 (m, 1H), 4.65-4.74 (m, 1H), 4.54-4.64 (m, 1H), 1.38 (d, J=6.4 Hz, 3H).

E) 1-[(2S)-2-[2-fluoro-5-(4,4,5,5-tetramethyl-1,3,2-dioxaborolan-2-yl)phenoxy]propyl]-1H-tetrazole A mixture of 1-[(2S)-2-(5-bromo-2-fluorophenoxy)propyl]-1H-tetrazole (29.3 g), $(Bpin)_2$ (37.1 g), $Pd(dppf)Cl_2$—$CH_2Cl_2$ (7.95 g) and KOAc (19.1 g) in DMSO (300 mL) was stirred under nitrogen atmosphere at 100° C. for 2 hr. The mixture was diluted with water (300 mL) and extracted with EtOAc (300 mL×3). The combined organic layer was washed with brine (300 mL), dried over $Na_2SO_4$ and concentrated under reduced pressure. The residue was purified by silica gel column chromatography (EtOAc/PE) to give the titled compound (33.0 g).

$^1$H NMR (400 MHz, $CDCl_3$) δ 8.44 (s, 1H), 7.33-7.35 (m, 1H), 7.26-7.29 (m, 1H), 6.94-6.99 (m, 1H), 4.89-4.93 (m, 2H), 4.70-4.76 (m, 1H), 1.35 (d, J=5.2 Hz, 3H), 1.27 (s, 12H).

F) 1-[(2S)-2-(2-fluoro-5-{2-methylpyrazolo[1,5-a]pyrimidin-5-yl}phenoxy)propyl]-1H-tetrazole The reaction and purification were performed according to Example 1 Step F to give the titled compound.

$^1$H NMR (300 MHz, $CDCl_3$) δ 8.87 (s, 1H), 8.59 (d, J=7.3 Hz, 1H), 7.72 (dd, J=2.2, 8.0 Hz, 1H), 7.61 (ddd, J=2.2, 4.4, 8.5 Hz, 1H), 7.20 (dd, J=8.5, 10.5 Hz, 1H), 7.08 (d, J=7.3 Hz, 1H), 6.48 (s, 1H), 4.87-4.95 (m, 1H), 4.80-4.86 (m, 1H), 4.65-4.73 (m, 1H), 2.53 (s, 3H), 1.45 (d, J=6.2 Hz, 3H); MS m/z 354.3 [M+H]$^+$.

G) 1-[(2S)-2-(5-{3-bromo-2-methylpyrazolo[1,5-a]pyrimidin-5-yl}-2-fluorophenoxy)propyl]-1H-tetrazole The reaction and purification were performed according to Example 1 Step G to give the titled compound.

$^1$H NMR (300 MHz, $CDCl_3$) δ 8.88 (s, 1H), 8.56 (d, J=7.3 Hz, 1H), 7.77 (dd, J=2.2, 7.9 Hz, 1H), 7.69 (ddd, J=2.2, 4.4, 8.6 Hz, 1H), 7.21 (dd, J=8.6, 10.5 Hz, 1H), 7.14 (d, J=7.4 Hz, 1H), 4.81-4.92 (m, 2H), 4.66-4.74 (m, 1H), 2.52 (s, 3H), 1.46 (d, J=6.2 Hz, 3H); MS m/z 432.2, 434.2 [M+H]$^+$.

H) 1-[(2S)-2-{2-fluoro-5-[2-methyl-3-(thiophen-2-yl)pyrazolo[1,5-a]pyrimidin-5-yl]phenoxy}propyl]-1H-tetrazole The reaction and purification were performed according to Example 1 Step H to give the titled compound.

$^1$H NMR (300 MHz, DMSO-$d_6$) δ 9.43 (s, 1H), 9.14 (d, J=7.3 Hz, 1H), 8.01-8.10 (m, 1H), 7.97 (ddd, J=1.9, 4.4, 8.5 Hz, 1H), 7.71 (d, J=7.4 Hz, 1H), 7.53-7.64 (m, 2H), 7.42 (dd, J=8.7, 10.9 Hz, 1H), 7.22 (dd, J=3.6, 5.1 Hz, 1H), 5.07-5.18 (m, 1H), 4.89-4.98 (m, 1H), 4.79-4.89 (m, 1H), 2.66 (s, 3H), 1.41 (d, J=6.2 Hz, 3H); MS m/z 436.4 [M+H]$^+$.

Example 61

1-[(2S)-2-{3-[3-(thiophen-2-yl)pyrazolo[1,5-a]pyrimidin-5-yl]phenoxy}propyl]-1H-1,2,4-triazole A) ((2S)-2-[3-(4,4,5,5-tetramethyl-1,3,2-dioxaborolan-2-yl)phenoxy]propan-1-ol To a mixture of (2S)-2-(3-bromophenoxy)propan-1-ol (35.0 g), $(Bpin)_2$ (45.9 g) and KOAc (44.3 g) in toluene (100 mL) was added $Pd(dppf)Cl_2$ (5.53 g). After being stirred under argon atmosphere at 100° C. for 3 hr, the mixture was poured into water and extracted with EtOAc. The organic layer was separated, washed with brine, dried over $MgSO_4$ and concentrated under reduced pressure. The residue was purified by silica gel column chromatography (EtOAc/hexane) to give the titled compound (36.0 g).

MS m/z 279.1 [M+H]$^+$.

B) (2S)-2-(3-{pyrazolo[1,5-a]pyrimidin-5-yl}phenoxy)propan-1-ol

The reaction and purification were performed according to Example 1 Step F to give the titled compound.
MS m/z 270.4 [M+H]$^+$.

C) (2S)-2-(3-{3-bromopyrazolo[1,5-a]pyrimidin-5-yl}phenoxy)propan-1-ol

The reaction and purification were performed according to Example 1 Step G to give the titled compound.
MS m/z 348.2 [M+H]$^+$.

D) (2S)-2-{3-[3-(thiophen-2-yl)pyrazolo[1,5-a]pyrimidin-5-yl]phenoxy}propan-1-ol The reaction and purification were performed according to Example 1 Step H to give the titled compound.
MS m/z 352.1 [M+H]$^+$.

E) (2S)-2-{3-[3-(thiophen-2-yl)pyrazolo[1,5-a]pyrimidin-5-yl]phenoxy}propyl methanesulfonate To a mixture of (2S)-2-{3-[3-(thiophen-2-yl)pyrazolo[1,5-a]pyrimidin-5-yl]phenoxy}propan-1-ol (1.80 g) and TEA (777 mg) in THF (10 mL) was added MsCl (644 mg). The mixture was stirred at room temperature for 30 min. The mixture was poured into water and extracted with EtOAc. The organic layer was separated, washed with brine, dried over $MgSO_4$ and concentrated under reduced pressure to give the crude titled compound (2.20 g). The crude product was used for the next step without further purification.

MS m/z 430.1 [M+H]$^+$.

F) 1-[(2S)-2-{3-[3-(thiophen-2-yl)pyrazolo[1,5-a]pyrimidin-5-yl]phenoxy}propyl]-1H-1,2,4-triazole To a mixture of (2S)-2-{3-[3-(thiophen-2-yl)pyrazolo[1,5-a]pyrimidin-5-yl]phenoxy}propyl methanesulfonate (100 mg), K$_2$CO$_3$ (64.3 mg) in DMF (5.0 mL) was added 1,2,4-triazole (32.1 mg). The mixture was stirred at 100° C. for 15 hr. The mixture was poured into water and extracted with EtOAc. The organic layer was separated, washed with brine, dried over MgSO$_4$ and concentrated under reduced pressure. The residue was purified by silica gel column chromatography (NH, EtOAc/hexane) to give the titled compound (75.0 mg) as a yellow solid.

$^1$H NMR (300 MHz, DMSO-d$_6$) δ 9.20 (d, J=7.4 Hz, 1H), 8.67 (s, 1H), 8.58 (s, 1H), 7.97 (s, 1H), 7.92 (d, J=7.9 Hz, 1H), 7.83 (s, 1H), 7.73 (d, J=7.4 Hz, 1H), 7.66 (dd, J=5.1, 3.6 Hz, 1H), 7.45-7.30 (m, 2H), 7.17 (dd, J=3.6, 1.1 Hz, 1H), 7.08 (dd, J=8.1, 2.2 Hz, 1H), 4.95-5.05 (m, 1H), 4.59 (d, J=5.6 Hz, 2H), 1.36 (d, J=6.2 Hz, 3H); MS m/z 403.1 [M+H]$^+$.

Example 121

2-[6-(4-fluoro-3-{[(2S)-1-(1H-tetrazol-1-yl)propan-2-yl]oxy}phenyl)imidazo[1,2-b]pyridazin-3-yl]benzonitrile A) 1-[(2S)-2-(2-fluoro-5-{imidazo[1,2-b]pyridazin-6-yl}phenoxy)propyl]-1H-tetrazole To a solution of 1-[(2S)-2-[2-fluoro-5-(4,4,5,5-tetramethyl-1,3,2-dioxaborolan-2-yl)phenoxy]propyl]-1H-tetrazole (33.0 g) and 6-chloroimidazo[1,2-b]pyridazine (14.6 g) in THF (320 mL) and water (80 mL) were added Cs$_2$CO$_3$ (61.8 g) and Pd(dppf)Cl$_2$—CH$_2$Cl$_2$ (7.74 g). The mixture was stirred under nitrogen atmosphere at 70° C. for 1 hr. The mixture was diluted with water (300 mL) and extracted with EtOAc (400 mL×3). The combined organic layer was washed with brine (500 mL), dried over Na$_2$SO$_4$ and concentrated under reduced pressure. The residue was purified by silica gel column chromatography (MeOH/EtOAc) to give the titled compound (13.0 g).

$^1$H NMR (400 MHz, CDCl$_3$) δ 8.51 (s, 1H), 7.99-8.01 (m, 2H), 7.79 (s, 1H), 7.55-7.57 (m, 2H), 7.39 (d, J=8.0 Hz, 1H), 7.16-7.20 (m, 1H), 5.01-5.06 (m, 2H), 4.83-4.85 (m, 1H), 1.51 (d, J=6.0 Hz, 3H).

B) 1-[(2S)-2-(5-{3-bromoimidazo[1,2-b]pyridazin-6-yl}-2-fluorophenoxy)propyl]-1H-tetrazole To a mixture of 1-[(2S)-2-(2-fluoro-5-{imidazo[1,2-b]pyridazin-6-yl}phenoxy)propyl]-1H-tetrazole (20.0 g) in DMF (300 mL) was added NBS (10.5 g). The mixture was stirred under nitrogen atmosphere at 25° C. for 12 hr. The mixture was diluted with water (200 mL) and extracted with EtOAc (300 mL×3). The combined organic layer was washed with brine (200 mL), dried over Na$_2$SO$_4$ and concentrated under reduced pressure. The residue was purified by silica gel column chromatography (EtOAc) to give the titled compound (15.1 g).

$^1$H NMR (400 MHz, CDCl$_3$) δ 8.54 (s, 1H), 7.99-8.01 (m, 1H), 7.80 (s, 1H), 7.62-7.64 (m, 2H), 7.46 (d, J=6.4 Hz, 1H), 7.21-7.23 (m, 1H), 5.04-5.07 (m, 2H), 4.84-4.86 (m, 1H), 1.52 (d, J=6.0 Hz, 3H).

C) 2-[6-(4-fluoro-3-{[(2S)-1-(1H-tetrazol-1-yl)propan-2-yl]oxy}phenyl)imidazo[1,2-b]pyridazin-3-yl]benzonitrile Pd(PPh$_3$)$_2$Cl$_2$ (4.33 mg) was added to a mixture of 1-[(2S)-2-(5-{3-bromoimidazo[1,2-b]pyridazin-6-yl}-2-fluorophenoxy)propyl]-1H-tetrazole (50.0 mg), (2-cyanophenyl)boronic acid (19.3 mg), Cs$_2$CO$_3$ (77.8 mg) in THF (5.0 mL) and water (1.0 mL). The mixture was stirred under nitrogen atmosphere at 70° C. for 1 hr. The mixture was poured into water and extracted with EtOAc. The organic layer was separated, washed with brine, dried over MgSO$_4$ and concentrated under reduced pressure. The residue was crystallized from EtOAc to give the titled compound (28.0 mg) as a white solid.

$^1$H NMR (300 MHz, DMSO-d$_6$) δ 9.40 (s, 1H), 8.39 (d, J=5.8 Hz, 1H), 8.23 (s, 1H), 8.07-8.13 (m, 2H), 7.97 (d, J=5.8 Hz, 1H), 7.90-7.97 (m, 1H), 7.81 (dd, J=5.8, 3.0 Hz, 1H), 7.68-7.72 (m, 2H), 7.35-7.38 (m, 1H), 5.01-5.09 (m, 1H), 4.78-4.94 (m, 2H), 1.36 (d, J=6.0 Hz, 3H); MS m/z 441.2 [M+H]$^+$.

Example 150

2-[5-(4-fluoro-3-{[(2S)-1-(1H-tetrazol-1-yl)propan-2-yl]oxy}phenyl)-3H-imidazo[4,5-b]pyridin-3-yl]pyridine-3-carbonitrile A) 5-chloro-3-{[2-(trimethylsilyl)ethoxy]methyl}-3H-imidazo[4,5-b]pyridine and 5-chloro-1-{[2-(trimethylsilyl)ethoxy]methyl}-1H-imidazo[4,5-b]pyridine To a mixture of 5-chloro-3H-imidazo[4,5-b]pyridine (3.90 g) and DIPEA (6.53 g) in DMF (40 mL) was added SEMCl (3.6 mL). After being stirred under nitrogen atmosphere at 80° C. for 14 hr, additional SEMCl (1.3 mL) was added to the mixture. After being stirred under nitrogen atmosphere at 80° C. for 4 hr, the mixture was quenched with water at room temperature and extracted with EtOAc. The organic layer was separated, washed with water and brine, dried over MgSO$_4$ and concentrated under reduced pressure. The residue was purified by silica gel column chromatography (NH, EtOAc/hexane) to give a mixture of the titled compounds (4.93 g).

MS m/z 284.2 [M+H]$^+$.

B) 1-[(2S)-2-[2-fluoro-5-(3-{[2-(trimethylsilyl)ethoxy]methyl}-3H-imidazo[4,5-b]pyridin-5-yl)phenoxy]propyl]-1H-tetrazole and 1-[(2S)-2-[2-fluoro-5-(1-{[2-(trimethylsilyl)ethoxy]methyl}-1H-imidazo[4,5-b]pyridin-5-yl)phenoxy]propyl]-1H-tetrazole The reaction and purification were performed according to Example 284 Step D to give the titled compound.

MS m/z 470.3 [M+H]$^+$.

C) 1-[(2S)-2-(2-fluoro-5-{3H-imidazo[4,5-b]pyridin-5-yl}phenoxy)propyl]-1H-tetrazole To a mixture of a mixture of 1-[(2S)-2-[2-fluoro-5-(3-{[2-(trimethylsilyl)ethoxy]methyl}-3H-imidazo[4,5-b]pyridin-5-yl)phenoxy]propyl]-1H-tetrazole and 1-[(2S)-2-[2-fluoro-5-(1-{[2-(trimethylsilyl)ethoxy]methyl}-1H-imidazo[4,5-b]pyridin-5-yl)phenoxy]propyl]-1H-tetrazole (7.48 g) in THF (40 mL) was added 1M TBAF THF solution (14 mL). The mixture was stirred under nitrogen atmosphere at 80° C. for 4 hr. The mixture was quenched with water at room temperature and extracted with EtOAc. The organic layer was separated, washed with water and brine, dried over $MgSO_4$ and concentrated under reduced pressure to give the crude titled compound (2.60 g). The crude product was used for the next step without further purification.

$^1$H NMR (300 MHz, DMSO-$d_6$) δ 12.62-13.31 (m, 1H), 9.42 (s, 1H), 8.39-8.51 (m, 1H), 7.98-8.18 (m, 1H), 7.68-7.86 (m, 3H), 7.25-7.36 (m, 1H), 5.01-5.12 (m, 1H), 4.75-4.93 (m, 2H), 1.36 (d, J=6.1 Hz, 3H); MS m/z 340.3 [M+H]$^+$.

D) 2-[5-(4-fluoro-3-{[(2S)-1-(1H-tetrazol-1-yl)propan-2-yl]oxy}phenyl)-3H-imidazo[4,5-b]pyridin-3-yl]pyridine-3-carbonitrile A mixture of 1-[(2S)-2-(2-fluoro-5-{3H-imidazo[4,5-b]pyridin-5-yl}phenoxy)propyl]-1H-tetrazole (250 mg), 2-chloropyridine-3-carbonitrile (152 mg), $K_3PO_4$ (233 mg), tBuXPhos (62.5 mg) and $Pd_2(dba)_3$ (67.4 mg) in DMA (15 mL) was stirred under microwave irradiation at 100° C. for 1 hr. The mixture was quenched with water at room temperature and extracted with EtOAc. The organic layer was separated, washed with water and brine, dried over $MgSO_4$ and concentrated under reduced pressure. The residue was purified by silica gel column chromatography (EtOAc/hexane) and silica gel column chromatography (NH, EtOAc/hexane) to give the titled compound (8.00 mg) as a white solid.

$^1$H NMR (300 MHz, CDCl$_3$) δ 8.91 (s, 1H), 8.83 (dd, J=1.8, 4.9 Hz, 1H), 8.65 (s, 1H), 8.48 (dd, J=1.8, 7.8 Hz, 1H), 8.22 (d, J=8.4 Hz, 1H), 7.97 (dd, J=2.1, 8.2 Hz, 1H), 7.72 (d, J=8.4 Hz, 1H), 7.61 (dd, J=4.9, 7.9 Hz, 1H), 7.53-7.58 (m, 1H), 7.18 (dd, J=8.5, 11 Hz, 1H), 4.92 (dt, J=2.9, 6.6 Hz, 1H), 4.80-4.87 (m, 1H), 4.65-4.74 (m, 1H), 1.42 (d, J=6.2 Hz, 3H); MS m/z 442.3 [M+H]$^+$.

Example 173

4-[5-(4-fluoro-3-{[(2S)-1-(1H-tetrazol-1-yl)propan-2-yl]oxy}phenyl)-3H-imidazo[4,5-b]pyridin-3-yl]-1-methyl-1H-imidazole-5-carbonitrile

A) 4-[(6-chloro-3-nitropyridin-2-yl)amino]-1-methyl-1H-imidazole-5-carbonitrile The reaction and purification were performed according to Example 284 Step A to give the titled compound.

$^1$H NMR (300 MHz, DMSO-$d_6$) δ 10.15 (s, 1H), 8.57 (d, J=8.5 Hz, 1H), 7.72 (s, 1H), 7.13 (d, J=8.5 Hz, 1H), 3.59 (s, 3H); MS m/z 279.0 [M+H]$^+$.

B) 4-{5-chloro-3H-imidazo[4,5-b]pyridin-3-yl}-1-methyl-1H-imidazole-5-carbonitrile The reaction and purification were performed according to Example 284 Step B and C to give the titled compound. MS m/z 259.1 [M+H]$^+$.

C) 4-[5-(4-fluoro-3-{[(2S)-1-(1H-tetrazol-1-yl)propan-2-yl]oxy}phenyl)-3H-imidazo[4,5-b]pyridin-3-yl]-1-methyl-1H-imidazole-5-carbonitrile The reaction and purification were performed according to Example 284 Step D to give the titled compound.

$^1$H NMR (300 MHz, DMSO-$d_6$) δ 9.41 (s, 1H), 8.83 (s, 1H), 8.32 (d, J=8.4 Hz, 1H), 8.24 (s, 1H), 8.08 (dd, J=2.0, 8.3 Hz, 1H), 8.03 (d, J=8.4 Hz, 1H), 7.84 (ddd, J=2.0, 4.4, 8.6 Hz, 1H), 7.32 (dd, J=8.6, 11 Hz, 1H), 5.08-5.19 (m, 1H), 4.88-4.96 (m, 1H), 4.76-4.87 (m, 1H), 3.97 (s, 3H), 1.37 (d, J=6.1 Hz, 3H); MS m/z 445.2 [M+H]$^+$.

Example 239

2-[6-(3-{[(2S)-1-(1H-tetrazol-1-yl)propan-2-yl]oxy}phenyl)imidazo[1,2-b]pyridazin-3-yl]benzonitrile

A) methyl (2S)-2-(3-bromophenoxy)propanoate

To a mixture of 3-bromophenol (75.0 g), methyl (2R)-2-hydroxypropanoate (90.3 g) and PPh$_3$ (171 g) in THF (1000 mL) was added DIAD (131 g) at 0° C. The mixture was stirred under nitrogen atmosphere at 20° C. for 12 hr. The mixture was diluted with water (1000 mL) and extracted with EtOAc (500 mL×3). The combined organic layer was washed with brine (1000 mL), dried over $Na_2SO_4$ and concentrated under reduced pressure. The residue was triturated with 15% EtOAc in PE (500 mL) and filtered. The filtrate was concentrated under reduced pressure. The residue was purified by silica gel column chromatography (EtOAc/PE) to give the titled compound (41.0 g).

$^1$H NMR (400 MHz, CDCl$_3$) δ 7.09-7.19 (m, 2H), 7.04 (d, J=2.0 Hz, 1H), 6.75-6.81 (m, 1H), 4.74 (q, J=6.8 Hz, 1H), 3.77 (s, 3H), 1.61 (d, J=6.8 Hz, 3H).

B) (2S)-2-(3-bromophenoxy)propan-1-ol

To a mixture of methyl (2S)-2-(3-bromophenoxy)propanoate (41.0 g) in THF (200 mL) and MeOH (400 mL) was added portionwise NaBH$_4$ (8.98 g) at 0° C. The mixture was stirred under nitrogen atmosphere at 20° C. for 12 hr. Saturated aqueous NH$_4$Cl solution (500 mL) and water (500 mL) were added to the mixture at 0° C. The organic solvent was removed under reduced pressure. The residue was extracted with EtOAc (400 mL×3). The combined organic layer was washed with brine (800 mL), dried over $Na_2SO_4$ and concentrated under reduced pressure to give the titled compound (35.0 g).

$^1$H NMR (400 MHz, CDCl$_3$) δ 7.01-7.16 (m, 3H), 6.80-6.90 (m, 1H), 4.41-4.52 (m, 1H), 3.64-3.75 (m, 2H), 2.06 (brs, 1H), 1.26 (d, J=6.0 Hz, 3H).

C) (2S)-2-(3-bromophenoxy)propyl methanesulfonate

To a mixture of (2S)-2-(3-bromophenoxy)propan-1-ol (64.0 g) and TEA (56.1 g) in THF (700 mL) was added dropwise MsCl (44.4 g) at 0° C. in 0.5 hr. The mixture was stirred under nitrogen atmosphere at 20° C. for 1 hr. The mixture was diluted with water (1000 mL) and extracted with EtOAc (500 mL×3). The combined organic layer was washed with brine (1000 mL), dried over Na₂SO₄, filtered and concentrated under reduced pressure to give the titled compound (82.0 g).
¹H NMR (400 MHz, CDCl₃) δ 7.06-7.19 (m, 3H), 6.81-6.92 (m, 1H), 4.59-4.70 (m, 1H), 4.25-4.36 (m, 2H), 3.03 (s, 3H), 1.36 (d, J=6.0 Hz, 3H).

D) 1-[(2S)-2-(3-bromophenoxy)propyl]-1H-tetrazole

To a mixture of (2S)-2-(3-bromophenoxy)propyl methanesulfonate (82.0 g) in DMF (800 mL) were added K₂CO₃ (73.3 g) and 1H-tetrazole (37.2 g). The mixture was stirred under nitrogen atmosphere at 80° C. for 12 hr. The mixture was concentrated under reduced pressure. The residue was poured into water (1500 mL) and extracted with EtOAc (800 mL×3). The combined organic layer was washed with brine (1000 mL), dried over Na₂SO₄ and concentrated under reduced pressure. The residue was purified by silica gel column chromatography (EtOAc/PE) to give the titled compound (72.0 g).
¹H NMR (400 MHz, CDCl₃) δ 8.71 (s, 1H), 7.09-7.18 (m, 2H), 6.95-7.03 (m, 1H), 6.67-6.73 (m, 1H), 4.66-4.79 (m, 2H), 4.53-4.65 (m, 1H), 1.36 (d, J=6.0 Hz, 3H).

E) 1-[(2S)-2-[3-(4,4,5,5-tetramethyl-1,3,2-dioxaborolan-2-yl)phenoxy]propyl]-1H-tetrazole To a mixture of 1-[(2S)-2-(3-bromophenoxy)propyl]-1H-tetrazole (36.0 g), (Bpin)₂ (48.4 g) and KOAc (25.0 g) in DMSO (500 mL) was added Pd(dppf)Cl₂—CH₂Cl₂ (10.4 g). The mixture was stirred at 100° C. for 2 hr. The mixture was diluted with water (2000 mL) and extracted with EtOAc (1000 mL×3). The combined organic layer was washed with water (1000 mL×2), dried over Na₂SO₄ and concentrated under reduced pressure. The residue was purified by silica gel column chromatography (EtOAc/PE) to give the titled compound (63.0 g).
¹H NMR (400 MHz, CDCl₃) δ 8.75 (s, 1H), 7.43 (d, J=7.2 Hz, 1H), 7.25-7.34 (m, 2H), 6.90-6.97 (m, 1H), 4.74-4.86 (m, 2H), 4.56-4.65 (m, 1H), 1.30-1.42 (m, 15H); MS m/z 331.0 [M+H]⁺.

F) 1-[(2S)-2-(3-{imidazo[1,2-b]pyridazin-6-yl}phenoxy)propyl]-1H-tetrazole

To a solution of 1-[(2S)-2-[3-(4,4,5,5-tetramethyl-1,3,2-dioxaborolan-2-yl)phenoxy]propyl]-1H-tetrazole (11.0 g), Cs₂CO₃ (21.7 g) and 6-chloroimidazo[1,2-b]pyridazine (5.12 g) in THF (100 mL) and water (25 mL) was added Pd(dppf)Cl₂—CH₂Cl₂ (2.72 g) The mixture was stirred under nitrogen atmosphere at 70° C. for 1 hr. The mixture was diluted with water (100 mL) and extracted with EtOAc (150 mL×3). The combined organic layer was washed with brine (100 mL), dried over Na₂SO₄ and concentrated under reduced pressure. The residue was purified by silica gel column chromatography (EtOAc/PE) to give the titled compound (8.00 g).
¹H NMR (400 MHz, CDCl₃) δ 8.78 (s, 1H), 7.99-8.05 (m, 2H), 7.83 (s, 1H), 7.53 (d, J=8.0 Hz, 1H), 7.39-7.46 (m, 3H), 6.93 (dd, J=8.4, 2.8 Hz, 1H), 4.87-4.93 (m, 1H), 4.79-4.83 (m, 1H), 4.62-4.67 (m, 1H), 1.43 (d, J=6.0 Hz, 3H).

G) 1-[(2S)-2-(3-{3-bromoimidazo[1,2-b]pyridazin-6-yl}phenoxy)propyl]-1H-tetrazole To a solution of 1-[(2S)-2-(3-{imidazo[1,2-b]pyridazin-6-yl}phenoxy)propyl]-1H-tetrazole (8.00 g) in DMF (70 mL) was added NBS (4.43 g). The mixture was stirred under nitrogen atmosphere at 25° C. for 12 hr. The mixture was diluted with water (60 mL) and extracted with EtOAc (100 mL×3). The combined organic layer was washed with brine (100 mL), dried over Na₂SO₄ and concentrated under reduced pressure. The residue was purified by silica gel column chromatography (EtOAc) to give the titled compound (8.75 g).
¹H NMR (400 MHz, CDCl₃) δ 8.79 (s, 1H), 7.98 (d, J=9.6 Hz, 1H), 7.78 (s, 1H), 7.58 (d, J=7.6 Hz, 1H), 7.47-7.52 (m, 2H), 7.41 (t, J=8.0 Hz, 1H), 6.92-6.94 (dd, J=8.4, 2.0 Hz, 1H), 4.85-4.91 (m, 1H), 4.78-4.82 (m, 1H), 4.62-4.68 (m, 1H), 1.43 (d, J=6.4 Hz, 3H).

H) 2-[6-(3-{[(2S)-1-(1H-tetrazol-1-yl)propan-2-yl]oxy}phenyl)imidazo[1,2-b]pyridazin-3-yl]benzonitrile The reaction and purification were performed according to Example 121 Step C to give the titled compound.
¹H NMR (400 MHz, CDCl₃) δ 8.76 (s, 1H), 8.18 (s, 1H), 8.13 (d, J=9.6 Hz, 1H), 7.96 (d, J=7.6 Hz, 1H), 7.91 (d, J=7.6 Hz, 1H), 7.74-7.79 (m, 1H), 7.51-7.58 (m, 4H), 7.41 (t, J=8.0 Hz, 1H), 6.94 (dd, J=8.4, 2.4 Hz, 1H), 4.86-4.90 (m, 1H), 4.76-4.83 (m, 1H), 4.60-4.70 (m, 1H), 1.41 (d, J=6.0 Hz, 3H). MS m/z 423.2 [M+H]⁺.

Example 244

2-[6-(5-{[(2S)-1-(1H-tetrazol-1-yl)propan-2-yl]oxy}pyridin-3-yl)imidazo[1,2-b]pyridazin-3-yl]benzonitrile

A) methyl (S)-2-((5-bromopyridin-3-yl)oxy)propanoate

The reaction and purification were performed according to Example 57 Step A to give the titled compound.
¹H NMR (400 MHz, CDCl₃) δ 8.26 (d, J=1.6 Hz, 1H), 8.17 (d, J=2.4 Hz, 1H), 7.29-7.30 (m, 1H), 4.75 (q, J=6.8 Hz, 1H), 3.74 (s, 3H), 1.60 (d, J=6.8 Hz, 3H).

B) (S)-2-((5-bromopyridin-3-yl)oxy)propan-1-ol

The reaction and purification were performed according to Example 57 Step B to give the titled compound.
¹H NMR (400 MHz, CDCl₃) δ 8.25 (d, J=1.6 Hz, 1H), 8.22 (d, J=2.8 Hz, 1H), 7.40-7.41 (m, 1H), 4.47-4.54 (m, 1H), 3.75-3.77 (m, 2H), 2.52 (brs, 1H), 1.29 (d, J=6.4 Hz, 3H).

C) (S)-2-((5-bromopyridin-3-yl)oxy)propyl methanesulfonate

The reaction and purification were performed according to Example 57 Step C to give the titled compound.
¹H NMR (400 MHz, CDCl₃) δ 8.29 (d, J=1.6 Hz, 1H), 8.22 (d, J=2.4 Hz, 1H), 7.39-7.40 (m, 1H), 4.66-4.70 (m, 1H), 4.32 (d, J=5.2 Hz, 2H), 3.02 (s, 3H), 1.37 (d, J=6.4 Hz, 3H).

D) 3-bromo-5-{[(2S)-1-(1H-tetrazol-1-yl)propan-2-yl]oxy}pyridine

The reaction and purification were performed according to Example 57 Step D to give the titled compound.

¹H NMR (400 MHz, CDCl₃) δ 8.69 (s, 1H), 8.31 (d, J=1.6 Hz, 1H), 8.14 (d, J=2.4 Hz, 1H), 7.26 (s, 1H), 4.73-4.82 (m, 2H), 4.58-4.63 (m, 1H), 1.40 (d, J=6.0 Hz, 3H).

E) 3-{imidazo[1,2-b]pyridazin-6-yl}-5-{[(2S)-1-(1H-tetrazol-1-yl)propan-2-yl]oxy}pyridine The reaction and purification were performed according to Example 57 Step E and Example 121 Step A to give the titled compound.
¹H NMR (300 MHz, CDCl₃) δ 8.76-8.82 (m, 2H), 8.37 (d, J=2.7 Hz, 1H), 8.03-8.12 (m, 2H), 7.85 (s, 1H), 7.74 (d, J=2.0 Hz, 1H), 7.47 (d, J=9.6 Hz, 1H), 4.94-5.02 (m, 1H), 4.81-4.88 (m, 1H), 4.65-4.73 (m, 1H), 1.49 (d, J=6.2 Hz, 3H); MS m/z 323.1 [M+H]⁺.

F) 3-{3-bromoimidazo[1,2-b]pyridazin-6-yl}-5-{[(2S)-1-(1H-tetrazol-1-yl)propan-2-yl]oxy}pyridine The reaction and purification were performed according to Example 121 Step B to give the titled compound.
¹H NMR (300 MHz, CDCl₃) δ 8.85 (d, J=1.4 Hz, 1H), 8.78 (s, 1H), 8.38 (d, J=2.8 Hz, 1H), 8.06 (d, J=9.4 Hz, 1H), 7.84 (s, 1H), 7.78-7.83 (m, 1H), 7.53 (d, J=9.5 Hz, 1H), 4.94-5.03 (m, 1H), 4.80-4.88 (m, 1H), 4.65-4.74 (m, 1H), 1.50 (d, J=6.1 Hz, 3H); MS m/z 401.1, 403.1 [M+H]⁺.

G) 2-[6-(5-{[(2S)-1-(1H-tetrazol-1-yl)propan-2-yl]oxy}pyridin-3-yl)imidazo[1,2-b]pyridazin-3-yl]benzonitrile The reaction and purification were performed according to Example 121 Step C to give the titled compound.
¹H NMR (300 MHz, DMSO-d₆) δ 9.47 (s, 1H), 8.86 (d, J=1.7 Hz, 1H), 8.45 (d, J=9.4 Hz, 1H), 8.40 (d, J=2.8 Hz, 1H), 8.27 (s, 1H), 8.09-8.14 (m, 2H), 8.04 (d, J=9.5 Hz, 1H), 7.91-7.99 (m, 2H), 7.70 (dt, J=1.2, 7.7 Hz, 1H), 5.13 (dt, J=3.6, 6.6 Hz, 1H), 4.87-4.95 (m, 1H), 4.76-4.85 (m, 1H), 1.35 (d, J=6.2 Hz, 3H); MS m/z 424.2 [M+H]⁺.

Example 247

2-[6-(4-fluoro-3-{[(2S)-1-(1H-tetrazol-1-yl)propan-2-yl]oxy}phenyl)imidazo[1,2-b]pyridazin-3-yl]pyridine-3-carbonitrile To a mixture of 1-[(2S)-2-(5-{3-bromoimidazo[1,2-b]pyridazin-6-yl}-2-fluorophenoxy)propyl]-1H-tetrazole (400 mg), 2-chloropyridine-3-carbonitrile (238 mg) and CsF (726 mg) in MeOH (10 mL) and water (1.0 mL) was added (Bpin)₂ (485 mg). After being stirred at room temperature for 10 min, a mixture of Pd(OAc)₂ (21.4 mg) and cataCXium® A (68.5 mg) in toluene (0.50 mL) was added to the mixture. The mixture was stirred under nitrogen atmosphere at 60° C. for 30 min and then at 90° C. for 14 hr. The insoluble material was removed by filtration and washed with MeOH and THF. The filtrate was concentrated under reduced pressure. The residue was diluted with water and extracted with EtOAc. The organic layer was separated, washed with water and brine, dried over MgSO₄ and concentrated under reduced pressure. The residue was purified by silica gel column chromatography (NH, EtOAc/hexane), and then preparative HPLC (water/CH₃CN containing 0.1% TFA). The desired fraction was neutralized with saturated aqueous NaHCO₃ solution and extracted with EtOAc. The organic layer was separated, dried over MgSO₄ and concentrated under reduced pressure. The residue was crystallized from EtOAc/IPE to give the titled compound (42.0 mg) as a white solid.
¹H NMR (300 MHz, DMSO-d₆) δ 9.40 (s, 1H), 9.05 (dd, J=1.74, 4.86 Hz, 1H), 8.59 (dd, J=1.70, 7.93 Hz, 1H), 8.43 (d, J=9.63 Hz, 1H), 8.31 (s, 1H), 8.03 (d, J=9.63 Hz, 1H), 7.86 (dd, J=2.02, 8.16 Hz, 1H), 7.68-7.77 (m, 2H), 7.39 (dd, J=8.57, 11.05 Hz, 1H), 5.05 (dt, J=3.76, 6.56 Hz, 1H), 4.77-4.96 (m, 2H), 1.37 (d, J=6.14 Hz, 3H); MS m/z 442.1 [M+H]⁺.

Example 251

3-[6-(3-{[(2S)-1-(1H-tetrazol-1-yl)propan-2-yl]oxy}phenyl)imidazo[1,2-b]pyridazin-3-yl]pyridine-4-carbonitrile A) 3-(tributylstannyl)pyridine-4-carbonitrile To a solution of 3-bromopyridine-4-carbonitrile (200 mg) in toluene (5.0 mL) were added hexabutylditin (1.27 g) and Pd(PPh₃)₄ (126 mg). The mixture was stirred under nitrogen atmosphere for 110° C. for 16 hr. The mixture was concentrated under reduced pressure to give the crude titled compound (860 mg). The crude product was used for next step without purification.

B) 3-[6-(3-{[(2S)-1-(1H-tetrazol-1-yl)propan-2-yl]oxy}phenyl)imidazo[1,2-b]pyridazin-3-yl]pyridine-2-carbonitrile A mixture of 3-(tributylstannyl)pyridine-4-carbonitrile (196 mg), 1-[(2S)-2-(3-{3-bromoimidazo[1,2-b]pyridazin-6-yl}phenoxy)propyl]-1H-tetrazole (200 mg), Pd(PPh₃)₄ (58.0 mg) and 1,4-dioxane (5.0 mL) was stirred under nitrogen atmosphere at 100° C. for 16 hr. The mixture was diluted with saturated aqueous KF solution (50 mL) and extracted with EtOAc. The organic layer was dried over Na₂SO₄ and concentrated under reduced pressure. The residue was purified by preparative HPLC (water/CH₃CN containing 0.05% NH₃—H₂O). Most of CH₃CN was removed under reduced pressure and the remaining solvent was removed by lyophilization to give the titled compound (54.0 mg) as a light yellow solid.
¹H NMR (400 MHz, CDCl₃) δ 9.36 (s, 1H), 8.82 (d, J=5.2 Hz, 1H), 8.78 (s, 1H), 8.28 (s, 1H), 8.16 (d, J=9.6 Hz, 1H), 7.79 (d, J=4.8 Hz, 1H), 7.60 (d, J=9.6 Hz, 1H), 7.49-7.55 (m, 2H), 7.36-7.45 (m, 1H), 6.91-6.98 (m, 1H), 4.86-4.90 (m, 1H), 4.76-4.83 (m, 1H), 4.61-4.70 (m, 1H), 1.42 (d, J=6.0 Hz, 3H). MS m/z 424.2 [M+H]⁺.

Example 253

1-methyl-3-[6-(3-{[(2S)-1-(1H-tetrazol-1-yl)propan-2-yl]oxy}phenyl)imidazo[1,2-b]pyridazin-3-yl]-1,2-dihydropyridin-2-one A) 3-[6-(3-{[(2S)-1-(1H-tetrazol-1-yl)propan-2-yl]oxy}phenyl)imidazo[1,2-b]pyridazin-3-yl]-1,2-dihydropyridin-2-one The reaction and purification were performed according to Example 121 Step C to give the titled compound.
¹H NMR (400 MHz, DMSO-d₆) δ 12.06 (brs, 1H), 9.48 (s, 1H), 8.98 (dd, J=7.2, 2.0 Hz, 1H), 8.71 (s, 1H), 8.31 (d, J=9.6 Hz, 1H), 7.87 (d, J=9.6 Hz, 1H), 7.69 (d, J=7.6 Hz, 1H), 7.61 (s, 1H), 7.40-7.52 (m, 2H), 7.09 (dd, J=8.4, 2.4 Hz, 1H), 6.51 (t, J=7.2 Hz, 1H), 5.01-5.11 (m, 1H), 4.81-4.91 (m, 1H), 4.69-4.79 (m, 1H), 1.36 (d, J=6.4 Hz, 3H); MS m/z 415.3 [M+H]$^+$.

B) 1-methyl-3-[6-(3-{[(2S)-1-(1H-tetrazol-1-yl)propan-2-yl]oxy}phenyl)imidazo[1,2-b]pyridazin-3-yl]-1,2-dihydropyridin-2-one To a solution of 3-[6-(3-{[(2S)-1-(1H-tetrazol-1-yl)propan-2-yl]oxy}phenyl)imidazo[1,2-b]pyridazin-3-yl]-1,2-dihydropyridin-2-one (100 mg) in DMF (3.0 mL) were added K$_2$CO$_3$ (67.0 mg) and iodomethane (41.0 mg). The mixture was stirred at 30° C. for 12 hr. The mixture was poured into water and extracted with EtOAc. The organic layer was washed with brine, dried over Na$_2$SO$_4$ and concentrated under reduced pressure. The residue was purified by preparative HPLC (water/CH$_3$CN containing 0.225% FA). The eluent was concentrated under reduced pressure to remove organic solvent. The residual aqueous solution was lyophilized to give the titled compound (18.0 mg) as a yellow solid.
$^1$H NMR (400 MHz, DMSO-d$_6$) δ 9.48 (s, 1H), 8.96 (dd, J=7.2, 2.0 Hz, 1H), 8.71 (s, 1H), 8.30 (d, J=9.6 Hz, 1H), 7.81-7.95 (m, 2H), 7.68 (d, J=7.6 Hz, 1H), 7.60 (s, 1H), 7.47 (t, J=8.0 Hz, 1H), 7.09 (dd, J=8.0, 2.0 Hz, 1H), 6.54 (t, J=7.2 Hz, 1H), 5.00-5.11 (m, 1H), 4.81-4.91 (m, 1H), 4.69-4.79 (m, 1H), 3.61 (s, 3H), 1.36 (d, J=6.0 Hz, 3H); MS m/z 429.2 [M+H]$^+$.

Example 259

1-methyl-2-oxo-4-[6-(3-{[(2S)-1-(1H-tetrazol-1-yl)propan-2-yl]oxy}phenyl)imidazo[1,2-b]pyridazin-3-yl]-1,2-dihydropyridine-3-carbonitrile A) 4-methoxy-1-methyl-2-oxo-1,2-dihydropyridine-3-carbonitrile The reaction and purification were performed according to Example 253 Step B to give the titled compound.
$^1$H NMR (400 MHz, CDCl$_3$) δ 7.53 (d, J=7.6 Hz, 1H), 6.07 (d, J=7.6 Hz, 1H), 3.99 (s, 3H), 3.55 (s, 3H); MS m/z 164.8 [M+H]$^+$.

B) 4-hydroxy-1-methyl-2-oxo-1,2-dihydropyridine-3-carbonitrile

To a solution of 4-methoxy-1-methyl-2-oxo-1,2-dihydropyridine-3-carbonitrile (1.10 g) in THF (3.0 mL) was added 5% aqueous NaOH solution (12 mL). The mixture was stirred at 110° C. for 2 hr. The mixture was cooled to room temperature and acidified with 2N aqueous HCl solution (pH 3). The resulting precipitate was collected by filtration and dried in air to give the titled compound (640 mg).
$^1$H NMR (400 MHz, DMSO-d$_6$) δ 12.58 (brs, 1H), 7.82 (d, J=7.6 Hz, 1H), 6.02 (d, J=7.6 Hz, 1H), 3.36 (s, 3H); MS m/z 150.8 [M+H]$^+$.

C) 4-bromo-1-methyl-2-oxo-1,2-dihydropyridine-3-carbonitrile

To a solution of 4-hydroxy-1-methyl-2-oxo-1,2-dihydropyridine-3-carbonitrile (440 mg) in DMF (8.0 mL) was added POBr$_3$ (1.68 g). The mixture was stirred at 110° C. for 3 hr. The mixture was poured into water and extracted with EtOAc. The organic layer was washed with brine, dried over Na$_2$SO$_4$ and concentrated under reduced pressure to give the titled compound (520 mg).
$^1$H NMR (400 MHz, CDCl$_3$) δ 7.40 (d, J=7.2 Hz, 1H), 6.50 (d, J=7.2 Hz, 1H), 3.58 (s, 3H); MS m/z 214.8 [M+H]$^+$.

D) 1-methyl-2-oxo-4-(tributylstannyl)-1,2-dihydropyridine-3-carbonitrile

The reaction and purification were performed according to Example 251 Step A to give the crude titled compound. The crude product was used for the next step without further purification.
MS m/z 425.1 [M+H]$^+$.

E) 1-methyl-2-oxo-4-[6-(3-{[(2S)-1-(1H-tetrazol-1-yl)propan-2-yl]oxy}phenyl)imidazo[1,2-b]pyridazin-3-yl]-1,2-dihydropyridine-3-carbonitrile The reaction and purification were performed according to Example 251 Step B to give the titled compound.
$^1$H NMR (400 MHz, DMSO-d$_6$) δ 9.48 (s, 1H), 8.46 (s, 1H), 8.42 (d, J=9.6 Hz, 1H), 8.23 (d, J=7.2 Hz, 1H), 8.05 (d, J=9.2 Hz, 1H), 7.70 (d, J=8.0 Hz, 1H), 7.63 (s, 1H), 7.46 (t, J=8.0 Hz, 1H), 7.15 (d, J=6.8 Hz, 1H), 7.10 (d, J=10.4 Hz, 1H), 4.95-5.05 (m, 1H), 4.81-4.91 (m, 1H), 4.69-4.79 (m, 1H), 3.58 (s, 3H), 1.34 (d, J=6.0 Hz, 3H); MS m/z 454.2 [M+H]$^+$.

Example 267

5-[6-(3-{[(2S)-1-(1H-tetrazol-1-yl)propan-2-yl]oxy}phenyl)imidazo[1,2-b]pyridazin-3-yl]pyrimidine-4-carbonitrile A) 5-bromopyrimidine N-oxide To a stirred solution of 5-bromopyrimidine (4.00 g) in CHCl$_3$ (40 mL) was added a solution of mCPBA (6.13 g) in DCM (40 mL) at 0° C. The mixture was stirred at 60° C. for 8 hr. The mixture was diluted with saturated aqueous NaHCO$_3$ solution (150 mL) and extracted with DCM. The organic layer was washed with brine, dried over Na$_2$SO$_4$ and concentrated under reduced pressure. The residue was triturated with 15% EtOAc in PE (50 mL). The resulting precipitate was collected by filtration and dried to give the tilted compound (1.40 g).
$^1$H NMR (400 MHz, CDCl$_3$) δ 8.89 (s, 1H), 8.50-8.52 (m, 1H), 8.28 (d, J=1.6 Hz, 1H).

B) 5-bromopyrimidine-4-carbonitrile

To a mixture of 5-bromopyrimidine N-oxide (1.60 g), CH$_3$CN (30 mL) and TEA (3.70 g) was added trimethylsilyl cyanide (1.81 g). The mixture was stirred under nitrogen atmosphere at 25° C. for 2 hr. The mixture was diluted with water and extracted with EtOAc. The organic layer was washed with brine, dried over Na$_2$SO$_4$ and concentrated under reduced pressure. The residue was purified by silica gel column chromatography (EtOAc/PE) to give the titled compound (770 mg).
$^1$H NMR (400 MHz, CDCl$_3$) δ 9.26 (s, 1H), 9.08 (s, 1H).

C) 1-[(2S)-2-{3-[3-(tributylstannyl)imidazo[1,2-b]pyridazin-6-yl]phenoxy}propyl]-1H-tetrazole To a solution of 1-[(2S)-2-(3-{3-bromoimidazo[1,2-b]pyridazin-6-yl}phenoxy)propyl]-1H-tetrazole (100 mg) in toluene (3.0 mL) was added hexabutylditin (290 mg). The mixture was degassed with nitrogen gas and then Pd(PPh$_3$)$_4$ (29.0 mg) was added to the mixture. The mixture was stirred under nitrogen atmosphere at 110° C. for 16 hr. The mixture was concentrated under reduced pressure to give the crude titled compound (200 mg). The crude product was used for the next step without purification.

MS m/z 612.1 [M+H]$^+$.

D) 5-[6-(3-{[(2S)-1-(1H-tetrazol-1-yl)propan-2-yl]oxy}phenyl)imidazo[1,2-b]pyridazin-3-yl]pyrimidine-4-carbonitrile A solution of 5-bromopyrimidine-4-carbonitrile (46.0 mg), 1-[(2S)-2-{3-[3-(tributylstannyl)imidazo[1,2-b]pyridazin-6-yl]phenoxy}propyl]-1H-tetrazole (200 mg) and Pd(PPh$_3$)$_2$Cl$_2$ (18.0 mg) in 1,4-dioxane (5.0 mL) was stirred under nitrogen atmosphere at 100° C. for 12 hr. The mixture was diluted with saturated aqueous KF solution (100 mL) and extracted with EtOAc. The organic layer was washed with brine, dried over Na$_2$SO$_4$ and concentrated under reduced pressure. The residue was purified by silica gel column chromatography (EtOAc/PE), and then preparative HPLC (water/CH$_3$CN containing 0.05% NH$_3$—H$_2$O). Most of CH$_3$CN was removed under reduced pressure and the remaining solvent was removed by lyophilization to give the titled compound (3.0 mg) as an off-white solid.

$^1$H NMR (400 MHz, DMSO-d$_6$) δ 9.63 (s, 1H), 9.35 (s, 1H), 8.75 (s, 1H), 8.40 (s, 1H), 8.20 (d, J=9.6 Hz, 1H), 7.65 (d, J=9.6 Hz, 1H), 7.50-7.55 (m, 1H), 7.46-7.50 (m, 1H), 7.39-7.46 (m, 1H), 6.96 (dd, J=7.6, 2.0 Hz, 1H), 4.84-4.94 (m, 1H), 4.78-4.84 (m, 1H), 4.61-4.70 (m, 1H), 1.46 (d, J=6.4 Hz, 3H); MS m/z 425.2 [M+H]$^+$.

Example 269

(S)-3-(6-(3-((1-(1H-tetrazol-1-yl)propan-2-yl)oxy)-4-fluorophenyl)imidazo[1,2-b]pyridazin-3-yl)-4-cyanopyridine N-oxide To a mixture of 3-[6-(4-fluoro-3-{[(2S)-1-(1H-tetrazol-1-yl)propan-2-yl]oxy}phenyl)imidazo[1,2-b]pyridazin-3-yl]pyridine-4-carbonitrile (44.0 mg) in CH$_3$CN (4.0 mL) was added mCPBA (24.0 mg) at 0° C. The mixture was stirred under nitrogen atmosphere at room temperature for 14 hr (Additional mCPBA was added to the mixture until the starting material was consumed). The mixture was quenched with Na$_2$S$_2$O$_3$-5H$_2$O at room temperature and extracted with EtOAc. The organic layer was separated, washed with water and brine, dried over MgSO$_4$ and concentrated under reduced pressure. The residue was purified by preparative HPLC (water/CH$_3$CN containing 0.1% TFA). The desired fraction was neutralized with saturated aqueous NaHCO$_3$ solution and extracted with EtOAc. The organic layer was separated, dried over MgSO$_4$ and concentrated under reduced pressure to give the titled compound (20.0 mg) as a white solid.

$^1$H NMR (300 MHz, DMSO-d$_6$) δ 9.40 (s, 1H), 9.08 (d, J=1.47 Hz, 1H), 8.42-8.50 (m, 2H), 8.39 (s, 1H), 8.16 (d, J=6.79 Hz, 1H), 8.05 (d, J=9.63 Hz, 1H), 7.85 (dd, J=2.15, 8.21 Hz, 1H), 7.72 (ddd, J=2.16, 4.42, 8.55 Hz, 1H), 7.42 (dd, J=8.62, 11.00 Hz, 1H), 5.05-5.15 (m, 1H), 4.87-4.95 (m, 1H), 4.77-4.86 (m, 1H), 1.38 (d, J=6.33 Hz, 3H); MS m/z 458.1 [M+H]$^+$.

Example 271

2-[6-(3-{[(2S)-1-(1H-tetrazol-1-yl)propan-2-yl]oxy}phenyl)imidazo[1,2-b]pyridazin-3-yl]pyridine-3-carbonitrile In a sealed tube, a mixture of 1-[(2S)-2-(3-{3-bromoimidazo[1,2-b]pyridazin-6-yl}phenoxy)propyl]-1H-tetrazole (200 mg), 2-chloropyridine-3-carbonitrile (206 mg), cataCXium® A (71.6 mg), CsF (226 mg), Pd(OAc)$_2$ (22.4 mg) and (Bpin)$_2$ (253 mg) in THF (5.0 mL) and water (0.50 mL) was stirred at 120° C. for 4 hr. The mixture was diluted with EtOAc (50 mL) and water (10 mL) and then the insoluble material was removed by filtration. The organic layer was separated, washed with aqueous NH$_4$Cl solution and brine, dried over MgSO$_4$ and concentrated under reduced pressure. The residue was purified by silica gel column chromatography (NH, MeOH/EtOAc) and crystallized from EtOAc four times to give the titled compound (72.0 mg) as a white solid.

$^1$H NMR (300 MHz, CDCl$_3$) δ 9.00-8.94 (m, 1H), 8.89-8.86 (m, 1H), 8.36-8.33 (m, 1H), 8.31-8.24 (m, 1H), 8.18-8.11 (m, 1H), 8.06-7.99 (m, 1H), 7.87-7.79 (m, 1H), 7.56-7.49 (m, 2H), 7.25-7.17 (m, 1H), 4.95-4.81 (m, 3H), 4.75-4.63 (m, 1H), 1.44 (d, J=6.4 Hz, 3H); MS m/z 424.2 [M+H]$^+$.

Example 275

3-[6-(4-fluoro-3-{[(2S)-1-(1H-tetrazol-1-yl)propan-2-yl]oxy}phenyl)imidazo[1,2-b]pyridazin-3-yl]pyridine-4-carbonitrile The reaction and purification were performed according to Example 121 Step C to give the titled compound.

$^1$H NMR (300 MHz, CDCl$_3$) δ 9.29 (d, J=0.73 Hz, 1H), 8.87 (s, 1H), 8.82-8.86 (m, 1H), 8.23-8.28 (m, 1H), 8.12-8.20 (m, 1H), 7.77-7.83 (m, 1H), 7.62-7.67 (m, 1H), 7.49-7.59 (m, 2H), 7.18-7.25 (m, 1H), 4.80-4.91 (m, 2H), 4.65-4.75 (m, 1H), 1.45 (d, J=6.24 Hz, 3H); MS m/z 442.2 [M+H]$^+$.

Example 284

2-[5-(3-{[(2S)-1-(1H-tetrazol-1-yl)propan-2-yl]oxy}phenyl)-3H-imidazo[4,5-b]pyridin-3-yl]pyridine-3-carbonitrile

A) 2-[(6-bromo-3-nitropyridin-2-yl)amino]pyridine-3-carbonitrile

To a cold mixture of 2,6-dibromo-3-nitropyridine (3.02 g) and 2-aminopyridine-3-carbonitrile (1.27 g) in THF (30 mL) was added portionwise 60% NaH in oil (638 mg) at 5° C. The mixture was stirred under argon atmosphere at room temperature for 1 hr. The mixture was poured into water at 0° C. and extracted with EtOAc. The organic layer was separated, washed with brine, dried over MgSO$_4$ and concentrated under reduced pressure. The residue was crystallized from THF/EtOAc to give the titled compound (2.43 g).

$^1$H NMR (300 MHz, CDCl$_3$) δ 10.07-10.19 (m, 1H), 8.62-8.68 (m, 1H), 8.32-8.41 (m, 1H), 8.03-8.10 (m, 1H), 7.28-7.34 (m, 1H), 7.17-7.22 (m, 1H); MS m/z 320.9 [M+H]$^+$.

B) 2-[(3-amino-6-bromopyridin-2-yl)amino]pyridine-3-carbonitrile

To a mixture of 2-[(6-bromo-3-nitropyridin-2-yl)amino]pyridine-3-carbonitrile (2.42 g) and saturated aqueous NH₄Cl solution (15 mL) in THF (20 mL) and EtOH (10 mL) was added iron powder (8.43 g). The mixture was stirred at 50° C. for 4 hr. The mixture was filtered through a Celite® pad and the filtrate was extracted with EtOAc. The organic layer was separated, washed with water and brine, dried over MgSO₄ and concentrated under reduced pressure to give the crude titled compound (2.20 g). The crude product was used for the next step without further purification.

¹H NMR (300 MHz, CDCl₃) δ 8.32-8.38 (m, 1H), 7.80-7.89 (m, 1H), 7.16-7.25 (m, 2H), 7.00-7.08 (m, 1H), 6.86-6.92 (m, 1H), 4.00-4.09 (m, 2H); MS m/z 290.9 [M+H]⁺.

C) 2-{5-bromo-3H-imidazo[4,5-b]pyridin-3-yl}pyridine-3-carbonitrile

A mixture of 2-[(3-amino-6-bromopyridin-2-yl)amino]pyridine-3-carbonitrile (2.18 g), triethyl orthoformate (55.5 g) and TsOH·H₂O (570 mg) in THF (7.0 mL) was stirred at 100° C. for 1 hr. The mixture was concentrated under reduced pressure at 50-60° C. The residue was dissolved in hot water (100 mL), EtOAc (100 mL) and THF (100 mL). The organic layer was separated, washed with water and brine, dried over MgSO₄ and concentrated under reduced pressure and crystallized from EtOAc to give the titled compound (1.98 g).

¹H NMR (300 MHz, DMSO-d₆) δ 9.00 (dd, J=1.8, 4.9 Hz, 1H), 8.94 (s, 1H), 8.74 (dd, J=1.8, 7.8 Hz, 1H), 8.27 (d, J=8.4 Hz, 1H), 7.89 (dd, J=5.0, 7.9 Hz, 1H), 7.67 (d, J=8.4 Hz, 1H); MS m/z 300.0 [M+H]⁺.

D) 2-[5-(3-{[(2S)-1-(1H-tetrazol-1-yl)propan-2-yl]oxy}phenyl)-3H-imidazo[4,5-b]pyridin-3-yl]pyridine-3-carbonitrile To a mixture of 2-{5-bromo-3H-imidazo[4,5-b]pyridin-3-yl}pyridine-3-carbonitrile (200 mg), 1-[(2S)-2-[3-(4,4,5,5-tetramethyl-1,3,2-dioxaborolan-2-yl)phenoxy]propyl]-1H-tetrazole (264 mg) and Cs₂CO₃ (325 mg) in THF (5.0 mL) and water (1.0 mL) was added Pd(dppf)Cl₂ (54.5 mg). The mixture was stirred under microwave irradiation at 100° C. for 1 hr. The mixture was quenched with water at room temperature and extracted with EtOAc. The organic layer was separated, washed with water and brine, dried over MgSO₄ and concentrated under reduced pressure. The residue was purified by silica gel column chromatography (NH, EtOAc/hexane) and crystallized from EtOAc to give the titled compound (112 mg) as an off-white solid.

¹H NMR (300 MHz, CDCl₃) δ 8.79-8.87 (m, 2H), 8.64-8.68 (m, 1H), 8.44-8.50 (m, 1H), 8.19-8.27 (m, 1H), 7.84-7.90 (m, 1H), 7.74-7.81 (m, 1H), 7.56-7.64 (m, 2H), 7.33-7.43 (m, 1H), 6.87-6.96 (m, 1H), 4.88-5.05 (m, 1H), 4.76-4.86 (m, 1H), 4.61-4.71 (m, 1H), 1.39 (d, J=6.2 Hz, 3H); MS m/z 424.2 [M+H]⁺.

Example 288

4-fluoro-2-[6-(5-{[(2S)-1-(1H-tetrazol-1-yl)propan-2-yl]oxy}pyridin-3-yl)imidazo[1,2-b]pyridazin-3-yl]benzonitrile hydrochloride 2N aqueous HCl solution (0.40 mL) was added to a suspension of 4-fluoro-2-[6-(5-{[(2S)-1-(1H-tetrazol-1-yl)propan-2-yl]oxy}pyridin-3-yl)imidazo[1,2-b]pyridazin-3-yl]benzonitrile (157 mg) in EtOH (5.0 mL) at room temperature. The mixture was slightly warmed for a while and the resulting mixture was cooled to room temperature and then concentrated under reduced pressure to give the titled compound (139 mg) as a light yellow solid.

¹H NMR (300 MHz, DMSO-d₆) δ 9.47 (s, 1H), 8.89 (d, J=1.7 Hz, 1H), 8.50 (d, J=9.5 Hz, 1H), 8.45 (d, J=2.7 Hz, 1H), 8.37 (s, 1H), 8.22 (dd, J=5.7, 8.8 Hz, 1H), 8.16-8.08 (m, 2H), 8.08-8.04 (m, 1H), 7.59 (dt, J=2.7, 8.5 Hz, 1H), 5.16 (dt, J=3.2, 6.3 Hz, 1H), 4.96-4.89 (m, 1H), 4.85-4.77 (m, 1H), 1.36 (d, J=6.1 Hz, 3H); MS m/z 442.2 [M+H]⁺.

Example 289

6-methoxy-4-[6-(3-{[(2S)-1-(1H-tetrazol-1-yl)propan-2-yl]oxy}phenyl)imidazo[1,2-b]pyridazin-3-yl]pyridine-3-carbonitrile A) (5-cyano-2-methoxypyridin-4-yl)boronic acid To a mixture of 6-methoxypyridine-3-carbonitrile (500 mg) in THF (10 mL) was added 2M lithium diisopropylamide heptane solution (2.2 mL) at −78° C. After being stirred at −78° C. for 30 min, triisopropyl borate (1.40 g) was added to the mixture. The mixture was stirred at 20° C. for 30 min. The mixture was quenched with water and washed with PE. The aqueous layer was adjusted to pH 6 by addition of 1M aqueous HCl solution and extracted with EtOAc. The organic layer was washed with brine, dried over Na₂SO₄ and concentrated under reduced pressure to give the titled compound (422 mg).

MS m/z 179.0 [M+H]⁺.

B) 6-methoxy-4-[6-(3-{[(2S)-1-(1H-tetrazol-1-yl)propan-2-yl]oxy}phenyl)imidazo[1,2-b]pyridazin-3-yl]pyridine-3-carbonitrile The reaction and purification were performed according to Example 121 Step C to give the titled compound.

¹H NMR (400 MHz, CDCl₃) δ 8.78 (s, 1H), 8.67 (s, 1H), 8.52 (s, 1H), 8.16 (d, J=5.6 Hz, 1H), 7.73 (s, 1H), 7.63 (d, J=9.6 Hz, 1H), 7.56-7.62 (m, 1H), 7.48-7.55 (m, 1H), 7.45 (t, J=8.0 Hz, 1H), 6.98 (dd, J=8.4, 2.0 Hz, 1H), 4.89-4.99 (m, 1H), 4.75-4.87 (m, 1H), 4.61-4.72 (m, 1H), 4.08 (s, 3H), 1.45 (d, J=6.0 Hz, 3H); MS m/z 454.3 [M+H]⁺.

Example 291

4-fluoro-2-[5-(3-{[(2S)-1-(1H-tetrazol-1-yl)propan-2-yl]oxy}phenyl)-3H-imidazo[4,5-b]pyridin-3-yl]benzonitrile A) 2-[(6-bromo-3-nitropyridin-2-yl)amino]-4-fluorobenzonitrile To a mixture of 2-amino-4-fluorobenzonitrile (1.05 g) and 2,6-dibromo-3-nitropyridine (2.60 g) in THF (20 mL) was added 60% NaH in oil (1.10 g) at 5° C. The mixture was stirred under nitrogen atmosphere at room temperature for 1 hr. The mixture was quenched with saturated aqueous NH₄Cl solution (50 mL) at 5° C. and extracted with EtOAc. The organic layer was separated, washed with brine, dried over MgSO₄ and concentrated under reduced pressure to give the titled compound (1.29 g).

¹H NMR (300 MHz, CDCl₃) δ 10.97-10.83 (m, 1H), 8.43 (d, J=8.5 Hz, 1H), 8.39-8.30 (m, 1H), 7.73-7.64 (m, 1H), 7.20 (d, J=8.5 Hz, 1H), 7.01-6.91 (m, 1H).

B) 2-[(3-amino-6-bromopyridin-2-yl)amino]-4-fluorobenzonitrile

To a mixture of 2-[(6-bromo-3-nitropyridin-2-yl)amino]-4-fluorobenzonitrile (1.28 g) and saturated aqueous NH₄Cl solution (15 mL) in THF (10 mL) and EtOH (5.0 mL) was added iron (4.23 g). The mixture was stirred at 50° C. for 3 hr. The mixture was filtered through a Celite® pad and the filtrate was extracted with EtOAc. The organic layer was separated, washed with water and brine, dried over MgSO$_4$ and concentrated under reduced pressure to give the crude titled compound (1.16 g). The crude product was used for the next step without further purification.

MS m/z 307.0 [M+H]$^+$.

C) 2-{5-bromo-3H-imidazo[4,5-b]pyridin-3-yl}-4-fluorobenzonitrile

A mixture of 2-[(3-amino-6-bromopyridin-2-yl)amino]-4-fluorobenzonitrile (1.16 g), triethyl orthoformate (16.7 g) and TsOH·H$_2$O (0.290 g) in THF (4.0 mL) was stirred at 100° C. for 1 hr. The mixture was concentrated under reduced pressure at 50-60° C. The residue was dissolved in hot water and EtOAc. The organic layer was separated, washed with water and brine, dried over MgSO$_4$ and concentrated under reduced pressure. The residue was purified by silica gel column chromatography (EtOAc/hexane) to give the titled compound (0.440 g).

$^1$H NMR (300 MHz, CDCl$_3$) δ 8.40-8.36 (m, 1H), 8.06 (d, J=8.3 Hz, 1H), 7.96-7.88 (m, 1H), 7.56 (s, 2H), 7.40-7.31 (m, 1H).

D) 4-fluoro-2-[5-(3-{[(2S)-1-(1H-tetrazol-1-yl)propan-2-yl]oxy}phenyl)-3H-imidazo[4,5-b]pyridin-3-yl]benzonitrile The reaction and purification were performed according to Example 284 Step D to give the titled compound.

$^1$H NMR (300 MHz, CDCl$_3$) δ 8.77 (s, 1H), 8.45 (s, 1H), 8.25 (d, J=8.4 Hz, 1H), 8.06-7.95 (m, 1H), 7.84-7.76 (m, 1H), 7.70-7.56 (m, 3H), 7.43-7.31 (m, 2H), 6.94-6.83 (m, 1H), 4.96-4.74 (m, 2H), 4.69-4.58 (m, 1H), 1.41 (d, J=6.1 Hz, 3H); MS m/z 441.1 [M+H]$^+$.

Example 298

4-fluoro-2-[6-(5-{[(2S)-1-(1H-tetrazol-1-yl)propan-2-yl]oxy}pyridazin-3-yl)imidazo[1,2-b]pyridazin-3-yl]benzonitrile A) 3-chloro-5-{[(2S)-1-(1H-tetrazol-1-yl)propan-2-yl]oxy}pyridazine The reaction and purification were performed according to Example 326 Step B to give the titled compound.

$^1$H NMR (300 MHz, CDCl$_3$) δ 8.78 (d, J=2.7 Hz, 1H), 8.73 (s, 1H), 6.90 (d, J=2.7 Hz, 1H), 5.03 (ttd, J=3.3, 6.5, 10.0 Hz, 1H), 4.86-4.65 (m, 2H), 1.51 (d, J=6.2 Hz, 3H); MS m/z 241.1 [M+H]$^+$.

B) 3-{imidazo[1,2-b]pyridazin-6-yl}-5-{[(2S)-1-(1H-tetrazol-1-yl)propan-2-yl]oxy}pyridazine A mixture of 3-chloro-5-{[(2S)-1-(1H-tetrazol-1-yl)propan-2-yl]oxy}pyridazine (70.0 mg), 6-chloroimidazo[1,2-b]pyridazine (100 mg), CsF (314 mg), Pd(OAc)$_2$ (18.6 mg), cataCXium® A (59.5 mg) and (Bpin)$_2$ (525 mg) in water (0.30 mL) and THF (3.0 mL) was stirred under microwave irradiation at 100° C. for 2 hr. The mixture was quenched with water at room temperature and extracted with EtOAc. The organic layer was separated, washed with brine, dried over MgSO$_4$ and concentrated under reduced pressure. To a solution of the residue in acetone (6.0 mL) was added manganese dioxide (360 mg). The mixture was stirred at room temperature for 14 hr. The insoluble material was removed by filtration and the filtrate was concentrated under reduced pressure. The residue was purified by silica gel column chromatography (MeOH/EtOAc) to give the titled compound (29.0 mg).

MS m/z 324.0 [M+H]$^+$.

C) 3-{3-bromoimidazo[1,2-b]pyridazin-6-yl}-5-{[(2S)-1-(1H-tetrazol-1-yl)propan-2-yl]oxy}pyridazine The reaction and purification were performed according to Example 121 Step B to give the titled compound.

MS m/z 402.1, 404.1 [M+H]$^+$.

D) 4-fluoro-2-[6-(5-{[(2S)-1-(1H-tetrazol-1-yl)propan-2-yl]oxy}pyridazin-3-yl)imidazo[1,2-b]pyridazin-3-yl]benzonitrile The reaction and purification were performed according to Example 121 Step C to give the titled compound.

$^1$H NMR (300 MHz, CD$_3$OD) δ 9.31 (s, 1H), 9.02 (d, J=2.9 Hz, 1H), 8.52-8.44 (m, 1H), 8.40-8.32 (m, 2H), 8.16-7.98 (m, 3H), 7.48 (dt, J=2.7, 8.3 Hz, 1H), 5.38-5.24 (m, 1H), 5.02-4.92 (m, 2H), 1.53 (d, J=6.2 Hz, 3H); MS m/z 443.2 [M+H]$^+$.

Example 300

4-methoxy-2-[6-(3-{[(2S)-1-(1H-tetrazol-1-yl)propan-2-yl]oxy}phenyl)imidazo[1,2-b]pyridazin-3-yl]pyridine-3-carbonitrile A mixture of 1-[(2S)-2-(3-{3-bromoimidazo[1,2-b]pyridazin-6-yl}phenoxy)propyl]-1H-tetrazole (120 mg), 2-chloro-4-methoxypyridine-3-carbonitrile (151 mg), cataCXium® A (42.9 mg), CsF (136 mg), Pd(OAc)$_2$ (13.4 mg) and (Bpin)$_2$ (228 mg) in water (0.50 mL) and THF (5.0 mL) was stirred under microwave irradiation at 120° C. for 4 hr. The mixture was poured into water and extracted with EtOAc. The organic layer was separated, washed with saturated aqueous NH$_4$Cl solution and brine, dried over MgSO$_4$ and concentrated under reduced pressure. The residue was purified by silica gel column chromatography (NH, MeOH/EtOAc) and crystallized from EtOAc/IPE to give the crude titled compound. The crude product was further purified by silica gel column chromatography (NH, MeOH/EtOAc) to the titled compound (40.0 mg) as a white solid.

$^1$H NMR (300 MHz, CDCl$_3$) δ 8.80 (s, 1H), 8.78-8.73 (m, 1H), 8.33-8.29 (m, 1H), 8.18-8.11 (m, 1H), 7.86-7.82 (m, 1H), 7.60-7.54 (m, 1H), 7.53-7.46 (m, 1H), 7.45-7.38 (m, 1H), 7.02-6.94 (m, 2H), 5.06-4.92 (m, 1H), 4.89-4.80 (m, 1H), 4.75-4.65 (m, 1H), 4.13 (s, 3H), 1.41 (d, J=6.2 Hz, 3H); MS m/z 454.1 [M+H]$^+$.

Example 305

4-fluoro-2-[5-(6-{[(2S)-1-(1H-tetrazol-1-yl)propan-2-yl]oxy}pyrimidin-4-yl)-3H-imidazo[4,5-b]pyridin-3-yl]benzonitrile A mixture of 4-chloro-6-{[(2S)-1-(1H-tetrazol-1-yl)propan-2-yl]oxy}pyrimidine (113 mg), 2-{5-bromo-3H-imidazo[4,5-b]pyridin-3-yl}-4-fluorobenzonitrile (30.0 mg), cataCXium® A (13.5 mg), CsF (71.8 mg), Pd(OAc)$_2$ (4.2 mg) and (Bpin)$_2$ (120 mg) in water (0.20 mL) and THF (2.5 mL) was stirred under microwave irradiation at 80° C. for 2 hr. The mixture was poured into water and extracted with EtOAc. The organic layer was separated, washed with saturated aqueous NH$_4$Cl solution and brine, dried over MgSO$_4$ and concentrated under reduced pressure. The residue was purified by silica gel column chromatography (NH, EtOAc/hexane) to give the titled compound (10.0 mg) as an off-white solid.

$^1$H NMR (300 MHz, CDCl$_3$) δ 8.81 (d, J=0.80 Hz, 1H), 8.68 (s, 1H), 8.64-8.57 (m, 1H), 8.49 (s, 1H), 8.36-8.30 (m, 1H), 8.04-7.96 (m, 1H), 7.67-7.58 (m, 2H), 7.47-7.35 (m, 1H), 5.87-5.72 (m, 1H), 4.88-4.79 (m, 1H), 4.78-4.67 (m, 1H), 1.43 (d, J=6.4 Hz, 3H); MS m/z 443.1 [M+H]$^+$.

Example 311

4-fluoro-2-[6-(4-{[(2S)-1-(1H-tetrazol-1-yl)propan-2-yl]oxy}pyridin-2-yl)imidazo[1,2-b]pyridazin-3-yl]benzonitrile A) 2-chloro-4-{[(2S)-1-(1H-tetrazol-1-yl)propan-2-yl]oxy}pyridine The reaction and purification were performed according to Example 326 Step B to give the titled compound.

$^1$H NMR (300 MHz, DMSO-d$_6$) δ 9.43 (s, 1H), 8.18 (d, J=5.8 Hz, 1H), 7.13 (d, J=2.2 Hz, 1H), 6.98 (dd, J=2.3, 5.8 Hz, 1H), 5.20-5.07 (m, 1H), 4.91-4.83 (m, 1H), 4.81-4.70 (m, 1H), 1.29 (d, J=6.1 Hz, 3H); MS m/z 240.0 [M+H]$^+$.

B) 2-{imidazo[1,2-b]pyridazin-6-yl}-4-{[(2S)-1-(1H-tetrazol-1-yl)propan-2-yl]oxy}pyridine The reaction and purification were performed according to Example 298 Step B to give the titled compound.
MS m/z 323.0 [M+H]$^+$.

C) 2-{3-bromoimidazo[1,2-b]pyridazin-6-yl}-4-{[(2S)-1-(1H-tetrazol-1-yl)propan-2-yl]oxy}pyridine The reaction and purification were performed according to Example 121 Step B to give the titled compound.

$^1$H NMR (300 MHz, DMSO-d$_6$) δ 9.51 (s, 1H), 8.58 (d, J=5.8 Hz, 1H), 8.32-8.27 (m, 1H), 8.19-8.14 (m, 1H), 8.01 (s, 1H), 7.79 (d, J=2.5 Hz, 1H), 7.20 (dd, J=2.6, 5.8 Hz, 1H), 5.30-5.16 (m, 1H), 4.98-4.89 (m, 1H), 4.88-4.78 (m, 1H), 1.38 (d, J=6.1 Hz, 3H); MS m/z 401.0, 403.0 [M+H]$^+$.

D) 4-fluoro-2-[6-(4-{[(2S)-1-(1H-tetrazol-1-yl)propan-2-yl]oxy}pyridin-2-yl)imidazo[1,2-b]pyridazin-3-yl]benzonitrile The reaction and purification were performed according to Example 121 Step C to give the titled compound.

$^1$H NMR (300 MHz, CDCl$_3$) δ 8.73 (s, 1H), 8.54 (d, J=5.7 Hz, 1H), 8.39-8.28 (m, 2H), 8.23-8.13 (m, 1H), 7.98-7.90 (m, 2H), 7.85 (d, J=2.5 Hz, 1H), 7.32-7.27 (m, 1H), 6.85 (dd, J=2.6, 5.7 Hz, 1H), 5.11-4.97 (m, 1H), 4.87-4.78 (m, 1H), 4.76-4.65 (m, 1H), 1.50 (d, J=6.2 Hz, 3H); MS m/z 442.1 [M+H]$^+$.

Example 313

6-methoxy-2-[6-(3-{[(2S)-1-(1H-tetrazol-1-yl)propan-2-yl]oxy}phenyl)imidazo[1,2-b]pyridazin-3-yl]pyridine-3-carbonitrile A) 2-chloro-6-methoxynicotinonitrile To a solution of 2,6-dichloronicotinonitrile (2.50 g) in MeOH (65 mL) was added slowly a solution of NaOMe (781 mg) in MeOH (15 mL). The mixture was stirred at 15° C. for 16 hr. The mixture was concentrated under reduced pressure. The residue was diluted with EtOAc, washed with water and brine, dried over Na$_2$SO$_4$ and concentrated under reduced pressure. The residue was purified by silica gel column chromatography (EtOAc/PE) to give the titled compound (675 mg).

$^1$H NMR (400 MHz, CDCl$_3$) δ 7.79 (d, J=8.4 Hz, 1H), 6.76 (d, J=8.8 Hz, 1H), 4.01 (s, 3H); MS m/z 169.1 [M+H]$^+$.

B) 6-methoxy-2-[6-(3-{[(2S)-1-(1H-tetrazol-1-yl)propan-2-yl]oxy}phenyl)imidazo[1,2-b]pyridazin-3-yl]pyridine-3-carbonitrile The reaction and purification were performed according to Example 321 to give the titled compound.

$^1$H NMR (300 MHz, CDCl$_3$) δ 8.79 (s, 1H), 8.32 (s, 1H), 8.14 (d, J=9.5 Hz, 1H), 8.04 (d, J=8.7 Hz, 1H), 7.79-7.73 (m, 1H), 7.61-7.52 (m, 2H), 7.46-7.36 (m, 1H), 7.00-6.92 (m, 1H), 6.91-6.84 (m, 1H), 5.03-4.89 (m, 1H), 4.87-4.76 (m, 1H), 4.71-4.59 (m, 1H), 4.04 (s, 3H), 1.41 (d, J=6.1 Hz, 3H); MS m/z 454.2 [M+1]$^+$.

Example 320

4-methoxy-6-[6-(3-{[(2S)-1-(1H-tetrazol-1-yl)propan-2-yl]oxy}phenyl)imidazo[1,2-b]pyridazin-3-yl]pyrimidine-5-carbonitrile A) 4-chloro-6-methoxypyrimidine-5-carbonitrile Sodium (0.170 g, cube) was added to MeOH (10 mL) at room temperature. After completely dissolved, the solution was slowly added to a mixture of 4,6-dichloropyrimidine-5-carbonitrile (1.30 g) in MeOH (10 mL) and THF (10 mL) at 5° C. The mixture was stirred under argon atmosphere at 5° C. to room temperature for 4 hr. The mixture was poured into EtOAc (50 mL) and water (50 mL). The organic layer was separated, washed with saturated aqueous NH$_4$Cl solution and brine, dried over MgSO$_4$ and concentrated under reduced pressure. The residue was washed with IPE to give the crude titled compound (0.560 g). The crude product was used for the next step without further purification.

$^1$H NMR (300 MHz, CDCl$_3$) δ 8.73-8.67 (m, 1H), 4.17 (s, 3H).

B) 4-methoxy-6-[6-(3-{[(2S)-1-(1H-tetrazol-1-yl)propan-2-yl]oxy}phenyl)imidazo[1,2-b]pyridazin-3-yl]pyrimidine-5-carbonitrile The reaction and purification were performed according to Example 321 to give the titled compound.

$^1$H NMR (300 MHz, CDCl$_3$) δ 8.98 (s, 1H), 8.81 (s, 1H), 8.47 (s, 1H), 8.17 (d, J=9.5 Hz, 1H), 7.89-7.84 (m, 1H), 7.68-7.62 (m, 1H), 7.56-7.49 (m, 1H), 7.46-7.39 (m, 1H), 7.03-6.94 (m, 1H), 5.07-4.94 (m, 1H), 4.89-4.81 (m, 1H), 4.75-4.64 (m, 1H), 4.24 (s, 3H), 1.43 (d, J=6.2 Hz, 3H); MS m/z 455.1 [M+H]$^+$.

Example 321

2-[6-(4-fluoro-3-{[(2S)-1-(1H-tetrazol-1-yl)propan-2-yl]oxy}phenyl)imidazo[1,2-b]pyridazin-3-yl]-4-methoxypyridine-3-carbonitrile A mixture of 1-[(2S)-2-(5-{3-bromoimidazo[1,2-b]pyridazin-6-yl}-2-fluorophenoxy)propyl]-1H-tetrazole (380 mg), 2-chloro-4-methoxypyridine-3-carbonitrile (305 mg), cataCXium® A (130 mg), CsF (413 mg), Pd(OAc)$_2$ (40.7 mg) and (Bpin)$_2$ (690 mg) in water (2.0 mL) and THF (20 mL) was stirred at 120° C. for 4 hr in a sealed tube. The mixture was poured into water and extracted with EtOAc. The organic layer was separated, washed with saturated aqueous NH$_4$Cl solution and brine, dried over MgSO$_4$ and concentrated under reduced pressure. The residue was purified by silica gel column chromatography (NH, MeOH/EtOAc) and crystallized from EtOAc/IPE to give the titled compound (97.0 mg) as an off-white solid.

$^1$H NMR (300 MHz, CDCl$_3$) δ 8.89 (s, 1H), 8.76 (d, J=6.1 Hz, 1H), 8.31 (s, 1H), 8.13 (d, J=9.5 Hz, 1H), 7.97 (dd, J=2.0, 8.1 Hz, 1H), 7.53 (d, J=9.5 Hz, 1H), 7.49-7.42 (m, 1H), 7.23-7.16 (m, 1H), 6.99 (d, J=6.1 Hz, 1H), 5.03-4.91 (m, 1H), 4.90-4.81 (m, 1H), 4.80-4.66 (m, 1H), 4.13 (s, 3H), 1.45 (d, J=6.2 Hz, 3H); MS m/z 472.1 [M+H]$^+$.

Example 325

4-fluoro-2-[6-(6-{[(2S)-1-(1H-tetrazol-1-yl)propan-2-yl]oxy}pyridin-2-yl)imidazo[1,2-b]pyridazin-3-yl]benzonitrile A) tert-butyl N-[(2R)-2-[(4-methylbenzenesulfonyl)oxy]propyl]carbamate To a mixture of tert-butyl N-[(2R)-2-hydroxypropyl]carbamate (22.6 g) in pyridine (100 mL) was added TsCl (26.6 g) at 25° C. The mixture was stirred at room temperature for 14 hr. The mixture was poured into water (500 mL) at room temperature and the stirring was continued for 2 hr. The precipitate was collected by filtration. The solid was dissolved in EtOAc (200 mL) and washed with water and saturated aqueous NH$_4$Cl solution, dried over MgSO$_4$ and concentrated under reduced pressure. The residue was triturated with hexane to give the titled compound (30.6 g).

$^1$H NMR (300 MHz, CDCl$_3$) δ 7.80 (d, J=8.3 Hz, 2H), 7.39-7.31 (m, 2H), 4.85-4.72 (m, 1H), 4.70-4.60 (m, 1H), 3.45-3.29 (m, 1H), 3.21-3.09 (m, 1H), 2.45 (s, 3H), 1.41 (s, 9H), 1.22 (d, J=6.4 Hz, 3H).

B) tert-butyl N-[(2S)-2-[(6-bromopyridin-2-yl)oxy]propyl]carbamate

A mixture of 6-bromopyridin-2-ol (200 mg), tert-butyl N-[(2R)-2-[(4-methylbenzenesulfonyl)oxy]propyl]carbamate (751 mg) and K$_2$CO$_3$ (472 mg) in DMA (1.2 mL) was stirred at 65° C. for 14 hr. The mixture was poured into water and extracted with EtOAc. The organic layer was separated, washed with saturated aqueous NH$_4$Cl solution and brine, dried over MgSO$_4$ and concentrated under reduced pressure. The residue was purified by silica gel column chromatography (EtOAc/hexane) to give the titled compound (341 mg).

$^1$H NMR (300 MHz, CDCl$_3$) δ 7.41 (dd, J=7.6, 8.1 Hz, 1H), 7.08-7.01 (m, 1H), 6.68-6.60 (m, 1H), 5.32-5.16 (m, 1H), 4.97-4.82 (m, 1H), 3.54-3.41 (m, 1H), 3.39-3.23 (m, 1H), 1.43 (s, 9H), 1.32 (d, J=6.3 Hz, 3H).

C) (2S)-2-[(6-bromopyridin-2-yl)oxy]propan-1-amine hydrochloride

To a mixture of tert-butyl N-[(2S)-2-[(6-bromopyridin-2-yl)oxy]propyl]carbamate (0.680 g) in EtOAc (2.0 mL) was added 4M HCl in EtOAc solution (2.0 mL). The mixture was stirred at 55° C. for 1 hr. After cooling, the precipitate was collected by filtration to give the titled compound (360 mg).

The filtrate was concentrated under reduced pressure to give the crude titled product (300 mg).

$^1$H NMR (300 MHz, DMSO-d$_6$) δ 8.26-8.00 (m, 3H), 7.77-7.66 (m, 1H), 7.32-7.21 (m, 1H), 6.87 (s, 1H), 5.34-5.16 (m, 1H), 3.24-3.00 (m, 2H), 1.31 (d, J=6.2 Hz, 3H).

D) N-[(2S)-2-[(6-bromopyridin-2-yl)oxy]propyl]formamide

To a mixture of (2S)-2-[(6-bromopyridin-2-yl)oxy]propan-1-amine hydrochloride (350 mg) in ethyl formate (3.5 mL) was added TEA (0.27 mL). The mixture was stirred under argon atmosphere at 45° C. for 4 hr. After cooling, EtOH (1.0 mL) and water (3.5 mL) were added thereto. The mixture was concentrated under reduced pressure and partitioned with EtOAc and water. The organic layer was separated, washed with saturated aqueous NH$_4$Cl solution and brine, dried over MgSO$_4$ and concentrated under reduced pressure. The residue was purified by silica gel column chromatography (EtOAc/hexane) to give the titled compound (320 mg).

$^1$H NMR (300 MHz, CDCl$_3$) δ 8.20 (s, 1H), 7.43 (d, J=0.6 Hz, 1H), 7.11-7.02 (m, 1H), 6.70-6.64 (m, 1H), 6.46-6.29 (m, 1H), 5.26 (dt, J=3.4, 6.6 Hz, 1H), 3.74-3.60 (m, 1H), 3.54-3.41 (m, 1H), 1.38-1.30 (m, 3H).

E) 2-bromo-6-{[(2S)-1-(1H-tetrazol-1-yl)propan-2-yl]oxy}pyridine

To a mixture of N-[(2S)-2-[(6-bromopyridin-2-yl)oxy]propyl]formamide (4.70 g) and TEA (7.6 mL) in THF (45 mL) was added POCl$_3$ (2.7 mL) at 5° C. The mixture was stirred at 5° C. for 2 hr. The mixture was quenched with saturated aqueous NaHCO$_3$ solution at 0° C. and extracted with EtOAc. The organic layer was separated, washed with brine, dried over MgSO$_4$ and concentrated under reduced pressure. To a mixture of the residue in TFE (45 mL) was added trimethylsilyl azide (3.6 mL) at room temperature. The mixture was stirred at 60° C. for 2 hr. Additional trimethylsilyl azide (1.2 mL) was added to the mixture at room temperature. The mixture was stirred at 60° C. for 1 hr. The mixture was quenched with saturated aqueous NaHCO$_3$ solution at room temperature and extracted with EtOAc. The organic layer was separated, washed with brine, dried over MgSO$_4$ and concentrated under reduced pressure. The residue was purified by silica gel column chromatography (EtOAc/hexane) to give the titled compound (5.13 g).

$^1$H NMR (300 MHz, CDCl$_3$) δ 8.67 (s, 1H), 7.51-7.41 (m, 1H), 7.11 (dd, J=0.6, 7.5 Hz, 1H), 6.67 (dd, J=0.6, 8.2 Hz, 1H), 5.63-5.50 (m, 1H), 4.84-4.60 (m, 2H), 1.39 (d, J=6.4 Hz, 3H).

F) 2-{imidazo[1,2-b]pyridazin-6-yl}-6-{[(2S)-1-(1H-tetrazol-1-yl)propan-2-yl]oxy}pyridine The reaction and purification were performed according to Example 298 Step B to give the titled compound.

$^1$H NMR (300 MHz, DMSO-d$_6$) δ 9.44 (s, 1H), 8.41-8.35 (m, 1H), 8.31-8.23 (m, 1H), 8.11-7.99 (m, 1H), 7.94-7.81 (m, 3H), 6.99-6.85 (m, 1H), 5.92-5.72 (m, 1H), 5.02-4.72 (m, 2H), 1.44-1.33 (m, 3H).

G) 2-{3-bromoimidazo[1,2-b]pyridazin-6-yl}-6-{[(2S)-1-(1H-tetrazol-1-yl)propan-2-yl]oxy}pyridine The reaction and purification were performed according to Example 121 Step B to give the crude titled compound. The crude product was used to the next step without further purification.

H) 4-fluoro-2-[6-(6-{[(2S)-1-(1H-tetrazol-1-yl)propan-2-yl]oxy}pyridin-2-yl)imidazo[1,2-b]pyridazin-3-yl]benzonitrile The reaction and purification were performed according to Example 121 Step C to give the titled compound.
$^1$H NMR (300 MHz, DMSO-$d_6$) δ 9.45 (s, 1H), 8.46 (d, J=9.6 Hz, 1H), 8.83 (s, 1H), 8.18-8.25 (m, 2H), 8.04 (dd, J=10.0, 2.7 Hz, 1H), 7.90 (d, J=8.0 Hz, 1H), 7.81 (d, J=8.0 Hz, 1H), 7.58 (dt, J=8.0, 2.7 Hz, H), 6.93 (d, J=8.0 Hz, 1H), 5.80-5.87 (m, 1H), 4.78-4.97 (m, 2H), 1.40 (d, J=6.0 Hz, 3H); MS m/z 442.1 [M+H]$^+$.

Example 326

4-fluoro-2-[6-(6-{[(2S)-1-(1H-tetrazol-1-yl)propan-2-yl]oxy}pyrazin-2-yl)imidazo[1,2-b]pyridazin-3-yl]benzonitrile A) (2S)-1-(1H-tetrazol-1-yl)propan-2-ol To a mixture of 1H-tetrazole (30.0 g) and THF (30 mL) was added (S)-propylene oxide (50.0 g). After being stirred at 40° C. for 72 hr, the mixture was concentrated under reduced pressure. The residue was purified by silica gel column chromatography (EtOAc/hexane) to give a colorless oil. To a mixture of the oil and THF (100 mL), were added TBSCl (7.05 g) and imidazole (3.18 g). After being stirred at room temperature for 15 hr, the mixture was concentrated under reduced pressure. The residue was purified by silica gel column chromatography (EtOAc/hexane) to give the titled compound (22.7 g).
$^1$H NMR (300 MHz, DMSO-$d_6$) δ 9.30 (s, 1H), 5.13 (d, J=5.0 Hz, 1H), 4.46 (dd, J=13.8, 3.8 Hz, 1H), 4.30 (dd, J=13.8, 5.0 Hz, 1H), 3.94-4.04 (m, 1H), 1.09 (d, J=6.3 Hz, 3H).

B) 2-chloro-6-{[(2S)-1-(1H-tetrazol-1-yl)propan-2-yl]oxy}pyrazine

To a mixture of (2S)-1-(1H-tetrazol-1-yl)propan-2-ol (2.14 g) in THF (50 mL) was added 60% NaH in oil (798 mg). After being stirred at room temperature for 10 min, 2,6-dichloropyrazine (2.48 g) was added to the mixture. After being stirred at room temperature for 1 hr, the mixture was poured into water and extracted with EtOAc. The organic layer was separated, washed with brine, dried over MgSO$_4$ and concentrated under reduced pressure. The residue was purified by silica gel column chromatography (EtOAc/hexane) to give the titled compound (2.65 g).
MS m/z 241.0 [M+H]$^+$.

C) 2-{imidazo[1,2-b]pyridazin-6-yl}-6-{[(2S)-1-(1H-tetrazol-1-yl)propan-2-yl]oxy}pyrazine The reaction and purification were performed according to Example 298 Step B to give the titled compound.
MS m/z 324.0 [M+H]$^+$.

D) 2-{3-bromoimidazo[1,2-b]pyridazin-6-yl}-6-{[(2S)-1-(1H-tetrazol-1-yl)propan-2-yl]oxy}pyrazine The reaction and purification were performed according to Example 121 Step B to give the titled compound.
$^1$H NMR (400 MHz, DMSO-$d_6$) δ 9.48 (s, 1H), 9.06 (s, 1H), 8.44 (s, 1H), 8.39 (d, J=9.5 Hz, 1H), 8.09 (d, J=9.5 Hz, 1H), 8.06 (s, 1H), 5.90-5.78 (m, 1H), 5.02-4.94 (m, 1H), 4.91-4.82 (m, 1H), 1.43 (d, J=6.4 Hz, 3H); MS m/z 402.0, 403.9 [M+H]$^+$.

E) 4-fluoro-2-[6-(6-{[(2S)-1-(1H-tetrazol-1-yl)propan-2-yl]oxy}pyrazin-2-yl)imidazo[1,2-b]pyridazin-3-yl]benzonitrile The reaction and purification were performed according to Example 121 Step C to give the titled compound.
$^1$H NMR (300 MHz, DMSO-$d_6$) δ 9.48 (s, 1H), 8.97 (s, 1H), 8.52 (d, J=9.6 Hz, 1H), 8.40 (d, J=13.3 Hz, 2H), 8.16-8.25 (m, 2H), 8.08 (dd, J=10.0, 2.7 Hz, 1H), 7.59 (dt, J=8.5, 2.7 Hz, 1H), 5.81-5.89 (m, 1H), 4.83-5.02 (m, 2H), 1.41 (d, J=6.0 Hz, 3H). MS m/z 443.1 [M+H]$^+$.

Example 342

4-fluoro-2-[5-(2-{[(2S)-1-(1H-tetrazol-1-yl)propan-2-yl]oxy}pyrimidin-4-yl)-3H-imidazo[4,5-b]pyridin-3-yl]benzonitrile A) 4-(benzyloxy)-2-{[(2S)-1-(1H-tetrazol-1-yl)propan-2-yl]oxy}pyrimidine The reaction and purification were performed according to Example 326 Step B to give the titled compound.
MS m/z 313.2 [M+H]$^+$.

B) 2-{[(2S)-1-(1H-tetrazol-1-yl)propan-2-yl]oxy}pyrimidin-4-ol

A mixture of 4-(benzyloxy)-2-{[(2S)-1-(1H-tetrazol-1-yl)propan-2-yl]oxy}pyrimidine (2.93 g) and 10% palladium-carbon (0.300 g) in EtOH (50 mL) was stirred under hydrogen atmosphere at room temperature for 14 hr. The catalyst was removed by filtration and then the filtrate was concentrated under reduced pressure to give the titled compound (2.00 g).
MS m/z 223.2 [M+H]$^+$.

C) 2-{[(2S)-1-(1H-tetrazol-1-yl)propan-2-yl]oxy}pyrimidin-4-yl trifluoromethanesulfonate To a mixture of 2-{[(2S)-1-(1H-tetrazol-1-yl)propan-2-yl]oxy}pyrimidin-4-ol (1.71 g) in DMF (15 mL) was added 60% NaH in oil (368 mg). After being stirred at room temperature for 10 min, N-phenyltrifluoromethanesulfonimide (3.01 g) was added to the mixture. After being stirred at room temperature for 30 min, the mixture was poured into water and extracted with EtOAc. The organic layer was separated, washed with brine, dried over MgSO$_4$ and concentrated under reduced pressure to give the titled compound (2.57 g).
$^1$H NMR (300 MHz, DMSO-$d_6$) δ 9.40 (s, 1H), 8.96-8.60 (m, 1H), 7.45-7.07 (m, 2H), 5.78-5.35 (m, 1H), 5.16-4.49 (m, 2H), 1.67-0.66 (m, 3H).

D) [3-(2-cyano-5-fluorophenyl)-3H-imidazo[4,5-b]pyridin-5-yl]boronic acid

Pd(dppf)Cl$_2$ (64.3 mg) was added to a mixture of 2-{5-bromo-3H-imidazo[4,5-b]pyridin-3-yl}-4-fluorobenzonitrile (250 mg), (Bpin)$_2$ (398 mg) and KOAc (154 mg) in toluene (5.0 mL). After being stirred under nitrogen atmosphere at 100° C. for 2 hr, the insoluble material was removed by filtration. The filtrate was concentrated under reduced pressure to give the crude titled compound (220 mg). The crude product was used for the next step without further purification.
MS m/z 282.9 [M+H]$^+$.

E) 4-fluoro-2-[5-(2-{[(2S)-1-(1H-tetrazol-1-yl)propan-2-yl]oxy}pyrimidin-4-yl)-3H-imidazo[4,5-b]pyridin-3-yl]benzonitrile The reaction and purification were performed according to Example 393 Step F to give the titled compound.
$^1$H NMR (300 MHz, DMSO-d$_6$) δ 9.43 (s, 1H), 9.02 (s, 1H), 8.66 (d, J=5.0 Hz, 1H), 8.47 (d, J=1.1 Hz, 2H), 8.33 (dd, J=8.7, 5.9 Hz, 1H), 8.05 (dd, J=8.5, 2.5 Hz, 1H), 7.84 (d, J=5.0 Hz, 1H), 7.74 (dd, J=9.3, 2.5 Hz, 1H), 5.71-5.78 (m, 1H), 4.82-4.98 (m, 2H), 1.42 (d, J=6.3 Hz, 3H). MS m/z 443.1 [M+H]$^+$.

Example 345

4-fluoro-2-[5-(6-{[(2S)-1-(1H-tetrazol-1-yl)propan-2-yl]oxy}pyridin-2-yl)-3H-imidazo[4,5-b]pyridin-3-yl]benzonitrile To a mixture of [3-(2-cyano-5-fluorophenyl)-3H-imidazo[4,5-b]pyridin-5-yl]boronic acid (180 mg), 2-bromo-6-{[(2S)-1-(1H-tetrazol-1-yl)propan-2-yl]oxy}pyridine (199 mg), Cs$_2$CO$_3$ (413 mg), THF (10 mL) and water (2.0 mL) was added Pd(dppf)Cl$_2$—CH$_2$Cl$_2$ (52.2 mg). After being stirred under nitrogen atmosphere at 70° C. for 1 hr, the mixture was poured into water and extracted with EtOAc. The organic layer was separated, washed with brine, dried over Na$_2$SO$_4$ and concentrated under reduced pressure. The residue was purified by silica gel column chromatography (EtOAc/hexane) to give the titled compound (60.0 mg) as a white solid.
$^1$H NMR (300 MHz, DMSO-d$_6$) δ 9.44 (s, 1H), 8.92 (s, 1H), 8.40 (s, 2H), 8.32 (dd, J=7.8, 5.8 Hz, 1H), 8.03 (dd, J=9.4, 2.6 Hz, 1H), 7.79-7.87 (m, 2H), 7.72 (dt, J=8.5, 2.6 Hz, 1H), 6.81 (dd, J=7.6, 1.3 Hz, 1H), 5.77-5.87 (m, 1H), 4.79-4.98 (m, 2H), 1.40 (d, J=6.3 Hz, 3H); MS m/z 442.1 [M+H]$^+$.

Example 347

4-fluoro-2-[5-(6-{[(2S)-1-(1H-tetrazol-1-yl)propan-2-yl]oxy}pyridazin-4-yl)-3H-imidazo[4,5-b]pyridin-3-yl]benzonitrile A) 5-chloro-3-{[(2S)-1-(1H-tetrazol-1-yl)propan-2-yl]oxy}pyridazine To a mixture of 5-chloropyridazin-3-ol (5.00 g), (2R)-1-(1H-tetrazol-1-yl)propan-2-ol (4.90 g) and PPh$_3$ (15.0 g) in THF (100 mL) was added DIAD (11.6 g). After being stirred under nitrogen atmosphere at room temperature for 1 hr, the mixture was concentrated under reduced pressure. The residue was purified by silica gel column chromatography (EtOAc/hexane) and silica gel column chromatography (NH, EtOAc/hexane) to give the titled compound (640 mg).
$^1$H NMR (300 MHz, DMSO-d$_6$) δ 9.45 (s, 1H), 9.03 (d, J=2.0 Hz, 1H), 7.51-7.61 (m, 1H), 5.73-5.83 (m, 1H), 4.79-4.97 (m, 2H), 1.34 (d, J=6.3 Hz, 3H).

B) 4-fluoro-2-[5-(6-{[(2S)-1-(1H-tetrazol-1-yl)propan-2-yl]oxy}pyridazin-4-yl)-3H-imidazo[4,5-b]pyridin-3-yl]benzonitrile The reaction and purification were performed according to Example 393 Step F to give the titled compound.
$^1$H NMR (300 MHz, DMSO-d$_6$) δ 9.61-9.53 (m, 1H), 9.49-9.42 (m, 1H), 9.04-8.97 (m, 1H), 8.51-8.43 (m, 1H), 8.40-8.26 (m, 2H), 8.11-8.03 (m, 1H), 7.79-7.68 (m, 2H), 5.96-5.80 (m, 1H), 5.02-4.82 (m, 2H), 1.41-1.36 (m, 3H); MS m/z 443.2 [M+H]$^+$.

Example 354

4-(2,2-difluoroethoxy)-2-[6-(3-{[(2S)-1-(1H-tetrazol-1-yl)propan-2-yl]oxy}phenyl)imidazo[1,2-b]pyridazin-3-yl]pyridine-3-carbonitrile A) 2-chloro-4-(2,2-difluoroethoxy)pyridine-3-carbonitrile To a mixture of 2,2-difluoroethan-1-ol (94.3 mg) in THF (2.0 mL) was added 60% NaH in oil (55.1 mg) at 0° C. The mixture was stirred under nitrogen atmosphere at 0° C. for 5 min. A solution of 2,4-dichloropyridine-3-carbonitrile (200 mg) in THF (2.0 mL) was added to the mixture at 0° C. The mixture was stirred under nitrogen atmosphere at room temperature for 4 hr. The mixture was quenched with water at room temperature and extracted with EtOAc. The organic layer was separated, washed with brine, dried over MgSO$_4$ and concentrated under reduced pressure. The residue was purified by silica gel column chromatography (EtOAc/hexane) to give the titled compound (185 mg).
MS m/z 219.1 [M+H]$^+$.

B) 4-(2,2-difluoroethoxy)-2-[6-(3-{[(2S)-1-(1H-tetrazol-1-yl)propan-2-yl]oxy}phenyl)imidazo[1,2-b]pyridazin-3-yl]pyridine-3-carbonitrile The reaction and purification were performed according to Example 321 to give the titled compound.
$^1$H NMR (300 MHz, DMSO-d$_6$) δ 9.44 (s, 1H), 8.90 (d, J=6.0 Hz, 1H), 8.41 (d, J=9.5 Hz, 1H), 8.28 (s, 1H), 7.99 (d, J=9.6 Hz, 1H), 7.68-7.61 (m, 2H), 7.54 (d, J=6.1 Hz, 1H), 7.44 (t, J=8.2 Hz, 1H), 7.06 (dd, J=1.9, 8.2 Hz, 1H), 6.77-6.32 (m, 1H), 5.07-4.93 (m, 1H), 4.91-4.68 (m, 4H), 1.34 (d, J=6.1 Hz, 3H); MS m/z 504.1 [M+H]$^+$.

Example 358

4-(methylamino)-2-[6-(3-{[(2S)-1-(1H-tetrazol-1-yl)propan-2-yl]oxy}phenyl)imidazo[1,2-b]pyridazin-3-yl]pyridine-3-carbonitrile A) 2-chloro-4-(methylamino)pyridine-3-carbonitrile A solution of 2N methylamine THF solution (2.4 mL) was added to a solution of 2,4-dichloropyridine-3-carbonitrile (400 mg) in DMF (6.0 mL) at 0° C. The mixture was stirred at 0° C. for 5 min and at room temperature for 2 hr. The reaction mixture was partitioned between EtOAc and water. The organic layer was washed with brine, dried over Na$_2$SO$_4$ and concentrated under reduced pressure. The residue was purified by recrystallization from EtOAc/hexane to give the titled compound (283 mg) as a white solid.
$^1$H NMR (300 MHz, CDCl$_3$) δ 8.12 (dd, J=0.5, 6.1 Hz, 1H), 6.50 (d, J=6.1 Hz, 1H), 5.46-5.15 (m, 1H), 3.01 (d, J=5.0 Hz, 3H); MS m/z 168.1 [M+1]$^+$.

B) 4-(methylamino)-2-[6-(3-{[(2S)-1-(1H-tetrazol-1-yl)propan-2-yl]oxy}phenyl)imidazo[1,2-b]pyridazin-3-yl]pyridine-3-carbonitrile The reaction and purification were performed according to Example 321 to give the titled compound.

¹H NMR (300 MHz, DMSO-d₆) δ 9.45 (s, 1H), 8.42 (d, J=6.0 Hz, 1H), 8.36 (d, J=9.5 Hz, 1H), 8.15 (s, 1H), 7.94 (d, J=9.6 Hz, 1H), 7.65 (d, J=7.7 Hz, 1H), 7.61 (d, J=2.2 Hz, 1H), 7.43 (t, J=8.0 Hz, 1H), 7.33 (q, J=4.3 Hz, 1H), 7.06 (dd, J=2.5, 7.9 Hz, 1H), 6.80 (d, J=6.1 Hz, 1H), 5.05-4.95 (m, 1H), 4.91-4.83 (m, 1H), 4.83-4.71 (m, 1H), 2.92 (d, J=4.7 Hz, 3H), 1.32 (d, J=6.1 Hz, 3H); MS m/z 455.3 [M+1]⁺.

Example 379

4-fluoro-2-[2-fluoro-5-(3-{[(2S)-1-(1H-tetrazol-1-yl)propan-2-yl]oxy}phenyl)pyrazolo[1,5-a]pyrimidin-3-yl]benzonitrile A) 2-fluoropyrazolo[1,5-a]pyrimidin-5-ol To a solution of methyl (2E)-3-methoxyprop-2-enoate (313 mg), 3-fluoro-1H-pyrazol-5-amine (300 mg) in THF (3.0 mL) was added Cs₂CO₃ (1.32 g) and the mixture was stirred at 80° C. for 12 hr. The mixture was diluted with water and extracted with EtOAc. The combined organic layer was washed with brine, dried over Na₂SO₄ and concentrated under reduced pressure. The residue was purified by silica gel column chromatography (EtOAc/PE) to give the titled compound (370 mg).
¹H NMR (400 MHz, CDCl₃) δ 12.0 (brs, 1H), 7.99 (d, J=8.0 Hz, 1H), 6.06 (d, J=8.0 Hz, 1H), 5.63 (d, J=5.2 Hz, 1H).

B) 5-chloro-2-fluoropyrazolo[1,5-a]pyrimidine

To a solution of 2-fluoropyrazolo[1,5-a]pyrimidin-5-ol (370 mg) in CH₃CN (5.0 mL) was added POCl₃ (1.48 g) and the mixture was stirred under nitrogen atmosphere at 80° C. for 12 hr. The mixture was concentrated under reduced pressure. The residue was poured into water and basified with 4M aqueous NaOH solution (pH 8). The resulting precipitate was collected by filtration and dried to give the crude titled compound (350 mg). The crude product was used for the next step without further purification.

C) 1-[(2S)-2-(3-{2-fluoropyrazolo[1,5-a]pyrimidin-5-yl}phenoxy)propyl]-1H-tetrazole The reaction and purification were performed according to Example 1 Step F to give the titled compound.
¹H NMR (400 MHz, CDCl₃) δ 8.77 (s, 1H), 8.52 (d, J=7.2 Hz, 1H), 7.61-7.63 (m, 2H), 7.40 (t, J=8.0 Hz, 1H), 7.24-7.26 (m, 1H), 6.93-6.96 (m, 1H), 6.22 (d, J=5.2 Hz, 1H), 4.88-4.95 (m, 1H), 4.77-4.82 (m, 1H), 4.60-4.67 (m, 1H), 1.42 (d, J=6.4 Hz, 3H).

D) 1-[(2S)-2-(3-{3-bromo-2-fluoropyrazolo[1,5-a]pyrimidin-5-yl}phenoxy)propyl]-1H-tetrazole The reaction and purification were performed according to Example 1 Step G to give the titled compound.
¹H NMR (400 MHz, CDCl₃) δ 8.78 (s, 1H), 8.51 (d, J=7.2 Hz, 1H), 7.66-7.69 (m, 2H), 7.42 (t, J=8.0 Hz, 1H), 7.30 (d, J=7.2 Hz, 1H), 6.96 (dd, J=8.0, 2.0 Hz, 1H), 4.87-4.95 (m, 1H), 4.79-4.83 (m, 1H), 4.63-4.68 (m, 1H), 1.44 (d, J=6.4 Hz, 3H).

E) 4-fluoro-2-[2-fluoro-5-(3-{[(2S)-1-(1H-tetrazol-1-yl)propan-2-yl]oxy}phenyl)pyrazolo[1,5-a]pyrimidin-3-yl]benzonitrile The reaction and purification were performed according to Example 1 Step H to give the titled compound.

¹H NMR (300 MHz, CDCl₃) δ 8.76 (s, 1H), 8.62 (d, J=7.3 Hz, 1H), 7.94-7.85 (m, 1H), 7.85-7.81 (m, 1H), 7.66-7.60 (m, 1H), 7.50-7.37 (m, 3H), 7.24-7.15 (m, 1H), 7.01-6.96 (m, 1H), 5.01-4.89 (m, 1H), 4.85-4.77 (m, 1H), 4.71-4.61 (m, 1H), 1.43 (d, J=6.2 Hz, 3H); MS m/z 459.1 [M+H]⁺.

Example 383

4-(difluoromethyl)-2-[5-(3-{[(2S)-1-(1H-tetrazol-1-yl)propan-2-yl]oxy}phenyl)-3H-imidazo[4,5-b]pyridin-3-yl]benzonitrile A) 1-bromo-4-(difluoromethyl)-2-nitrobenzene The reaction and purification were performed according to Example 413 Step A to give the titled compound.
¹H NMR (300 MHz, DMSO-d₆) δ 8.26-8.31 (m, 1H), 8.10 (d, J=8.3 Hz, 1H), 7.82 (dt, J=8.3, 0.9 Hz, 1H), 7.16 (d, J=57.0 Hz, 1H).

B) 4-(difluoromethyl)-2-nitrobenzonitrile

To a mixture of 1-bromo-4-(difluoromethyl)-2-nitrobenzene (4.00 g) in DMF (100 mL) were added Pd(PPh₃)₄ (1.82 g) and Zn(CN)₂ (5.56 g). After being stirred under argon atmosphere at 110° C. for 15 hr, the mixture was poured into water and extracted with EtOAc. The organic layer was separated, washed with brine, dried over MgSO₄ and concentrated under reduced pressure. The residue was purified by silica gel column chromatography (EtOAc/hexane) to give the titled compound (1.80 g).
¹H NMR (300 MHz, DMSO-d₆) δ 8.56 (s, 1H), 8.35 (d, J=8.0 Hz, 1H), 8.19 (d, J=8.0 Hz, 1H), 7.29 (t, J=57.0 Hz, 1H).

C) 2-amino-4-(difluoromethyl)benzonitrile

The reaction and purification were performed according to Example 413 Step C to give the titled compound.
¹H NMR (300 MHz, DMSO-d₆) δ 7.53 (d, J=8.1 Hz, 1H), 6.96 (s, 1H), 6.95 (t, J=54.0 Hz, 1H), 6.70-6.73 (m, 1H), 6.37 (brs, 2H).

D) 2-[(6-bromo-3-nitropyridin-2-yl)amino]-4-(difluoromethyl)benzonitrile

The reaction and purification were performed according to Example 284 Step A to give the titled compound.
MS m/z 369.0 [M+H]⁺.

E) 2-[(3-amino-6-bromopyridin-2-yl)amino]-4-(difluoromethyl)benzonitrile

The reaction and purification were performed according to Example 284 Step B to give the titled compound.
MS m/z 339.0 [M+H]⁺.

F) 2-{5-bromo-3H-imidazo[4,5-b]pyridin-3-yl}-4-(difluoromethyl)benzonitrile

The reaction and purification were performed according to Example 284 Step C to give the titled compound.
¹H NMR (300 MHz, CDCl₃) δ 8.35 (s, 1H), 8.09-7.99 (m, 2H), 7.91 (s, 1H), 7.79 (d, J=8.1 Hz, 1H), 7.55 (d, J=8.4 Hz, 1H), 6.81 (t, J=1.0 Hz, 1H); MS m/z 349.0 [M+H]⁺.

G) 4-(difluoromethyl)-2-[5-(3-{[(2S)-1-(1H-tetrazol-1-yl)propan-2-yl]oxy}phenyl)-3H-imidazo[4,5-b]pyridin-3-yl]benzonitrile The reaction and purification were performed according to Example 284 Step D to give the titled compound.
$^1$H NMR (300 MHz, CDCl$_3$) δ 8.75 (s, 1H), 8.47 (s, 1H), 8.26 (d, J=8.4 Hz, 1H), 8.13-8.06 (m, 2H), 7.86-7.74 (m, 2H), 7.64-7.57 (m, 2H), 7.41-7.32 (m, 1H), 7.06-6.66 (m, 2H), 4.91-4.74 (m, 2H), 4.69-4.58 (m, 1H), 1.40-1.35 (m, 3H); MS m/z 473.1 [M+H]$^+$.

Example 392

4-fluoro-2-methoxy-6-[6-(6-{[(2S)-1-(1H-tetrazol-1-yl)propan-2-yl]oxy}pyrazin-2-yl)imidazo[1,2-b]pyridazin-3-yl]benzonitrile To a mixture of 2-bromo-4-fluoro-6-methoxybenzonitrile (110 mg), (Bpin)$_2$ (182 mg), KOAc (140 mg) and toluene (10 mL) was added Pd(dppf)Cl$_2$—CH$_2$Cl$_2$ (39.0 mg). After being stirred under nitrogen atmosphere at 100° C. for 3 hr, the mixture was filtered and concentrated under reduced pressure.
To a mixture of the residue, 2-{3-bromoimidazo[1,2-b]pyridazin-6-yl}-6-{[(2S)-1-(1H-tetrazol-1-yl)propan-2-yl]oxy}pyrazine (92.0 mg), Cs$_2$CO$_3$ (151 mg), DME (5.0 mL) and water (1.0 mL) was added Pd(amphos)Cl$_2$ (16.0 mg). After being stirred under nitrogen atmosphere at 80° C. for 1 hr, the mixture was poured into water and extracted with EtOAc. The organic layer was separated, washed with brine, dried over Na$_2$SO$_4$ and concentrated under reduced pressure. The residue was purified by silica gel column chromatography (EtOAc/hexane), silica gel column chromatography (NH, EtOAc/hexane) and recrystallization from EtOAc/hexane to give the titled compound (52.0 mg) as a pale yellow solid.
$^1$H NMR (300 MHz, DMSO-d$_6$) δ 9.48 (s, 1H), 8.95 (s, 1H), 8.50 (d, J=9.5 Hz, 1H), 8.43 (s, 1H), 8.34 (s, 1H), 8.16 (d, J=9.5 Hz, 1H), 7.60 (dd, J=2.3, 9.6 Hz, 1H), 7.39 (dd, J=2.3, 10.9 Hz, 1H), 5.90-5.77 (m, 1H), 5.04-4.94 (m, 1H), 4.92-4.82 (m, 1H), 4.04 (s, 3H), 1.42 (d, J=6.4 Hz, 3H); MS m/z 473.1 [M+H]$^+$.

Example 393

4-fluoro-2-methoxy-6-[5-(6-{[(2S)-1-(1H-tetrazol-1-yl)propan-2-yl]oxy}pyridin-2-yl)-3H-imidazo[4,5-b]pyridin-3-yl]benzonitrile A) 2-amino-4,6-difluorobenzonitrile To a solution of 2,4,6-trifluorobenzonitrile (10.5 g) in CH$_3$CN (80 mL) was added 28% aqueous NH$_3$ solution (45 mL). After being stirred under nitrogen atmosphere at room temperature for 72 hr, the mixture was concentrated under reduced pressure. The mixture was quenched with water and extracted with EtOAc. The organic layer was separated, washed with brine, dried over MgSO$_4$ and concentrated under reduced pressure. The residue was purified by silica gel column chromatography (EtOAc/hexane) to give the titled compound (4.58 g).
$^1$H NMR (300 MHz, CDCl$_3$) δ 6.31-6.18 (m, 2H), 4.68 (brs, 2H); m/z 153.1 [M-H]$^-$.

B) 2-amino-4-fluoro-6-methoxybenzonitrile and 2-amino-6-fluoro-4-methoxybenzonitrile To a solution of 2-amino-4,6-difluorobenzonitrile (4.58 g) in DMF (50 mL) was added 28% NaOMe in MeOH solution (7.9 mL) at 0° C. The mixture was stirred under nitrogen atmosphere at room temperature for 72 hr. The mixture was quenched with water at room temperature and extracted with EtOAc. The organic layer was separated, washed with brine, dried over MgSO$_4$ and concentrated under reduced pressure. The residue was purified by silica gel column chromatography (EtOAc/hexane) to give 2-amino-4-fluoro-6-methoxybenzonitrile (1.92 g) and 2-amino-6-fluoro-4-methoxybenzonitrile (1.04 g).
Data of 2-amino-4-fluoro-6-methoxybenzonitrile
$^1$H NMR (300 MHz, DMSO-d$_6$) δ 6.32 (s, 2H), 6.14 (dt, J=2.2, 11.6 Hz, 2H), 3.80 (s, 3H).
Data of 2-amino-6-fluoro-4-methoxybenzonitrile
$^1$H NMR (300 MHz, DMSO-d$_6$) δ 6.38 (s, 2H), 6.20-6.09 (m, 2H), 3.73 (s, 3H).

C) 2-[(6-bromo-3-nitropyridin-2-yl)amino]-4-fluoro-6-methoxybenzonitrile

To a mixture of 2-amino-4-fluoro-6-methoxybenzonitrile (1.93 g) and 2,6-dibromo-3-nitropyridine (3.91 g) in THF (60 mL) was added 60% NaH in oil (1.85 g) at 0° C. The mixture was stirred under nitrogen atmosphere at room temperature for 1 hr. The mixture was quenched with water at 0° C. and the precipitating solid was collected by filtration. The solid was washed with water and dried under reduced pressure to give the crude titled compound (4.95 g). The crude product was used for the next step without further purification.
$^1$H NMR (300 MHz, DMSO-d$_6$) δ 10.50 (s, 1H), 8.49 (d, J=8.6 Hz, 1H), 7.60 (dd, J=2.3, 11.0 Hz, 1H), 7.35 (d, J=8.5 Hz, 1H), 7.07 (dd, J=2.2, 10.9 Hz, 1H), 3.97 (s, 3H); m/z 366.9 [M+H]$^+$.

D) 2-{5-bromo-3H-imidazo[4,5-b]pyridin-3-yl}-4-fluoro-6-methoxybenzonitrile

To a mixture of crude 2-[(6-bromo-3-nitropyridin-2-yl)amino]-4-fluoro-6-methoxybenzonitrile (1.90 g) and saturated aqueous NH$_4$Cl solution (30 mL) in THF (60 mL) and EtOH (10 mL) was added iron (3.46 g). The mixture was stirred at 50° C. for 14 hr. The mixture was filtered through a Celite® pad and the filtrate was extracted with EtOAc. The organic layer was separated, washed with water and brine, dried over MgSO$_4$ and concentrated under reduced pressure.
To a mixture of the residue and TsOH-H$_2$O (391 mg) in THF (40 mL) was added triethyl orthoformate (18 mL). After being stirred at 100° C. for 3 hr, the mixture was concentrated under reduced pressure at 60° C. The residue was purified by silica gel column chromatography (EtOAc/hexane) to give the titled compound (640 mg).
$^1$H NMR (300 MHz, DMSO-d$_6$) δ 8.84 (s, 1H), 8.24 (d, J=8.3 Hz, 1H), 7.63 (d, J=8.3 Hz, 1H), 7.57-7.47 (m, 2H), 4.05 (s, 3H); m/z 346.9 [M+H]$^+$.

E) [3-(2-cyano-5-fluoro-3-methoxyphenyl)-3H-imidazo[4,5-b]pyridin-5-yl]boronic acid To a mixture of 2-{5-bromo-3H-imidazo[4,5-b]pyridin-3-yl}-4-fluoro-6-methoxybenzonitrile (100 mg), (Bpin)$_2$ (87.6 mg), KOAc (84.7 mg) in toluene (8.0 mL) was added Pd(dppf)Cl$_2$—CH$_2$Cl$_2$ (23.5 mg). After being stirred under nitrogen atmosphere at 100° C. for 1 hr, the mixture was filtered through Celite®. The filtrate was concentrated under reduced pressure to give the crude titled compound (90.0 mg). The crude product was used for the next step without further purification.
MS m/z 312.9 [M+H]$^+$.

F) 4-fluoro-2-methoxy-6-[5-(6-{[(2S)-1-(1H-tetrazol-1-yl)propan-2-yl]oxy}pyridin-2-yl)-3H-imidazo[4,5-b]pyridin-3-yl]benzonitrile To a mixture of crude [3-(2-cyano-5-fluoro-3-methoxyphenyl)-3H-imidazo[4,5-b]pyridin-5-yl]boronic acid (90.0 mg), 2-bromo-6-{[(2S)-1-(1H-tetrazol-1-yl)propan-2-yl]oxy}pyridine (98.0 mg) and $Cs_2CO_3$ (187 mg) in THF (5.0 mL) and water (0.50 mL) was added Pd(amphos)$Cl_2$ (20.3 mg). After being stirred under nitrogen atmosphere at 70° C. for 1 hr, the mixture was poured into water and extracted with EtOAc. The organic layer was separated, washed with brine, dried over $MgSO_4$ and concentrated under reduced pressure. The residue was purified by silica gel column chromatography (NH, EtOAc/hexane) and recrystallized from EtOAc/IPE to give the titled compound (45.0 mg) as an off-white solid.

$^1$H NMR (300 MHz, DMSO-$d_6$) δ 9.44 (s, 1H), 8.87 (s, 1H), 8.39 (s, 2H), 7.89-7.78 (m, 2H), 7.58-7.46 (m, 2H), 6.85-6.76 (m, 1H), 5.90-5.76 (m, 1H), 5.00-4.76 (m, 2H), 4.07 (s, 3H), 1.40 (d, J=6.3 Hz, 3H); MS m/z 472.2 [M+H]$^+$.

Example 399

4-[6-(4-fluoro-3-{[(2S)-1-(1H-tetrazol-1-yl)propan-2-yl]oxy}phenyl)imidazo[1,2-b]pyridazin-3-yl]-2-methoxypyridine-3-carbonitrile

A) 4-chloro-2-methoxypyridine-3-carbonitrile

To a cold mixture of diisopropylamine (3.30 g) in THF (50 mL) under argon atmosphere was added dropwise 1.6M n-BuLi hexane solution (20 mL) at −78° C. The mixture was stirred under argon atmosphere at −78° C. for 30 min. Then a mixture of 2-methoxypyridine-3-carbonitrile (4.00 g) in THF (25 mL) was added to the mixture. After being stirred under argon atmosphere at −78° C. for 1 hr, a mixture of hexachloroethane (14.1 g) in THF (50 mL) was added to the mixture. The mixture was warmed to −40° C. and stirred for 15 min. The mixture was quenched with water (100 mL) at the same temperature and extracted with EtOAc. The organic layer was separated, washed with saturated aqueous $NH_4Cl$ solution, dried over $MgSO_4$ and concentrated under reduced pressure. The residue was purified by silica gel column chromatography (EtOAc/hexane) to give the titled compound (0.850 g).

$^1$H NMR (300 MHz, $CDCl_3$) δ 8.24 (d, J=5.5 Hz, 1H), 7.06 (d, J=5.6 Hz, 1H), 4.09-4.06 (m, 3H).

B) 4-[6-(4-fluoro-3-{[(2S)-1-(1H-tetrazol-1-yl)propan-2-yl]oxy}phenyl)imidazo[1,2-b]pyridazin-3-yl]-2-methoxypyridine-3-carbonitrile The reaction and purification were performed according to Example 321 to give the titled compound.

$^1$H NMR (300 MHz, $CDCl_3$) δ 8.90-8.83 (m, 1H), 8.45 (s, 1H), 8.38-8.34 (m, 1H), 8.20-8.13 (m, 1H), 7.80-7.72 (m, 1H), 7.59-7.52 (m, 2H), 7.52-7.46 (m, 1H), 7.26-7.18 (m, 1H), 4.98-4.82 (m, 2H), 4.78-4.63 (m, 1H), 4.16 (s, 3H), 1.48 (d, J=6.2 Hz, 3H); MS m/z 472.1 [M+H]$^+$.

Example 409

2-(difluoromethoxy)-4-fluoro-6-[6-(6-{[(2S)-1-(1H-tetrazol-1-yl)propan-2-yl]oxy}pyridin-2-yl)imidazo[1,2-b]pyridazin-3-yl]benzonitrile

A) 2-amino-6-(benzyloxy)-4-fluorobenzonitrile

To a mixture of benzyl alcohol (2.55 g) in DMF (30 mL) was added 60% NaH in oil (1.03 g). After being stirred at room temperature for 10 min, 2-amino-4,6-difluorobenzonitrile (3.64 g) was added to the mixture. After being stirred at 100° C. for 3 hr, the mixture was poured into water and extracted with EtOAc. The organic layer was separated, washed with brine, dried over $MgSO_4$ and concentrated under reduced pressure. The residue was purified by silica gel column chromatography (EOAc/hexane) to give the titled compound (660 mg) as a white solid.

MS m/z 241.1 [M−H]$^-$.

B) tert-butyl N-[3-(benzyloxy)-2-cyano-5-fluorophenyl]-N-[(tert-butoxy)carbonyl]carbamate DMAP (16.6 mg) was added to a mixture of 2-amino-6-(benzyloxy)-4-fluorobenzonitrile (0.660 g), TEA (825 mg) and (Boc)$_2$O (1.30 g) in THF (10 mL). The mixture was stirred at room temperature for 15 hr. The mixture was poured into water and extracted with EtOAc. The organic layer was separated, washed with brine, dried over $MgSO_4$ and concentrated under reduced pressure. The residue was purified by silica gel column chromatography (EtOAc/hexane) to give the titled compound (1.05 g).

MS m/z 441.2 [M−H]$^-$.

C) tert-butyl N-[(tert-butoxy)carbonyl]-N-(2-cyano-5-fluoro-3-hydroxyphenyl)carbamate A mixture of tert-butyl N-[3-(benzyloxy)-2-cyano-5-fluorophenyl]-N-[(tert-butoxy)carbonyl]carbamate (1.05 g) and 10% palladium-carbon (100 mg) in EtOH (10 mL) was stirred under hydrogen atmosphere at room temperature for 4 hr. The catalyst was removed by filtration. The filtrate was concentrated under reduced pressure to give the crude titled compound (840 mg). The crude product was used for the next step without further purification.

MS m/z 351.1 [M−H]$^-$.

D) 2-amino-6-(difluoromethoxy)-4-fluorobenzonitrile

To a mixture of tert-butyl N-[(tert-butoxy)carbonyl]-N-(2-cyano-5-fluoro-3-hydroxyphenyl)carbamate (840 mg), ethyl bromodifluoroacetate (966 mg) in DMF (10 mL) and water (2.0 mL) was added $K_2CO_3$ (12.4 g). After being stirred at 100° C. for 1 hr, the mixture was poured into water and extracted with EtOAc. The organic layer was separated, washed with brine, dried over $MgSO_4$ and concentrated under reduced pressure. The residue was diluted with THF (2.0 mL) and TFA (2.0 mL) was added to the mixture. After being stirred at 50° C. for 15 hr, the mixture was neutralized with saturated aqueous $NaHCO_3$ solution and extracted with EtOAc. The organic layer was separated, washed with brine, dried over $MgSO_4$ and concentrated under reduced pressure. The residue was purified by silica gel column chromatography (EtOAc/hexane) to give the titled compound (342 mg).

MS m/z 201.1 [M−H]$^-$.

E) 2-bromo-6-(difluoromethoxy)-4-fluorobenzonitrile

To a mixture of 2-amino-6-(difluoromethoxy)-4-fluorobenzonitrile (672 mg), CuBr (1.42 g) in $CH_3CN$ (10 mL) was added amyl nitrite (1.35 g). The mixture was stirred under nitrogen atmosphere at room temperature for 2 hr. The mixture was quenched with water at room temperature, diluted with EtOAc and filtered through a Celite® pad. The filtrate was partitioned two layers and the organic layer was washed with brine, dried over MgSO$_4$ and concentrated under reduced pressure. The residue was purified by silica gel column chromatography (EtOAc/hexane) to give the titled compound (550 mg).

$^1$H NMR (300 MHz, DMSO-d$_6$) δ 7.86 (dd, J=8.3, 2.3 Hz, 2H), 7.58 (dd, J=9.8, 2.2 Hz, 1H), 7.47 (t, J=79.0 Hz, 1H).

F) 2-(difluoromethoxy)-4-fluoro-6-[6-(6-{[(2S)-1-(1H-tetrazol-1-yl)propan-2-yl]oxy}pyridin-2-yl)imidazo[1,2-b]pyridazin-3-yl]benzonitrile The reaction and purification were performed according to Example 392 to give the titled compound.

$^1$H NMR (300 MHz, DMSO-d$_6$) δ 9.44 (s, 1H), 8.47 (d, J=9.5 Hz, 1H), 7.90-7.97 (m, 2H), 7.79-7.82 (m, 1H), 7.60-7.66 (m, 1H), 7.47 (t, J=72.0 Hz, 1H), 6.92-6.94 (m, 1H), 5.78-5.90 (m, 1H), 4.78-4.97 (m, 2H), 1.41 (d, J=6.4 Hz, 3H); MS m/z 508.1 [M+H]$^+$.

Example 410

4-fluoro-2-methoxy-6-[6-(6-{[(2S)-1-(1H-tetrazol-1-yl)propan-2-yl]oxy}pyridin-2-yl)imidazo[1,2-b]pyridazin-3-yl]benzonitrile The reaction and purification were performed according to Example 392 to give the titled compound.

$^1$H NMR (300 MHz, DMSO-d$_6$) δ 9.44 (s, 1H), 8.44 (d, J=9.6 Hz, 1H), 8.29 (s, 1H), 8.21 (d, J=9.5 Hz, 1H), 7.97-7.88 (m, 1H), 7.79 (d, J=7.0 Hz, 1H), 7.56 (dd, J=2.3, 9.6 Hz, 1H), 7.37 (dd, J=2.2, 10.9 Hz, 1H), 6.94 (d, J=7.8 Hz, 1H), 5.89-5.76 (m, 1H), 5.00-4.89 (m, 1H), 4.88-4.76 (m, 1H), 4.03 (s, 3H), 1.40 (d, J=6.3 Hz, 3H); MS m/z 472.1 [M+H]$^+$.

Example 412

2-(difluoromethoxy)-6-[6-(3-{[(2S)-1-(1H-tetrazol-1-yl)propan-2-yl]oxy}phenyl)imidazo[1,2-b]pyridazin-3-yl]benzonitrile A) 2-bromo-6-(difluoromethoxy)-4-fluorobenzonitrile To a mixture of 2-amino-6-(difluoromethoxy)-4-fluorobenzonitrile (2.67 g), CuBr (5.66 g) in CH$_3$CN (30 mL) was added amyl nitrite (1.35 g). The mixture was stirred under nitrogen atmosphere at room temperature for 2 hr. The mixture was quenched with water, diluted with EtOAc and filtered through a Celite® pad. The filtrate was partitioned two layers and the organic layer was washed with brine, dried over MgSO$_4$ and concentrated under reduced pressure. The residue was purified by silica gel column chromatography (EtOAc/hexane) to give the titled compound (2.28 g).

$^1$H NMR (300 MHz, DMSO-d$_6$) δ 7.69-7.78 (m, 2H), 7.47-7.51 (m, 1H), 7.47 (t, J=72.0 Hz, 1H).

B) 2-(difluoromethoxy)-6-[6-(3-{[(2S)-1-(1H-tetrazol-1-yl)propan-2-yl]oxy}phenyl)imidazo[1,2-b]pyridazin-3-yl]benzonitrile The reaction and purification were performed according to Example 392 to give the titled compound.

$^1$H NMR (300 MHz, DMSO-d$_6$) δ 9.43 (s, 1H), 8.38-8.41 (m, 1H), 8.27 (s, 1H), 7.95-7.99 (m, 3H), 7.63-7.65 (m, 3H), 7.63 (t, J=72 Hz, 1H), 7.44 (t, J=8.0 Hz, 1H), 7.06 (dd, J=2.0, 8.3 Hz, 1H), 4.95-5.03 (m, 1H), 4.70-4.89 (m, 2H), 1.36 (d, J=6.1 Hz, 3H); MS m/z 489.1 [M+H]$^+$.

Example 413

2-(difluoromethyl)-6-[6-(3-{[(2S)-1-(1H-tetrazol-1-yl)propan-2-yl]oxy}phenyl)imidazo[1,2-b]pyridazin-3-yl]benzonitrile A) 2-bromo-1-(difluoromethyl)-3-nitrobenzene Deoxo-Fluor® (9.60 g) was added to a mixture of 2-bromo-3-nitrobenzaldehyde (5.00 g) in toluene (50 mL). The mixture was stirred at room temperature for 1 hr. The mixture was neutralized with saturated aqueous NaHCO$_3$ solution and extracted with EtOAc. The organic layer was separated, washed with brine, dried over MgSO$_4$ and concentrated under reduced pressure to give the crude titled compound (5.40 g). The crude product was used for the next step without further purification.

$^1$H NMR (300 MHz, DMSO-d$_6$) δ 8.15-8.19 (m, 1H), 7.94-7.97 (m, 1H), 7.77-7.82 (m, 1H), 7.26 (t, J=84.0 Hz, 1H).

B) 2-(difluoromethyl)-6-nitrobenzonitrile

To a mixture of 2-bromo-1-(difluoromethyl)-3-nitrobenzene (2.00 g) in NMP (20 mL) were added LiBr (688 mg) and CuCN (851 mg). The mixture was stirred under microwave irradiation at 200° C. for 1 hr. The mixture was poured into water and the insoluble material was removed by filtration through a Celite® pad. The filtrate was extracted with EtOAc. The organic layer was separated, washed with brine dried over MgSO$_4$ and concentrated under reduced pressure. The residue was purified by silica gel column chromatography (EtOAc/hexane) to give the titled compound (540 mg).

$^1$H NMR (300 MHz, DMSO-d$_6$) δ 8.54-8.57 (m, 1H), 8.23-8.26 (m, 1H), 8.10-8.16 (m, 1H), 7.41 (t, J=56.0 Hz, 1H).

C) 2-amino-6-(difluoromethyl)benzonitrile

A mixture of 2-(difluoromethyl)-6-nitrobenzonitrile (540 mg) and 10% palladium-carbon (60.0 mg) in EtOH (5.0 mL) was stirred under hydrogen atmosphere at room temperature for 14 hr. The catalyst was removed by filtration, and then the filtrate was concentrated under reduced pressure to give the titled compound (460 mg).

MS m/z 167.2 [M−H]$^-$.

D) 2-bromo-6-(difluoromethyl)benzonitrile

The reaction and purification were performed according to Example 409 Step E to give the titled compound.

$^1$H NMR (300 MHz, DMSO-d$_6$) δ 8.08-8.12 (m, 1H), 7.75-7.88 (m, 2H), 7.27 (t, J=54.0 Hz, 1H).

E) 2-(difluoromethyl)-6-[6-(3-{[(2S)-1-(1H-tetrazol-1-yl)propan-2-yl]oxy}phenyl)imidazo[1,2-b]pyridazin-3-yl]benzonitrile The reaction and purification were performed according to Example 392 to give the titled compound.

$^1$H NMR (300 MHz, DMSO-d$_6$) δ 9.42 (s, 1H), 8.38-8.41 (m, 1H), 8.28 (s, 1H), 8.22-8.28 (m, 1H), 8.06-8.11 (m, 1H), 7.95-8.01 (m, 2H), 7.61-7.64 (m, 1H), 7.55-7.58 (m, 1H), 7.40-7.45 (m, 1H), 7.63 (t, J=54.0 Hz, 1H), 7.04-7.08 (m, 1H), 4.95-5.03 (m, 1H), 4.70-4.89 (m, 2H), 1.30 (d, J=6.1 Hz, 3H); MS m/z 473.1 [M+H]$^+$.

Example 416

4-fluoro-2-[5-(6-{[(2S)-1-(1H-tetrazol-1-yl)propan-2-yl]oxy}pyridin-2-yl)pyrazolo[1,5-a]pyrimidin-3-yl]benzonitrile A) 2-{pyrazolo[1,5-a]pyrimidin-5-yl}-6-{[(2S)-1-(1H-tetrazol-1-yl)propan-2-yl]oxy}pyridine A mixture of 2-bromo-6-{[(2S)-1-(1H-tetrazol-1-yl)propan-2-yl]oxy}pyridine (510 mg), 5-chloropyrazolo[1,5-a]pyrimidine (549 mg), (Bpin)$_2$ (2.27 g), cataCXium® A (256 mg), Pd(OAc)$_2$ (80.3 mg) and CsF (1.35 g) in THF (10 mL) and water (2.5 mL) was stirred under microwave irradiation at 120° C. for 2 hr. The mixture was partitioned between EtOAc and aqueous NaHCO$_3$ solution. The organic layer was washed with brine, dried over Na$_2$SO$_4$ and concentrated under reduced pressure. The residue was purified by silica gel column chromatography (NH, EtOAc/hexane) to give the titled compound (133 mg).
$^1$H NMR (300 MHz, CDCl$_3$) δ 8.76 (dd, J=0.9, 7.3 Hz, 1H), 8.69 (s, 1H), 8.19-8.14 (m, 2H), 7.83-7.75 (m, 2H), 6.83 (dd, J=0.8, 8.2 Hz, 1H), 6.75 (dd, J=0.8, 2.4 Hz, 1H), 5.86-5.76 (m, 1H), 4.89-4.82 (m, 1H), 4.77-4.70 (m, 1H), 1.49 (d, J=6.4 Hz, 3H); MS m/z 323.1 [M+1]$^+$.

B) 2-{3-bromopyrazolo[1,5-a]pyrimidin-5-yl}-6-{[(2S)-1-(1H-tetrazol-1-yl)propan-2-yl]oxy}pyridine The reaction and purification were performed according to Example 1 Step G to give the titled compound.
$^1$H NMR (300 MHz, CDCl$_3$) δ 8.71 (d, J=7.3 Hz, 1H), 8.67 (s, 1H), 8.30 (dd, J=0.7, 7.5 Hz, 1H), 8.14 (s, 1H), 7.87-7.78 (m, 2H), 6.85 (dd, J=0.7, 8.2 Hz, 1H), 5.82 (dt, J=3.6, 6.6 Hz, 1H), 4.89-4.81 (m, 1H), 4.78-4.70 (m, 1H), 1.49 (d, J=6.3 Hz, 3H); MS m/z 401.1, 403.1 [M+1]$^+$.

C) 4-fluoro-2-[5-(6-{[(2S)-1-(1H-tetrazol-1-yl)propan-2-yl]oxy}pyridin-2-yl)pyrazolo[1,5-a]pyrimidin-3-yl]benzonitrile The reaction and purification were performed according to Example 1 Step H to give the titled compound.
$^1$H NMR (300 MHz, DMSO-d$_6$) δ 9.45 (s, 1H), 9.40 (d, J=7.3 Hz, 1H), 8.83 (s, 1H), 8.12-8.04 (m, 4H), 7.99-7.93 (m, 1H), 7.42 (dt, J=2.7, 8.4 Hz, 1H), 6.98 (dd, J=0.7, 8.2 Hz, 1H), 5.87 (dt, J=3.5, 6.6 Hz, 1H), 5.00-4.91 (m, 1H), 4.88-4.79 (m, 1H), 1.42 (d, J=6.3 Hz, 3H); MS m/z 442.2 [M+1]$^+$.

Example 417

2-(difluoromethyl)-4-fluoro-6-[6-(6-{[(2S)-1-(1H-tetrazol-1-yl)propan-2-yl]oxy}pyridin-2-yl)imidazo[1,2-b]pyridazin-3-yl]benzonitrile A) 2-bromo-1-(difluoromethyl)-5-fluoro-3-nitrobenzene To a mixture of 1-bromo-2-(difluoromethyl)-4-fluorobenzene (4.70 g) and sulfuric acid (30 mL) was added nitric acid (2.7 mL) at 0° C. After being stirred at 0° C. for 4 hr, the mixture was poured into iced water and extracted with EtOAc. The organic layer was separated, washed with brine, dried over Na$_2$SO$_4$ and concentrated under reduced pressure. The residue was purified by silica gel column chromatography (EtOAc/hexane) to give the titled compound containing a regioisomer (4.10 g).
$^1$H NMR (300 MHz, DMSO-d$_6$) δ 8.33 (dd, J=2.9, 7.8 Hz, 1H), 7.94 (dd, J=3.0, 8.5 Hz, 1H), 7.26 (t, J=53.5 Hz, 1H).

B) 2-(difluoromethyl)-4-fluoro-6-nitrobenzonitrile

The reaction and purification were performed according to Example 413 Step B to give the titled compound.
$^1$H NMR (300 MHz, DMSO-d$_6$) δ 8.58 (dd, J=2.6, 8.3 Hz, 1H), 8.24 (dd, J=2.5, 8.0 Hz, 1H), 7.40 (t, J=53.4 Hz, 1H).

C) 2-amino-6-(difluoromethyl)-4-fluorobenzonitrile

The reaction and purification were performed according to Example 413 Step C to give the titled compound.
$^1$H NMR (300 MHz, DMSO-d$_6$) δ 7.04 (t, J=54.3 Hz, 1H), 6.77-6.63 (m, 4H); m/z 185.1 [M+H]$^+$.

D) 2-bromo-6-(difluoromethyl)-4-fluorobenzonitrile

The reaction and purification were performed according to Example 409 Step E to give the titled compound.
$^1$H NMR (300 MHz, DMSO-d$_6$) δ 8.20 (dd, J=2.5, 8.2 Hz, 1H), 7.82 (dd, J=2.3, 8.7 Hz, 1H), 7.26 (t, J=53.9 Hz, 1H).

E) 2-(difluoromethyl)-4-fluoro-6-[6-(6-{[(2S)-1-(1H-tetrazol-1-yl)propan-2-yl]oxy}pyridin-2-yl)imidazo[1,2-b]pyridazin-3-yl]benzonitrile The reaction and purification were performed according to Example 392 to give the titled compound.
$^1$H NMR (300 MHz, DMSO-d$_6$) δ 9.44 (s, 1H), 8.47 (d, J=9.6 Hz, 1H), 8.37 (s, 1H), 8.30-8.18 (m, 2H), 7.94-7.86 (m, 2H), 7.82-7.76 (m, 1H), 7.39 (t, J=53.8 Hz, 1H), 6.99-6.90 (m, 1H), 5.92-5.73 (m, 1H), 4.98-4.90 (m, 1H), 4.88-4.77 (m, 1H), 1.41 (d, J=6.3 Hz, 3H); m/z 492.1 [M+H]$^+$.

Example 426

2-acetyl-6-[6-(3-{[(2S)-1-(1H-tetrazol-1-yl)propan-2-yl]oxy}phenyl)imidazo[1,2-b]pyridazin-3-yl]benzonitrile A) 2-acetyl-6-aminobenzonitrile To a mixture of 2-amino-6-bromobenzonitrile (1.00 g) and tributyl(1-ethoxyvinyl)tin (2.19 g) in toluene (20 mL) was added Pd(PPh$_3$)$_2$Cl$_2$ (177 mg). After being stirred under argon atmosphere at 100° C. for 4 hr, 1N aqueous HCl solution was added to the mixture at room temperature. After being stirred for 2 hr, the mixture was poured into water and extracted with EtOAc. The organic layer was separated, washed with brine, dried over MgSO$_4$ and concentrated under reduced pressure to give the crude titled compound (820 mg). The crude product was used for the next step without further purification.
MS m/z 161.0 [M+H]$^+$.

B) 2-acetyl-6-bromobenzonitrile

The reaction and purification were performed according to Example 409 Step E to give the titled compound.

¹H NMR (300 MHz, DMSO-d₆) δ 8.15-8.18 (m, 1H), 8.10-8.14 (m, 1H), 7.75-7.80 (m, 1H), 2.65 (s, 3H).

C) 2-acetyl-6-(4,4,5,5-tetramethyl-1,3,2-dioxaborolan-2-yl)benzonitrile

To a mixture of 2-acetyl-6-bromobenzonitrile (510 mg), (Bpin)₂ (1.15 g), KOAc (445 mg) in toluene (10 mL) was added Pd(dppf)Cl₂ (185 mg). The mixture was stirred under nitrogen atmosphere at 100° C. for 4 hr. The mixture was passed through a Celite® pad to remove insoluble materials and the filtrate was concentrated under reduced pressure to give the crude titled compound (620 mg). The crude product was used for the next step without further purification.
MS m/z 272.0 [M+H]+(detected as the boronic acid).

D) 2-acetyl-6-[6-(3-{[(2S)-1-(1H-tetrazol-1-yl)propan-2-yl]oxy}phenyl)imidazo[1,2-b]pyridazin-3-yl]benzonitrile The reaction and purification were performed according to Example 121 Step C to give the titled compound.
¹H NMR (300 MHz, DMSO-d₆) δ 9.42 (s, 1H), 8.37-8.40 (m, 1H), 8.26-8.29 (m, 1H), 8.21 (s, 1H), 8.00-8.06 (m, 1H), 7.92-7.95 (m, 1H), 7.56-7.61 (m, 2H), 7.36-7.45 (m, 1H), 7.02-7.07 (m, 1H), 4.95-5.03 (m, 1H), 4.70-4.89 (m, 2H), 2.75 (s, 3H), 1.31 (d, J=6.1 Hz, 3H); MS m/z 465.1 [M+H]⁺.

Example 427

2-(1,1-difluoroethyl)-6-[6-(3-{[(2S)-1-(1H-tetrazol-1-yl)propan-2-yl]oxy}phenyl)imidazo[1,2-b]pyridazin-3-yl]benzonitrile The reaction and purification were performed according to Example 413 Step A to give the titled compound.
¹H NMR (300 MHz, DMSO-d₆) δ 9.42 (s, 1H), 8.39 (d, J=9.5 Hz, 1H), 8.26 (s, 1H), 8.16 (d, J=8.0 Hz, 1H), 7.89-8.01 (m, 3H), 7.59-7.63 (m, 1H), 7.51-7.56 (m, 1H), 7.40-7.45 (m, 1H), 7.04-7.09 (m, 1H), 4.95-5.03 (m, 1H), 4.70-4.89 (m, 2H), 2.18 (t, J=19.1 Hz, 3H), 1.31 (d, J=6.1 Hz, 3H); MS m/z 487.1 [M+H]⁺.

Example 435

2-[6-(4-fluoro-3-{[(2S)-1-(1H-tetrazol-1-yl)propan-2-yl]oxy}phenyl)imidazo[1,2-b]pyridazin-3-yl]-4-(fluoromethoxy)pyridine-3-carbonitrile A) 2-[6-(4-fluoro-3-{[(2S)-1-(1H-tetrazol-1-yl)propan-2-yl]oxy}phenyl)imidazo[1,2-b]pyridazin-3-yl]-4-oxo-1,4-dihydropyridine-3-carbonitrile A mixture of 2-[6-(4-fluoro-3-{[(2S)-1-(1H-tetrazol-1-yl)propan-2-yl]oxy}phenyl)imidazo[1,2-b]pyridazin-3-yl]-4-methoxypyridine-3-carbonitrile (604 mg), TMSCl (2.78 g) and NaI (959 mg) in CH₃CN (30 mL) was stirred at 80° C. for 6 hr. Then 5% aqueous Na₂S₂O₃ solution was added to the mixture. The mixture was concentrated under reduced pressure. The residue was diluted with EtOAc and water. The mixture was stirred at room temperature for a while and then the precipitate was collected by filtration to give the titled compound (373 mg).
¹H NMR (300 MHz, DMSO-d₆) 12.58 (brs, 1H), 9.40 (s, 1H), 8.47 (d, J=9.6 Hz, 1H), 8.41 (s, 1H), 8.08 (d, J=9.6 Hz, 1H), 7.97 (brs, 1H), 7.88 (dd, J=2.0, 8.1 Hz, 1H), 7.74 (ddd, J=2.1, 4.4, 8.6 Hz, 1H), 7.42 (dd, J=8.6, 11.0 Hz, 1H), 6.44 (brs, 1H), 5.07 (dt, J=3.5, 6.7 Hz, 1H), 4.96-4.88 (m, 1H), 4.87-4.79 (m, 1H), 1.38 (d, J=6.1 Hz, 3H); MS m/z 458.3 [M+1]⁺.

B) 2-[6-(4-fluoro-3-{[(2S)-1-(1H-tetrazol-1-yl)propan-2-yl]oxy}phenyl)imidazo[1,2-b]pyridazin-3-yl]-4-(fluoromethoxy)pyridine-3-carbonitrile A mixture of 2-[6-(4-fluoro-3-{[(2S)-1-(1H-tetrazol-1-yl)propan-2-yl]oxy}phenyl)imidazo[1,2-b]pyridazin-3-yl]-4-oxo-1,4-dihydropyridine-3-carbonitrile (200 mg), fluoromethyl 4-methylbenzenesulfonate (445 mg) and Cs₂CO₃ (426 mg) in DMF (6.0 mL) was stirred at 70° C. for 16.5 hr. The mixture was partitioned between EtOAc and water. The organic layer was washed with brine, dried over Na₂SO₄ and concentrated under reduced pressure. The residue was purified by silica gel column chromatography (MeOH/EtOAc) and recrystallization from EtOAc to give the titled compound (108 mg) as a white solid.
¹H NMR (300 MHz, DMSO-d₆) δ 9.39 (s, 1H), 8.96 (d, J=5.9 Hz, 1H), 8.44 (d, J=9.5 Hz, 1H), 8.32 (s, 1H), 8.03 (d, J=9.6 Hz, 1H), 7.88 (dd, J=2.1, 8.1 Hz, 1H), 7.71 (ddd, J=2.0, 4.3, 8.6 Hz, 1H), 7.60 (d, J=5.2 Hz, 1H), 7.40 (dd, J=8.6, 11.0 Hz, 1H), 6.36-6.11 (m, 2H), 5.11-5.00 (m, 1H), 4.94-4.88 (m, 1H), 4.86-4.78 (m, 1H), 1.38 (d, J=6.1 Hz, 3H); MS m/z 490.3 [M+1]⁺.

Example 447

4-fluoro-2-[6-(5-fluoro-6-{[(2S)-1-(1H-tetrazol-1-yl)propan-2-yl]oxy}pyridin-2-yl)imidazo[1,2-b]pyridazin-3-yl]-6-methoxybenzonitrile A) 6-bromo-3-fluoro-2-{[(2S)-1-(1H-tetrazol-1-yl)propan-2-yl]oxy}pyridine The reaction and purification were performed according to Example 326 Step B to give the titled compound.
¹H NMR (300 MHz, CDCl₃) δ 8.75 (s, 1H), 7.29-7.20 (m, 4H), 7.06 (dd, J=2.8, 8.2 Hz, 1H), 5.57 (dquin, J=3.7, 6.4 Hz, 1H), 4.84-4.77 (m, 1H), 4.74-4.67 (m, 1H), 1.45 (d, J=6.3 Hz, 3H); MS m/z 302.0, 304.0 [M+1]⁺.

B) 3-fluoro-6-{imidazo[1,2-b]pyridazin-6-yl}-2-{[(2S)-1-(1H-tetrazol-1-yl)propan-2-yl]oxy}pyridine The reaction and purification were performed according to Example 298 Step B to give the titled compound.
¹H NMR (300 MHz, CDCl₃) δ 8.79 (s, 1H), 8.06-7.97 (m, 3H), 7.92-7.88 (m, 1H), 7.81 (d, J=1.2 Hz, 1H), 7.52 (dd, J=8.3, 9.4 Hz, 1H), 5.83-5.72 (m, 1H), 4.91-4.85 (m, 1H), 4.81-4.73 (m, 1H), 1.56 (d, J=6.3 Hz, 3H); MS m/z 341.2 [M+1]⁺.

C) 6-{3-bromoimidazo[1,2-b]pyridazin-6-yl}-3-fluoro-2-{[(2S)-1-(1H-tetrazol-1-yl)propan-2-yl]oxy}pyridine The reaction and purification were performed according to Example 1 Step G to give the titled compound.
¹H NMR (300 MHz, CDCl₃) δ 8.78 (s, 1H), 8.13 (dd, J=3.2, 8.3 Hz, 1H), 8.05-8.01 (m, 1H), 7.98-7.94 (m, 1H), 7.81 (s, 1H), 7.55 (dd, J=8.3, 9.4 Hz, 1H), 5.82-5.73 (m, 1H), 4.92-4.84 (m, 1H), 4.82-4.73 (m, 1H), 1.56 (d, J=6.3 Hz, 3H); MS m/z 419.0, 421.0 [M+1]⁺.

D) 4-fluoro-2-[6-(5-fluoro-6-{[(2S)-1-(1H-tetrazol-1-yl)propan-2-yl]oxy}pyridin-2-yl)imidazo[1,2-b]pyridazin-3-yl]-6-methoxybenzonitrile The reaction and purification were performed according to Example 321 to give the titled compound.
$^1$H NMR (300 MHz, DMSO-$d_6$) δ 9.42 (s, 1H), 8.44 (d, J=9.5 Hz, 1H), 8.28 (s, 1H), 8.16 (d, J=9.5 Hz, 1H), 7.97-7.87 (m, 1H), 7.84-7.76 (m, 1H), 7.55 (dd, J=2.1, 9.4 Hz, 1H), 7.37 (dd, J=1.8, 10.9 Hz, 1H), 5.99-5.86 (m, 1H), 5.03-4.92 (m, 1H), 4.92-4.81 (m, 1H), 4.03 (s, 3H), 1.45 (d, J=6.3 Hz, 3H); MS m/z 490.3 [M+1]$^+$.

Example 448

4-chloro-2-methoxy-6-[5-(6-{[(2S)-1-(1H-tetrazol-1-yl)propan-2-yl]oxy}pyrazin-2-yl)-3H-imidazo[4,5-b]pyridin-3-yl]benzonitrile A) 2-bromo-5-chloro-1-methoxy-3-nitrobenzene To a mixture of 4-chloro-2-methoxy-6-nitroaniline (23.4 g) in CH$_3$CN (200 mL) was added 48% aqueous HBr solution (96.8 g) Then a solution of NaNO$_2$ (8.69 g) in water (100 mL) was added portionwise to the mixture. The mixture was stirred at room temperature for 1 hr. CuBr (19.7 g) was added portionwise to the mixture. After being stirred at room temperature for 1 hr, the mixture was poured into water and extracted with EtOAc. The organic layer was separated, washed with brine, dried over MgSO$_4$ and concentrated under reduced pressure. The residue was passed through an NH silica gel pad to give the titled compound (23.5 g).
$^1$H NMR (300 MHz, DMSO-$d_6$) δ 7.78 (d, J=2.3 Hz, 1H), 7.53 (d, J=2.3 Hz, 1H), 3.98 (s, 3H).

B) 4-chloro-2-methoxy-6-nitrobenzonitrile

The reaction and purification were performed according to Example 413 Step B to give the titled compound.
$^1$H NMR (300 MHz, DMSO-$d_6$) δ 8.02 (d, J=1.8 Hz, 1H), 7.89 (d, J=1.8 Hz, 1H), 4.06 (s, 3H).

C) 2-amino-4-chloro-6-methoxybenzonitrile

To a mixture of 4-chloro-2-methoxy-6-nitrobenzonitrile (7.46 g) and in AcOH (100 mL) was added iron (19.5 g). The mixture was stirred at 80° C. for 1 hr. The mixture was filtered through a Celite® pad and the filtrate was extracted with EtOAc. The organic layer was separated, washed with water and brine, dried over MgSO$_4$ and concentrated under reduced pressure to give the titled compound (4.60 g).
$^1$H NMR (300 MHz, DMSO-$d_6$) δ 6.42 (d, J=1.7 Hz, 1H), 6.32 (brs, 2H), 6.31 (d, J=1.7 Hz, 1H), 3.82 (s, 3H).

D) 2-[(6-bromo-3-nitropyridin-2-yl)amino]-4-chloro-6-methoxybenzonitrile

The reaction and purification were performed according to Example 284 Step A to give the titled compound.
MS m/z 384.9 [M+H]$^+$.

E) 2-{5-bromo-3H-imidazo[4,5-b]pyridin-3-yl}-4-chloro-6-methoxybenzonitrile

The reaction and purification were performed according to Example 284 Step B and C to give the titled compound.

$^1$H NMR (300 MHz, DMSO-$d_6$) δ 8.83 (s, 1H), 8.23 (d, J=8.3 Hz, 1H), 7.68 (s, 2H), 7.63 (d, J=8.3 Hz, 1H), 4.07 (s, 3H); MS m/z 364.8 [M+H]$^+$.

F) 2-bromo-6-{[(2S)-1-(1H-tetrazol-1-yl)propan-2-yl]oxy}pyrazine

The reaction and purification were performed according to Example 326 Step B to give the titled compound.
$^1$H NMR (400 MHz, CDCl$_3$) δ 8.68 (s, 1H), 8.29 (s, 1H), 8.13 (s, 1H), 5.56-5.59 (m, 1H), 4.75-4.83 (m, 1H), 4.66-4.74 (m, 1H), 1.44 (d, J=6.4 Hz, 3H); MS m/z=285.2, 286.7 [M+H]$^+$.

G) 4-chloro-2-methoxy-6-[5-(6-{[(2S)-1-(1H-tetrazol-1-yl)propan-2-yl]oxy}pyrazin-2-yl)-3H-imidazo[4,5-b]pyridin-3-yl]benzonitrile The reaction and purification were performed according to Example 393 Step E and F to give the titled compound.
$^1$H NMR (300 MHz, DMSO-$d_6$) δ 9.48 (s, 1H), 8.95 (d, J=8.1 Hz, 2H), 8.44 (d, J=8.3 Hz, 1H), 8.34 (d, J=8.4 Hz, 1H), 8.30 (s, 1H), 7.74 (d, J=1.7 Hz, 1H), 7.67 (d, J=1.7 Hz, 1H), 5.89-5.79 (m, 1H), 5.02-4.83 (m, 2H), 4.18-4.06 (m, 3H), 1.42 (d, J=6.3 Hz, 3H); MS m/z 489.1 [M+H]$^+$.

Example 452

4-fluoro-2-methoxy-6-[6-(6-{[(2S)-1-(1H-1,2,4-triazol-1-yl)propan-2-yl]oxy}pyridin-2-yl)imidazo[1,2-b]pyridazin-3-yl]benzonitrile A) 2-{6-chloroimidazo[1,2-b]pyridazin-3-yl}-4-fluoro-6-methoxybenzonitrile To a mixture of 2-bromo-4-fluoro-6-methoxybenzonitrile (301 mg), 6-chloroimidazo[1,2-b]pyridazine (205 mg), KOAc (256 mg) and xylene (30 mL) was added Pd(PPh$_3$)$_4$ (151 mg). After being stirred under nitrogen atmosphere at 130° C. for 14 hr, the mixture was poured into water and extracted with EtOAc. The organic layer was separated, washed with brine, dried over Na$_2$SO$_4$ and concentrated under reduced pressure. The residue was purified by silica gel column chromatography (EtOAc/hexane) and washed with IPE to give the titled compound (236 mg).
$^1$H NMR (300 MHz, DMSO-$d_6$) δ 8.38 (d, J=9.5 Hz, 1H), 8.25 (s, 1H), 7.54 (d, J=9.5 Hz, 1H), 7.43 (dd, J=2.3, 9.4 Hz, 1H), 7.38 (dd, J=2.3, 10.9 Hz, 1H), 4.02 (s, 3H); MS m/z 302.9 [M+H]$^+$.

B) (2S)-1-(1H-1,2,4-triazol-1-yl)propan-2-ol

A mixture of 1,2,4-triazole (2.00 g,) and (S)-(−)-propylene oxide (1.85 g) was stirred at 32° C. for 24 hr. The mixture was concentrated under reduced pressure. The residue was purified by silica gel column chromatography (MeOH/EtOAc) to give the titled compound (2.40 g).
$^1$H NMR (400 MHz, CDCl$_3$) δ 8.09 (s, 1H), 7.89 (s, 1H), 4.15-4.30 (m, 2H), 4.00-4.10 (m, 1H), 3.45 (d, J=4.0 Hz, 1H), 1.26 (d, J=6.4 Hz, 3H).

C) 2-bromo-6-{[(2S)-1-(1H-1,2,4-triazol-1-yl)propan-2-yl]oxy}pyridine

To a mixture of (2S)-1-(1H-1,2,4-triazol-1-yl)propan-2-ol (271 mg) and THF (5.0 mL) was added 60% NaH in oil (92.0 mg). After being stirred at room temperature for 10 min, 2,6-dibromopyridine (499 mg) was added to the mixture. After being stirred at room temperature for 3 days, 60% NaH in oil (92.0 mg) was added to the mixture. After being stirred at 70° C. for 2 hr, the mixture was poured into water and extracted with EtOAc. The organic layer was separated, washed with brine, dried over $Na_2SO_4$ and concentrated under reduced pressure. The residue was purified by silica gel column chromatography (EtOAc/hexane) to give the titled compound (287 mg).
$^1$H NMR (300 MHz, DMSO-$d_6$) δ 8.49 (s, 1H), 7.92 (s, 1H), 7.62 (dd, J=7.6, 8.1 Hz, 1H), 7.19 (dd, J=0.6, 7.5 Hz, 1H), 6.78 (dd, J=0.6, 8.2 Hz, 1H), 5.46-5.36 (m, 1H), 4.51-4.44 (m, 2H), 1.28 (d, J=6.4 Hz, 3H); MS m/z 282.9, 284.9 [M+H]$^+$.

D) 4-fluoro-2-methoxy-6-[6-(6-{[(2S)-1-(1H-1,2,4-triazol-1-yl)propan-2-yl]oxy}pyridin-2-yl)imidazo[1,2-b]pyridazin-3-yl]benzonitrile The reaction and purification were performed according to Example 298 Step B to give the titled compound.
$^1$H NMR (300 MHz, DMSO-$d_6$) δ 8.52 (s, 1H), 8.44 (d, J=9.5 Hz, 1H), 8.28 (s, 1H), 8.23 (d, J=9.5 Hz, 1H), 7.96-7.87 (m, 2H), 7.79 (d, J=6.8 Hz, 1H), 7.56 (dd, J=2.2, 9.5 Hz, 1H), 7.37 (dd, J=2.3, 10.9 Hz, 1H), 6.92 (dd, J=0.6, 8.1 Hz, 1H), 5.82-5.67 (m, 1H), 4.60-4.52 (m, 2H), 4.03 (s, 3H), 1.39 (d, J=6.4 Hz, 3H); m/z 471.1 [M+H]$^+$.

Example 466

4-(fluoromethoxy)-2-[6-(3-{[(2S)-1-(1H-tetrazol-1-yl)propan-2-yl]oxy}phenyl)imidazo[1,2-b]pyridazin-3-yl]pyridine-3-carbonitrile A) 4-oxo-2-[6-(3-{[(2S)-1-(1H-tetrazol-1-yl)propan-2-yl]oxy}phenyl)imidazo[1,2-b]pyridazin-3-yl]-1,4-dihydropyridine-3-carbonitrile The reaction and purification were performed according to Example 435 Step A to give the titled compound.
$^1$H NMR (300 MHz, DMSO-$d_6$) δ 9.46 (s, 1H), 8.45 (d, J=9.5 Hz, 1H), 8.39 (s, 1H), 8.06 (d, J=9.5 Hz, 1H), 8.03-7.94 (m, 1H), 7.71-7.65 (m, 2H), 7.46 (t, J=7.9 Hz, 1H), 7.09 (dd, J=2.1, 7.8 Hz, 1H), 6.54-6.36 (m, 1H), 5.10-4.96 (m, 1H), 4.92-4.83 (m, 1H), 4.82-4.72 (m, 1H), 1.34 (d, J=6.1 Hz, 3H), NH was not assigned; m/z 440.3 [M+H]$^+$.

B) 4-(fluoromethoxy)-2-[6-(3-{[(2S)-1-(1H-tetrazol-1-yl)propan-2-yl]oxy}phenyl)imidazo[1,2-b]pyridazin-3-yl]pyridine-3-carbonitrile The reaction and purification were performed according to Example 435 Step B to give the titled compound.
$^1$H NMR (300 MHz, DMSO-$d_6$) δ 9.44 (s, 1H), 8.96 (d, J=6.0 Hz, 1H), 8.42 (d, J=9.6 Hz, 1H), 8.31 (s, 1H), 8.00 (d, J=9.6 Hz, 1H), 7.68-7.59 (m, 3H), 7.44 (t, J=8.1 Hz, 1H), 7.10-7.03 (m, 1H), 6.24 (d, J=51.5 Hz, 2H), 5.05-4.94 (m, 1H), 4.92-4.83 (m, 1H), 4.81-4.73 (m, 1H), 1.34 (d, J=6.1 Hz, 3H); m/z 472.3 [M+H]$^+$.

Example 467

6-fluoro-2-[6-(3-{[(2S)-1-(1H-tetrazol-1-yl)propan-2-yl]oxy}phenyl)imidazo[1,2-b]pyridazin-3-yl]pyridine-3-carbonitrile A) 2-chloro-6-fluoropyridine-3-carbonitrile To a mixture of 2,6-dichloropyridine-3-carbonitrile (1.68 g) in DMSO (15 mL) was added portionwise KF (1.81 g) at 0° C. The mixture was stirred at room temperature for 48 hr. The mixture was quenched with water and extracted with EtOAc. The organic layer was separated, washed with water and brine, dried over $MgSO_4$ and concentrated under reduced pressure. The residue was purified by silica gel column chromatography (EtOAc/hexane) to give the titled compound (175 mg).
$^1$H NMR (300 MHz, DMSO-$d_6$) δ 8.63 (dd, J=8.1, 8.8 Hz, 1H), 7.80 (dd, J=1.2, 8.1 Hz, 1H).

B) 6-fluoro-2-[6-(3-{[(2S)-1-(1H-tetrazol-1-yl)propan-2-yl]oxy}phenyl)imidazo[1,2-b]pyridazin-3-yl]pyridine-3-carbonitrile The reaction and purification were performed according to Example 321 to give the titled compound.
$^1$H NMR (300 MHz, DMSO-$d_6$) δ 9.44 (s, 1H), 8.78 (dd, J=7.6, 8.5 Hz, 1H), 8.43 (d, J=9.6 Hz, 1H), 8.38 (s, 1H), 8.05 (d, J=9.6 Hz, 1H), 7.73-7.63 (m, 2H), 7.56 (dd, J=3.0, 8.6 Hz, 1H), 7.45 (t, J=8.0 Hz, 1H), 7.10-7.03 (m, 1H), 5.06-4.95 (m, 1H), 4.91-4.71 (m, 2H), 1.34 (d, J=6.1 Hz, 3H); m/z 442.2 [M+H]$^+$.

Example 472

4-fluoro-2-hydroxy-6-[5-(6-{[(2S)-1-(1H-tetrazol-1-yl)propan-2-yl]oxy}pyridin-2-yl)-3H-imidazo[4,5-b]pyridin-3-yl]benzonitrile To a solution of 1-dodecanethiol (858 mg) in DCM (12 mL) was added $AlCl_3$ (565 mg) was added at 0° C. After being stirred at room temperature for 5 min, 4-fluoro-2-methoxy-6-[5-(6-{[(2S)-1-(1H-tetrazol-1-yl)propan-2-yl]oxy}pyridin-2-yl)-3H-imidazo[4,5-b]pyridin-3-yl]benzonitrile (100 mg) was added. After being stirred at room temperature for 14.5 hr, the mixture was concentrated under reduced pressure. The mixture was partitioned between EtOAc and 0.1N aqueous HCl solution. The organic layer was washed with brine, dried over $Na_2SO_4$ and concentrated under reduced pressure. The residue was purified by silica gel column chromatography (MeOH/EtOAc) and then preparative HPLC (water/$CH_3CN$ containing 0.1% TFA). The desired fraction was neutralized with saturated aqueous $NaHCO_3$ solution and extracted with EtOAc. The organic layer was separated, dried over $Na_2SO_4$ and concentrated under reduced pressure to give the titled compound (10.7 mg) as a white solid.
$^1$H NMR (300 MHz, DMSO-$d_6$) δ 9.44 (s, 1H), 8.76 (s, 1H), 8.38-8.31 (m, 2H), 7.91-7.87 (m, 1H), 7.85-7.79 (m, 1H), 6.81 (dd, J=1.1, 7.9 Hz, 1H), 6.79-6.65 (m, 1H), 6.62-6.46 (m, 1H), 5.88-5.76 (m, 1H), 4.99-4.90 (m, 1H), 4.87-4.79 (m, 1H), 1.40 (d, J=6.4 Hz, 3H) (The OH proton was not observed); MS m/z 458.2 [M+H]$^+$.

Example 473

2-[6-(4-fluoro-3-{[(2S)-1-(1H-tetrazol-1-yl)propan-2-yl]oxy}phenyl)imidazo[1,2-b]pyridazin-3-yl]-4-(methoxy-d3)pyridine-3-carbonitrile A mixture of 2-[6-(4-fluoro-3-{[(2S)-1-(1H-tetrazol-1-yl)propan-2-yl]oxy}phenyl)imidazo[1,2-b]pyridazin-3-yl]-4-oxo-1,4-dihydropyridine-3-carbonitrile (161 mg), iodomethane-d3 (152 mg) and $K_2CO_3$ (97.1 mg) in DMF (5.0 mL) was stirred at room temperature for 1 hr. Then the mixture was partitioned between EtOAc and water. The organic layer was washed with 5% aqueous $Na_2S_2O_3$ solution and brine, dried over Na$_2$SO$_4$ and concentrated under reduced pressure. The residue was purified by silica gel column chromatography (MeOH/EtOAc) to give the titled compound (23.8 mg) as a light yellow solid.

$^1$H NMR (300 MHz, DMSO-d$_6$) δ 9.40 (s, 1H), 8.85 (d, J=6.1 Hz, 1H), 8.42 (d, J=9.4 Hz, 1H), 8.27 (s, 1H), 8.01 (d, J=9.5 Hz, 1H), 7.88 (d, J=7.3 Hz, 1H), 7.76-7.67 (m, 1H), 7.48-7.36 (m, 2H), 5.03 (dd, J=3.2, 6.0 Hz, 1H), 4.97-4.88 (m, 1H), 4.87-4.77 (m, 1H), 1.38 (d, J=5.9 Hz, 3H); MS m/z 475.2 [M+H]$^+$.

Example 474

4-fluoro-2-(methoxy-d3)-6-[5-(6-{[(2S)-1-(1H-tetrazol-1-yl)propan-2-yl]oxy}pyridin-2-yl)-3H-imidazo[4,5-b]pyridin-3-yl]benzonitrile The reaction and purification were performed according to example 473 to give the titled compound.
$^1$H NMR (300 MHz, DMSO-d$_6$) δ 9.44 (s, 1H), 8.87 (s, 1H), 8.39 (s, 2H), 7.87-7.80 (m, 2H), 7.59-7.47 (m, 2H), 6.86-6.78 (m, 1H), 5.91-5.77 (m, 1H), 5.00-4.89 (m, 1H), 4.87-4.78 (m, 1H), 1.40 (d, J=6.0 Hz, 3H); MS m/z 475.2 [M+H]$^+$.

Example 475

2-[6-(4-fluoro-3-{[(2R)-1-fluoro-3-(1H-tetrazol-1-yl)propan-2-yl]oxy}phenyl)imidazo[1,2-b]pyridazin-3-yl]-4-methoxypyridine-3-carbonitrile A) 1-[(2R)-2-(5-bromo-2-fluorophenoxy)-3-fluoropropyl]-1H-tetrazole A mixture of (2R)-2-(5-bromo-2-fluorophenoxy)-3-(1H-tetrazol-1-yl)propan-1-ol (386 mg), nonafluorobutanesulfonyl fluoride (2.19 g), triethylamine trihydrofluoride (1.16 g) and TEA (1.46 g) in THF (15 mL) was stirred at room temperature for 1.5 hr. Then the mixture was partitioned between EtOAc and water. The organic layer was washed with brine, dried over Na$_2$SO$_4$ and concentrated under reduced pressure. The residue was purified by silica gel column chromatography (EtOAc/hexane) to give the titled compound (376 mg).
$^1$H NMR (300 MHz, CDCl$_3$) δ 8.77 (s, 1H), 7.20-7.14 (m, 1H), 7.09 (dd, J=2.3, 7.3 Hz, 1H), 6.98 (dd, J=8.8, 10.7 Hz, 1H), 4.96-4.80 (m, 2H), 4.79-4.63 (m, 2H), 4.61-4.46 (m, 1H); MS m/z 319.1, 321.1 [M+H]$^+$.

B) 2-[6-(4-fluoro-3-{[(2R)-1-fluoro-3-(1H-tetrazol-1-yl)propan-2-yl]oxy}phenyl)imidazo[1,2-b]pyridazin-3-yl]-4-methoxypyridine-3-carbonitrile A mixture of 1-[(2R)-2-(5-bromo-2-fluorophenoxy)-3-fluoropropyl]-1H-tetrazole (124 mg), (Bpin)$_2$ (118 mg), Pd(dppf)Cl$_2$—CH$_2$Cl$_2$ (15.8 mg) and KOAc (76.2 mg) in DME (4.0 mL) was stirred under argon atmosphere at 100° C. for 2 hr. Then the mixture was partitioned between EtOAc and water. The organic layer was washed with brine, dried over Na$_2$SO$_4$ and concentrated under reduced pressure.
A mixture of the residue, 2-{6-chloroimidazo[1,2-b]pyridazin-3-yl}-4-methoxypyridine-3-carbonitrile (100 mg), Pd(PPh$_3$)$_4$ (20.2 mg) and K$_2$CO$_3$ (143 mg) in THF (10 mL) and water (1.0 mL) was stirred under argon atmosphere at 70° C. for 4 hr. Then the mixture was partitioned between EtOAc and water. The organic layer was washed with brine, dried over Na$_2$SO$_4$ and concentrated under reduced pressure. The residue was purified by silica gel column chromatography (MeOH/EtOAc) to give the titled compound (13.9 mg) as a white solid.
$^1$H NMR (300 MHz, DMSO-d$_6$) δ 9.43 (s, 1H), 8.86 (d, J=6.1 Hz, 1H), 8.44 (d, J=9.6 Hz, 1H), 8.27 (s, 1H), 8.00 (d, J=9.6 Hz, 1H), 7.86 (dd, J=2.0, 8.1 Hz, 1H), 7.74 (ddd, J=2.1, 4.4, 8.5 Hz, 1H), 7.45-7.38 (m, 2H), 5.33-5.19 (m, 1H), 5.09-4.96 (m, 2H), 4.96-4.64 (m, 2H), 4.11 (s, 3H); MS m/z 490.0 [M+H]$^+$.

Example 477

2-[6-(4-fluoro-3-{[(2R)-1-hydroxy-3-(1H-tetrazol-1-yl)propan-2-yl]oxy}phenyl)imidazo[1,2-b]pyridazin-3-yl]-4-methoxypyridine-3-carbonitrile A) methyl (2R)-3-[(tert-butyldimethylsilyl)oxy]-2-hydroxypropanoate To a mixture of methyl (2R)-2,3-dihydroxypropanoate (6.88 g) in DCM (45 mL) were added imidazole (7.80 g) and TBSCl (9.50 g) at 0° C. After being stirred under nitrogen atmosphere at room temperature for 2 hr, the mixture was poured into water and extracted with DCM. The organic layer was washed with brine, dried over Na$_2$SO$_4$ and concentrated under reduced pressure. The residue was purified by silica gel column chromatography (EtOAc/PE) to give the titled compound (9.19 g).
$^1$H NMR (400 MHz, DMSO-d$_6$) δ 4.20-4.24 (m, 1H), 3.87-3.92 (m, 1H), 3.84-3.86 (m, 1H), 3.78 (s, 3H), 3.02 (d, J=7.6 Hz, 1H), 0.87 (s, 9H), 0.05 (d, J=6.0 Hz, 6H).

B) methyl (2S)-2-(5-bromo-2-fluorophenoxy)-3-[(tert-butyldimethylsilyl)oxy]propanoate To a mixture of methyl (2R)-3-[(tert-butyldimethylsilyl)oxy]-2-hydroxypropanoate (9.10 g), 5-bromo-2-fluorophenol (4.94 g), PPh$_3$ (10.2 g) in THF (100 mL) was added DIAD (7.85 g) at 0° C. After being stirred under nitrogen atmosphere at 10° C. for 12 hr, the mixture was poured into water and extracted with EtOAc. The organic layer was washed with brine, dried over Na$_2$SO$_4$ and concentrated under reduced pressure. The residue was purified by silica gel column chromatography (EtOAc/PE) to give the titled compound (10.0 g).
$^1$H NMR (400 MHz, CDCl$_3$) δ 7.06-7.12 (m, 2H), 6.96 (dd, J=8.8, 2.0 Hz, 1H), 4.73 (d, J=4.8 Hz, 1H), 4.09 (d, J=4.8 Hz, 2H), 3.79 (s, 3H), 0.88 (s, 9H), 0.08 (d, J=7.6 Hz, 6H).

C) (2R)-2-(5-bromo-2-fluorophenoxy)-3-[(tert-butyldimethylsilyl)oxy]propan-1-ol

To a solution of (2S)-2-(5-bromo-2-fluorophenoxy)-3-[(tert-butyldimethylsilyl)oxy]propanoate (10.0 g) in THF (40 mL) and MeOH (60 mL) was portionwise added NaBH$_4$ (2.49 g) at 0° C. After being stirred at 10° C. for 12 hr, the mixture was quenched with saturated aqueous NH$_4$Cl solution and water at 0° C. and extracted with EtOAc. The organic layer was washed with brine, dried over Na$_2$SO$_4$ and concentrated under reduced pressure. The residue was purified by silica gel column chromatography (EtOAc/PE) to give the titled compound (8.90 g).
$^1$H NMR (400 MHz, CDCl$_3$) δ 7.29 (dd, J=7.6, 2.4 Hz, 1H), 7.02-7.08 (m, 1H), 6.91-6.98 (m, 1H), 4.30-4.38 (m, 1H), 3.82-3.92 (m, 4H), 0.88 (s, 9H), 0.62 (d, J=6.8 Hz, 6H). (The OH proton was not observed.)

D) (2S)-2-(5-bromo-2-fluorophenoxy)-3-[(tert-butyldimethylsilyl)oxy]propyl methanesulfonate To a solution of (2R)-2-(5-bromo-2-fluorophenoxy)-3-[(tert-butyldimethylsilyl)oxy]propan-1-ol (8.90 g) and TEA (4.75 g) in THF (80 mL) was dropwise added MsCl (5.27 g) at 0° C. After being stirred under nitrogen atmosphere at 10° C. for 1 hr, the mixture was diluted with water and extracted with EtOAc. The organic layer was washed with brine, dried over $Na_2SO_4$ and concentrated under reduced pressure to give the titled compound (9.77 g).
$^1$H NMR (400 MHz, $CDCl_3$) δ 7.24 (dd, J=7.2, 2.4 Hz, 1H), 7.06-7.12 (m, 1H), 6.97 (dd, J=10.8, 8.8 Hz, 1H), 4.42-4.55 (m, 3H), 3.80-3.89 (m, 2H), 3.05 (s, 3H), 0.88 (s, 9H), 0.61 (d, J=6.4 Hz, 6H).

E) 1-[(2R)-2-(5-bromo-2-fluorophenoxy)-3-[(tert-butyldimethylsilyl)oxy]propyl]-1H-tetrazole To a mixture of (2S)-2-(5-bromo-2-fluorophenoxy)-3-[(tert-butyldimethylsilyl)oxy]propyl methanesulfonate (9.77 g) and 1H-tetrazole (2.99 g) in DMF (80 mL) was added $K_2CO_3$ (5.90 g). After being stirred under nitrogen atmosphere at 80° C. for 12 hr, the mixture was poured into water and extracted with EtOAc. The organic layer was washed with brine, dried over $Na_2SO_4$ and concentrated under reduced pressure. The residue was purified by silica gel column chromatography (EtOAc/PE) to give the titled compound (3.30 g).
$^1$H NMR (400 MHz, $CDCl_3$) δ 8.76 (s, 1H), 7.08-7.13 (m, 2H), 6.91-6.97 (m, 1H), 4.84-4.89 (m, 1H), 4.72-4.79 (m, 1H), 4.56-4.64 (m, 1H), 3.71-3.82 (m, 2H), 0.90 (s, 9H), 0.62 (d, J=7.6 Hz, 6H).

F) (2R)-2-(5-bromo-2-fluorophenoxy)-3-(1H-tetrazol-1-yl)propan-1-ol

To a mixture of 1-[(2R)-2-(5-bromo-2-fluorophenoxy)-3-[(tert-butyldimethylsilyl)oxy]propyl]-1H-tetrazole (3.30 g) in THF (30 mL) was added 1M TBAF THF solution (15 mL) at 0° C. After being stirred under nitrogen atmosphere at 10° C. for 12 hr, the mixture was diluted with saturated aqueous $NaHCO_3$ solution and water and extracted with EtOAc. The organic layer was washed with brine, dried over $Na_2SO_4$ and concentrated under reduced pressure. The residue was purified by silica gel column chromatography (EtOAc/PE) to give the titled compound (2.16 g).
$^1$H NMR (400 MHz, $CDCl_3$) δ 8.78 (s, 1H), 7.10-7.15 (m, 1H), 7.08 (dd, J=7.2, 2.0 Hz, 1H), 6.97 (dd, J=10.8, 8.8 Hz, 1H), 4.86-4.90 (m, 2H), 4.60-4.68 (m, 1H), 3.76-3.89 (m, 2H), 2.36 (brs, 1H); MS m/z 317.1, 319.1 $[M+H]^+$.

G) (2R)-2-[2-fluoro-5-(4,4,5,5-tetramethyl-1,3,2-dioxaborolan-2-yl)phenoxy]-3-(1H-tetrazol-1-yl)propan-1-ol To a mixture of (2R)-2-(5-bromo-2-fluorophenoxy)-3-(1H-tetrazol-1-yl)propan-1-ol (300 mg) and $(Bpin)_2$ (360 mg) in DMSO (4.0 mL) were added KOAc (186 mg) and $Pd(dppf)Cl_2$ (35.0 mg). After being stirred under nitrogen atmosphere at 100° C. for 2 hr, the mixture was poured into water and extracted with EtOAc. The organic layer was washed with brine, dried over $Na_2SO_4$ and concentrated under reduced pressure. The residue was purified by silica gel column chromatography (EtOAc/PE) to give the titled compound (262 mg).
$^1$H NMR (400 MHz, $CDCl_3$) δ 8.79 (s, 1H), 7.45-7.49 (m, 1H), 7.34 (dd, J=8.8, 1.2 Hz, 1H), 7.09 (dd, J=11.2, 8.0 Hz, 1H), 4.83-4.93 (m, 2H), 4.66-4.71 (m, 1H), 3.73-3.85 (m, 2H), 1.33 (s, 12H). (The OH proton was not observed.)

H) 2-[6-(4-fluoro-3-{[(2R)-1-hydroxy-3-(1H-tetrazol-1-yl)propan-2-yl]oxy}phenyl)imidazo[1,2-b]pyridazin-3-yl]-4-methoxypyridine-3-carbonitrile To a mixture of (2R)-2-[2-fluoro-5-(4,4,5,5-tetramethyl-1,3,2-dioxaborolan-2-yl)phenoxy]-3-(1H-tetrazol-1-yl)propan-1-ol (262 mg) and 2-{6-chloroimidazo[1,2-b]pyridazin-3-yl}-4-methoxypyridine-3-carbonitrile (137 mg) in DME (3.0 mL) and water (0.30 mL) were added $Cs_2CO_3$ (313 mg) and $Pd(PPh_3)_4$ (55.0 mg). After being stirred under nitrogen atmosphere at 70° C. for 4 hr, the mixture was poured into water and extracted with EtOAc. The organic layer was washed with brine, dried over $Na_2SO_4$ and concentrated under reduced pressure. The residue was purified by silica gel column chromatography (MeOH/EtOAc) to give the titled compound (170 mg) as a yellow solid.
$^1$H NMR (400 MHz, DMSO-$d_6$) δ 9.39 (s, 1H), 8.85 (d, J=6.0 Hz, 1H), 8.42 (d, J=9.2 Hz, 1H), 8.26 (s, 1H), 7.98 (d, J=9.2 Hz, 1H), 7.86 (dd, J=8.4, 2.0 Hz, 1H), 7.67-7.72 (m, 1H), 7.43 (d, J=6.0 Hz, 1H), 7.38 (dd, J=10.8, 8.4 Hz, 1H), 5.25 (t, J=5.2 Hz, 1H), 4.90-4.94 (m, 3H), 4.11 (s, 3H), 3.74-3.80 (m, 1H), 3.65-3.71 (m, 1H); MS m/z 488.0 $[M+H]^+$.

Example 478

2-[6-(4-fluoro-3-{[(2S)-1-(1H-tetrazol-1-yl)propan-2-yl]amino}phenyl)imidazo[1,2-b]pyridazin-3-yl]-4-methoxypyridine-3-carbonitrile

A) N-(5-bromo-2-fluorophenyl)-4-nitrobenzene-1-sulfonamide

To a mixture of 4-nitrobenzenesulfonyl chloride (6.41 g) in DCM (55 mL) were added 5-bromo-2-fluoroaniline (5.00 g) and pyridine (2.50 g) at 0° C. After being stirred under nitrogen atmosphere at 10° C. for 12 hr, the mixture was diluted with water and extracted with EtOAc. The organic layer was washed with brine, dried over $Na_2SO_4$ and concentrated under reduced pressure. The residue was purified by silica gel column chromatography (EtOAc/PE) to give the titled compound (9.00 g).
$^1$H NMR (400 MHz, $CDCl_3$) δ 8.31-8.34 (m, 2H), 7.96-7.99 (m, 2H), 7.79 (dd, J=6.8, 2.4 Hz, 1H), 7.27-7.29 (m, 1H), 6.91 (dd, J=10.0, 8.8 Hz, 1H), 6.77 (s, 1H).

B) tert-butyl N-[(2S)-2-[N-(5-bromo-2-fluorophenyl)-4-nitrobenzenesulfonamido]propyl]carbamate To a mixture of N-(5-bromo-2-fluorophenyl)-4-nitrobenzene-1-sulfonamide (5.00 g), tert-butyl N-[(2R)-2-hydroxypropyl]carbamate (2.57 g) and $PPh_3$ (5.24 g) in THF (50 mL) was added DIAD (4.04 g) at 0° C., After being stirred under nitrogen atmosphere at 10° C. for 12 hr, the mixture was diluted with water and extracted with EtOAc. The organic layer was washed with brine, dried over $Na_2SO_4$ and concentrated under reduced pressure. The residue was purified by silica gel column chromatography (EtOAc/PE) to give the titled compound (3.20 g).

¹H NMR (400 MHz, CDCl₃) δ 8.31-8.36 (m, 2H), 7.86-7.99 (m, 2H), 7.54-7.27 (m, 1H), 7.25-7.01 (m, 2H), 6.81-6.91 (m, 1H), 3.02-3.31 (m, 2H), 2.53-2.85 (m, 1H), 1.45 (s, 9H), 1.02-1.11 (m, 3H).

C) N-[(2S)-1-aminopropan-2-yl]-N-(5-bromo-2-fluorophenyl)-4-nitrobenzene-1-sulfonamide hydrochloride The reaction and purification were performed according to Example 325 Step C to give the titled compound.

¹H NMR (400 MHz, DMSO-d₆) δ 8.47 (d, J=8.8 Hz, 2H), 8.05-8.19 (m, 5H), 7.76-7.81 (m, 1H), 7.31-7.55 (m, 2H), 4.46-4.63 (m, 1H), 2.91-3.05 (m, 1H), 2.71-2.81 (m, 1H), 0.95-1.11 (m, 3H); MS m/z 432.0, 434.0 [M+H]⁺.

D) N-[(2S)-2-[N-(5-bromo-2-fluorophenyl)4-nitrobenzenesulfonamido]propyl]formamide The reaction and purification were performed according to Example 325 Step D to give the titled compound.
MS m/z 460.0, 462.0 [M+H]⁺.

E) N-(5-bromo-2-fluorophenyl)-4-nitro-N-[(2S)-1-(1H-tetrazol-1-yl)propan-2-yl]benzene-1-sulfonamide The reaction and purification were performed according to Example 325 Step E to give the titled compound.

¹H NMR (400 MHz, CDCl₃) δ 8.72 (s, 1H), 8.34 (d, J=8.8 Hz, 2H), 7.81 (d, J=8.4 Hz, 2H), 7.56-7.60 (m, 1H), 6.96-7.24 (m, 2H), 4.66-4.76 (m, 2H), 4.35-4.42 (m, 1H), 1.15-1.31 (m, 3H).

F) N-[2-fluoro-5-(4,4,5,5-tetramethyl-1,3,2-dioxaborolan-2-yl)phenyl]-4-nitro-N-[(2S)-1-(1H-tetrazol-1-yl)propan-2-yl]benzene-1-sulfonamide The reaction and purification were performed according to Example 57 Step E to give the titled compound.

¹H NMR (400 MHz, CDCl₃) δ 8.71 (s, 1H), 8.31 (d, J=9.2 Hz, 2H), 7.82-7.91 (m, 3H), 7.43-7.71 (m, 1H), 7.19 (s, 1H), 4.56-4.91 (m, 2H), 4.30-4.41 (m, 1H), 1.33 (s, 12H), 1.24-1.28 (m, 3H); MS m/z 533.2 [M+H]⁺.

G) 2-fluoro-5-(4,4,5,5-tetramethyl-1,3,2-dioxaborolan-2-yl)-N-[(2S)-1-(1H-tetrazol-1-yl)propan-2-yl]aniline To a mixture of mercaptoacetic acid (125 mg), N-[2-fluoro-5-(4,4,5,5-tetramethyl-1,3,2-dioxaborolan-2-yl)phenyl]-4-nitro-N-[(2S)-1-(1H-tetrazol-1-yl)propan-2-yl]benzene-1-sulfonamide (240 mg) in DMF (4.0 mL) was added LiOH (49.0 mg). After being stirred under nitrogen atmosphere at 10° C. for 4 hr, the mixture was quenched with saturated aqueous NaHCO₃ solution and water and extracted with EtOAc. The organic layer was washed with brine, dried over Na₂SO₄ and concentrated under reduced pressure. The residue was purified by silica gel column chromatography (EtOAc/PE) to give the titled compound (65.0 mg).

¹H NMR (400 MHz, CDCl₃) δ 8.57 (s, 1H), 7.18-7.22 (m, 1H), 7.10 (d, J=9.2 Hz, 1H), 7.02 (dd, J=12.0, 8.0 Hz, 1H), 4.51-4.67 (m, 2H), 4.09-4.14 (m, 1H), 1.34 (s, 12H), 1.27 (d, J=6.4 Hz, 3H) (The NH proton was not observed); MS m/z 348.1 [M+H]⁺.

H) 2-[6-(4-fluoro-3-{[(2S)-1-(1H-tetrazol-1-yl)propan-2-yl]amino}phenyl)imidazo[1,2-b]pyridazin-3-yl]-4-methoxypyridine-3-carbonitrile To a mixture of 2-fluoro-5-(4,4,5,5-tetramethyl-1,3,2-dioxaborolan-2-yl)-N-[(2S)-1-(1H-tetrazol-1-yl)propan-2-yl]aniline (65.0 mg) and 2-{6-chloroimidazo[1,2-b]pyridazin-3-yl}-4-methoxypyridine-3-carbonitrile (36.0 mg) in DME (1.0 mL) and water (0.10 mL) were added Pd(PPh₃)₄ (14.0 mg) and Cs₂CO₃ (81.0 mg). After being stirred under nitrogen atmosphere at 70° C. for 4 hr, the mixture was diluted with water and extracted with EtOAc. The organic layer was washed with brine, dried over Na₂SO₄ and concentrated under reduced pressure. The residue was purified by silica gel column chromatography (MeOH/DCM) and then preparative TLC (MeOH/DCM) to give the titled compound (13.0 mg) as a yellow solid.

¹H NMR (400 MHz, DMSO-d₆) δ 9.32 (s, 1H), 8.85 (d, J=6.0 Hz, 1H), 8.38 (d, J=9.6 Hz, 1H), 8.24 (s, 1H), 7.95 (d, J=9.6 Hz, 1H), 7.40-7.49 (m, 2H), 7.17-7.28 (m, 2H), 5.74 (d, J=8.0 Hz, 1H), 4.61-4.73 (m, 2H), 4.16-4.25 (m, 1H), 4.01 (s, 3H), 1.21 (d, J=6.4 Hz, 3H); MS m/z 471.1 [M+H]⁺.

The compounds of the Examples 1 to 486 in the following Table 1 were produced according to the methods described in the above-mentioned Examples, or methods analogous thereto. The MS of the compounds of Examples 1 to 486 are shown in the following Table 1. MS in the tables means actual measured value.

| Ex. No. | IUPAC NAME | Act | MS |
|---|---|---|---|
| 1 | 3-[5-(4-cyano-3-{[(2S)-1-(1H-tetrazol-1-yl)propan-2-yl]oxy}phenyl)pyrazolo[1,5-a]pyrimidin-3-yl]-N-[2-(diethylamino)ethyl]benzamide | B | 564.9 |
| 2 | methyl 3-[5-(4-cyano-3-{[(2S)-1-(1H-tetrazol-1-yl)propan-2-yl]oxy}phenyl)pyrazolo[1,5-a]pyrimidin-3-yl]benzoate | C | 481.2 |
| 3 | 1-[(2S)-2-{2-fluoro-5-[3-(thiophen-2-yl)pyrazolo[1,5-a]pyrimidin-5-yl]phenoxy}propyl]-1H-tetrazole | A | 422.2 |
| 4 | 2-[5-(4-fluoro-3-{[(2S)-1-(1H-tetrazol-1-yl)propan-2-yl]oxy}phenyl)pyrazolo[1,5-a]pyrimidin-3-yl]pyridine | A | 417.2 |
| 5 | 1-[(2S)-2-(2-fluoro-5-{3-phenylpyrazolo[1,5-a]pyrimidin-5-yl}phenoxy)propyl]-1H-tetrazole | A | 416.2 |
| 6 | methyl 3-[5-(4-fluoro-3-{[(2S)-1-(1H-tetrazol-1-yl)propan-2-yl]oxy}phenyl)pyrazolo[1,5-a]pyrimidin-3-yl]benzoate | A | 474.2 |
| 7 | 3-[5-(4-fluoro-3-{[(2S)-1-(1H-tetrazol-1-yl)propan-2-yl]oxy}phenyl)pyrazolo[1,5-a]pyrimidin-3-yl]benzoic acid | A | 460.1 |
| 8 | N-ethyl-3-[5-(4-fluoro-3-{[(2S)-1-(1H-tetrazol-1-yl)propan-2-yl]oxy}phenyl)pyrazolo[1,5-a]pyrimidin-3-yl]benzamide | A | 487.2 |
| 9 | 3-[5-(4-fluoro-3-{[(2S)-1-(1H-tetrazol-1-yl)propan-2-yl]oxy}phenyl)pyrazolo[1,5-a]pyrimidin-3-yl]-N-(3-methoxypropyl)benzamide | A | 531.2 |
| 10 | 4-(1-{3-[5-(4-fluoro-3-{[(2S)-1-(1H-tetrazol-1-yl)propan-2-yl]oxy}phenyl)pyrazolo[1,5-a]pyrimidin-3-yl]benzoyl}piperidin-4-yl)morpholine | A | 612.3 |
| 11 | 3-[5-(4-cyano-3-{[(2S)-1-(1H-tetrazol-1-yl)propan-2-yl]oxy}phenyl)-3H-imidazo[4,5-b]pyridin-3-yl]-N-[2-(diethylamino)ethyl]benzamide | C | 565.2 |
| 12 | N-[2-(diethylamino)ethyl]-3-[5-(4-fluoro-3-{[(2S)-1-(1H-tetrazol-1-yl)propan-2-yl]oxy}phenyl)-3H-imidazo[4,5-b]pyridin-3-yl]benzamide | A | 558.2 |
| 13 | methyl 3-[5-(4-fluoro-3-{[(2S)-1-(1H-tetrazol-1-yl)propan-2-yl]oxy}phenyl)-3H-imidazo[4,5-b]pyridin-3-yl]benzoate | A | 474.2 |

| Ex. No. | IUPAC NAME | Act | MS |
|---|---|---|---|
| 14 | methyl 2-[5-(4-fluoro-3-{[(2S)-1-(1H-tetrazol-1-yl)propan-2-yl]oxy}phenyl)-3H-imidazo[4,5-b]pyridin-3-yl]pyridine-4-carboxylate | A | 475.2 |
| 15 | 4-{4-[5-(3-{[(2S)-1-(1H-tetrazol-1-yl)propan-2-yl]oxy}phenyl)pyrazolo[1,5-a]pyrimidin-3-yl]phenyl}morpholine | B | 483.2 |
| 16 | 3-[5-(3-{[(2S)-1-(1H-tetrazol-1-yl)propan-2-yl]oxy}phenyl)pyrazolo[1,5-a]pyrimidin-3-yl]benzoic acid | A | 442.2 |
| 17 | 1-[(2S)-2-{2-fluoro-5-[3-(thiophen-2-yl)imidazo[1,2-a]pyridin-6-yl]phenoxy}propyl]-1H-tetrazole | B | 421.1 |
| 18 | 1-[(2S)-2-{2-fluoro-5-[3-(furan-2-yl)pyrazolo[1,5-a]pyrimidin-5-yl]phenoxy}propyl]-1H-tetrazole | A | 406.0 |
| 19 | 1-[(2S)-2-{2-fluoro-5-[3-(furan-3-yl)pyrazolo[1,5-a]pyrimidin-5-yl]phenoxy}propyl]-1H-tetrazole | A | 406.1 |
| 20 | 3-[5-(4-fluoro-3-{[(2S)-1-(1H-tetrazol-1-yl)propan-2-yl]oxy}phenyl)pyrazolo[1,5-a]pyrimidin-3-yl]pyridine | A | 417.0 |
| 21 | 4-[5-(4-fluoro-3-{[(2S)-1-(1H-tetrazol-1-yl)propan-2-yl]oxy}phenyl)pyrazolo[1,5-a]pyrimidin-3-yl]pyridine | A | 417.0 |
| 22 | 5-[5-(4-fluoro-3-{[(2S)-1-(1H-tetrazol-1-yl)propan-2-yl]oxy}phenyl)pyrazolo[1,5-a]pyrimidin-3-yl]pyrimidine | A | 418.1 |
| 23 | 1-[(2S)-2-{2-fluoro-5-[3-(1-methyl-1H-pyrazol-4-yl)pyrazolo[1,5-a]pyrimidin-5-yl]phenoxy}propyl]-1H-tetrazole | A | 420.0 |
| 24 | 1-[(2S)-2-{2-fluoro-5-[3-(1-methyl-1H-pyrazol-5-yl)pyrazolo[1,5-a]pyrimidin-5-yl]phenoxy}propyl]-1H-tetrazole | B | 420.0 |
| 25 | 1-[(2S)-2-{2-fluoro-5-[3-(1-methyl-1H-pyrazol-3-yl)pyrazolo[1,5-a]pyrimidin-5-yl]phenoxy}propyl]-1H-tetrazole | A | 420.0 |
| 26 | 1-[(2S)-2-{2-fluoro-5-[3-(thiophen-3-yl)pyrazolo[1,5-a]pyrimidin-5-yl]phenoxy}propyl]-1H-tetrazole | A | 422.0 |
| 27 | 1-[(2S)-2-{2-fluoro-5-[3-(1,3-thiazol-5-yl)pyrazolo[1,5-a]pyrimidin-5-yl]phenoxy}propyl]-1H-tetrazole | A | 423.0 |
| 28 | 2-[5-(4-fluoro-3-{[(2S)-1-(1H-tetrazol-1-yl)propan-2-yl]oxy}phenyl)pyrazolo[1,5-a]pyrimidin-3-yl]benzonitrile | A | 441.0 |
| 29 | 3-[5-(4-fluoro-3-{[(2S)-1-(1H-tetrazol-1-yl)propan-2-yl]oxy}phenyl)pyrazolo[1,5-a]pyrimidin-3-yl]benzonitrile | A | 441.0 |
| 30 | 1-[(2S)-2-{2-fluoro-5-[3-(4-methoxyphenyl)pyrazolo[1,5-a]pyrimidin-5-yl]phenoxy}propyl]-1H-tetrazole | A | 446.0 |
| 31 | 1-[(2S)-2-{2-fluoro-5-[3-(2-methoxyphenyl)pyrazolo[1,5-a]pyrimidin-5-yl]phenoxy}propyl]-1H-tetrazole | A | 446.0 |
| 32 | 1-[(2S)-2-{2-fluoro-5-[3-(3-methoxyphenyl)pyrazolo[1,5-a]pyrimidin-5-yl]phenoxy}propyl]-1H-tetrazole | A | 446.0 |
| 33 | 2-{3-[5-(4-fluoro-3-{[(2S)-1-(1H-tetrazol-1-yl)propan-2-yl]oxy}phenyl)pyrazolo[1,5-a]pyrimidin-3-yl]phenoxy}acetonitrile | A | 471.0 |
| 34 | 2-[5-(4-fluoro-3-{[(2S)-1-(1H-tetrazol-1-yl)propan-2-yl]oxy}phenyl)pyrazolo[1,5-a]pyrimidin-3-yl]-N-methylbenzamide | C | 473.0 |
| 35 | 3-[5-(4-fluoro-3-{[(2S)-1-(1H-tetrazol-1-yl)propan-2-yl]oxy}phenyl)pyrazolo[1,5-a]pyrimidin-3-yl]-N-methylbenzamide | A | 473.1 |
| 36 | N-{3-[5-(4-fluoro-3-{[(2S)-1-(1H-tetrazol-1-yl)propan-2-yl]oxy}phenyl)pyrazolo[1,5-a]pyrimidin-3-yl]phenyl}acetamide | A | 473.0 |
| 37 | 4-[5-(4-fluoro-3-{[(2S)-1-(1H-tetrazol-1-yl)propan-2-yl]oxy}phenyl)pyrazolo[1,5-a]pyrimidin-3-yl]-N-methylbenzamide | A | 473.0 |
| 38 | N-{4-[5-(4-fluoro-3-{[(2S)-1-(1H-tetrazol-1-yl)propan-2-yl]oxy}phenyl)pyrazolo[1,5-a]pyrimidin-3-yl]phenyl}acetamide | A | 473.0 |
| 39 | N-{2-[5-(4-fluoro-3-{[(2S)-1-(1H-tetrazol-1-yl)propan-2-yl]oxy}phenyl)pyrazolo[1,5-a]pyrimidin-3-yl]phenyl}acetamide | C | 473.0 |
| 40 | ([3-[5-(4-fluoro-3-{[(2S)-1-(1H-tetrazol-1-yl)propan-2-yl]oxy}phenyl)pyrazolo[1,5-a]pyrimidin-3-yl]phenyl]methyl)dimethylamine | A | 473.0 |
| 41 | ({4-[5-(4-fluoro-3-{[(2S)-1-(1H-tetrazol-1-yl)propan-2-yl]oxy}phenyl)pyrazolo[1,5-a]pyrimidin-3-yl]phenyl}methyl)dimethylamine | A | 473.0 |
| 42 | 1-(4-{4-[5-(4-fluoro-3-{[(2S)-1-(1H-tetrazol-1-yl)propan-2-yl]oxy}phenyl)pyrazolo[1,5-a]pyrimidin-3-yl]phenyl}piperazin-1-yl)ethan-1-one | B | 541.9 |
| 43 | 1-[(2S)-2-(2-fluoro-5-{3-[2-(2-methoxyethoxy)phenyl]pyrazolo[1,5-a]pyrimidin-5-yl}phenoxy)propyl]-1H-tetrazole | A | 490.0 |
| 44 | 1-[(2S)-2-(2-fluoro-5-{3-[4-(2-methoxyethoxy)phenyl]pyrazolo[1,5-a]pyrimidin-5-yl}phenoxy)propyl]-1H-tetrazole | B | 490.0 |
| 45 | 1-[(2S)-2-(2-fluoro-5-{3-[2-(trifluoromethoxy)phenyl]pyrazolo[1,5-a]pyrimidin-5-yl}phenoxy)propyl]-1H-tetrazole | B | 499.9 |
| 46 | 1-[(2S)-2-(2-fluoro-5-{3-[3-(trifluoromethoxy)phenyl]pyrazolo[1,5-a]pyrimidin-5-yl}phenoxy)propyl]-1H-tetrazole | B | 500.1 |
| 47 | 4-{3-[5-(4-fluoro-3-{[(2S)-1-(1H-tetrazol-1-yl)propan-2-yl]oxy}phenyl)pyrazolo[1,5-a]pyrimidin-3-yl]phenyl}morpholine | B | 501.0 |
| 48 | 4-{2-[5-(4-fluoro-3-{[(2S)-1-(1H-tetrazol-1-yl)propan-2-yl]oxy}phenyl)pyrazolo[1,5-a]pyrimidin-3-yl]phenyl}morpholine | B | 501.0 |
| 49 | 4-{4-[5-(4-fluoro-3-{[(2S)-1-(1H-tetrazol-1-yl)propan-2-yl]oxy}phenyl)pyrazolo[1,5-a]pyrimidin-3-yl]phenyl}morpholine | B | 501.0 |
| 50 | 1-[(2S)-2-{2-fluoro-5-[3-(3-fluorophenyl)pyrazolo[1,5-a]pyrimidin-5-yl]phenoxy}propyl]-1H-tetrazole | A | 434.0 |
| 51 | 1-[(2S)-2-{2-fluoro-5-[3-(4-fluorophenyl)pyrazolo[1,5-a]pyrimidin-5-yl]phenoxy}propyl]-1H-tetrazole | A | 434.1 |
| 52 | 1-[(2S)-2-{2-fluoro-5-[3-(2-fluorophenyl)pyrazolo[1,5-a]pyrimidin-5-yl]phenoxy}propyl]-1H-tetrazole | A | 434.2 |
| 53 | 1-[(2S)-2-{2-fluoro-5-[3-[4-(propan-2-yl)phenyl]pyrazolo[1,5-a]pyrimidin-5-yl}phenoxy)propyl]-1H-tetrazole | C | 458.0 |
| 54 | 1-[(2S)-2-(5-{3-[3-(cyclopropylmethoxy)phenyl]pyrazolo[1,5-a]pyrimidin-5-yl}-2-fluorophenoxy)propyl]-1H-tetrazole | B | 486.0 |
| 55 | 1-{2-[5-(4-fluoro-3-{[(2S)-1-(1H-tetrazol-1-yl)propan-2-yl]oxy}phenyl)pyrazolo[1,5-a]pyrimidin-3-yl]phenyl}piperazine | C | 500.0 |
| 56 | 1-{4-[5-(4-fluoro-3-{[(2S)-1-(1H-tetrazol-1-yl)propan-2-yl]oxy}phenyl)pyrazolo[1,5-a]pyrimidin-3-yl]phenyl}piperazine | A | 500.1 |
| 57 | 1-[(2S)-2-{2-fluoro-5-[2-methyl-3-(thiophen-2-yl)pyrazolo[1,5-a]pyrimidin-5-yl]phenoxy}propyl]-1H-tetrazole | B | 436.2 |
| 58 | 2-[(2S)-2-{3-[3-(thiophen-2-yl)pyrazolo[1,5-a]pyrimidin-5-yl]phenoxy}propyl]-2H-tetrazol-5-amine | C | 419.2 |
| 59 | 1-[(2S)-2-{3-[3-(thiophen-2-yl)pyrazolo[1,5-a]pyrimidin-5-yl]phenoxy}propyl]-1H-tetrazol-5-amine | A | 419.1 |
| 60 | 1-[(2S)-2-{2-fluoro-5-[3-(thiophen-2-yl)imidazo[1,2-b]pyridazin-6-yl]phenoxy}propyl]-1H-tetrazole | A | 422.2 |
| 61 | 1-[(2S)-2-{3-[3-(thiophen-2-yl)pyrazolo[1,5-a]pyrimidin-5-yl]phenoxy}propyl]-1H-1,2,4-triazole | A | 403.2 |
| 62 | 3-[5-(4-fluoro-3-{[(2S)-1-(1H-tetrazol-1-yl)propan-2-yl]oxy}phenyl)-3H-imidazo[4,5-b]pyridin-3-yl]benzoic acid | B | 460.1 |
| 63 | N-(cyclopropylmethyl)-3-[5-(3-{[(2S)-1-(1H-tetrazol-1-yl)propan-2-yl]oxy}phenyl)pyrazolo[1,5-a]pyrimidin-3-yl]benzamide | A | 495.0 |

| Ex. No. | IUPAC NAME | Act | MS |
|---|---|---|---|
| 64 | N-(3-methylbutyl)-3-[5-(3-{[(2S)-1-(1H-tetrazol-1-yl)propan-2-yl]oxy}phenyl)pyrazolo[1,5-a]pyrimidin-3-yl]benzamide | A | 511.1 |
| 65 | N-(1H-pyrazol-4-yl)-3-[5-(3-{[(2S)-1-(1H-tetrazol-1-yl)propan-2-yl]oxy}phenyl)pyrazolo[1,5-a]pyrimidin-3-yl]benzamide | A | 506.9 |
| 66 | N-[3-(3-hydroxyazetidin-1-yl)propyl]-3-[5-(3-{[(2S)-1-(1H-tetrazol-1-yl)propan-2-yl]oxy}phenyl)pyrazolo[1,5-a]pyrimidin-3-yl]benzamide | A | 554.1 |
| 67 | N-[2-(morpholin-4-yl)ethyl]-3-[5-(3-{[(2S)-1-(1H-tetrazol-1-yl)propan-2-yl]oxy}phenyl)pyrazolo[1,5-a]pyrimidin-3-yl]benzamide | A | 554.2 |
| 68 | N,N-diethyl-2-({3-[5-(3-{[(2S)-1-(1H-tetrazol-1-yl)propan-2-yl]oxy}phenyl)pyrazolo[1,5-a]pyrimidin-3-yl]phenyl}formamido)acetamide | A | 554.1 |
| 69 | N-[3-(diethylamino)propyl]-3-[5-(3-{[(2S)-1-(1H-tetrazol-1-yl)propan-2-yl]oxy}phenyl)pyrazolo[1,5-a]pyrimidin-3-yl]benzamide | A | 554.1 |
| 70 | N-(1-methylazetidin-3-yl)-3-[5-(3-{[(2S)-1-(1H-tetrazol-1-yl)propan-2-yl]oxy}phenyl)pyrazolo[1,5-a]pyrimidin-3-yl]benzamide | A | 510.0 |
| 71 | 4-{3-[5-(3-{[(2S)-1-(1H-tetrazol-1-yl)propan-2-yl]oxy}phenyl)pyrazolo[1,5-a]pyrimidin-3-yl]benzoyl}morpholine | B | 511.0 |
| 72 | N-(2,2-dimethylpropyl)-3-[5-(3-{[(2S)-1-(1H-tetrazol-1-yl)propan-2-yl]oxy}phenyl)pyrazolo[1,5-a]pyrimidin-3-yl]benzamide | A | 511.0 |
| 73 | N-(1-{3-[5-(3-{[(2S)-1-(1H-tetrazol-1-yl)propan-2-yl]oxy}phenyl)pyrazolo[1,5-a]pyrimidin-3-yl]benzoyl}piperidin-4-yl)acetamide | B | 566.0 |
| 74 | N-[3-(2-oxopyrrolidin-1-yl)propyl]-3-[5-(3-{[(2S)-1-(1H-tetrazol-1-yl)propan-2-yl]oxy}phenyl)pyrazolo[1,5-a]pyrimidin-3-yl]benzamide | A | 566.0 |
| 75 | N-(1-acetylpiperidin-4-yl)-3-[5-(3-{[(2S)-1-(1H-tetrazol-1-yl)propan-2-yl]oxy}phenyl)pyrazolo[1,5-a]pyrimidin-3-yl]benzamide | A | 566.0 |
| 76 | N-[2-(1-methylpiperidin-4-yl)ethyl]-3-[5-(3-{[(2S)-1-(1H-tetrazol-1-yl)propan-2-yl]oxy}phenyl)pyrazolo[1,5-a]pyrimidin-3-yl]benzamide | A | 566.1 |
| 77 | N-methyl-2-({3-[5-(3-{[(2S)-1-(1H-tetrazol-1-yl)propan-2-yl]oxy}phenyl)pyrazolo[1,5-a]pyrimidin-3-yl]phenyl}formamido)acetamide | A | 512.0 |
| 78 | N-[3-(morpholin-4-yl)propyl]-3-[5-(3-{[(2S)-1-(1H-tetrazol-1-yl)propan-2-yl]oxy}phenyl)pyrazolo[1,5-a]pyrimidin-3-yl]benzamide | A | 568.0 |
| 79 | N-(4-hydroxybutyl)-3-[5-(3-{[(2S)-1-(1H-tetrazol-1-yl)propan-2-yl]oxy}phenyl)pyrazolo[1,5-a]pyrimidin-3-yl]benzamide | A | 513.0 |
| 80 | N-(2-hydroxy-2-methylpropyl)-3-[5-(3-{[(2S)-1-(1H-tetrazol-1-yl)propan-2-yl]oxy}phenyl)pyrazolo[1,5-a]pyrimidin-3-yl]benzamide | A | 513.0 |
| 81 | N-phenyl-3-[5-(3-{[(2S)-1-(1H-tetrazol-1-yl)propan-2-yl]oxy}phenyl)pyrazolo[1,5-a]pyrimidin-3-yl]benzamide | B | 517.0 |
| 82 | N-(pyridin-4-yl)-3-[5-(3-{[(2S)-1-(1H-tetrazol-1-yl)propan-2-yl]oxy}phenyl)pyrazolo[1,5-a]pyrimidin-3-yl]benzamide | A | 518.0 |
| 83 | N-(pyridin-2-yl)-3-[5-(3-{[(2S)-1-(1H-tetrazol-1-yl)propan-2-yl]oxy}phenyl)pyrazolo[1,5-a]pyrimidin-3-yl]benzamide | A | 518.0 |
| 84 | N-(pyridin-3-yl)-3-[5-(3-{[(2S)-1-(1H-tetrazol-1-yl)propan-2-yl]oxy}phenyl)pyrazolo[1,5-a]pyrimidin-3-yl]benzamide | A | 518.0 |
| 85 | N-(1-methyl-1H-pyrazol-4-yl)-3-[5-(3-{[(2S)-1-(1H-tetrazol-1-yl)propan-2-yl]oxy}phenyl)pyrazolo[1,5-a]pyrimidin-3-yl]benzamide | A | 521.0 |
| 86 | N-(1-benzylazetidin-3-yl)-3-[5-(3-{[(2S)-1-(1H-tetrazol-1-yl)propan-2-yl]oxy}phenyl)pyrazolo[1,5-a]pyrimidin-3-yl]benzamide | A | 586.0 |
| 87 | N-[2-(1,1-dioxo-1$\lambda^6$-thiomorpholin-4-yl)ethyl]-3-[5-(3-{[(2S)-1-(1H-tetrazol-1-yl)propan-2-yl]oxy}phenyl)pyrazolo[1,5-a]pyrimidin-3-yl]benzamide | A | 601.9 |
| 88 | N-(1-methylpyrrolidin-3-yl)-3-[5-(3-{[(2S)-1-(1H-tetrazol-1-yl)propan-2-yl]oxy}phenyl)pyrazolo[1,5-a]pyrimidin-3-yl]benzamide | A | 524.0 |
| 89 | 1-{3-[5-(3-{[(2S)-1-(1H-tetrazol-1-yl)propan-2-yl]oxy}phenyl)pyrazolo[1,5-a]pyrimidin-3-yl]benzoyl}piperidin-4-ol | B | 525.0 |
| 90 | N-[2-({3-[5-(3-{[(2S)-1-(1H-tetrazol-1-yl)propan-2-yl]oxy}phenyl)pyrazolo[1,5-a]pyrimidin-3-yl]phenyl}formamido)ethyl]acetamide | A | 526.1 |
| 91 | N-benzyl-3-[5-(3-{[(2S)-1-(1H-tetrazol-1-yl)propan-2-yl]oxy}phenyl)pyrazolo[1,5-a]pyrimidin-3-yl]benzamide | A | 531.0 |
| 92 | N-[(pyridin-2-yl)methyl]-3-[5-(3-{[(2S)-1-(1H-tetrazol-1-yl)propan-2-yl]oxy}phenyl)pyrazolo[1,5-a]pyrimidin-3-yl]benzamide | A | 532.1 |
| 93 | N-[(pyridin-4-yl)methyl]-3-[5-(3-{[(2S)-1-(1H-tetrazol-1-yl)propan-2-yl]oxy}phenyl)pyrazolo[1,5-a]pyrimidin-3-yl]benzamide | A | 532.0 |
| 94 | N-[(pyridin-3-yl)methyl]-3-[5-(3-{[(2S)-1-(1H-tetrazol-1-yl)propan-2-yl]oxy}phenyl)pyrazolo[1,5-a]pyrimidin-3-yl]benzamide | A | 532.0 |
| 95 | N-[2-(1H-imidazol-1-yl)ethyl]-3-[5-(3-{[(2S)-1-(1H-tetrazol-1-yl)propan-2-yl]oxy}phenyl)pyrazolo[1,5-a]pyrimidin-3-yl]benzamide | A | 535.1 |
| 96 | 3-[5-(3-{[(2S)-1-(1H-tetrazol-1-yl)propan-2-yl]oxy}phenyl)pyrazolo[1,5-a]pyrimidin-3-yl]-N-[2-(1H-1,2,4-triazol-1-yl)ethyl]benzamide | A | 536.1 |
| 97 | N-(1-methyl-5-oxopyrrolidin-3-yl)-3-[5-(3-{[(2S)-1-(1H-tetrazol-1-yl)propan-2-yl]oxy}phenyl)pyrazolo[1,5-a]pyrimidin-3-yl]benzamide | A | 537.9 |
| 98 | N-(1-methylpiperidin-4-yl)-3-[5-(3-{[(2S)-1-(1H-tetrazol-1-yl)propan-2-yl]oxy}phenyl)pyrazolo[1,5-a]pyrimidin-3-yl]benzamide | A | 538.0 |
| 99 | 4-methyl-1-{3-[5-(3-{[(2S)-1-(1H-tetrazol-1-yl)propan-2-yl]oxy}phenyl)pyrazolo[1,5-a]pyrimidin-3-yl]benzoyl}piperidin-4-ol | B | 539.0 |
| 100 | N-(oxan-4-yl)methyl]-3-[5-(3-{[(2S)-1-(1H-tetrazol-1-yl)propan-2-yl]oxy}phenyl)pyrazolo[1,5-a]pyrimidin-3-yl]benzamide | A | 539.0 |
| 101 | 4-methoxy-1-{3-[5-(3-{[(2S)-1-(1H-tetrazol-1-yl)propan-2-yl]oxy}phenyl)pyrazolo[1,5-a]pyrimidin-3-yl]benzoyl[piperidine | B | 539.0 |
| 102 | N-[3-({3-[5-(3-{[(2S)-1-(1H-tetrazol-1-yl)propan-2-yl]oxy}phenyl)pyrazolo[1,5-a]pyrimidin-3-yl]phenyl}formamido)propyl]acetamide | A | 540.0 |
| 103 | N-[2-(diethylamino)ethyl]-3-[5-(3-{[(2S)-1-(1H-tetrazol-1-yl)propan-2-yl]oxy}phenyl)pyrazolo[1,5-a]pyrimidin-3-yl]benzamide | A | 540.0 |
| 104 | N-[4-(dimethylamino)butyl]-3-[5-(3-{[(2S)-1-(1H-tetrazol-1-yl)propan-2-yl]oxy}phenyl)pyrazolo[1,5-a]pyrimidin-3-yl]benzamide | A | 540.0 |

| Ex. No. | IUPAC NAME | Act | MS |
|---|---|---|---|
| 105 | N-(2-phenylethyl)-3-[5-(3-{[(2S)-1-(1H-tetrazol-1-yl)propan-2-yl]oxy}phenyl)pyrazolo[1,5-a]pyrimidin-3-yl]benzamide | B | 545.0 |
| 106 | N-[2-(pyridin-2-yl)ethyl]-3-[5-(3-{[(2S)-1-(1H-tetrazol-1-yl)propan-2-yl]oxy}phenyl)pyrazolo[1,5-a]pyrimidin-3-yl]benzamide | A | 546.0 |
| 107 | N-[2-(pyridin-4-yl)ethyl]-3-[5-(3-{[(2S)-1-(1H-tetrazol-1-yl)propan-2-yl]oxy}phenyl)pyrazolo[1,5-a]pyrimidin-3-yl]benzamide | A | 546.0 |
| 108 | N-[2-(pyridin-3-yl)ethyl]-3-[5-(3-{[(2S)-1-(1H-tetrazol-1-yl)propan-2-yl]oxy}phenyl)pyrazolo[1,5-a]pyrimidin-3-yl]benzamide | A | 546.1 |
| 109 | 1-[(2S)-2-{3-[3-(3-{5H,6H,7H,8H-imidazo[1,2-a]pyrazine-7-carbonyl[phenyl]pyrazolo[1,5-a]pyrimidin-5-yl]phenoxy}propyl]-1H-tetrazole | B | 547.0 |
| 110 | 1-[(2S)-2-{3-[3-(3-{5H,6H,7H,8H-[1,2,4]triazolo[1,5-a]pyrazine-7-carbonyl}phenyl)pyrazolo[1,5-a]pyrimidin-5-yl]phenoxy}propyl]-1H-tetrazole | B | 548.1 |
| 111 | N-(2-cyclohexylethyl)-3-[5-(3-{[(2S)-1-(1H-tetrazol-1-yl)propan-2-yl]oxy}phenyl)pyrazolo[1,5-a]pyrimidin-3-yl]benzamide | B | 551.1 |
| 112 | N-(1-methyl-2-oxopiperidin-4-yl)-3-[5-(3-{[(2S)-1-(1H-tetrazol-1-yl)propan-2-yl]oxy}phenyl)pyrazolo[1,5-a]pyrimidin-3-yl]benzamide | A | 552.1 |
| 113 | N-[2-(2-oxopyrrolidin-1-yl)ethyl]-3-[5-(3-{[(2S)-1-(1H-tetrazol-1-yl)propan-2-yl]oxy}phenyl)pyrazolo[1,5-a]pyrimidin-3-yl]benzamide | A | 552.0 |
| 114 | 5-[(2S)-2-{3-[3-(thiophen-2-yl)pyrazolo[1,5-a]pyrimidin-5-yl]phenoxy}propyl]-1H-tetrazole | B | 404.2 |
| 115 | 3-[5-(4-fluoro-3-{[(2S)-1-(1H-tetrazol-1-yl)propan-2-yl]oxy}phenyl)-3H-imidazo[4,5-b]pyridin-3-yl]-N-methylbenzamide | A | 473.2 |
| 116 | 2-[5-(4-fluoro-3-{[(2S)-1-(1H-tetrazol-1-yl)propan-2-yl]oxy}phenyl)-3H-imidazo[4,5-b]pyridin-3-yl]-N-methylpyridine-4-carboxamide | A | 474.2 |
| 117 | N-[2-(diethylamino)ethyl]-2-[5-(4-fluoro-3-{[(2S)-1-(1H-tetrazol-1-yl)propan-2-yl]oxy}phenyl)-3H-imidazo[4,5-b]pyridin-3-yl]pyridine-4-carboxamide | A | 559.3 |
| 118 | tert-butyl 4-[5-(4-fluoro-3-{[(2S)-1-(1H-tetrazol-1-yl)propan-2-yl]oxy}phenyl)-3H-imidazo[4,5-b]pyridin-3-yl]-1H-pyrazole-1-carboxylate | A | 506.2 |
| 119 | 1-[(2S)-2-{2-fluoro-5-[3-(1H-pyrazol-4-yl)-3H-imidazo[4,5-b]pyridin-5-yl]phenoxy}propyl]-1H-tetrazole | A | 406.2 |
| 120 | 1-[(2S)-2-{2-fluoro-5-[3-(1-methyl-1H-pyrazol-4-yl)-3H-imidazo[4,5-b]pyridin-5-yl]phenoxy}propyl]-1H-tetrazole | B | 420.2 |
| 121 | 2-[6-(4-fluoro-3-{[(2S)-1-(1H-tetrazol-1-yl)propan-2-yl]oxy}phenyl)imidazo[1,2-b]pyridazin-3-yl]benzonitrile | A | 441.0 |
| 122 | 1-[(2S)-2-{2-fluoro-5-[3-(1-methyl-1H-pyrazol-3-yl)-3H-imidazo[4,5-b]pyridin-5-yl]phenoxy}propyl]-1H-tetrazole | A | 420.2 |
| 123 | 2-[5-(4-fluoro-3-{[(2S)-1-(1H-tetrazol-1-yl)propan-2-yl]oxy}phenyl)pyrazolo[1,5-a]pyrimidin-3-yl]benzaldehyde | A | 444.2 |
| 124 | benzyl 2-{3-cyano-4-[6-(4-fluoro-3-{[(2S)-1-(1H-tetrazol-1-yl)propan-2-yl]oxy}phenyl)imidazo[1,2-b]pyridazin-3-yl]-1H-pyrazol-1-yl}acetate | B | 579.2 |
| 125 | 2-{3-cyano-4-[6-(4-fluoro-3-{[(2S)-1-(1H-tetrazol-1-yl)propan-2-yl]oxy}phenyl)imidazo[1,2-b]pyridazin-3-yl]-1H-pyrazol-1-yl}acetic acid | B | 489.1 |
| 126 | 2-{3-cyano-4-[6-(4-fluoro-3-{[(2S)-1-(1H-tetrazol-1-yl)propan-2-yl]oxy}phenyl)imidazo[1,2-b]pyridazin-3-yl]-1H-pyrazol-1-yl}-N-(3-methoxypropyl)acetamide | C | 560.3 |
| 127 | 2-{3-cyano-4-[6-(4-fluoro-3-{[(2S)-1-(1H-tetrazol-1-yl)propan-2-yl]oxy}phenyl)imidazo[1,2-b]pyridazin-3-yl]-1H-pyrazol-1-yl}-N-[2-(morpholin-4-yl)ethyl]acetamide | C | 601.3 |
| 128 | methyl 2-chloro-3-[5-(4-fluoro-3-{[(2S)-1-(1H-tetrazol-1-yl)propan-2-yl]oxy}phenyl)pyrazolo[1,5-a]pyrimidin-3-yl]benzoate | B | 508.3 |
| 129 | 1-[(2S)-2-(2-fluoro-5-{3-[2-(trifluoromethyl)phenyl]pyrazolo[1,5-a]pyrimidin-5-yl}phenoxy)propyl]-1H-tetrazole | C | 484.1 |
| 130 | 1-[(2S)-2-(2-fluoro-5-{3-[3-(trifluoromethyl)phenyl]pyrazolo[1,5-a]pyrimidin-5-yl}phenoxy)propyl]-1H-tetrazole | B | 484.1 |
| 131 | 1-[(2S)-2-{5-{3-[3-(difluoromethyl)phenyl]pyrazolo[1,5-a]pyrimidin-5-yl}-2-fluorophenoxy)propyl]-1H-tetrazole | A | 466.1 |
| 132 | 1-[(2S)-2-(5-{3-[4-(difluoromethyl)phenyl]pyrazolo[1,5-a]pyrimidin-5-yl}-2-fluorophenoxy)propyl]-1H-tetrazole | B | 466.2 |
| 133 | 1-[(2S)-2-{5-[3-(2-chlorophenyl)pyrazolo[1,5-a]pyrimidin-5-yl]-2-fluorophenoxy)propyl]-1H-tetrazole | B | 450.1 |
| 134 | 1-[(2S)-2-{5-[3-(3-chlorophenyl)pyrazolo[1,5-a]pyrimidin-5-yl]-2-fluorophenoxy)propyl]-1H-tetrazole | A | 450.1 |
| 135 | 1-[(2S)-2-{5-[3-(4-chlorophenyl)pyrazolo[1,5-a]pyrimidin-5-yl]-2-fluorophenoxy)propyl]-1H-tetrazole | B | 450.1 |
| 136 | 4-[5-(4-fluoro-3-{[(2S)-1-(1H-tetrazol-1-yl)propan-2-yl]oxy}phenyl)pyrazolo[1,5-a]pyrimidin-3-yl]benzonitrile | B | 441.2 |
| 137 | 3-[5-(4-fluoro-3-{[(2S)-1-(1H-tetrazol-1-yl)propan-2-yl]oxy}phenyl)pyrazolo[1,5-a]pyrimidin-3-yl]pyridine-2-carbonitrile | A | 442.2 |
| 138 | 3-[5-(4-fluoro-3-{[(2S)-1-(1H-tetrazol-1-yl)propan-2-yl]oxy}phenyl)pyrazolo[1,5-a]pyrimidin-3-yl]pyridine-4-carbonitrile | A | 442.2 |
| 139 | 5-[5-(4-fluoro-3-{[(2S)-1-(1H-tetrazol-1-yl)propan-2-yl]oxy}phenyl)pyrazolo[1,5-a]pyrimidin-3-yl]thiophene-2-carbonitrile | A | 447.1 |
| 140 | 2-[5-(4-fluoro-3-{[(2S)-1-(1H-tetrazol-1-yl)propan-2-yl]oxy}phenyl)pyrazolo[1,5-a]pyrimidin-3-yl]-4-methoxypyridine | B | 447.2 |
| 141 | 1-[(2S)-2-{2-fluoro-5-[3-(2-methyl-1,3-thiazol-5-yl)pyrazolo[1,5-a]pyrimidin-5-yl]phenoxy}propyl]-1H-tetrazole | A | 437.2 |
| 142 | 1-[(2S)-2-{5-[3-(1,3-dimethyl-1H-pyrazol-4-yl)pyrazolo[1,5-a]pyrimidin-5-yl]-2-fluorophenoxy)propyl]-1H-tetrazole | B | 434.2 |
| 143 | 1-[(2S)-2-{5-[3-(1,5-dimethyl-1H-pyrazol-4-yl)pyrazolo[1,5-a]pyrimidin-5-yl]-2-fluorophenoxy)propyl]-1H-tetrazole | A | 434.2 |
| 144 | 1-[(2S)-2-(5-{3-[1-(difluoromethyl)-1H-pyrazol-4-yl]pyrazolo[1,5-a]pyrimidin-5-yl}-2-fluorophenoxy)propyl]-1H-tetrazole | A | 456.1 |
| 145 | 4-(2-{4-[5-(4-fluoro-3-{[(2S)-1-(1H-tetrazol-1-yl)propan-2-yl]oxy}phenyl)pyrazolo[1,5-a]pyrimidin-3-yl]-1H-pyrazol-1-yl}ethyl)morpholine | B | 519.2 |
| 146 | ethyl 4-cyano-3-[6-(4-fluoro-3-{[(2S)-1-(1H-tetrazol-1-yl)propan-2-yl]oxy}phenyl)imidazo[1,2-b]pyridazin-3-yl]benzoate | A | 513.2 |
| 147 | 4-cyano-3-[6-(4-fluoro-3-{[(2S)-1-(1H-tetrazol-1-yl)propan-2-yl]oxy}phenyl)imidazo[1,2-b]pyridazin-3-yl]benzoic acid | B | 485.1 |
| 148 | 4-cyano-3-[6-(4-fluoro-3-{[(2S)-1-(1H-tetrazol-1-yl)propan-2-yl]oxy}phenyl)imidazo[1,2-b]pyridazin-3-yl]-N-[2-(morpholin-4-yl)ethyl]benzamide | B | 597.3 |

| Ex. No. | IUPAC NAME | Act | MS |
|---|---|---|---|
| 149 | 1-[(2S)-2-(5-{3-[2-(difluoromethyl)phenyl]pyrazolo[1,5-a]pyrimidin-5-yl}-2-fluorophenoxy)propyl]-1H-tetrazole | B | 466.1 |
| 150 | 2-[5-(4-fluoro-3-{[(2S)-1-(1H-tetrazol-1-yl)propan-2-yl]oxy}phenyl)-3H-imidazo[4,5-b]pyridin-3-yl]pyridine-3-carbonitrile | A | 441.9 |
| 151 | 2-[5-(4-fluoro-3-{[(2S)-1-(1H-tetrazol-1-yl)propan-2-yl]oxy}phenyl)-3H-imidazo[4,5-b]pyridin-3-yl]benzonitrile | A | 441.0 |
| 152 | 3-[5-(4-fluoro-3-{[(2S)-1-(1H-tetrazol-1-yl)propan-2-yl]oxy}phenyl)pyrazolo[1,5-a]pyrimidin-3-yl]-2-methoxy-N-[2-(morpholin-4-yl)ethyl]benzamide | A | 602.3 |
| 153 | 2-[5-(4-fluoro-3-{[(2S)-1-(1H-tetrazol-1-yl)propan-2-yl]oxy}phenyl)-3H-imidazo[4,5-b]pyridin-3-yl]pyridine | A | 417.2 |
| 154 | 2-fluoro-6-[5-(4-fluoro-3-{[(2S)-1-(1H-tetrazol-1-yl)propan-2-yl]oxy}phenyl)pyrazolo[1,5-a]pyrimidin-3-yl]benzonitrile | A | 459.1 |
| 155 | 2-fluoro-6-[5-(4-fluoro-3-{[(2S)-1-(1H-tetrazol-1-yl)propan-2-yl]oxy}phenyl)pyrazolo[1,5-a]pyrimidin-3-yl]benzamide | B | 477.2 |
| 156 | 5-[5-(4-fluoro-3-{[(2S)-1-(1H-tetrazol-1-yl)propan-2-yl]oxy}phenyl)pyrazolo[1,5-a]pyrimidin-3-yl]pyridine-3-carbonitrile | A | 442.2 |
| 157 | 4-fluoro-2-[5-(4-fluoro-3-{[(2S)-1-(1H-tetrazol-1-yl)propan-2-yl]oxy}phenyl)pyrazolo[1,5-a]pyrimidin-3-yl]benzonitrile | A | 458.9 |
| 158 | 1-[(2S)-2-{2-fluoro-5-[3-(1H-pyrazol-3-yl)pyrazolo[1,5-a]pyrimidin-5-yl]phenoxy}propyl]-1H-tetrazole | A | 406.0 |
| 159 | 6-[5-(4-fluoro-3-{[(2S)-1-(1H-tetrazol-1-yl)propan-2-yl]oxy}phenyl)-3H-imidazo[4,5-b]pyridin-3-yl]pyridine-2-carbonitrile | A | 441.9 |
| 160 | 4-(2-{3-[5-(4-fluoro-3-{[(2S)-1-(1H-tetrazol-1-yl)propan-2-yl]oxy}phenyl)pyrazolo[1,5-a]pyrimidin-3-yl]-1H-pyrazol-1-yl}ethyl)morpholine | A | 519.2 |
| 161 | 2-{3-[5-(4-fluoro-3-{[(2S)-1-(1H-tetrazol-1-yl)propan-2-yl]oxy}phenyl)pyrazolo[1,5-a]pyrimidin-3-yl]-1H-pyrazol-1-yl}acetonitrile | A | 445.2 |
| 162 | 3-[5-(4-fluoro-3-{[(2S)-1-(1H-tetrazol-1-yl)propan-2-yl]oxy}phenyl)pyrazolo[1,5-a]pyrimidin-3-yl]thiophene-2-carbonitrile | A | 447.1 |
| 163 | 4-[5-(4-fluoro-3-{[(2S)-1-(1H-tetrazol-1-yl)propan-2-yl]oxy}phenyl)pyrazolo[1,5-a]pyrimidin-3-yl]-1-methyl-1H-pyrazole-5-carbonitrile | A | 445.2 |
| 164 | 4-[5-(4-fluoro-3-{[(2S)-1-(1H-tetrazol-1-yl)propan-2-yl]oxy}phenyl)pyrazolo[1,5-a]pyrimidin-3-yl]-1-methyl-1H-pyrazole-3-carbonitrile | A | 445.2 |
| 165 | N-(cyclopropanesulfonyl)-3-[5-(3-{[(2S)-1-(1H-tetrazol-1-yl)propan-2-yl]oxy}phenyl)pyrazolo[1,5-a]pyrimidin-3-yl]benzamide | A | 545.2 |
| 166 | 3-[5-(4-fluoro-3-{[(2S)-1-(1H-tetrazol-1-yl)propan-2-yl]oxy}phenyl)pyrazolo[1,5-a]pyrimidin-3-yl]-2-methoxypyridine | A | 447.3 |
| 167 | 3-[5-(4-fluoro-3-{[(2S)-1-(1H-tetrazol-1-yl)propan-2-yl]oxy}phenyl)pyrazolo[1,5-a]pyrimidin-3-yl]-1,2-dihydropyridin-2-one | A | 433.2 |
| 168 | 4-cyano-3-[6-(4-fluoro-3-{[(2S)-1-(1H-tetrazol-1-yl)propan-2-yl]oxy}phenyl)imidazo[1,2-b]pyridazin-3-yl]-N-methylbenzamide | A | 498.0 |
| 169 | 2-[6-(4-fluoro-3-{[(2S)-1-(1H-tetrazol-1-yl)propan-2-yl]oxy}phenyl)imidazo[1,2-b]pyridazin-3-yl]-6-(methoxymethoxy)benzonitrile | A | 501.0 |
| 170 | 2-[6-(4-fluoro-3-{[(2S)-1-(1H-tetrazol-1-yl)propan-2-yl]oxy}phenyl)imidazo[1,2-b]pyridazin-3-yl]-6-hydroxybenzonitrile | A | 456.9 |
| 171 | 2-[6-(4-fluoro-3-{[(2S)-1-(1H-tetrazol-1-yl)propan-2-yl]oxy}phenyl)imidazo[1,2-b]pyridazin-3-yl]-6-[3-(morpholin-4-yl)propoxy]benzonitrile | A | 584.0 |
| 172 | 2-[6-(4-fluoro-3-{[(2S)-1-(1H-tetrazol-1-yl)propan-2-yl]oxy}phenyl)imidazo[1,2-b]pyridazin-3-yl]-6-(3-methoxypropoxy)benzonitrile | A | 529.0 |
| 173 | 4-[5-(4-fluoro-3-{[(2S)-1-(1H-tetrazol-1-yl)propan-2-yl]oxy}phenyl)-3H-imidazo[4,5-b]pyridin-3-yl]-1-methyl-1H-imidazole-5-carbonitrile | A | 445.0 |
| 174 | 3-[5-(4-fluoro-3-{[(2S)-1-(1H-tetrazol-1-yl)propan-2-yl]oxy}phenyl)-3H-imidazo[4,5-b]pyridin-3-yl]-2-methoxypyridine | B | 447.0 |
| 175 | 3-[5-(4-fluoro-3-{[(2S)-1-(1H-tetrazol-1-yl)propan-2-yl]oxy}phenyl)-3H-imidazo[4,5-b]pyridin-3-yl]-1,2-dihydropyridin-2-one | B | 433.0 |
| 176 | 3-[5-(4-fluoro-3-{[(2S)-1-(1H-tetrazol-1-yl)propan-2-yl]oxy}phenyl)-3H-imidazo[4,5-b]pyridin-3-yl]-1-methyl-1,2-dihydropyridin-2-one | B | 446.9 |
| 177 | 2-(cyanomethoxy)-6-[6-(4-fluoro-3-{[(2S)-1-(1H-tetrazol-1-yl)propan-2-yl]oxy}phenyl)imidazo[1,2-b]pyridazin-3-yl]benzonitrile | A | 495.9 |
| 178 | 2-[6-(4-fluoro-3-{[(2S)-1-(1H-tetrazol-1-yl)propan-2-yl]oxy}phenyl)imidazo[1,2-b]pyridazin-3-yl]-6-[(2-oxopyrrolidin-3-yl)oxy]benzonitrile | A | 539.9 |
| 179 | methyl 2-cyano-3-[5-(4-fluoro-3-{[(2S)-1-(1H-tetrazol-1-yl)propan-2-yl]oxy}phenyl)-3H-imidazo[4,5-b]pyridin-3-yl]benzoate | B | 498.9 |
| 180 | 2-[5-(4-fluoro-3-{[(2S)-1-(1H-tetrazol-1-yl)propan-2-yl]oxy}phenyl)pyrazolo[1,5-a]pyrimidin-3-yl]-6-[(2-methoxyethyl)amino]benzonitrile | A | 514.0 |
| 181 | 2-amino-6-[6-(4-fluoro-3-{[(2S)-1-(1H-tetrazol-1-yl)propan-2-yl]oxy}phenyl)imidazo[1,2-b]pyridazin-3-yl]benzonitrile | A | 456.0 |
| 182 | N-{2-cyano-3-[6-(4-fluoro-3-{[(2S)-1-(1H-tetrazol-1-yl)propan-2-yl]oxy}phenyl)imidazo[1,2-b]pyridazin-3-yl]phenyl}-3-methoxypropanamide | A | 542.0 |
| 183 | 1-[(2S)-2-{5-[3-(2-ethynylphenyl)imidazo[1,2-b]pyridazin-6-yl]-2-fluorophenoxy}propyl]-1H-tetrazole | A | 440.0 |
| 184 | 2-[6-(4-fluoro-3-{[(2S)-1-(1H-tetrazol-1-yl)propan-2-yl]oxy}phenyl)imidazo[1,2-b]pyridazin-3-yl]benzene-1,4-dicarboxamide | C | 502.1 |
| 185 | 2-[6-(4-fluoro-3-{[(2S)-1-(1H-tetrazol-1-yl)propan-2-yl]oxy}phenyl)imidazo[1,2-b]pyridazin-3-yl]benzene-1,4-dicarbonitrile | A | 466.1 |
| 186 | 3-[6-(4-fluoro-3-{[(2S)-1-(1H-tetrazol-1-yl)propan-2-yl]oxy}phenyl)imidazo[1,2-b]pyridazin-3-yl]benzene-1,2-dicarbonitrile | A | 466.1 |
| 187 | 1-[(2S)-2-{5-[3-(5-bromo-2,3-dihydro-1-benzofuran-7-yl)imidazo[1,2-b]pyridazin-6-yl]-2-fluorophenoxy}propyl]-1H-tetrazole | A | 536.0 |
| 188 | methyl 6-[5-(4-fluoro-3-{[(2S)-1-(1H-tetrazol-1-yl)propan-2-yl]oxy}phenyl)-3H-imidazo[4,5-b]pyridin-3-yl]pyridine-2-carboxylate | A | 475.2 |
| 189 | 2-cyano-3-[5-(4-fluoro-3-{[(2S)-1-(1H-tetrazol-1-yl)propan-2-yl]oxy}phenyl)-3H-imidazo[4,5-b]pyridin-3-yl]benzoic acid | B | 485.1 |
| 190 | 1-[(2S)-2-{5-[3-(2-ethenylphenyl)imidazo[1,2-b]pyridazin-6-yl]-2-fluorophenoxy}propyl]-1H-tetrazole | A | 442.2 |
| 191 | 2-{[dimethyl(oxo)-$\lambda^6$-sulfanylidene]amino}-6-[6-(4-fluoro-3-{[(2S)-1-(1H-tetrazol-1-yl)propan-2-yl]oxy}phenyl)imidazo[1,2-b]pyridazin-3-yl]benzonitrile | A | 532.2 |
| 192 | 4-[5-(4-fluoro-3-{[(2S)-1-(1H-tetrazol-1-yl)propan-2-yl]oxy}phenyl)-3H-imidazo[4,5-b]pyridin-3-yl]-2-(2-methoxyethyl)-2,3-dihydro-1H-isoindole-1,3-dione | C | 543.1 |

-continued

| Ex. No. | IUPAC NAME | Act | MS |
|---|---|---|---|
| 193 | 4-[5-(4-fluoro-3-{[(2S)-1-(1H-tetrazol-1-yl)propan-2-yl]oxy}phenyl)-3H-imidazo[4,5-b]pyridin-3-yl]-2-methyl-2,3-dihydro-1H-isoindole-1,3-dione | C | 499.0 |
| 194 | 3-[6-(4-fluoro-3-{[(2S)-1-(1H-tetrazol-1-yl)propan-2-yl]oxy}phenyl)imidazo[1,2-b]pyridazin-3-yl]pyridin-2-amine | B | 432.2 |
| 195 | 2-[6-(4-fluoro-3-{[(2S)-1-(1H-tetrazol-1-yl)propan-2-yl]oxy}phenyl)imidazo[1,2-b]pyridazin-3-yl]-6-{[(1r,4r)-4-[(2R,6S)-2,6-dimethylmorpholin-4-yl]cyclohexyl]oxy}benzonitrile | A | 652.3 |
| 196 | 3-[6-(4-fluoro-3-{[(2S)-1-(1H-tetrazol-1-yl)propan-2-yl]oxy}phenyl)imidazo[1,2-b]pyridazin-3-yl]-1-methyl-1,2-dihydropyridin-2-one | A | 447.2 |
| 197 | 2-[6-(4-fluoro-3-{[(2S)-1-(1H-tetrazol-1-yl)propan-2-yl]oxy}phenyl)imidazo[1,2-b]pyridazin-3-yl]-6-methoxybenzonitrile | A | 471.1 |
| 198 | 2-[6-(4-fluoro-3-{[(2S)-1-(1H-tetrazol-1-yl)propan-2-yl]oxy}phenyl)imidazo[1,2-b]pyridazin-3-yl]-6-[(2-oxopyrrolidin-3-yl)methoxy]benzonitrile | A | 554.1 |
| 199 | 2-[6-(4-fluoro-3-{[(2S)-1-(1H-tetrazol-1-yl)propan-2-yl]oxy}phenyl)imidazo[1,2-b]pyridazin-3-yl]-6-[(5-oxopyrrolidin-3-yl)methoxy]benzonitrile | A | 554.2 |
| 200 | 2-[6-(4-fluoro-3-{[(2S)-1-(1H-tetrazol-1-yl)propan-2-yl]oxy}phenyl)imidazo[1,2-b]pyridazin-3-yl]-6-[(5-oxopyrrolidin-2-yl)methoxy]benzonitrile | A | 554.1 |
| 201 | 2-[6-(4-fluoro-3-{[(2S)-1-(1H-tetrazol-1-yl)propan-2-yl]oxy}phenyl)imidazo[1,2-b]pyridazin-3-yl]-6-[(1-methylpyrrolidin-3-yl)methoxy]benzonitrile | A | 554.2 |
| 202 | 2-{2-cyano-3-[6-(4-fluoro-3-{[(2S)-1-(1H-tetrazol-1-yl)propan-2-yl]oxy}phenyl)imidazo[1,2-b]pyridazin-3-yl]phenoxy}acetamide | A | 514.1 |
| 203 | 2-[6-(4-fluoro-3-{[(2S)-1-(1H-tetrazol-1-yl)propan-2-yl]oxy}phenyl)imidazo[1,2-b]pyridazin-3-yl]-6-[(oxan-4-yl)methoxy]benzonitrile | A | 555.2 |
| 204 | N-(3-{2-cyano-3-[6-(4-fluoro-3-{[(2S)-1-(1H-tetrazol-1-yl)propan-2-yl]oxy}phenyl)imidazo[1,2-b]pyridazin-3-yl]phenoxy}propyl)acetamide | A | 556.1 |
| 205 | N-(2-{2-cyano-3-[6-(4-fluoro-3-{[(2S)-1-(1H-tetrazol-1-yl)propan-2-yl]oxy}phenyl)imidazo[1,2-b]pyridazin-3-yl]phenoxy}ethyl)-N-methylacetamide | A | 556.2 |
| 206 | 2-(2,2-difluoroethoxy)-6-[6-(4-fluoro-3-{[(2S)-1-(1H-tetrazol-1-yl)propan-2-yl]oxy}phenyl)imidazo[1,2-b]pyridazin-3-yl]benzonitrile | A | 521.2 |
| 207 | 2-[6-(4-fluoro-3-{[(2S)-1-(1H-tetrazol-1-yl)propan-2-yl]oxy}phenyl)imidazo[1,2-b]pyridazin-3-yl]-6-[2-(2-oxopyrrolidin-1-yl)ethoxy]benzonitrile | A | 568.2 |
| 208 | 2-[6-(4-fluoro-3-{[(2S)-1-(1H-tetrazol-1-yl)propan-2-yl]oxy}phenyl)imidazo[1,2-b]pyridazin-3-yl]-6-[2-(piperidin-4-yl)ethoxy]benzonitrile | A | 568.3 |
| 209 | 2-{2-[2-(dimethylamino)ethoxy]ethoxy]-6-[6-(4-fluoro-3-{[(2S)-1-(1H-tetrazol-1-yl)propan-2-yl]oxy}phenyl)imidazo[1,2-b]pyridazin-3-yl]benzonitrile | A | 572.2 |
| 210 | 2-(cyclobutylmethoxy)-6-[6-(4-fluoro-3-{[(2S)-1-(1H-tetrazol-1-yl)propan-2-yl]oxy}phenyl)imidazo[1,2-b]pyridazin-3-yl]benzonitrile | A | 525.1 |
| 211 | 2-[2-(2,5-dioxopyrrolidin-1-yl)ethoxy]-6-[6-(4-fluoro-3-{[(2S)-1-(1H-tetrazol-1-yl)propan-2-yl]oxy}phenyl)imidazo[1,2-b]pyridazin-3-yl]benzonitrile | A | 582.2 |
| 212 | 2-[6-(4-fluoro-3-{[(2S)-1-(1H-tetrazol-1-yl)propan-2-yl]oxy}phenyl)imidazo[1,2-b]pyridazin-3-yl]-6-{2-[2-(2-methoxyethoxy)ethoxy]ethoxy}benzonitrile | A | 603.2 |
| 213 | 2-[6-(4-fluoro-3-{[(2S)-1-(1H-tetrazol-1-yl)propan-2-yl]oxy}phenyl)imidazo[1,2-b]pyridazin-3-yl]-6-(propan-2-yloxy)benzonitrile | A | 499.1 |
| 214 | 2-[6-(4-fluoro-3-{[(2S)-1-(1H-tetrazol-1-yl)propan-2-yl]oxy}phenyl)imidazo[1,2-b]pyridazin-3-yl]-6-(2,2,2-trifluoroethoxy)benzonitrile | A | 539.1 |
| 215 | 2-[2-(azetidin-1-yl)ethoxy]-6-[6-(4-fluoro-3-{[(2S)-1-(1H-tetrazol-1-yl)propan-2-yl]oxy}phenyl)imidazo[1,2-b]pyridazin-3-yl]benzonitrile | A | 540.1 |
| 216 | 2-{2-cyano-3-[6-(4-fluoro-3-{[(2S)-1-(1H-tetrazol-1-yl)propan-2-yl]oxy}phenyl)imidazo[1,2-b]pyridazin-3-yl]phenoxy}acetic acid | A | 515.1 |
| 217 | 4-{2-cyano-3-[6-(4-fluoro-3-{[(2S)-1-(1H-tetrazol-1-yl)propan-2-yl]oxy}phenyl)imidazo[1,2-b]pyridazin-3-yl]phenoxy}butanoic acid | A | 543.1 |
| 218 | (S)-2-(6-(3-((1-(1H-tetrazol-1-yl)propan-2-yl)oxy)-4-fluorophenyl)imidazo[1,2-b]pyridazin-3-yl)pyridine N-oxide | B | 433.0 |
| 219 | 5-[6-(4-fluoro-3-{[(2S)-1-(1H-tetrazol-1-yl)propan-2-yl]oxy}phenyl)imidazo[1,2-b]pyridazin-3-yl]-6-methoxypyridine-3-carbonitrile | A | 471.9 |
| 220 | 5-[6-(4-fluoro-3-{[(2S)-1-(1H-tetrazol-1-yl)propan-2-yl]oxy}phenyl)imidazo[1,2-b]pyridazin-3-yl]-6-oxo-1,6-dihydropyridine-3-carbonitrile | A | 457.9 |
| 221 | 5-[6-(4-fluoro-3-{[(2S)-1-(1H-tetrazol-1-yl)propan-2-yl]oxy}phenyl)imidazo[1,2-b]pyridazin-3-yl]-1-methyl-6-oxo-1,6-dihydropyridine-3-carbonitrile | A | 472.0 |
| 222 | 4-[6-(4-fluoro-3-{[(2S)-1-(1H-tetrazol-1-yl)propan-2-yl]oxy}phenyl)imidazo[1,2-b]pyridazin-3-yl]-1-(3-hydroxypropyl)-1H-pyrazole-3-carbonitrile | B | 489.0 |
| 223 | 4-[6-(4-fluoro-3-{[(2S)-1-(1H-tetrazol-1-yl)propan-2-yl]oxy}phenyl)imidazo[1,2-b]pyridazin-3-yl]-1-(3-methoxypropyl)-1H-pyrazole-5-carbonitrile | A | 502.9 |
| 224 | 3-methoxypropyl 4-[6-(4-fluoro-3-{[(2S)-1-(1H-tetrazol-1-yl)propan-2-yl]oxy}phenyl)imidazo[1,2-b]pyridazin-3-yl]-1-(3-methoxypropyl)-1H-pyrazole-5-carboxylate | C | 594.0 |
| 225 | 4-[6-(4-fluoro-3-{[(2S)-1-(1H-tetrazol-1-yl)propan-2-yl]oxy}phenyl)imidazo[1,2-b]pyridazin-3-yl]-1-(3-hydroxypropyl)-1H-pyrazole-5-carbonitrile | A | 488.9 |
| 226 | 2-(2-cyano-2,2-dimethylethoxy)-6-[6-(4-fluoro-3-{[(2S)-1-(1H-tetrazol-1-yl)propan-2-yl]oxy}phenyl)imidazo[1,2-b]pyridazin-3-yl]benzonitrile | A | 537.9 |
| 227 | 2-[6-(4-fluoro-3-{[(2S)-1-(1H-tetrazol-1-yl)propan-2-yl]oxy}phenyl)imidazo[1,2-b]pyridazin-3-yl]pyridine | A | 417.0 |
| 228 | 2-cyano-3-[5-(4-fluoro-3-{[(2S)-1-(1H-tetrazol-1-yl)propan-2-yl]oxy}phenyl)-3H-imidazo[4,5-b]pyridin-3-yl]-N,N-dimethylbenzamide | C | 511.9 |
| 229 | 2-[5-(4-fluoro-3-{[(2S)-1-(1H-tetrazol-1-yl)propan-2-yl]oxy}phenyl)-3H-imidazo[4,5-b]pyridin-3-yl]-6-(3-methoxyazetidine-1-carbonyl)benzonitrile | B | 553.9 |
| 230 | 4-[6-(4-fluoro-3-{[(2S)-1-(1H-tetrazol-1-yl)propan-2-yl]oxy}phenyl)imidazo[1,2-b]pyridazin-3-yl]-1-(3-methoxypropyl)-1H-pyrazole-5-carboxylic acid | C | 522.1 |
| 231 | tert-butyl N-{3-cyano-2-[6-(4-fluoro-3-{[(2S)-1-(1H-tetrazol-1-yl)propan-2-yl]oxy}phenyl)imidazo[1,2-b]pyridazin-3-yl]pyridin-4-yl}carbamate | A | 557.1 |

| Ex. No. | IUPAC NAME | Act | MS |
|---|---|---|---|
| 232 | tert-butyl N-[(tert-butoxy)carbonyl]-N-{3-cyano-2-[6-(4-fluoro-3-{[(2S)-1-(1H-tetrazol-1-yl)propan-2-yl]oxy}phenyl)imidazo[1,2-b]pyridazin-3-yl]pyridin-4-yl}carbamate | A | 657.3 |
| 233 | 2-amino-4-[6-(4-fluoro-3-{[(2S)-1-(1H-tetrazol-1-yl)propan-2-yl]oxy}phenyl)imidazo[1,2-b]pyridazin-3-yl]pyridine-3-carbonitrile | A | 457.1 |
| 234 | 4-amino-2-[6-(4-fluoro-3-{[(2S)-1-(1H-tetrazol-1-yl)propan-2-yl]oxy}phenyl)imidazo[1,2-b]pyridazin-3-yl]pyridine-3-carbonitrile | A | 457.1 |
| 235 | 4-[6-(4-fluoro-3-{[(2S)-1-(1H-tetrazol-1-yl)propan-2-yl]oxy}phenyl)imidazo[1,2-b]pyridazin-3-yl]-1-(3-methoxypropyl)-N-methyl-1H-pyrazole-5-carboxamide | C | 535.1 |
| 236 | 4-[6-(4-fluoro-3-{[(2S)-1-(1H-tetrazol-1-yl)propan-2-yl]oxy}phenyl)imidazo[1,2-b]pyridazin-3-yl]-1-(3-methoxypropyl)-N,N-dimethyl-1H-pyrazole-5-carboxamide | C | 549.1 |
| 237 | 4-[6-(4-fluoro-3-{[(2S)-1-(1H-tetrazol-1-yl)propan-2-yl]oxy}phenyl)imidazo[1,2-b]pyridazin-3-yl]-N-(2-methoxyethyl)-1-(3-methoxypropyl)-1H-pyrazole-5-carboxamide | C | 579.1 |
| 238 | methyl 3-[6-(4-fluoro-3-{[(2S)-1-(1H-tetrazol-1-yl)propan-2-yl]oxy}phenyl)imidazo[1,2-b]pyridazin-3-yl]thiophene-2-carboxylate | B | 480.1 |
| 239 | 2-[6-(3-{[(2S)-1-(1H-tetrazol-1-yl)propan-2-yl]oxy}phenyl)imidazo[1,2-b]pyridazin-3-yl]benzonitrile | A | 423.2 |
| 240 | 4-[6-(4-fluoro-3-{[(2S)-1-(1H-tetrazol-1-yl)propan-2-yl]oxy}phenyl)imidazo[1,2-b]pyridazin-3-yl]-6-methoxypyridine-3-carbonitrile | A | 472.1 |
| 241 | 4-[6-(4-fluoro-3-{[(2S)-1-(1H-tetrazol-1-yl)propan-2-yl]oxy}phenyl)imidazo[1,2-b]pyridazin-3-yl]-6-oxo-1,6-dihydropyridine-3-carbonitrile | A | 458.1 |
| 242 | 4-[6-(4-fluoro-3-{[(2S)-1-(1H-tetrazol-1-yl)propan-2-yl]oxy}phenyl)imidazo[1,2-b]pyridazin-3-yl]-1-methyl-6-oxo-1,6-dihydropyridine-3-carbonitrile | A | 472.1 |
| 243 | 3-[6-(4-fluoro-3-{[(2S)-1-(1H-tetrazol-1-yl)propan-2-yl]oxy}phenyl)imidazo[1,2-b]pyridazin-3-yl]thiophene-2-carboxylic acid | C | 466.1 |
| 244 | 2-[6-(5-{[(2S)-1-(1H-tetrazol-1-yl)propan-2-yl]oxy}pyridin-3-yl)imidazo[1,2-b]pyridazin-3-yl]benzonitrile | A | 424.2 |
| 245 | 3-[6-(4-fluoro-3-{[(2S)-1-(1H-tetrazol-1-yl)propan-2-yl]oxy}phenyl)imidazo[1,2-b]pyridazin-3-yl]-N-methylthiophene-2-carboxamide | B | 479.2 |
| 246 | 4-fluoro-2-[6-(4-fluoro-3-{[(2S)-1-(1H-tetrazol-1-yl)propan-2-yl]oxy}phenyl)imidazo[1,2-b]pyridazin-3-yl]benzonitrile | A | 459.1 |
| 247 | 2-[6-(4-fluoro-3-{[(2S)-1-(1H-tetrazol-1-yl)propan-2-yl]oxy}phenyl)imidazo[1,2-b]pyridazin-3-yl]pyridine-3-carbonitrile | A | 442.2 |
| 248 | 3-[6-(4-fluoro-3-{[(2S)-1-(1H-tetrazol-1-yl)propan-2-yl]oxy}phenyl)imidazo[1,2-b]pyridazin-3-yl]pyridine-2-carbonitrile | A | 442.2 |
| 249 | 3-[6-(4-fluoro-3-{[(2S)-1-(1H-tetrazol-1-yl)propan-2-yl]oxy}phenyl)imidazo[1,2-b]pyridazin-3-yl]-6-methoxypyridine-2-carbonitrile | A | 472.1 |
| 250 | 7-[6-(4-fluoro-3-{[(2S)-1-(1H-tetrazol-1-yl)propan-2-yl]oxy}phenyl)imidazo[1,2-b]pyridazin-3-yl]imidazo[1,2-a]pyridine-8-carbonitrile | A | 481.1 |
| 251 | 3-[6-(3-{[(2S)-1-(1H-tetrazol-1-yl)propan-2-yl]oxy}phenyl)imidazo[1,2-b]pyridazin-3-yl]pyridine-4-carbonitrile | A | 424.2 |
| 252 | 3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 415.2 |
| 253 | 1-methyl-3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 429.2 |
| 254 | 1-(2-methoxyethyl)-3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 473.2 |
| 255 | 3-[6-(4-fluoro-3-{[(2S)-1-(1H-tetrazol-1-yl)propan-2-yl]oxy}phenyl)imidazo[1,2-b]pyridazin-3-yl]-6-oxo-1,6-dihydropyridine-2-carbonitrile | A | 458.1 |
| 256 | 3-[6-(4-fluoro-3-{[(2S)-1-(1H-tetrazol-1-yl)propan-2-yl]oxy}phenyl)imidazo[1,2-b]pyridazin-3-yl]-1-methyl-6-oxo-1,6-dihydropyridine-2-carbonitrile | C | 472.1 |
| 257 | 3-[6-(3-{[(2S)-1-(1H-tetrazol-1-yl)propan-2-yl]oxy}phenyl)imidazo[1,2-b]pyridazin-3-yl]pyridine-2-carbonitrile | A | 424.1 |
| 258 | 2-[6-(4-fluoro-3-{[(2S)-1-(1H-tetrazol-1-yl)propan-2-yl]oxy}phenyl)imidazo[1,2-b]pyridazin-3-yl]-6-[(1-oxo-1λ$^6$-thiolan-1-ylidene)amino]benzonitrile | A | 557.9 |
| 259 | 1-methyl-2-oxo-4-[6-(3-{[(2S)-1-(1H-tetrazol-1-yl)propan-2-yl]oxy}phenyl)imidazo[1,2-b]pyridazin-3-yl]-1,2-dihydropyridine-3-carbonitrile | A | 453.9 |
| 260 | 2-chloro-4-[6-(3-{[(2S)-1-(1H-tetrazol-1-yl)propan-2-yl]oxy}phenyl)imidazo[1,2-b]pyridazin-3-yl]pyridine-3-carbonitrile | A | 457.9 |
| 261 | 2-ethoxy-4-[6-(3-{[(2S)-1-(1H-tetrazol-1-yl)propan-2-yl]oxy}phenyl)imidazo[1,2-b]pyridazin-3-yl]pyridine-3-carbonitrile | A | 468.0 |
| 262 | 3-[6-(3-{[(2S)-1-(1H-tetrazol-1-yl)propan-2-yl]oxy}phenyl)imidazo[1,2-b]pyridazin-3-yl]pyrazine-2-carbonitrile | A | 425.2 |
| 263 | 4-{[dimethyl(oxo)-λ$^6$-sulfanylidene]amino}-2-[6-(4-fluoro-3-{[(2S)-1-(1H-tetrazol-1-yl)propan-2-yl]oxy}phenyl)imidazo[1,2-b]pyridazin-3-yl]benzonitrile | C | 532.2 |
| 264 | 2-[6-(4-fluoro-3-{[(2S)-1-(1H-tetrazol-1-yl)propan-2-yl]oxy}phenyl)imidazo[1,2-b]pyridazin-3-yl]-4-[(1-oxo-1λ$^6$-thiolan-1-ylidene)amino]benzonitrile | C | 558.1 |
| 265 | 1-[(2S)-2-(2-fluoro-5-{3-[1-methyl-3-(trifluoromethyl)-1H-pyrazol-4-yl]imidazo[1,2-b]pyridazin-6-yl}phenoxy)propyl]-1H-tetrazole | B | 488.1 |
| 266 | 1-[(2S)-2-(5-{3-[1,5-dimethyl-3-(trifluoromethyl)-1H-pyrazol-4-yl]imidazo[1,2-b]pyridazin-6-yl}-2-fluorophenoxy)propyl]-1H-tetrazole | C | 502.2 |
| 267 | 5-[6-(3-{[(2S)-1-(1H-tetrazol-1-yl)propan-2-yl]oxy}phenyl)imidazo[1,2-b]pyridazin-3-yl]pyrimidine-4-carbonitrile | A | 425.2 |
| 268 | 2-[6-(4-fluoro-3-{[(2S)-1-(1H-tetrazol-1-yl)propan-2-yl]oxy}phenyl)imidazo[1,2-b]pyridazin-3-yl]-3-methoxypyrazine | B | 448.2 |
| 269 | (S)-3-(6-(3-((1-(1H-tetrazol-1-yl)propan-2-yl)oxy)-4-fluorophenyl)imidazo[1,2-b]pyridazin-3-yl)-4-cyanopyridine N-oxide | A | 458.2 |
| 270 | 5-fluoro-3-[6-(4-fluoro-3-{[(2S)-1-(1H-tetrazol-1-yl)propan-2-yl]oxy}phenyl)imidazo[1,2-b]pyridazin-3-yl]-2-methoxypyridine | A | 465.1 |
| 271 | 2-[6-(3-{[(2S)-1-(1H-tetrazol-1-yl)propan-2-yl]oxy}phenyl)imidazo[1,2-b]pyridazin-3-yl]pyridine-3-carbonitrile | A | 424.1 |
| 272 | 2-oxo-4-[6-(3-{[(2S)-1-(1H-tetrazol-1-yl)propan-2-yl]oxy}phenyl)imidazo[1,2-b]pyridazin-3-yl]-1,2-dihydropyridine-3-carbonitrile | A | 440.1 |
| 273 | 4-[6-(3-{[(2S)-1-(1H-tetrazol-1-yl)propan-2-yl]oxy}phenyl)imidazo[1,2-b]pyridazin-3-yl]pyrimidine-5-carbonitrile | B | 425.1 |
| 274 | 4-cyclopropyl-2-[6-(3-{[(2S)-1-(1H-tetrazol-1-yl)propan-2-yl]oxy}phenyl)imidazo[1,2-b]pyridazin-3-yl]pyridine-3-carbonitrile | A | 464.2 |
| 275 | 3-[6-(4-fluoro-3-{[(2S)-1-(1H-tetrazol-1-yl)propan-2-yl]oxy}phenyl)imidazo[1,2-b]pyridazin-3-yl]pyridine-4-carbonitrile | A | 442.2 |

| Ex. No. | IUPAC NAME | Act | MS |
|---|---|---|---|
| 276 | (S)-3-(6-(3-((1-(1H-tetrazol-1-yl)propan-2-yl)oxy)phenyl)imidazo[1,2-b]pyridazin-3-yl)-4-cyanopyridine N-oxide | A | 440.2 |
| 277 | 5-methyl-3-[6-(3-{[(2S)-1-(1H-tetrazol-1-yl)propan-2-yl]oxy}phenyl)imidazo[1,2-b]pyridazin-3-yl]pyrazine-2-carbonitrile | A | 439.2 |
| 278 | 6-methyl-2-[6-(3-{[(2S)-1-(1H-tetrazol-1-yl)propan-2-yl]oxy}phenyl)imidazo[1,2-b]pyridazin-3-yl]pyridine-3-carbonitrile | A | 438.2 |
| 279 | 4-[6-(3-{[(2S)-1-(1H-tetrazol-1-yl)propan-2-yl]oxy}phenyl)imidazo[1,2-b]pyridazin-3-yl]pyridine-3-carbonitrile | A | 424.2 |
| 280 | 3-[6-(3-{[(2S)-1-(1H-tetrazol-1-yl)propan-2-yl]oxy}phenyl)imidazo[1,2-b]pyridazin-3-yl]pyridazine-4-carbonitrile | A | 425.3 |
| 281 | 5-methoxy-2-[6-(3-{[(2S)-1-(1H-tetrazol-1-yl)propan-2-yl]oxy}phenyl)imidazo[1,2-b]pyridazin-3-yl]pyridine-3-carbonitrile | A | 454.2 |
| 282 | (S)-4-(6-(3-((1-(1H-tetrazol-1-yl)propan-2-yl)oxy)phenyl)imidazo[1,2-b]pyridazin-3-yl)-3-cyanopyridine N-oxide | B | 440.2 |
| 283 | 2-[6-(3-{[(2S)-1-(1H-tetrazol-1-yl)propan-2-yl]oxy}phenyl)imidazo[1,2-b]pyridazin-3-yl]pyrazine | A | 400.3 |
| 284 | 2-[5-(3-{[(2S)-1-(1H-tetrazol-1-yl)propan-2-yl]oxy}phenyl)-3H-imidazo[4,5-b]pyridin-3-yl]pyridine-3-carbonitrile | A | 424.3 |
| 285 | 5-methoxy-3-[6-(3-{[(2S)-1-(1H-tetrazol-1-yl)propan-2-yl]oxy}phenyl)imidazo[1,2-b]pyridazin-3-yl]pyrazine-2-carbonitrile | A | 455.3 |
| 286 | 4-fluoro-2-[5-(2-{[(2S)-1-(1H-1,2,4-triazol-1-yl)propan-2-yl]oxy}pyridin-4-yl)pyrazolo[1,5-a]pyrimidin-3-yl]benzonitrile | A | 441.2 |
| 287 | 4-fluoro-2-[6-(5-{[(2S)-1-(1H-tetrazol-1-yl)propan-2-yl]oxy}pyridin-3-yl)imidazo[1,2-b]pyridazin-3-yl]benzonitrile | A | 442.2 |
| 288 | 4-fluoro-2-[6-(5-{[(2S)-1-(1H-tetrazol-1-yl)propan-2-yl]oxy}pyridin-3-yl)imidazo[1,2-b]pyridazin-3-yl]benzonitrile hydrochloride | A | 442.2 |
| 289 | 6-methoxy-4-[6-(3-{[(2S)-1-(1H-tetrazol-1-yl)propan-2-yl]oxy}phenyl)imidazo[1,2-b]pyridazin-3-yl]pyridine-3-carbonitrile | A | 454.3 |
| 290 | 3-[6-(4-fluoro-3-{[(2S)-1-(1H-tetrazol-1-yl)propan-2-yl]oxy}phenyl)imidazo[1,2-b]pyridazin-3-yl]pyrazine-2-carbonitrile | A | 443.2 |
| 291 | 4-fluoro-2-[5-(3-{[(2S)-1-(1H-tetrazol-1-yl)propan-2-yl]oxy}phenyl)-3H-imidazo[4,5-b]pyridin-3-yl]benzonitrile | A | 441.2 |
| 292 | 4-fluoro-2-[5-(4-fluoro-3-{[(2S)-1-(1H-tetrazol-1-yl)propan-2-yl]oxy}phenyl)-3H-imidazo[4,5-b]pyridin-3-yl]benzonitrile | A | 459.2 |
| 293 | 2-[6-(2-fluoro-5-{[(2S)-1-(1H-tetrazol-1-yl)propan-2-yl]oxy}phenyl)imidazo[1,2-b]pyridazin-3-yl]pyridine-3-carbonitrile | B | 442.2 |
| 294 | 3-[5-(4-fluoro-3-{[(2S)-1-(1H-tetrazol-1-yl)propan-2-yl]oxy}phenyl)pyrazolo[1,5-a]pyrimidin-3-yl]pyrazine-2-carbonitrile | A | 443.2 |
| 295 | 2-[5-(4-fluoro-3-{[(2S)-1-(1H-tetrazol-1-yl)propan-2-yl]oxy}phenyl)pyrazolo[1,5-a]pyrimidin-3-yl]pyridine-3-carbonitrile | A | 442.2 |
| 296 | 2-[6-(3-fluoro-5-{[(2S)-1-(1H-tetrazol-1-yl)propan-2-yl]oxy}phenyl)imidazo[1,2-b]pyridazin-3-yl]pyridine-3-carbonitrile | A | 442.2 |
| 297 | (S)-2-(6-(3-((1-(1H-tetrazol-1-yl)propan-2-yl)oxy)-4-fluorophenyl)imidazo[1,2-b]pyridazin-3-yl)-3-cyanopyridine N-oxide | B | 458.2 |
| 298 | 4-fluoro-2-[6-(5-{[(2S)-1-(1H-tetrazol-1-yl)propan-2-yl]oxy}pyridazin-3-yl)imidazo[1,2-b]pyridazin-3-yl]benzonitrile | B | 443.2 |
| 299 | 4-fluoro-2-[6-(6-{[(2S)-1-(1H-tetrazol-1-yl)propan-2-yl]oxy}pyrimidin-4-yl)imidazo[1,2-b]pyridazin-3-yl]benzonitrile | B | 443.2 |
| 300 | 4-methoxy-2-[6-(3-{[(2S)-1-(1H-tetrazol-1-yl)propan-2-yl]oxy}phenyl)imidazo[1,2-b]pyridazin-3-yl]pyridine-3-carbonitrile | A | 454.2 |
| 301 | 4-oxo-2-[6-(3-{[(2S)-1-(1H-tetrazol-1-yl)propan-2-yl]oxy}phenyl)imidazo[1,2-b]pyridazin-3-yl]-1,4-dihydropyridine-3-carbonitrile | B | 440.2 |
| 302 | 3-[5-(3-{[(2S)-1-(1H-tetrazol-1-yl)propan-2-yl]oxy}phenyl)pyrazolo[1,5-a]pyrimidin-3-yl]pyrazine-2-carbonitrile | A | 425.2 |
| 303 | 2-[6-(3-{[(2S)-1-(1H-tetrazol-1-yl)propan-2-yl]oxy}phenyl)imidazo[1,2-b]pyridazin-3-yl]benzaldehyde | A | 426.2 |
| 304 | 2-[5-(3-{[(2S)-1-(1H-tetrazol-1-yl)propan-2-yl]oxy}phenyl)pyrazolo[1,5-a]pyrimidin-3-yl]pyridine-3-carbonitrile | A | 424.2 |
| 305 | 4-fluoro-2-[5-(6-{[(2S)-1-(1H-tetrazol-1-yl)propan-2-yl]oxy}pyrimidin-4-yl)-3H-imidazo[4,5-b]pyridin-3-yl]benzonitrile | B | 443.2 |
| 306 | dimethyl[({2-[6-(3-{[(2S)-1-(1H-tetrazol-1-yl)propan-2-yl]oxy}phenyl)imidazo[1,2-b]pyridazin-3-yl]phenyl}methyl)imino]-λ$^6$-sulfanone | B | 503.2 |
| 307 | dimethyl({2-[6-(3-{[(2S)-1-(1H-tetrazol-1-yl)propan-2-yl]oxy}phenyl)imidazo[1,2-b]pyridazin-3-yl]phenyl}methyl)amine | B | 455.3 |
| 308 | {2-[6-(3-{[(2S)-1-(1H-tetrazol-1-yl)propan-2-yl]oxy}phenyl)imidazo[1,2-b]pyridazin-3-yl]phenyl}methanol | A | 428.3 |
| 309 | 3-[5-(3-{[(2S)-1-(1H-tetrazol-1-yl)propan-2-yl]oxy}phenyl)pyrazolo[1,5-a]pyrimidin-3-yl]pyridine-4-carboxamide | B | 442.2 |
| 310 | 3-[5-(3-{[(2S)-1-(1H-tetrazol-1-yl)propan-2-yl]oxy}phenyl)pyrazolo[1,5-a]pyrimidin-3-yl]pyridine-4-carbonitrile | A | 424.1 |
| 311 | 4-fluoro-2-[6-(4-{[(2S)-1-(1H-tetrazol-1-yl)propan-2-yl]oxy}pyridin-2-yl)imidazo[1,2-b]pyridazin-3-yl]benzonitrile | A | 442.1 |
| 312 | 2-methoxy-6-[6-(3-{[(2S)-1-(1H-tetrazol-1-yl)propan-2-yl]oxy}phenyl)imidazo[1,2-b]pyridazin-3-yl]pyridine-3-carbonitrile | A | 454.2 |
| 313 | 6-methoxy-2-[6-(3-{[(2S)-1-(1H-tetrazol-1-yl)propan-2-yl]oxy}phenyl)imidazo[1,2-b]pyridazin-3-yl]pyridine-3-carbonitrile | A | 454.1 |
| 314 | 5-fluoro-3-[6-(4-fluoro-3-{[(2S)-1-(1H-tetrazol-1-yl)propan-2-yl]oxy}phenyl)imidazo[1,2-b]pyridazin-3-yl]-1,2-dihydropyridin-2-one | A | 451.1 |
| 315 | 5-fluoro-2-methoxy-3-[6-(3-{[(2S)-1-(1H-tetrazol-1-yl)propan-2-yl]oxy}phenyl)imidazo[1,2-b]pyridazin-3-yl]pyridine | A | 447.2 |
| 316 | 4-fluoro-2-[5-(5-{[(2S)-1-(1H-tetrazol-1-yl)propan-2-yl]oxy}pyridin-3-yl)-3H-imidazo[4,5-b]pyridin-3-yl]benzonitrile | A | 442.2 |
| 317 | 5-fluoro-3-[6-(4-fluoro-3-{[(2S)-1-(1H-tetrazol-1-yl)propan-2-yl]oxy}phenyl)imidazo[1,2-b]pyridazin-3-yl]-1-methyl-1,2-dihydropyridin-2-one | A | 465.2 |
| 318 | 6-oxo-4-[6-(3-{[(2S)-1-(1H-tetrazol-1-yl)propan-2-yl]oxy}phenyl)imidazo[1,2-b]pyridazin-3-yl]-1,6-dihydropyridine-3-carbonitrile | A | 440.2 |
| 319 | 4-fluoro-2-[5-(2-{[(2S)-1-(1H-tetrazol-1-yl)propan-2-yl]oxy}pyridin-4-yl)pyrazolo[1,5-a]pyrimidin-3-yl]benzonitrile | A | 442.2 |
| 320 | 4-methoxy-6-[6-(3-{[(2S)-1-(1H-tetrazol-1-yl)propan-2-yl]oxy}phenyl)imidazo[1,2-b]pyridazin-3-yl]pyrimidine-5-carbonitrile | A | 455.2 |
| 321 | 2-[6-(4-fluoro-3-{[(2S)-1-(1H-tetrazol-1-yl)propan-2-yl]oxy}phenyl)imidazo[1,2-b]pyridazin-3-yl]-4-methoxypyridine-3-carbonitrile | A | 472.1 |
| 322 | 2-methoxy-6-[6-(3-{[(2S)-1-(1H-tetrazol-1-yl)propan-2-yl]oxy}phenyl)imidazo[1,2-b]pyridazin-3-yl]benzonitrile | A | 453.2 |
| 323 | 5-chloro-2-methoxy-3-[6-(3-{[(2S)-1-(1H-tetrazol-1-yl)propan-2-yl]oxy}phenyl)imidazo[1,2-b]pyridazin-3-yl]pyridine | A | 463.1 |

| Ex. No. | IUPAC NAME | Act | MS |
|---|---|---|---|
| 324 | 5-fluoro-3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 433.2 |
| 325 | 4-fluoro-2-[6-(6-{[(2S)-1-(1H-tetrazol-1-yl)propan-2-yl]oxy}pyridin-2-yl)imidazo[1,2-b]pyridazin-3-yl]benzonitrile | A | 442.2 |
| 326 | 4-fluoro-2-[6-(6-{[(2S)-1-(1H-tetrazol-1-yl)propan-2-yl]oxy}pyrazin-2-yl)imidazo[1,2-b]pyridazin-3-yl]benzonitrile | A | 443.2 |
| 327 | 2-methoxy-5-methyl-3-[6-(3-{[(2S)-1-(1H-tetrazol-1-yl)propan-2-yl]oxy}phenyl)imidazo[1,2-b]pyridazin-3-yl]pyridine | A | 443.2 |
| 328 | 5-chloro-3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 449.2 |
| 329 | 5-methyl-3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 429.2 |
| 330 | 4-fluoro-2-[5-(4-{[(2S)-1-(1H-tetrazol-1-yl)propan-2-yl]oxy}pyridin-2-yl)-3H-imidazo[4,5-b]pyridin-3-yl]benzonitrile | A | 442.2 |
| 331 | 5-fluoro-1-methyl-3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 447.2 |
| 332 | 2-methoxy-3-[6-(3-{[(2S)-1-(1H-tetrazol-1-yl)propan-2-yl]oxy}phenyl)imidazo[1,2-b]pyridazin-3-yl]pyridine | A | 429.2 |
| 333 | 6-methyl-4-[6-(3-{[(2S)-1-(1H-tetrazol-1-yl)propan-2-yl]oxy}phenyl)imidazo[1,2-b]pyridazin-3-yl]pyridine-3-carbonitrile | A | 438.1 |
| 334 | 5-chloro-1-methyl-3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 463.2 |
| 335 | 1,5-dimethyl-3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 443.2 |
| 336 | 2-(2,2-difluoroethoxy)-5-fluoro-3-[6-(3-{[(2S)-1-(1H-tetrazol-1-yl)propan-2-yl]oxy}phenyl)imidazo[1,2-b]pyridazin-3-yl]pyridine | A | 497.1 |
| 337 | 1-(2,2-difluoroethyl)-5-fluoro-3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 497.1 |
| 338 | 5-fluoro-3-[6-(3-{[(2S)-1-(1H-tetrazol-1-yl)propan-2-yl]oxy}phenyl)imidazo[1,2-b]pyridazin-3-yl]-2-(2,2,2-trifluoroethoxy)pyridine | A | 515.2 |
| 339 | 5-fluoro-3-[6-(3-{[(2S)-1-(1H-tetrazol-1-yl)propan-2-yl]oxy}phenyl)imidazo[1,2-b]pyridazin-3-yl]-1-(2,2,2-trifluoroethyl)-1,2-dihydropyridin-2-one | A | 515.1 |
| 340 | 1-(2,2-difluoroethyl)-3-[6-(3-{[(2S)-1-(1H-tetrazol-1-yl)propan-2-yl]oxy}phenyl)imidazo[1,2-b]pyridazin-3-yl]-1,2-dihydropyridin-2-one | A | 479.2 |
| 341 | 3-[6-(3-{[(2S)-1-(1H-tetrazol-1-yl)propan-2-yl]oxy}phenyl)imidazo[1,2-b]pyridazin-3-yl]-1-[2-(2,2,2-trifluoroethoxy)ethyl]-1,2-dihydropyridin-2-one | A | 541.2 |
| 342 | 4-fluoro-2-[5-(2-{[(2S)-1-(1H-tetrazol-1-yl)propan-2-yl]oxy}pyrimidin-4-yl)-3H-imidazo[4,5-b]pyridin-3-yl]benzonitrile | B | 443.2 |
| 343 | 4-fluoro-2-[5-(2-{[(2S)-1-(1H-tetrazol-1-yl)propan-2-yl]oxy}pyridin-4-yl)-3H-imidazo[4,5-b]pyridin-3-yl]benzonitrile | A | 442.2 |
| 344 | 2-[6-(3-{[(2S)-1-(1H-tetrazol-1-yl)propan-2-yl]oxy}phenyl)imidazo[1,2-b]pyridazin-3-yl]-4-(2,2,2-trifluoroethoxy)pyridine-3-carbonitrile | A | 522.1 |
| 345 | 4-fluoro-2-[5-(6-{[(2S)-1-(1H-tetrazol-1-yl)propan-2-yl]oxy}pyridin-2-yl)-3H-imidazo[4,5-b]pyridin-3-yl]benzonitrile | A | 442.2 |
| 346 | 4-fluoro-2-[5-(4-{[(2S)-1-(1H-tetrazol-1-yl)propan-2-yl]oxy}pyrimidin-2-yl)-3H-imidazo[4,5-b]pyridin-3-yl]benzonitrile | B | 443.2 |
| 347 | 4-fluoro-2-[5-(6-{[(2S)-1-(1H-tetrazol-1-yl)propan-2-yl]oxy}pyridazin-4-yl)-3H-imidazo[4,5-b]pyridin-3-yl]benzonitrile | B | 443.2 |
| 348 | 1-methyl-6-oxo-4-[6-(3-{[(2S)-1-(1H-tetrazol-1-yl)propan-2-yl]oxy}phenyl)imidazo[1,2-b]pyridazin-3-yl]-1,6-dihydropyridine-3-carbonitrile | A | 454.1 |
| 349 | 2-[6-(3-{[(2S)-1-(1H-tetrazol-1-yl)propan-2-yl]oxy}phenyl)imidazo[1,2-b]pyridazin-3-yl]-6-(trifluoromethyl)pyridine-3-carbonitrile | B | 492.1 |
| 350 | 6-(dimethylamino)-2-[6-(3-{[(2S)-1-(1H-tetrazol-1-yl)propan-2-yl]oxy}phenyl)imidazo[1,2-b]pyridazin-3-yl]pyridine-3-carbonitrile | B | 467.2 |
| 351 | 5-fluoro-2-methoxy-4-[6-(3-{[(2S)-1-(1H-tetrazol-1-yl)propan-2-yl]oxy}phenyl)imidazo[1,2-b]pyridazin-3-yl]pyridine | A | 447.2 |
| 352 | 4-[(oxetan-3-yl)methoxy]-2-[6-(3-{[(2S)-1-(1H-tetrazol-1-yl)propan-2-yl]oxy}phenyl)imidazo[1,2-b]pyridazin-3-yl]pyridine-3-carbonitrile | A | 510.2 |
| 353 | 4-methoxy-2-[5-(3-{[(2S)-1-(1H-tetrazol-1-yl)propan-2-yl]oxy}phenyl)-3H-imidazo[4,5-b]pyridin-3-yl]pyridine-3-carbonitrile | A | 454.1 |
| 354 | 4-(2,2-difluoroethoxy)-2-[6-(3-{[(2S)-1-(1H-tetrazol-1-yl)propan-2-yl]oxy}phenyl)imidazo[1,2-b]pyridazin-3-yl]pyridine-3-carbonitrile | A | 504.1 |
| 355 | 2-[5-(4-fluoro-3-{[(2S)-1-(1H-tetrazol-1-yl)propan-2-yl]oxy}phenyl)-3H-imidazo[4,5-b]pyridin-3-yl]-4-methoxypyridine-3-carbonitrile | A | 472.2 |
| 356 | 4-(dimethylamino)-2-[6-(3-{[(2S)-1-(1H-tetrazol-1-yl)propan-2-yl]oxy}phenyl)imidazo[1,2-b]pyridazin-3-yl]pyridine-3-carbonitrile | A | 467.2 |
| 357 | 3-[6-(3-fluoro-5-{[(2S)-1-(1H-tetrazol-1-yl)propan-2-yl]oxy}phenyl)imidazo[1,2-b]pyridazin-3-yl]-1-methyl-1,2-dihydropyridin-2-one | A | 447.2 |
| 358 | 4-(methylamino)-2-[6-(3-{[(2S)-1-(1H-tetrazol-1-yl)propan-2-yl]oxy}phenyl)imidazo[1,2-b]pyridazin-3-yl]pyridine-3-carbonitrile | A | 453.2 |
| 359 | 2-({5-fluoro-3-[6-(3-{[(2S)-1-(1H-tetrazol-1-yl)propan-2-yl]oxy}phenyl)imidazo[1,2-b]pyridazin-3-yl]pyridin-2-yl}oxy)acetonitrile | A | 472.1 |
| 360 | 2-{5-fluoro-2-oxo-3-[6-(3-{[(2S)-1-(1H-tetrazol-1-yl)propan-2-yl]oxy}phenyl)imidazo[1,2-b]pyridazin-3-yl]-1,2-dihydropyridin-1-yl}acetonitrile | A | 472.2 |
| 361 | 6-(methylamino)-2-[6-(3-{[(2S)-1-(1H-tetrazol-1-yl)propan-2-yl]oxy}phenyl)imidazo[1,2-b]pyridazin-3-yl]pyridine-3-carbonitrile | A | 453.2 |
| 362 | 2-methoxy-4-[6-(3-{[(2S)-1-(1H-tetrazol-1-yl)propan-2-yl]oxy}phenyl)imidazo[1,2-b]pyridazin-3-yl]pyrimidine-5-carbonitrile | A | 455.1 |
| 363 | 4-(pyrrolidin-1-yl)-2-[6-(3-{[(2S)-1-(1H-tetrazol-1-yl)propan-2-yl]oxy}phenyl)imidazo[1,2-b]pyridazin-3-yl]pyridine-3-carbonitrile | B | 493.2 |
| 364 | 6-oxo-2-[6-(3-{[(2S)-1-(1H-tetrazol-1-yl)propan-2-yl]oxy}phenyl)imidazo[1,2-b]pyridazin-3-yl]-1,6-dihydropyridine-3-carbonitrile | A | 440.2 |
| 365 | 4-ethoxy-6-[6-(3-{[(2S)-1-(1H-tetrazol-1-yl)propan-2-yl]oxy}phenyl)imidazo[1,2-b]pyridazin-3-yl]pyrimidine-5-carbonitrile | A | 469.2 |
| 366 | 4-ethoxy-2-[6-(3-{[(2S)-1-(1H-tetrazol-1-yl)propan-2-yl]oxy}phenyl)imidazo[1,2-b]pyridazin-3-yl]pyridine-3-carbonitrile | A | 468.2 |
| 367 | 4-[(2,2-difluoroethyl)amino]-2-[6-(3-{[(2S)-1-(1H-tetrazol-1-yl)propan-2-yl]oxy}phenyl)imidazo[1,2-b]pyridazin-3-yl]pyridine-3-carbonitrile | B | 503.1 |

| Ex. No. | IUPAC NAME | Act | MS |
|---|---|---|---|
| 368 | 2-[5-(4-chloro-3-{[(2S)-1-(1H-tetrazol-1-yl)propan-2-yl]oxy}phenyl)-3H-imidazo[4,5-b]pyridin-3-yl]pyridine-3-carbonitrile | B | 458.2 |
| 369 | 2-[6-(3-{[(2S)-1-(1H-tetrazol-1-yl)propan-2-yl]oxy}phenyl)imidazo[1,2-b]pyridazin-3-yl]-4-[(2,2,2-trifluoroethyl)amino]pyridine-3-carbonitrile | B | 521.1 |
| 370 | 4-(azetidin-1-yl)-2-[6-(3-{[(2S)-1-(1H-tetrazol-1-yl)propan-2-yl]oxy}phenyl)imidazo[1,2-b]pyridazin-3-yl]pyridine-3-carbonitrile | B | 479.2 |
| 371 | 6-ethyl-2-[6-(3-{[(2S)-1-(1H-tetrazol-1-yl)propan-2-yl]oxy}phenyl)imidazo[1,2-b]pyridazin-3-yl]pyridine-3-carbonitrile | A | 452.2 |
| 372 | 4-(dimethylamino)-6-[6-(3-{[(2S)-1-(1H-tetrazol-1-yl)propan-2-yl]oxy}phenyl)imidazo[1,2-b]pyridazin-3-yl]pyrimidine-5-carbonitrile | B | 468.2 |
| 373 | 2-[6-(3-{[(2S)-1-(1H-tetrazol-1-yl)propan-2-yl]oxy}phenyl)-[1,2,4]triazolo[4,3-b]pyridazin-3-yl]benzonitrile | C | 424.2 |
| 374 | 4-ethoxy-2-[5-(3-{[(2S)-1-(1H-tetrazol-1-yl)propan-2-yl]oxy}phenyl)-3H-imidazo[4,5-b]pyridin-3-yl]pyridine-3-carbonitrile | A | 468.2 |
| 375 | 4-ethoxy-2-[5-(2-{[(2S)-1-(1H-tetrazol-1-yl)propan-2-yl]oxy}pyridin-4-yl)-3H-imidazo[4,5-b]pyridin-3-yl]pyridine-3-carbonitrile | B | 469.2 |
| 376 | 4-[(2,2-difluoroethyl)(methyl)amino]-2-[6-(3-{[(2S)-1-(1H-tetrazol-1-yl)propan-2-yl]oxy}phenyl)imidazo[1,2-b]pyridazin-3-yl]pyridine-3-carbonitrile | B | 517.2 |
| 377 | 2-[2-fluoro-5-(3-{[(2S)-1-(1H-tetrazol-1-yl)propan-2-yl]oxy}phenyl)pyrazolo[1,5-a]pyrimidin-3-yl]-4-methoxypyridine-3-carbonitrile | B | 472.2 |
| 378 | 4-methyl-2-[6-(3-{[(2S)-1-(1H-tetrazol-1-yl)propan-2-yl]oxy}phenyl)imidazo[1,2-b]pyridazin-3-yl]pyridine-3-carbonitrile | A | 438.2 |
| 379 | 4-fluoro-2-[2-fluoro-5-(3-{[(2S)-1-(1H-tetrazol-1-yl)propan-2-yl]oxy}phenyl)pyrazolo[1,5-a]pyrimidin-3-yl]benzonitrile | A | 459.2 |
| 380 | 4-ethyl-2-[6-(3-{[(2S)-1-(1H-tetrazol-1-yl)propan-2-yl]oxy}phenyl)imidazo[1,2-b]pyridazin-3-yl]pyridine-3-carbonitrile | A | 452.1 |
| 381 | 6-oxo-4-[6-(3-{[(2S)-1-(1H-tetrazol-1-yl)propan-2-yl]oxy}phenyl)imidazo[1,2-b]pyridazin-3-yl]-1,6-dihydropyrimidine-5-carbonitrile | A | 441.2 |
| 382 | 4-(difluoromethyl)-2-[5-(6-{[(2S)-1-(1H-tetrazol-1-yl)propan-2-yl]oxy}pyridin-2-yl)-3H-imidazo[4,5-b]pyridin-3-yl]benzonitrile | C | 474.3 |
| 383 | 4-(difluoromethyl)-2-[5-(3-{[(2S)-1-(1H-tetrazol-1-yl)propan-2-yl]oxy}phenyl)-3H-imidazo[4,5-b]pyridin-3-yl]benzonitrile | A | 473.3 |
| 384 | 4-(difluoromethyl)-2-[5-(6-{[(2S)-1-(1H-tetrazol-1-yl)propan-2-yl]oxy}pyrazin-2-yl)-3H-imidazo[4,5-b]pyridin-3-yl]benzonitrile | C | 475.2 |
| 385 | 4-(difluoromethoxy)-2-[5-(6-{[(2S)-1-(1H-tetrazol-1-yl)propan-2-yl]oxy}pyridin-2-yl)-3H-imidazo[4,5-b]pyridin-3-yl]benzonitrile | C | 490.2 |
| 386 | 6-chloro-2-[6-(3-{[(2S)-1-(1H-tetrazol-1-yl)propan-2-yl]oxy}phenyl)imidazo[1,2-b]pyridazin-3-yl]pyridine-3-carbonitrile | A | 458.1 |
| 387 | 4-fluoro-2-[6-(3-{[(2S)-1-(1H-tetrazol-1-yl)propan-2-yl]oxy}phenyl)-[1,2,4]triazolo[4,3-b]pyridazin-3-yl]benzonitrile | C | 442.2 |
| 388 | 6-(difluoromethyl)-2-[6-(3-{[(2S)-1-(1H-tetrazol-1-yl)propan-2-yl]oxy}phenyl)imidazo[1,2-b]pyridazin-3-yl]pyridine-3-carbonitrile | A | 474.2 |
| 389 | 6-acetyl-2-[6-(3-{[(2S)-1-(1H-tetrazol-1-yl)propan-2-yl]oxy}phenyl)imidazo[1,2-b]pyridazin-3-yl]pyridine-3-carbonitrile | B | 466.2 |
| 390 | 6-(1-hydroxyethyl)-2-[6-(3-{[(2S)-1-(1H-tetrazol-1-yl)propan-2-yl]oxy}phenyl)imidazo[1,2-b]pyridazin-3-yl]pyridine-3-carbonitrile | A | 468.2 |
| 391 | 2-[6-(3-{[(2S)-1-(1H-tetrazol-1-yl)propan-2-yl]oxy}phenyl)-[1,2,4]triazolo[4,3-b]pyridazin-3-yl]pyridine-3-carbonitrile | C | 425.2 |
| 392 | 4-fluoro-2-methoxy-6-[6-(6-{[(2S)-1-(1H-tetrazol-1-yl)propan-2-yl]oxy}pyrazin-2-yl)imidazo[1,2-b]pyridazin-3-yl]benzonitrile | A | 473.2 |
| 393 | 4-fluoro-2-methoxy-6-[5-(6-{[(2S)-1-(1H-tetrazol-1-yl)propan-2-yl]oxy}pyridin-2-yl)-3H-imidazo[4,5-b]pyridin-3-yl]benzonitrile | A | 472.2 |
| 394 | 4-amino-6-[6-(3-{[(2S)-1-(1H-tetrazol-1-yl)propan-2-yl]oxy}phenyl)imidazo[1,2-b]pyridazin-3-yl]pyrimidine-5-carbonitrile | B | 440.2 |
| 395 | 2-(difluoromethyl)-6-[5-(3-{[(2S)-1-(1H-tetrazol-1-yl)propan-2-yl]oxy}phenyl)-3H-imidazo[4,5-b]pyridin-3-yl]benzonitrile | A | 473.2 |
| 396 | 4-fluoro-2-methoxy-6-[5-(6-{[(2S)-1-(1H-tetrazol-1-yl)propan-2-yl]oxy}pyrazin-2-yl)-3H-imidazo[4,5-b]pyridin-3-yl]benzonitrile | A | 473.2 |
| 397 | 2-(difluoromethyl)-6-[5-(6-{[(2S)-1-(1H-tetrazol-1-yl)propan-2-yl]oxy}pyridin-2-yl)-3H-imidazo[4,5-b]pyridin-3-yl]benzonitrile | C | 474.2 |
| 398 | 2-(difluoromethoxy)-6-[5-(6-{[(2S)-1-(1H-tetrazol-1-yl)propan-2-yl]oxy}pyridin-2-yl)-3H-imidazo[4,5-b]pyridin-3-yl]benzonitrile | B | 490.2 |
| 399 | 4-[6-(4-fluoro-3-{[(2S)-1-(1H-tetrazol-1-yl)propan-2-yl]oxy}phenyl)imidazo[1,2-b]pyridazin-3-yl]-2-methoxypyridine-3-carbonitrile | A | 472.2 |
| 400 | 2-methoxy-4-[6-(3-{[(2S)-1-(1H-tetrazol-1-yl)propan-2-yl]oxy}phenyl)imidazo[1,2-b]pyridazin-3-yl]pyridine-3-carbonitrile | A | 454.2 |
| 401 | 4-(difluoromethyl)-2-[6-(3-{[(2S)-1-(1H-tetrazol-1-yl)propan-2-yl]oxy}phenyl)imidazo[1,2-b]pyridazin-3-yl]pyridine-3-carbonitrile | A | 474.2 |
| 402 | 4-[6-(4-fluoro-3-{[(2S)-1-(1H-tetrazol-1-yl)propan-2-yl]oxy}phenyl)imidazo[1,2-b]pyridazin-3-yl]-6-methoxypyrimidine-5-carbonitrile | A | 473.2 |
| 403 | 2-methoxy-4-[6-(6-{[(2S)-1-(1H-tetrazol-1-yl)propan-2-yl]oxy}pyridin-2-yl)imidazo[1,2-b]pyridazin-3-yl]pyridine-3-carbonitrile | A | 455.3 |
| 404 | 2-methoxy-6-[6-(6-{[(2S)-1-(1H-tetrazol-1-yl)propan-2-yl]oxy}pyridin-2-yl)imidazo[1,2-b]pyridazin-3-yl]benzonitrile | A | 454.3 |
| 405 | 2-(difluoromethoxy)-4-fluoro-6-[5-(6-{[(2S)-1-(1H-tetrazol-1-yl)propan-2-yl]oxy}pyridin-2-yl)-3H-imidazo[4,5-b]pyridin-3-yl]benzonitrile | A | 508.2 |
| 406 | 2-(difluoromethoxy)-4-fluoro-6-[5-(6-{[(2S)-1-(1H-tetrazol-1-yl)propan-2-yl]oxy}pyrazin-2-yl)-3H-imidazo[4,5-b]pyridin-3-yl]benzonitrile | B | 509.3 |
| 407 | 2-(difluoromethyl)-4-fluoro-6-[5-(6-{[(2S)-1-(1H-tetrazol-1-yl)propan-2-yl]oxy}pyridin-2-yl)-3H-imidazo[4,5-b]pyridin-3-yl]benzonitrile | B | 492.4 |
| 408 | 2-fluoro-4-methoxy-6-[6-(6-{[(2S)-1-(1H-tetrazol-1-yl)propan-2-yl]oxy}pyridin-2-yl)imidazo[1,2-b]pyridazin-3-yl]benzonitrile | A | 472.3 |
| 409 | 2-(difluoromethoxy)-4-fluoro-6-[6-(6-{[(2S)-1-(1H-tetrazol-1-yl)propan-2-yl]oxy}pyridin-2-yl)imidazo[1,2-b]pyridazin-3-yl]benzonitrile | A | 508.2 |
| 410 | 4-fluoro-2-methoxy-6-[6-(6-{[(2S)-1-(1H-tetrazol-1-yl)propan-2-yl]oxy}pyridin-2-yl)imidazo[1,2-b]pyridazin-3-yl]benzonitrile | A | 472.3 |
| 411 | 4-fluoro-2-methoxy-6-[5-(4-{[(2S)-1-(1H-tetrazol-1-yl)propan-2-yl]oxy}pyridin-2-yl)-3H-imidazo[4,5-b]pyridin-3-yl]benzonitrile | A | 472.3 |
| 412 | 2-(difluoromethoxy)-6-[6-(3-{[(2S)-1-(1H-tetrazol-1-yl)propan-2-yl]oxy}phenyl)imidazo[1,2-b]pyridazin-3-yl]benzonitrile | A | 489.3 |
| 413 | 2-(difluoromethyl)-6-[6-(3-{[(2S)-1-(1H-tetrazol-1-yl)propan-2-yl]oxy}phenyl)imidazo[1,2-b]pyridazin-3-yl]benzonitrile | A | 473.2 |

| Ex. No. | IUPAC NAME | Act | MS |
|---|---|---|---|
| 414 | 4-methoxy-2-[6-(6-{[(2S)-1-(1H-tetrazol-1-yl)propan-2-yl]oxy}pyridin-2-yl)imidazo[1,2-b]pyridazin-3-yl]pyridine-3-carbonitrile | B | 455.3 |
| 415 | 3-[6-(6-{[(2S)-1-(1H-tetrazol-1-yl)propan-2-yl]oxy}pyridin-2-yl)imidazo[1,2-b]pyridazin-3-yl]pyridine-4-carbonitrile | A | 425.4 |
| 416 | 4-fluoro-2-[5-(6-{[(2S)-1-(1H-tetrazol-1-yl)propan-2-yl]oxy}pyridin-2-yl)pyrazolo[1,5-a]pyrimidin-3-yl]benzonitrile | A | 442.2 |
| 417 | 2-(difluoromethyl)-4-fluoro-6-[6-(6-{[(2S)-1-(1H-tetrazol-1-yl)propan-2-yl]oxy}pyridin-2-yl)imidazo[1,2-b]pyridazin-3-yl]benzonitrile | A | 492.2 |
| 418 | 5-fluoro-2-[6-(6-{[(2S)-1-(1H-tetrazol-1-yl)propan-2-yl]oxy}pyridin-2-yl)imidazo[1,2-b]pyridazin-3-yl]benzonitrile | B | 442.2 |
| 419 | 2-fluoro-6-[6-(6-{[(2S)-1-(1H-tetrazol-1-yl)propan-2-yl]oxy}pyridin-2-yl)imidazo[1,2-b]pyridazin-3-yl]benzonitrile | A | 442.2 |
| 420 | 4-methoxy-2-[6-(6-{[(2S)-1-(1H-tetrazol-1-yl)propan-2-yl]oxy}pyridin-2-yl)imidazo[1,2-b]pyridazin-3-yl]benzonitrile | A | 454.2 |
| 421 | 2,4-difluoro-6-[6-(6-{[(2S)-1-(1H-tetrazol-1-yl)propan-2-yl]oxy}pyridin-2-yl)imidazo[1,2-b]pyridazin-3-yl]benzonitrile | A | 460.2 |
| 422 | 3,4-difluoro-2-[6-(6-{[(2S)-1-(1H-tetrazol-1-yl)propan-2-yl]oxy}pyridin-2-yl)imidazo[1,2-b]pyridazin-3-yl]benzonitrile | A | 460.1 |
| 423 | 3,6-difluoro-2-[6-(6-{[(2S)-1-(1H-tetrazol-1-yl)propan-2-yl]oxy}pyridin-2-yl)imidazo[1,2-b]pyridazin-3-yl]benzonitrile | A | 460.1 |
| 424 | 2-fluoro-4-methoxy-6-[5-(6-{[(2S)-1-(1H-tetrazol-1-yl)propan-2-yl]oxy}pyridin-2-yl)-3H-imidazo[4,5-b]pyridin-3-yl]benzonitrile | A | 472.2 |
| 425 | 2-[6-(6-{[(2S)-1-(1H-tetrazol-1-yl)propan-2-yl]oxy}pyridin-2-yl)imidazo[1,2-b]pyridazin-3-yl]benzonitrile | A | 424.3 |
| 426 | 2-acetyl-6-[6-(3-{[(2S)-1-(1H-tetrazol-1-yl)propan-2-yl]oxy}phenyl)imidazo[1,2-b]pyridazin-3-yl]benzonitrile | A | 465.2 |
| 427 | 2-(1,1-difluoroethyl)-6-[6-(3-{[(2S)-1-(1H-tetrazol-1-yl)propan-2-yl]oxy}phenyl)imidazo[1,2-b]pyridazin-3-yl]benzonitrile | A | 487.2 |
| 428 | 2-methoxy-6-[6-(6-{[(2S)-1-(1H-tetrazol-1-yl)propan-2-yl]oxy}pyrazin-2-yl)imidazo[1,2-b]pyridazin-3-yl]benzonitrile | A | 455.2 |
| 429 | 4-methoxy-2-[6-(6-{[(2S)-1-(1H-tetrazol-1-yl)propan-2-yl]oxy}pyrazin-2-yl)imidazo[1,2-b]pyridazin-3-yl]pyridine-3-carbonitrile | C | 456.2 |
| 430 | 4-methoxy-2-[5-(6-{[(2S)-1-(1H-tetrazol-1-yl)propan-2-yl]oxy}pyridin-2-yl)pyrazolo[1,5-a]pyrimidin-3-yl]pyridine-3-carbonitrile | C | 455.2 |
| 431 | 2-[6-(4-fluoro-3-{[(2S)-1-(1H-tetrazol-1-yl)propan-2-yl]oxy}phenyl)imidazo[1,2-b]pyridazin-3-yl]-4-oxo-1,4-dihydropyridine-3-carbonitrile | C | 458.2 |
| 432 | 2-[6-(4-fluoro-3-{[(2S)-1-(1H-tetrazol-1-yl)propan-2-yl]oxy}phenyl)imidazo[1,2-b]pyridazin-3-yl]-6-methoxypyridine | A | 447.2 |
| 433 | 4,5-difluoro-2-[6-(6-{[(2S)-1-(1H-tetrazol-1-yl)propan-2-yl]oxy}pyridin-2-yl)imidazo[1,2-b]pyridazin-3-yl]benzonitrile | A | 460.2 |
| 434 | 5-fluoro-3-[6-(3-{[(2S)-1-(1H-tetrazol-1-yl)propan-2-yl]oxy}phenyl)imidazo[1,2-b]pyridazin-3-yl]pyridine-2-carbonitrile | A | 442.3 |
| 435 | 2-[6-(4-fluoro-3-{[(2S)-1-(1H-tetrazol-1-yl)propan-2-yl]oxy}phenyl)imidazo[1,2-b]pyridazin-3-yl]-4-(fluoromethoxy)pyridine-3-carbonitrile | A | 490.3 |
| 436 | 2-[6-(4-fluoro-3-{[(2S)-1-(1H-tetrazol-1-yl)propan-2-yl]oxy}phenyl)imidazo[1,2-b]pyridazin-3-yl]-1-(fluoromethyl)-4-oxo-1,4-dihydropyridine-3-carbonitrile | B | 490.2 |
| 437 | 2-[5-(4-fluoro-3-{[(2S)-1-(1H-tetrazol-1-yl)propan-2-yl]oxy}phenyl)pyrazolo[1,5-a]pyrimidin-3-yl]-4-methoxypyridine-3-carbonitrile | A | 472.3 |
| 438 | 4-fluoro-2-methoxy-6-[6-(4-{[(2S)-1-(1H-tetrazol-1-yl)propan-2-yl]oxy}pyridin-2-yl)imidazo[1,2-b]pyridazin-3-yl]benzonitrile | A | 472.3 |
| 439 | 4-fluoro-2-[5-(5-fluoro-6-{[(2S)-1-(1H-tetrazol-1-yl)propan-2-yl]oxy}pyridin-2-yl)-3H-imidazo[4,5-b]pyridin-3-yl]-6-methoxybenzonitrile | A | 490.3 |
| 440 | 2,4-dimethoxy-6-[5-(6-{[(2S)-1-(1H-tetrazol-1-yl)propan-2-yl]oxy}pyridin-2-yl)-3H-imidazo[4,5-b]pyridin-3-yl]benzonitrile | B | 484.2 |
| 441 | 4-chloro-2-[6-(6-{[(2S)-1-(1H-tetrazol-1-yl)propan-2-yl]oxy}pyrazin-2-yl)imidazo[1,2-b]pyridazin-3-yl]benzonitrile | A | 459.3 |
| 442 | 4-chloro-2-[5-(6-{[(2S)-1-(1H-tetrazol-1-yl)propan-2-yl]oxy}pyridin-2-yl)-3H-imidazo[4,5-b]pyridin-3-yl]benzonitrile | A | 458.3 |
| 443 | 4-fluoro-2-methoxy-6-[6-(6-{[(2S)-1-(1H-1,2,4-triazol-1-yl)propan-2-yl]oxy}pyrazin-2-yl)imidazo[1,2-b]pyridazin-3-yl]benzonitrile | A | 472.2 |
| 444 | 2-[6-(4-fluoro-3-{[(2S)-1-(2H-tetrazol-2-yl)propan-2-yl]oxy}phenyl)imidazo[1,2-b]pyridazin-3-yl]-4-methoxypyridine-3-carbonitrile | A | 472.2 |
| 445 | 4-chloro-2-[5-(6-{[(2S)-1-(1H-tetrazol-1-yl)propan-2-yl]oxy}pyrazin-2-yl)-3H-imidazo[4,5-b]pyridin-3-yl]benzonitrile | B | 459.2 |
| 446 | 2-chloro-6-[5-(6-{[(2S)-1-(1H-tetrazol-1-yl)propan-2-yl]oxy}pyrazin-2-yl)-3H-imidazo[4,5-b]pyridin-3-yl]benzonitrile | C | 459.2 |
| 447 | 4-fluoro-2-[6-(5-fluoro-6-{[(2S)-1-(1H-tetrazol-1-yl)propan-2-yl]oxy}pyridin-2-yl)imidazo[1,2-b]pyridazin-3-yl]-6-methoxybenzonitrile | A | 490.2 |
| 448 | 4-chloro-2-methoxy-6-[5-(6-{[(2S)-1-(1H-tetrazol-1-yl)propan-2-yl]oxy}pyrazin-2-yl)-3H-imidazo[4,5-b]pyridin-3-yl]benzonitrile | A | 489.1 |
| 449 | 4-fluoro-2-[6-(5-fluoro-6-{[(2S)-1-(1H-tetrazol-1-yl)propan-2-yl]oxy}pyridin-2-yl)imidazo[1,2-b]pyridazin-3-yl]benzonitrile | A | 460.2 |
| 450 | 5-fluoro-2-[6-(3-{[(2S)-1-(1H-tetrazol-1-yl)propan-2-yl]oxy}phenyl)imidazo[1,2-b]pyridazin-3-yl]pyridine-3-carbonitrile | A | 442.3 |
| 451 | 5,6-difluoro-2-[6-(3-{[(2S)-1-(1H-tetrazol-1-yl)propan-2-yl]oxy}phenyl)imidazo[1,2-b]pyridazin-3-yl]pyridine-3-carbonitrile | A | 460.2 |
| 452 | 4-fluoro-2-methoxy-6-[6-(6-{[(2S)-1-(1H-1,2,4-triazol-1-yl)propan-2-yl]oxy}pyridin-2-yl)imidazo[1,2-b]pyridazin-3-yl]benzonitrile | A | 471.3 |
| 453 | 2-chloro-6-[5-(6-{[(2S)-1-(1H-tetrazol-1-yl)propan-2-yl]oxy}pyridin-2-yl)-3H-imidazo[4,5-b]pyridin-3-yl]benzonitrile | B | 458.2 |
| 454 | 4-chloro-2-methoxy-6-[5-(6-{[(2S)-1-(1H-tetrazol-1-yl)propan-2-yl]oxy}pyridin-2-yl)-3H-imidazo[4,5-b]pyridin-3-yl]benzonitrile | A | 488.3 |
| 455 | 4-chloro-2-methoxy-6-[6-(6-{[(2S)-1-(1H-tetrazol-1-yl)propan-2-yl]oxy}pyrazin-2-yl)imidazo[1,2-b]pyridazin-3-yl]benzonitrile | A | 489.3 |
| 456 | 2,4-dimethoxy-6-[6-(6-{[(2S)-1-(1H-tetrazol-1-yl)propan-2-yl]oxy}pyridin-2-yl)imidazo[1,2-b]pyridazin-3-yl]benzonitrile | A | 484.4 |
| 457 | 4-(difluoromethyl)-2-[6-(6-{[(2S)-1-(1H-tetrazol-1-yl)propan-2-yl]oxy}pyridin-2-yl)imidazo[1,2-b]pyridazin-3-yl]pyridine-3-carbonitrile | B | 475.3 |
| 458 | 2-[6-(6-{[(2S)-1-(1H-tetrazol-1-yl)propan-2-yl]oxy}pyridin-2-yl)imidazo[1,2-b]pyridazin-3-yl]pyridine-3-carbonitrile | C | 425.4 |
| 459 | 4-methoxy-6-[6-(6-{[(2S)-1-(1H-tetrazol-1-yl)propan-2-yl]oxy}pyridin-2-yl)imidazo[1,2-b]pyridazin-3-yl]pyrimidine-5-carbonitrile | C | 456.3 |
| 460 | 2,3-difluoro-6-[6-(6-{[(2S)-1-(1H-tetrazol-1-yl)propan-2-yl]oxy}pyridin-2-yl)imidazo[1,2-b]pyridazin-3-yl]benzonitrile | B | 460.3 |
| 461 | 3-fluoro-2-[6-(6-{[(2S)-1-(1H-tetrazol-1-yl)propan-2-yl]oxy}pyridin-2-yl)imidazo[1,2-b]pyridazin-3-yl]benzonitrile | B | 442.3 |

| Ex. No. | IUPAC NAME | Act | MS |
|---|---|---|---|
| 462 | 4-fluoro-2-(methoxymethyl)-6-[6-(6-{[(2S)-1-(1H-tetrazol-1-yl)propan-2-yl]oxy}pyridin-2-yl)imidazo[1,2-b]pyridazin-3-yl]benzonitrile | A | 486.3 |
| 463 | 6-methoxy-4-[6-(6-{[(2S)-1-(1H-tetrazol-1-yl)propan-2-yl]oxy}pyridin-2-yl)imidazo[1,2-b]pyridazin-3-yl]pyridine-3-carbonitrile | A | 455.3 |
| 464 | 6-oxo-4-[6-(6-{[(2S)-1-(1H-tetrazol-1-yl)propan-2-yl]oxy}pyridin-2-yl)imidazo[1,2-b]pyridazin-3-yl]-1,6-dihydropyridine-3-carbonitrile | A | 441.3 |
| 465 | 1-methyl-6-oxo-4-[6-(6-{[(2S)-1-(1H-tetrazol-1-yl)propan-2-yl]oxy}pyridin-2-yl)imidazo[1,2-b]pyridazin-3-yl]-1,6-dihydropyridine-3-carbonitrile | A | 455.3 |
| 466 | 4-(fluoromethoxy)-2-[6-(3-{[(2S)-1-(1H-tetrazol-1-yl)propan-2-yl]oxy}phenyl)imidazo[1,2-b]pyridazin-3-yl]pyridine-3-carbonitrile | A | 472.3 |
| 467 | 6-fluoro-2-[6-(3-{[(2S)-1-(1H-tetrazol-1-yl)propan-2-yl]oxy}phenyl)imidazo[1,2-b]pyridazin-3-yl]pyridine-3-carbonitrile | A | 442.3 |
| 468 | 2-fluoro-6-[6-(3-{[(2S)-1-(1H-tetrazol-1-yl)propan-2-yl]oxy}phenyl)imidazo[1,2-b]pyridazin-3-yl]pyridine-3-carbonitrile | A | 442.3 |
| 469 | 4-(2-methoxyethoxy)-2-[6-(3-{[(2S)-1-(1H-tetrazol-1-yl)propan-2-yl]oxy}phenyl)imidazo[1,2-b]pyridazin-3-yl]pyridine-3-carbonitrile | A | 498.3 |
| 470 | 3-[6-(4-fluoro-3-{[(2S)-1-(1H-tetrazol-1-yl)propan-2-yl]oxy}phenyl)imidazo[1,2-b]pyridazin-3-yl]-5-methoxypyridine-4-carbonitrile | A | 472.3 |
| 471 | 4-(difluoromethyl)-2-[6-(6-{[(2S)-1-(1H-tetrazol-1-yl)propan-2-yl]oxy}pyrazin-2-yl)imidazo[1,2-b]pyridazin-3-yl]pyridine-3-carbonitrile | C | 476.3 |
| 472 | 4-fluoro-2-hydroxy-6-[5-(6-{[(2S)-1-(1H-tetrazol-1-yl)propan-2-yl]oxy}pyridin-2-yl)-3H-imidazo[4,5-b]pyridin-3-yl]benzonitrile | A | 458.2 |
| 473 | 2-[6-(4-fluoro-3-{[(2S)-1-(1H-tetrazol-1-yl)propan-2-yl]oxy}phenyl)imidazo[1,2-b]pyridazin-3-yl]-4-(methoxy-d3)pyridine-3-carbonitrile | A | 475.2 |
| 474 | 4-fluoro-2-(methoxy-d3)-6-[5-(6-{[(2S)-1-(1H-tetrazol-1-yl)propan-2-yl]oxy}pyridin-2-yl)-3H-imidazo[4,5-b]pyridin-3-yl]benzonitrile | A | 475.2 |
| 475 | 2-[6-(4-fluoro-3-{[(2R)-1-fluoro-3-(1H-tetrazol-1-yl)propan-2-yl]oxy}phenyl)imidazo[1,2-b]pyridazin-3-yl]-4-methoxypyridine-3-carbonitrile | A | 490.0 |
| 476 | 2-[6-(4-fluoro-3-{[(2S)-1-(1H-tetrazol-1-yl)butan-2-yl]oxy}phenyl)imidazo[1,2-b]pyridazin-3-yl]-4-methoxypyridine-3-carbonitrile | A | 486.2 |
| 477 | 2-[6-(4-fluoro-3-{[(2R)-1-hydroxy-3-(1H-tetrazol-1-yl)propan-2-yl]oxy}phenyl)imidazo[1,2-b]pyridazin-3-yl]-4-methoxypyridine-3-carbonitrile | A | 488.0 |
| 478 | 2-[6-(4-fluoro-3-{[(2S)-1-(1H-tetrazol-1-yl)propan-2-yl]amino}phenyl)imidazo[1,2-b]pyridazin-3-yl]-4-methoxypyridine-3-carbonitrile | A | 471.1 |
| 479 | 2-[6-(4-fluoro-3-[methyl[(2S)-1-(1H-tetrazol-1-yl)propan-2-yl]amino}phenyl)imidazo[1,2-b]pyridazin-3-yl]-4-methoxypyridine-3-carbonitrile | C | 485.1 |
| 480 | 4-fluoro-2-methoxy-6-[6-(6-{[(2S)-1-(1H-tetrazol-1-yl)propan-2-yl]amino}pyridin-2-yl)imidazo[1,2-b]pyridazin-3-yl]benzonitrile | A | 471.1 |
| 481 | 4-fluoro-2-methoxy-6-[6-(4-{[(2S)-1-(1H-tetrazol-1-yl)propan-2-yl]amino}pyridin-2-yl)imidazo[1,2-b]pyridazin-3-yl]benzonitrile | A | 471.1 |
| 482 | 4-fluoro-2-methoxy-6-[6-(5-{[(2S)-1-(1H-tetrazol-1-yl)propan-2-yl]amino}pyridin-3-yl)imidazo[1,2-b]pyridazin-3-yl]benzonitrile | A | 471.1 |
| 483 | 4-fluoro-2-[6-(4-{[(2S)-1-(1H-tetrazol-1-yl)propan-2-yl]amino}pyridin-2-yl)imidazo[1,2-b]pyridazin-3-yl]benzonitrile | A | 441.1 |
| 484 | 4-fluoro-2-[6-(6-{[(2S)-1-(1H-tetrazol-1-yl)propan-2-yl]amino}pyrazin-2-yl)imidazo[1,2-b]pyridazin-3-yl]benzonitrile | A | 442.2 |
| 485 | 2-[6-(4-fluoro-3-{[(2S)-1-(1H-tetrazol-1-yl)propan-2-yl]amino}phenyl)imidazo[1,2-b]pyridazin-3-yl]pyridine-3-carbonitrile | A | 441.1 |
| 486 | 4-methoxy-2-[6-(4-{[(2S)-1-(1H-tetrazol-1-yl)propan-2-yl]oxy}pyridin-2-yl)imidazo[1,2-b]pyridazin-3-yl]pyridine-3-carbonitrile | B | 455.3 |

Experimental Example 1

Evaluation of In Vitro CaMKII Inhibitory Activity (Binding Assay)

(i) Objective

In vitro CaMKIIδ inhibitory activity was evaluated by a binding assay.

(ii) Materials

Full-length, glutathione-S-transferase (GST)-tagged, human CaMKIIδ was purchased from Carna Biosciences (product #02-111, Kobe, Japan). Full-length bovine calmodulin was purchased from Wako Pure Chemical Industries (Osaka, Japan). Terbium-labeled anti-GST antibody (Tb-anti-GST Ab) was purchased from Life Technologies (Carlsbad, CA, USA). Fluorescent probe ligand, 5,5-difluoro-7,9-dimethyl-3-(3-oxo-3-((3-((4-(3-(piperazin-1-yl)phenyl)pyrimidin-2-yl)amino)phenyl)amino)propyl)-5H-dipyrrolo[1,2-c:2',1'-f][1,3,2]diazaborinin-4-ium-5-uide, was described in WO 2018/183112 A1.

(iii) Methods

Time-Resolved Fluorescence Resonance Energy Transfer (TR-FRET) Assay

All assays were conducted using 384-well, white, flat-bottomed plates (product #784075, Greiner Bio-One, Frickenhausen, Germany) in kinase assay buffer, which consists of 50 mM HEPES pH 7.2-7.5, 10 mM $MgCl_2$, 1 mM EGTA, 0.01% Brig-35, 0.1 mM DTT). The fluorescent probe ligand, 5,5-difluoro-7,9-dimethyl-3-(3-oxo-3-((3-((4-(3-(piperazin-1-yl)phenyl)pyrimidin-2-yl)amino)phenyl)amino)propyl)-5H-dipyrrolo[1,2-c:2',1'-f][1,3,2]diazaborinin-4-ium-5-uide was added at a final concentration of 300 nM to solutions containing 0.21 nM Tb-anti-GST Ab, 1 mM $CaCl_2$, 10 μg/mL calmodulin, and 0.5 nM GST-tagged CaMKIIδ. After shaded incubation of the protein-probe mixture on ice for 30 min, the premix was dispensed in the assay plate including test inhibitors with 4 fold dilution series of eight concentrations. After 1 hr incubation at room temperature, TR-FRET signals were measured in duplicate using an EnVision microplate reader (Perkin Elmer, Waltham, MA, USA). The solution in each well was excited with a laser ($\lambda$=340 nm) reflected by a dichroic mirror (D400/D505 (Perkin Elmer) through an excitation filter (UV (TRF) 340, (Perkin Elmer)), and fluorescence from Tb and BODIPY were detected through two emission filters (CFP 495 (Perkin Elmer) for Tb, Emission 520 (Perkin Elmer) for BODIPY).

The percentage of inhibition of test compounds was calculated according to equation (1)

$$\text{Inhibition (\%)} = 100 \times (\mu_H - T)/(\mu_H - \mu_L) \quad (1)$$

Where T is the value of the wells containing test compounds and $\mu_H$, and $\mu_L$ are the mean values of the 0% and 100% inhibition control wells, respectively. The values of the 0 and 100% inhibition controls were the signals obtained in the absence and presence of high concentration (3 μM) of a parent compound of the fluorescent probe ligand (without the fluorophore), respectively. The half maximal inhibitory concentration ($IC_{50}$) of test compounds was calculated by fitting the data with the logistic equation using XLfit (IDBS, Guildford, UK). The $IC_{50}$ was classified according to the following activity ranks.
A: less than 10 nM
B: 10 nM or more and less than 100 nM
C: 100 nM or more
The results are shown in Table 1.

Experimental Example 2

Evaluation of In Vivo Cardiac CaMKII Inhibition (Oral Administration)
(i) Objective
To evaluate potency of test compounds to inhibit cardiac CaMKII in vivo, phosphorylation levels of the CaMKII-specific phosphorylation site of phospholamban (Thr17, P-PLN) were measured in the heart of rats administered orally with test compounds.
(ii) Materials and Methods
Test compounds were suspended in 0.5% [w/v]methylcellulose/water solution and administered (30 mg/kg) to male CD (SD) IGS rats (6-8 weeks old, n=4) by oral gavage (5 mL/kg). At 2 hours after the administration, rats were sacrificed and the hearts were harvested. After washing the isolated hearts with ice-cold saline, connective tissues were removed on ice, and the isolated left ventricle were frozen into liquid nitrogen gas and stored at –80° C.
The left ventricle samples were homogenized in RIPA-buffer containing phosphatase inhibitors and protease inhibitors. Samples were analyzed by Western blotting using anti-P-PLN (Thr17) antibody (Santa Cruz Biotechnology, sc-17024-R). The band intensities were quantified using an imaging system and were normalized relative to the vehicle-treated group.
(iii) Results
Four compounds from the examples were tested two hours after administration at a dose of 30 mg/kg and each compound had a P-PLN reduction rate of >25% compared to the vehicle-treated group.

Formulation Examples

Medicaments containing the compound of the present invention as an active ingredient can be produced, for example, by the following formulations.
1. Capsule

| (1) | compound obtained in Example 1 | 10 mg |
| (2) | lactose | 90 mg |
| (3) | microcrystalline cellulose | 70 mg |
| (4) | magnesium stearate | 10 mg |
| | 1 capsule | 180 mg |

The total amount of the above-mentioned (1), (2) and (3) and 5 mg of (4) are blended and granulated, and 5 mg of the remaining (4) is added. The whole mixture is sealed in a gelatin capsule.
2. Tablet

| (1) | compound obtained in Example 1 | 10 mg |
| (2) | lactose | 35 mg |
| (3) | cornstarch | 150 mg |
| (4) | microcrystalline cellulose | 30 mg |
| (5) | magnesium stearate | 5 mg |
| | 1 tablet | 230 mg |

The total amount of the above-mentioned (1), (2) and (3), 20 mg of (4) and 2.5 mg of (5) are blended and granulated, and 10 mg of the remaining (4) and 2.5 mg of the remaining (5) are added and the mixture is compression formed to give a tablet.

According to the present invention, a fused heteroaryl compound having a superior CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like can be provided.

The invention claimed is:
1. A compound represented by formula (I):

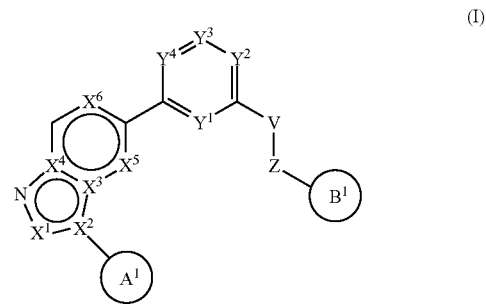

or a pharmaceutically acceptable salt thereof,
wherein:

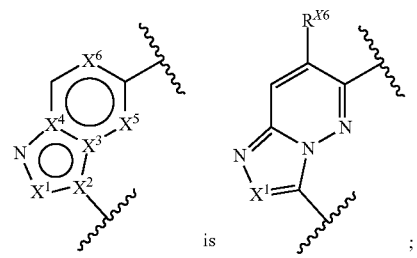

$X^1$ is $CR^{X1}$ or N;
$R^{X1}$ is H, halogen, or $C_{1-6}$ alkyl;
$R^{X6}$ is H;
$Y^1$ is $CR^{Y1}$ or N;
$Y^2$ is $CR^{Y2}$ or N;
$Y^3$ is $CR^{Y3}$ or N;
$Y^4$ is $CR^{Y4}$ or N;
$R^{Y1}$ is H;
$R^{Y2}$ is H, halogen, or CN;

$R^{Y3}$ is H or halogen;
$R^{Y4}$ is H or halogen;
V is —O—;
Z is $C_{1-6}$ alkylene;
Ring $A^1$ is $C_{6-14}$ aryl or heteroaryl, wherein the $C_{6-14}$ aryl or heteroaryl is optionally substituted with one or more substituents independently selected from the group consisting of halogen, CN, $NO_2$, $C_{1-6}$ alkyl, $C_{1-6}$ haloalkyl, $C_{7-16}$ aralkyl, $C_{2-6}$ alkenyl, $C_{2-6}$ alkynyl, C(O)H, C(O)$C_{1-6}$ alkyl, C(O)$C_{1-6}$ haloalkyl, C(O)$C_{7-16}$ aralkyl, C(O)$C_{2-6}$ alkenyl, C(O)$C_{3-10}$ cycloalkyl, C(O)$C_{3-10}$ cycloalkenyl, C(O)-(3- to 14-membered heterocyclyl), C(O)$C_{6-14}$ aryl, C(O)-(5- to 14-membered heteroaryl), C(O)$NH_2$, C(O)NH$C_{1-6}$ alkyl, C(O)NH$C_{1-6}$ haloalkyl, C(O)NH$C_{7-16}$ aralkyl, C(O)NH$C_{2-6}$ alkenyl, C(O)NH$C_{3-10}$ cycloalkyl, C(O)NH$C_{3-10}$ cycloalkenyl, C(O)NH-(3- to 14-membered heterocyclyl), C(O)NH$C_{6-14}$ aryl, C(O)NH-(5- to 14-membered heteroaryl), C(O)N($C_{1-6}$ alkyl)$_2$, C(O)OH, C(O)O$C_{1-6}$ alkyl, C(O)O$C_{1-6}$ haloalkyl, C(O)O$C_{7-16}$ aralkyl, C(O)O$C_{2-6}$ alkenyl, C(O)O$C_{3-10}$ cycloalkyl, C(O)O$C_{3-10}$ cycloalkenyl, C(O)O-(3- to 14-membered heterocyclyl), C(O)O$C_{6-14}$ aryl, C(O)O-(5- to 14-membered heteroaryl), C(S)$NH_2$, C(S)NH$C_{1-6}$ alkyl, C(S)NH$C_{1-6}$ haloalkyl, C(S)NH$C_{7-16}$ aralkyl, C(S)NH$C_{2-6}$ alkenyl, C(S)NH$C_{3-10}$ cycloalkyl, C(S)NH$C_{3-10}$ cycloalkenyl, C(S)NH-(3- to 14-membered heterocyclyl), C(S)NH$C_{6-14}$ aryl, C(S)NH-(5- to 14-membered heteroaryl), $NH_2$, NH$C_{1-6}$ alkyl, N($C_{1-6}$ alkyl)$_2$, NH$C_{7-16}$ aralkyl, NH$C_{2-6}$ alkenyl, NHC(O)$C_{1-6}$ alkyl, NHC(O)$C_{7-16}$ aralkyl, NHC(O)O$C_{1-6}$ alkyl, NHC(O)O$C_{7-16}$ aralkyl, NH$C_{3-10}$ cycloalkyl, NH$C_{3-10}$ cycloalkenyl, NH-(3- to 14-membered heterocyclyl), NH$C_{6-14}$ aryl, NH-(5- to 14-membered heteroaryl), OH, O$C_{1-6}$ alkyl, O$C_{1-6}$ haloalkyl, O$C_{7-16}$ aralkyl, O$C_{2-6}$ alkenyl, O$C_{3-10}$ cycloalkyl, O$C_{3-10}$ cycloalkenyl, O-(3- to 14-membered heterocyclyl), O$C_{6-14}$ aryl, O-(5- to 14-membered heteroaryl), P(O)(OH)$_2$, SH, S$C_{1-6}$ alkyl, S$C_{1-6}$ haloalkyl, S$C_{7-16}$ aralkyl, S$C_{2-6}$ alkenyl, S$C_{3-10}$ cycloalkyl, S$C_{3-10}$ cycloalkenyl, S-(3- to 14-membered heterocyclyl), S$C_{6-14}$ aryl, S-(5- to 14-membered heteroaryl), S(O)$C_{1-6}$ alkyl, S(O)$C_{1-6}$ haloalkyl, S(O)$C_{7-16}$ aralkyl, S(O)$C_{2-6}$ alkenyl, S(O)$C_{3-10}$ cycloalkyl, S(O)$C_{3-10}$ cycloalkenyl, S(O)-(3- to 14-membered heterocyclyl), S(O)$C_{6-14}$ aryl, S(O)-(5- to 14-membered heteroaryl), S(O)$_2C_{1-6}$ alkyl, S(O)$_2C_{1-6}$ haloalkyl, S(O)$_2C_{7-166}$ aralkyl, S(O)$_2C_{2-6}$ alkenyl, S(O)$_2C_{3-10}$ cycloalkyl, S(O)$_2C_{3-10}$ cycloalkenyl, S(O)$_2$-(3- to 14-membered heterocyclyl), S(O)$_2C_{6-14}$ aryl, S(O)$_2$-(5- to 14-membered heteroaryl), S(O)$_2NH_2$, S(O)$_2NH_2$, S(O)$_2$NH$C_{1-6}$ alkyl, S(O)$_2$N($C_{1-6}$ alkyl)$_2$, S(O)$_2$NH$C_{7-16}$ aralkyl, S(O)$_2$NH$C_{2-6}$ alkenyl, S(O)$_2$NH$C_{3-10}$ cycloalkyl, S(O)$_2$NH$C_{3-10}$ cycloalkenyl, S(O)$_2$NH-(3- to 14-membered heterocyclyl), S(O)$_2$NH$C_{6-14}$ aryl, S(O)$_2$NH-(5- to 14-membered heteroaryl), $SiH_3$, Si($C_{1-6}$ alkyl)$_3$, Si($C_{7-16}$ aralkyl)$_3$, Si($C_{2-6}$ alkenyl)$_3$, Si($C_{3-10}$ cycloalkyl)$_3$, Si($C_{3-10}$ cycloalkenyl)$_3$, Si-(3- to 14-membered heterocyclyl)$_3$, Si($C_{6-14}$ aryl)$_3$, Si-(5- to 14-membered heteroaryl)$_3$, $C_{3-10}$ cycloalkyl, $C_{3-10}$ cycloalkenyl, heterocyclyl, $C_{6-14}$ aryl, and heteroaryl; and Ring $B^1$ is heteroaryl, wherein the heteroaryl is optionally substituted with one or more substituents independently selected from the group consisting of halogen, CN, $NO_2$, $C_{1-6}$ alkyl, $C_{1-6}$ haloalkyl, $C_{7-16}$ aralkyl, $C_{2-6}$ alkenyl, $C_{2-6}$ alkynyl, C(O)H, C(O)$C_{1-6}$ alkyl, C(O)$C_{1-6}$ haloalkyl, C(O)$C_{7-16}$ aralkyl, C(O)$C_{2-6}$ alkenyl, C(O)$C_{3-10}$ cycloalkyl, C(O)$C_{3-10}$ cycloalkenyl, C(O)-(3- to 14-membered heterocyclyl), C(O)$C_{6-14}$ aryl, C(O)-(5- to 14-membered heteroaryl), C(O)$NH_2$, C(O)NH$C_{1-6}$ alkyl, C(O)NH$C_{1-6}$ haloalkyl, C(O)NH$C_{7-16}$ aralkyl, C(O)NH$C_{2-6}$ alkenyl, C(O)NH$C_{3-10}$ cycloalkyl, C(O)NH$C_{3-10}$ cycloalkenyl, C(O)NH-(3- to 14-membered heterocyclyl), C(O)NH$C_{6-14}$ aryl, C(O)NH-(5- to 14-membered heteroaryl), C(O)N($C_{1-6}$ alkyl)$_2$, C(O)OH, C(O)O$C_{1-6}$ alkyl, C(O)O$C_{1-6}$ haloalkyl, C(O)O$C_{7-16}$ aralkyl, C(O)O$C_{2-6}$ alkenyl, C(O)O$C_{3-10}$ cycloalkyl, C(O)O$C_{3-10}$ cycloalkenyl, C(O)O-(3- to 14-membered heterocyclyl), C(O)O$C_{6-14}$ aryl, C(O)O-(5- to 14-membered heteroaryl), C(S)$NH_2$, C(S)NH$C_{1-6}$ alkyl, C(S)NH$C_{1-6}$ haloalkyl, C(S)NH$C_{7-16}$ aralkyl, C(S)NH$C_{2-6}$ alkenyl, C(S)NH$C_{3-10}$ cycloalkyl, C(S)NH$C_{3-10}$ cycloalkenyl, C(S)NH-(3- to 14-membered heterocyclyl), C(S)NH$C_{6-14}$ aryl, C(S)NH-(5- to 14-membered heteroaryl), $NH_2$, NH$C_{1-6}$ alkyl, N($C_{1-6}$ alkyl)$_2$, NH$C_{7-16}$ aralkyl, NH$C_{2-6}$ alkenyl, NHC(O)$C_{1-6}$ alkyl, NHC(O)$C_{7-16}$ aralkyl, NHC(O)O$C_{1-6}$ alkyl, NHC(O)O$C_{7-16}$ aralkyl, NH$C_{3-10}$ cycloalkyl, NH$C_{3-10}$ cycloalkenyl, NH-(3- to 14-membered heterocyclyl), NH$C_{6-14}$ aryl, NH-(5- to 14-membered heteroaryl), OH, O$C_{1-6}$ alkyl, O$C_{1-6}$ haloalkyl, O$C_{7-16}$ aralkyl, O$C_{2-6}$ alkenyl, O$C_{3-10}$ cycloalkyl, O$C_{3-10}$ cycloalkenyl, O-(3- to 14-membered heterocyclyl), O$C_{6-14}$ aryl, O-(5- to 14-membered heteroaryl), P(O)(OH)$_2$, SH, S$C_{1-6}$ alkyl, S$C_{1-6}$ haloalkyl, S$C_{7-16}$ aralkyl, S$C_{2-6}$ alkenyl, S$C_{3-10}$ cycloalkyl, S$C_{3-10}$ cycloalkenyl, S-(3- to 14-membered heterocyclyl), S$C_{6-14}$ aryl, S-(5- to 14-membered heteroaryl), S(O)$C_{1-6}$ alkyl, S(O)$C_{1-6}$ haloalkyl, S(O)$C_{7-16}$ aralkyl, S(O)$C_{2-6}$ alkenyl, S(O)$C_{3-10}$ cycloalkyl, S(O)$C_{3-10}$ cycloalkenyl, S(O)-(3- to 14-membered heterocyclyl), S(O)$C_{6-14}$ aryl, S(O)-(5- to 14-membered heteroaryl), S(O)$_2C_{1-6}$ alkyl, S(O)$_2C_{1-6}$ haloalkyl, S(O)$_2C_{7-166}$ aralkyl, S(O)$_2C_{2-6}$ alkenyl, S(O)$_2C_{3-10}$ cycloalkyl, S(O)$_2C_{3-10}$ cycloalkenyl, S(O)$_2$-(3- to 14-membered heterocyclyl), S(O)$_2C_{6-14}$ aryl, S(O)$_2$-(5- to 14-membered heteroaryl), S(O)$_2NH_2$, S(O)$_2NH_2$, S(O)$_2$NH$C_{1-6}$ alkyl, S(O)$_2$N($C_{1-6}$ alkyl)$_2$, S(O)$_2$NH$C_{7-16}$ aralkyl, S(O)$_2$NH$C_{2-6}$ alkenyl, S(O)$_2$NH$C_{3-10}$ cycloalkyl, S(O)$_2$NH$C_{3-10}$ cycloalkenyl, S(O)$_2$NH-(3- to 14-membered heterocyclyl), S(O)$_2$NH$C_{6-14}$ aryl, S(O)$_2$NH-(5- to 14-membered heteroaryl), $SiH_3$, Si($C_{1-6}$ alkyl)$_3$, Si($C_{7-16}$ aralkyl)$_3$, Si($C_{2-6}$ alkenyl)$_3$, Si($C_{3-10}$ cycloalkyl)$_3$, Si($C_{3-10}$ cycloalkenyl)$_3$, Si-(3- to 14-membered heterocyclyl)$_3$, Si($C_{6-14}$ aryl)$_3$, Si-(5- to 14-membered heteroaryl)$_3$, $C_{3-10}$ cycloalkyl, $C_{3-10}$ cycloalkenyl, heterocyclyl, $C_{6-14}$ aryl, and heteroaryl.

2. The compound according to claim 1, or a pharmaceutically acceptable salt thereof, wherein:
Z is —CHR$^1$CH$_2$—; and
R$^1$ is —C$_{1-4}$ alkyl.

3. The compound according to claim 1, or a pharmaceutically acceptable salt thereof, wherein Ring $B^1$ is a 5-membered heteroaryl, wherein the 5-membered heteroaryl is optionally substituted.

4. The compound according to claim 1, wherein the compound is represented by the following formula:

or a pharmaceutically acceptable salt thereof.

5. The compound according to claim 1, wherein the compound is represented by the following formula:

or a pharmaceutically acceptable salt thereof,
wherein:
  $R^1$ is $C_{1-4}$ alkyl;
  Ring $A^2$ is phenyl or a 5- or 6-membered heteroaryl, wherein the phenyl or 5- or 6-membered heteroaryl is optionally substituted; and
  Ring $B^2$ is a 5-membered heteroaryl, wherein the 5-membered heteroaryl is optionally substituted.

6. The compound according to claim 5, or a pharmaceutically acceptable salt thereof, wherein:
  (i) $Y^1$ is N; or
  (ii) $Y^2$ is N; or
  (iii) $Y^3$ is N; or
  (iv) $Y^4$ is N.

7. The compound according to claim 5, or a pharmaceutically acceptable salt thereof, wherein $R^1$ is $CH_3$.

8. The compound according to claim 5, or a pharmaceutically acceptable salt thereof, wherein Ring $A^2$ is phenyl or a 6-membered heteroaryl, wherein the phenyl or 6-membered heteroaryl is optionally substituted with at least one CN substituent.

9. The compound according to claim 5, or a pharmaceutically acceptable salt thereof, wherein:
  $X^1$ is $CR^{X1}$;
  $R^{X1}$ is H; and
  Ring $B^2$ is triazol-1-yl or tetrazol-1-yl.

10. The compound according to claim 5, wherein the compound is represented by the following formula:

(II)

or a pharmaceutically acceptable salt thereof,
wherein:
  Ring $B^2$ is triazol-1-yl or tetrazol-1-yl.

11. The compound according to claim 1, wherein the compound is represented by the following formula:

or a pharmaceutically acceptable salt thereof,
wherein:
  Ring $A^3$ is phenyl or a 6-membered nitrogen-containing heteroaryl, wherein the phenyl or 6-membered nitrogen-containing heteroaryl is optionally substituted; and
  W is CH or N.

12. The compound according to claim 11, or a pharmaceutically acceptable salt thereof, wherein is formula ($A^3$-1):

($A^3$-1)

-continued

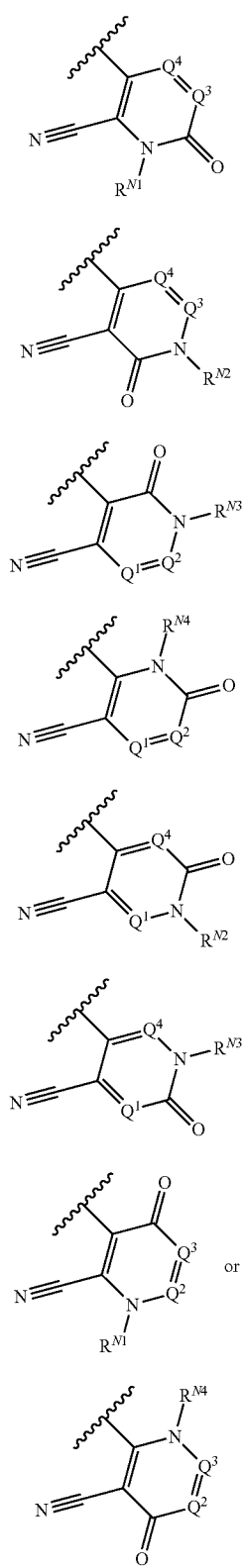

$Q^1$ is $CR^{Q1}$ or N;
$Q^2$ is $CR^{Q2}$ or N;
$Q^3$ is $CR^{Q3}$ or N;
$Q^4$ is $CR^{Q4}$ or N;

$R^{Q1}$ is H, halogen, CN, $C_{1-6}$ alkyl, $C_{1-6}$ haloalkyl, $C_{7-16}$ aralkyl, $C(O)C_{1-6}$ alkyl, $C(O)$-(monocyclic 3- to 8-membered heterocyclyl), $C(O)NHC_{1-6}$ alkyl, $C(O)N(C_{1-6}$ alkyl$)_2$, $C(O)OH$, $C(O)OC_{1-6}$ alkyl, $NH_2$, $NHC_{1-6}$ alkyl, $N(C_{1-6}$ alkyl$)_2$, $NHC_{7-16}$ aralkyl, $NHC(O)C_{1-6}$ alkyl, $NHC(O)C_{7-16}$ aralkyl, $NHC(O)OC_{1-6}$ alkyl, $NHC(O)OC_{7-16}$ aralkyl, OH, $OC_{1-6}$ alkyl, $OC_{1-6}$ haloalkyl, $OC_{7-16}$ aralkyl, $OC_{3-10}$ cycloalkyl, O-(monocyclic 3- to 8-membered heterocyclyl), $C_{3-10}$ cycloalkyl, or a monocyclic 3- to 8-membered heterocyclyl;

$R^{Q2}$ is H, halogen, or $OC_{1-6}$ alkyl;

$R^{Q3}$ is H, halogen, CN, $C_{1-6}$ alkyl, $C(O)C_{1-6}$ alkyl, $C(O)NHC_{1-6}$ alkyl, $C(O)N(C_{1-6}$ alkyl$)_2$, $C(O)OH$, $C(O)OC_{1-6}$ alkyl, $NHC_{1-6}$ alkyl, $N(C_{1-6}$ alkyl$)_2$, or $OC_{1-6}$ alkyl; and $R^{Q4}$ is H or halogen.

13. The compound according to claim 11, wherein the compound is represented by the following formula:

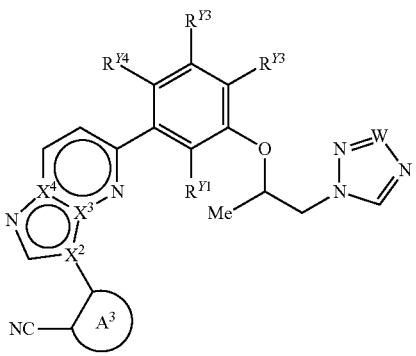

or a pharmaceutically acceptable salt thereof.

14. A pharmaceutical composition comprising a pharmaceutically acceptable excipient and the compound according to claim 1, or a pharmaceutically acceptable salt thereof.

15. A compound selected from the group consisting of:

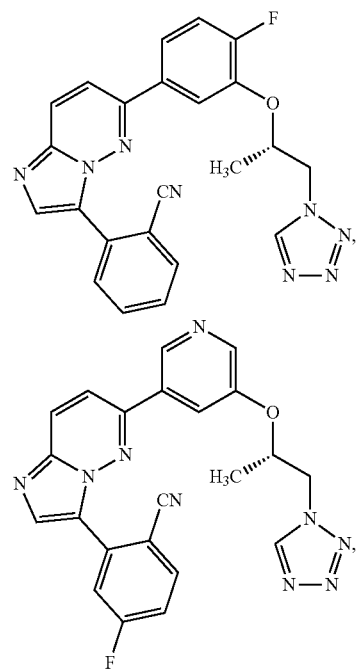

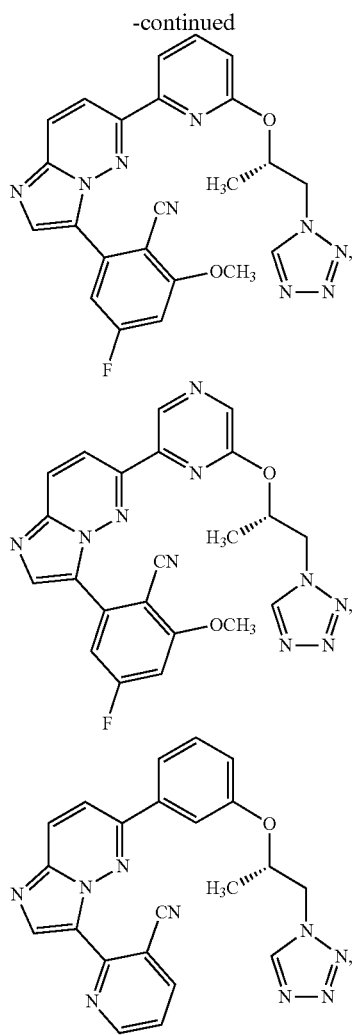
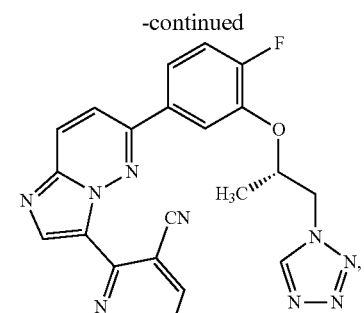
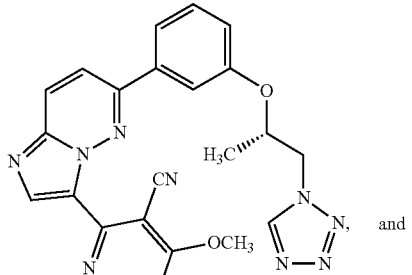
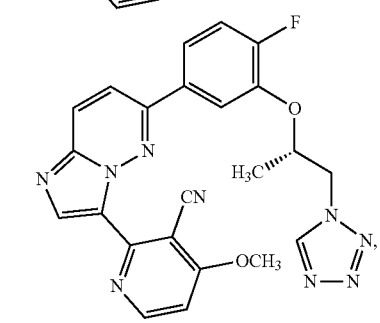
or a pharmaceutically acceptable salt thereof.
* * * * *